(12) United States Patent
Evans et al.

(10) Patent No.: US 9,051,249 B2
(45) Date of Patent: Jun. 9, 2015

(54) BENZYLAMINE DERIVATIVES AS INHIBITORS OF PLASMA KALLIKREIN

(75) Inventors: David Michael Evans, Salisbury (GB); Rebecca Louise Davie, Salisbury (GB); Hannah Joy Edwards, Salisbury (GB); David Philip Rooker, Salisbury (GB)

(73) Assignee: KalVista Pharmaceuticals Limited, Wiltshire (GB)

( * ) Notice: Subject to any disclaimer, the term of this patent is extended or adjusted under 35 U.S.C. 154(b) by 0 days.

(21) Appl. No.: 14/131,351

(22) PCT Filed: Jul. 6, 2012

(86) PCT No.: PCT/GB2012/051588
§ 371 (c)(1),
(2), (4) Date: Apr. 2, 2014

(87) PCT Pub. No.: WO2013/005045
PCT Pub. Date: Jan. 10, 2013

(65) Prior Publication Data
US 2014/0213611 A1    Jul. 31, 2014

Related U.S. Application Data

(60) Provisional application No. 61/505,305, filed on Jul. 7, 2011.

(30) Foreign Application Priority Data

Jul. 7, 2011    (GB) .................................. 1111682.9

(51) Int. Cl.

| | |
|---|---|
| *C07D 333/38* | (2006.01) |
| *C07D 207/16* | (2006.01) |
| *C07D 213/81* | (2006.01) |
| *C07D 215/48* | (2006.01) |
| *C07D 261/18* | (2006.01) |
| *C07C 237/20* | (2006.01) |
| *C07C 317/28* | (2006.01) |
| *C07C 237/22* | (2006.01) |
| *C07K 5/062* | (2006.01) |
| *C07K 5/06* | (2006.01) |
| *C07K 5/065* | (2006.01) |
| *C07D 231/14* | (2006.01) |
| *C07D 333/24* | (2006.01) |
| *C07D 333/60* | (2006.01) |
| *C07D 233/90* | (2006.01) |
| *C07D 409/12* | (2006.01) |
| *C07D 413/12* | (2006.01) |
| *C07D 417/12* | (2006.01) |
| *C07D 207/34* | (2006.01) |
| *C07D 277/30* | (2006.01) |
| *C07D 277/56* | (2006.01) |
| *C07D 209/18* | (2006.01) |
| *C07D 213/56* | (2006.01) |

(Continued)

(52) U.S. Cl.
CPC ............. *C07C 317/28* (2013.01); *C07C 237/22* (2013.01); *C07D 207/16* (2013.01); *A61K 38/00* (2013.01); *C07K 5/06026* (2013.01); *C07K 5/06191* (2013.01); *C07K 5/06078* (2013.01); *C07K 5/06034* (2013.01); *C07D 213/81* (2013.01); *C07D 215/48* (2013.01); *C07D 231/14* (2013.01); *C07D 333/24* (2013.01); *C07D 333/38* (2013.01); *C07D 333/60* (2013.01); *C07D 233/90* (2013.01); *C07D 409/12* (2013.01); *C07D 413/12* (2013.01); *C07D 417/12* (2013.01); *C07D 261/18* (2013.01); *C07D 207/34* (2013.01); *C07D 277/30* (2013.01); *C07D 277/56* (2013.01); *C07D 209/18* (2013.01); *C07D 213/56* (2013.01); *C07D 307/68* (2013.01); *C07K 5/06* (2013.01); *C07C 237/20* (2013.01)

(58) Field of Classification Search
None
See application file for complete search history.

(56) References Cited

U.S. PATENT DOCUMENTS

| | | | |
|---|---|---|---|
| 5,187,157 A | 2/1993 | Kettner et al. | |
| 8,207,378 B2 * | 6/2012 | Steinmetzer et al. | ........... 564/92 |

FOREIGN PATENT DOCUMENTS

| | | |
|---|---|---|
| EP | 2281885 A | 2/2011 |
| WO | WO 92/04371 | 3/1992 |

(Continued)

OTHER PUBLICATIONS

Clermont et al., "Plasma kallikrein mediates retinal vascular dysfunction and induces retinal thickening in diabetic rats", Diabetes, May 2011, 60, 1590-1598.

(Continued)

*Primary Examiner* — Timothy R Rozof
(74) *Attorney, Agent, or Firm* — Baker & Hostetler LLP

(57) ABSTRACT

The present invention provides compounds of formula (I): compositions comprising such compounds; the use of such compounds in therapy (for example in the treatment or prevention of a disease or condition in which plasma kallikrein activity is implicated); and methods of treating patients with such compounds; wherein $R^1$ to $R^9$ are as defined herein.

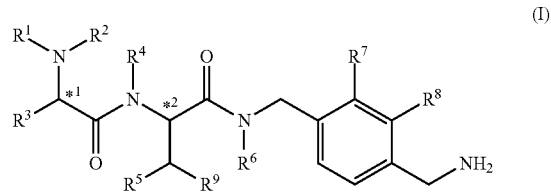

17 Claims, 1 Drawing Sheet

(51) Int. Cl.
C07D 307/68 (2006.01)
A61K 38/00 (2006.01)

(56) References Cited

FOREIGN PATENT DOCUMENTS

| WO | WO 94/29335 | 12/1994 |
|---|---|---|
| WO | WO 95/07921 | 3/1995 |
| WO | WO 03/076458 | 9/2003 |
| WO | WO 2004/062657 A1 | 7/2004 |
| WO | WO 2008/016883 | 2/2008 |
| WO | WO 2008/049595 | 5/2008 |
| WO | WO 2008/049595 A1 | 5/2008 |
| WO | WO 2011/075684 | 6/2011 |
| WO | WO 2011/094496 A2 | 8/2011 |
| WO | WO 2011/118672 | 9/2011 |
| WO | WO 2012/004678 | 1/2012 |
| WO | WO 2012/017020 | 2/2012 |
| WO | WO 2012/142308 | 10/2012 |

OTHER PUBLICATIONS

Evans et al., "Selective inhibitors of plasma kallikrein", Immunolpharmocology, 1996, 32, 115-116.

Garrett et al., "Peptide aldehyde inhibitors of the kallikreins: an investigation of subsite interactions with tripeptides containing structural variations at the amino terminus", J. Peptide Res., 1998, 52, 62-71.

Griesbacher et al., "Involvement of tissue kallikrein but not plsma kallikrein in the development of symptoms mediated by endogenous kinins in acute pancreatitus in rats", British Journal of Pharmacology, 2002, 137, 692-700.

Kolte et al., "Biochemical characterization of a novel high-affinity and specific plasma kallikrein inhibitor", British Journal of Pharmacology, Nov. 25, 2010, 162, 1639-1649.

Lehmann, "Ecallantide (DX-88), a plasma kallikrein inhibitor for the treatment of hereditary angioedema and the prevention of blood loss in on-pump cardiothoracic surgery", Expert Opinion Biol. Ther., Aug. 2008, 8, 1187-1199.

Marceau et al., "Bradykinin receptor ligands: therapeutic perspectives", Nature Review, Drug Discovery 2004, Oct. 2004, vol. 3, 845-852.

Okada et al., "Development of potent and selective plasmin and plasma kallikrein inhibitors and studies on the structure-activity relationship", Chem. Pharm. Bull., 2000, 48, 12, 1964-1972.

Stürzbecher et al., "Novel plasma kallikrein inhibitors of the benzamidine type", Brazilian J. med. Biol. Res., 1994, 27, 1929-1934.

Teno et al., "Development of Active Center-Directed Plasmin and Plasma Kallikrein Inhibitors and Studies on the Structure-Inhibitory Activity Relationship", Chem. Pharm. Bull., Jun. 1993, 41, 1079-1090.

Young et al., "Small molecule inhibitors of plasma kallikrein", Bioorg. Med. Chem. Letts., Apr. 2006, 16, 7, 2034-2036.

Zhang et al., "Discovery of highly potent small molecule kallikrein inhibitors", Medicinal Chemistry 2, 2006, 545-553.

* cited by examiner

BENZYLAMINE DERIVATIVES AS INHIBITORS OF PLASMA KALLIKREIN

CROSS-REFERENCE TO RELATED APPLICATIONS

This application is the National Stage of International Application No. PCT/GB2012/051588, filed Jul. 6, 2012, which claims the benefit of Great Britain Application No. 1111682.9, filed Jul. 7, 2011, and U.S. Patent Application No. 61/505,305, filed Jul. 7, 20011, the disclosures of which are incorporated herein by reference in their entireties.

This invention relates to benzylamine derivatives and to pharmaceutical compositions containing and the uses of, such derivatives.

BACKGROUND TO THE INVENTION

The benzylamine derivatives of the present invention are inhibitors of plasma kallikrein and have a number of therapeutic applications, particularly in the treatment of retinal vascular permeability associated with diabetic retinopathy and diabetic macular oedema.

Plasma kallikrein is a trypsin-like serine protease that can liberate kinins from kininogens (see K. D. Bhoola et al., "Kallikrein-Kinin Cascade", *Encyclopedia of Respiratory Medicine*, p 483-493; J. W. Bryant et al., "Human plasma kallikrein-kinin system: physiological and biochemical parameters" *Cardiovascular and haematological agents in medicinal chemistry*, 7, p 234-250, 2009; K. D. Bhoola et al., *Pharmacological Rev.*, 1992, 44, 1; and D. J. Campbell, "Towards understanding the kallikrein-kinin system: insights from the measurement of kinin peptides", *Brazilian Journal of Medical and Biological Research* 2000, 33, 665-677). It is an essential member of the intrinsic blood coagulation cascade although its role in this cascade does not involve the release of bradykinin or enzymatic cleavage. Plasma prekallikrein is encoded by a single gene and synthesized in the liver. It is secreted by hepatocytes as an inactive plasma prekallikrein that circulates in plasma as a heterodimer complex bound to high molecular weight kininogen which is activated to give the active plasma kallikrein Kinins are potent mediators of inflammation that act through G protein-coupled receptors and antagonists of kinins (such as bradykinin antagonists) have previously been investigated as potential therapeutic agents for the treatment of a number of disorders (F. Marceau and D. Regoli, Nature Rev., Drug Discovery, 2004, 3, 845-852).

Plasma kallikrein is thought to play a role in a number of inflammatory disorders. The major inhibitor of plasma kallikrein is the serpin C1 esterase inhibitor. Patients who present with a genetic deficiency in C1 esterase inhibitor suffer from hereditary angioedema (HAE) which results in intermittent swelling of face, hands, throat, gastro-intestinal tract and genitals. Blisters formed during acute episodes contain high levels of plasma kallikrein which cleaves high molecular weight kininogen liberating bradykinin leading to increased vascular permeability. Treatment with a large protein plasma kallikrein inhibitor has been shown to effectively treat HAE by preventing the release of bradykinin which causes increased vascular permeability (A. Lehmann "Ecallantide (DX-88), a plasma kallikrein inhibitor for the treatment of hereditary angioedema and the prevention of blood loss in on-pump cardiothoracic surgery" *Expert Opin. Biol. Ther.* 8, p 1187-99).

The plasma kallikrein-kinin system is abnormally abundant in patients with advanced diabetic macular oedema. It has been recently published that plasma kallikrein contributes to retinal vascular dysfunctions in diabetic rats (A. Clermont et al. "Plasma kallikrein mediates retinal vascular dysfunction and induces retinal thickening in diabetic rats" *Diabetes*, 2011, 60, p 1590-98). Furthermore, administration of the plasma kallikrein inhibitor ASP-440 ameliorated both retinal vascular permeability and retinal blood flow abnormalities in diabetic rats. Therefore a plasma kallikrein inhibitor should have utility as a treatment to reduce retinal vascular permeability associated with diabetic retinopathy and diabetic macular oedema.

Synthetic and small molecule plasma kallikrein inhibitors have been described previously, for example by Garrett et al. ("Peptide aldehyde . . . " *J. Peptide Res.* 52, p 62-71 (1998)), T. Griesbacher et al. ("Involvement of tissue kallikrein but not plasma kallikrein in the development of symptoms mediated by endogenous kinins in acute pancreatitis in rats" *British Journal of Pharmacology* 137, p 692-700 (2002)), Evans ("Selective dipeptide inhibitors of kallikrein" WO03/076458), Szelke et al. ("Kininogenase inhibitors" WO92/04371), D. M. Evans et al. (*Immunolpharmacology*, 32, p 115-116 (1996)), Szelke et al. ("Kininogen inhibitors" WO95/07921), Antonsson et al. ("New peptides derivatives" WO94/29335), J. Stürzbecher et al. (*Brazilian J. Med. Biol. Res* 27, p 1929-34 (1994)), Kettner et al. (U.S. Pat. No. 5,187,157), N. Teno et al. (*Chem. Pharm. Bull.* 41, p 1079-1090 (1993)), W. B. Young et al. ("Small molecule inhibitors of plasma kallikrein" *Bioorg. Med. Chem. Letts.* 16, p 2034-2036 (2006)), Okada et al. ("Development of potent and selective plasmin and plasma kallikrein inhibitors and studies on the structure-activity relationship" *Chem. Pharm. Bull.* 48, p 1964-72 (2000)), Steinmetzer et al. ("Trypsin-like serine protease inhibitors and their preparation and use" WO08/049, 595), Zhang et al. ("Discovery of highly potent small molecule kallikrein inhibitors" *Medicinal Chemistry* 2, p 545-553 (2006)), Sinha et al. ("Inhibitors of plasma kallikrein" WO08/016,883), and Brandl et al. ("N-((6-amino-pyridin-3-yl)methyl)-heteroaryl-carboxamides as inhibitors of plasma kallikrein" WO2012/017020). Also, Steinmetzer et al. ("Serine protease inhibitors" WO2012/004678) describes cyclized peptide analogs which are inhibitors of human plasmin and plasma kallikrein.

To date, no small molecule synthetic plasma kallikrein inhibitor has been approved for medical use. The molecules described in the known art suffer from limitations such as poor selectivity over related enzymes such as KLK1, thrombin and other serine proteases, and poor oral availability. The large protein plasma kallikrein inhibitors present risks of anaphylactic reactions, as has been reported for Ecallantide. Thus there remains a need for compounds that selectively inhibit plasma kallikrein, that do not induce anaphylaxis and that are orally available. Furthermore, the molecules in the known art feature a highly polar and ionisable guanidine or amidine functionality. It is well known that such functionalities may be limiting to gut permeability and therefore to oral availability.

Other complications of diabetes such as cerebral haemorrhage, nepropathy, cardiomyopathy and neuropathy, all of which have associations with plasma kallikrein may also be considered as targets for a plasma kallikrein inhibitor.

SUMMARY OF THE INVENTION

The present invention relates to a series of benzylamines that are inhibitors of plasma kallikrein. These compounds demonstrate good selectivity for plasma kallikrein and are potentially useful in the treatment of impaired visual acuity, diabetic retinopathy, macular oedema, hereditary angioedema, diabetes, pancreatitis, cerebral haemorrhage, nepropathy, cardiomyopathy, neuropathy, inflammatory bowel disease, arthritis, inflammation, septic shock, hypotension, cancer, adult respiratory distress syndrome, disseminated intravascular coagulation, cardiopulmonary bypass surgery and bleeding from post operative surgery. The invention further relates to pharmaceutical compositions of the inhibitors, to the use of the compositions as therapeutic agents, and to methods of treatment using these compositions.

In an aspect, the present invention provides compounds of formula I

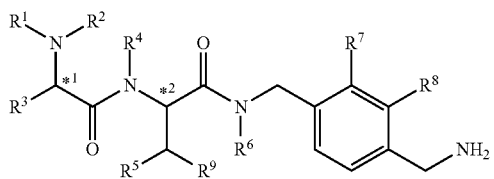

(I)

wherein:
R¹ is selected from H, alkyl, —COalkyl, —COaryl, —CO-heteroaryl, —CO₂alkyl, —(CH₂)$_a$OH, —(CH₂)$_b$COOR¹⁰, —(CH₂)$_c$CONH₂, —SO₂alkyl, —SO₂aryl, —SO₂(CH₂)$_h$R¹³, —CO(CH₂)$_i$R¹⁴, —COcycloalkyl, —COCH=CHR¹⁵, —CO(CH₂)$_j$NHCO(CH₂)$_k$R¹⁶ and —CONR¹⁷R¹⁸;
R² is selected from H and alkyl;
R³ is selected from H, alkyl, —(CH₂)$_d$aryl, —(CH₂)$_e$heteroaryl, —(CH₂)$_f$cycloalkyl, —(CH₂)$_g$heterocycloalkyl, —CH(cycloalkyl)₂, —CH(heterocycloalkyl)₂ and —(CH₂)$_l$aryl-O—(CH₂)$_m$-aryl;
R⁴ and R⁶ are independently selected from H and alkyl;
R⁵ is selected from H, alkyl, alkoxy and OH;
or R⁴ and R⁵, together with the atoms to which they are attached, may join to form a 5- or 6-membered azacycloalkyl structure;
R⁷ and R⁸ are independently selected from H, alkyl, alkoxy, CN, halo and CF₃;
R⁹ is aryl or heteroaryl;
R¹⁰ is H or alkyl;
a, b, c, d, e, f g, h, i, j, l and m are independently 1, 2 or 3;
k is 0, 1, 2 or 3;
*1 and *2 denote chiral centres;
alkyl is a linear saturated hydrocarbon having up to 10 carbon atoms (C₁-C₁₀) or a branched saturated hydrocarbon of between 3 and 10 carbon atoms (C₃-C₁₀); alkyl may optionally be substituted with 1 or 2 substituents independently selected from (C₃-C₁₀)cycloalkyl, (C₁-C₆)alkoxy, OH, CN, CF₃, COOR¹¹, fluoro and NR¹¹R¹²;
cycloalkyl is a mono- or bi-cyclic saturated hydrocarbon of between 3 and 10 carbon atoms; cycloalkyl may optionally be fused to an aryl group; or cycloalkyl is adamantyl;
heterocycloalkyl is a C-linked or N-linked 3 to 10 membered saturated, mono- or bi-cyclic ring, wherein said heterocycloalkyl ring contains, where possible, 1, 2 or 3 heteroatoms independently selected from N, NR¹¹ and O;
alkoxy is a linear O-linked hydrocarbon of between 1 and 6 carbon atoms (C₁-C₆) or a branched O-linked hydrocarbon of between 3 and 6 carbon atoms (C₃-C₆); alkoxy may optionally be substituted with 1 or 2 substituents independently selected from (C₃-C₁₀)cycloalkyl, OH, CN, CF₃, COOR¹¹, fluoro and NR¹¹R¹²;
aryl is phenyl, biphenyl or naphthyl; aryl may be optionally substituted with up to 5 substituents independently selected from alkyl, alkoxy, OH, halo, CN, COOR¹¹, CF₃ and NR¹¹R¹²;
heteroaryl is a 5, 6, 9 or 10 membered mono- or bi-cyclic aromatic ring, containing, where possible, 1, 2 or 3 ring members independently selected from N, NR¹¹, S and O; heteroaryl may be optionally substituted with 1, 2 or 3 substituents independently selected from alkyl, alkoxy, OH, halo, CN, COOR¹¹, CF₃, NR¹¹R¹² and NHR¹⁹;
R¹¹ and R¹² are independently selected from H and alkyl;
R¹³ is aryl or heteroaryl;
R¹⁴ is aryl, heteroaryl, cycloalkyl or heterocycloalkyl;
R¹⁵ is H, alkyl, aryl, heteroaryl, cycloalkyl or heterocycloalkyl;
R¹⁶ is H, aryl or heteroaryl;
R¹⁷ is H, alkyl, aryl, heteroaryl or heterocycloalkyl;
R¹⁸ is —(CH₂)$_m$R²¹, where m is 0, 1, 2 or 3 and R²¹ is H, aryl or heteroaryl;
R¹⁹ —COalkyl, —COaryl or —COheteroaryl;
and tautomers, isomers, stereoisomers (including enantiomers, diastereoisomers and racemic and scalemic mixtures thereof), pharmaceutically acceptable salts and solvates thereof.

In another aspect the present invention provides a prodrug of a compound of formula (I) as herein defined, or a pharmaceutically acceptable salt thereof.

In yet another aspect the present invention provides an N-oxide of a compound of formula (I) as herein defined, or a prodrug or pharmaceutically acceptable salt thereof.

It will be understood that certain compounds of the present invention may exist in solvated, for example hydrated, as well as unsolvated forms. It is to be understood that the present invention encompasses all such solvated forms.

In an aspect, the invention comprises a subset of the compounds of formula (I) wherein:
R¹ is selected from H, alkyl, —COalkyl, —COaryl, —CO-heteroaryl, —CO₂alkyl, —(CH₂)$_a$OH, —(CH₂)$_b$COOR¹⁰, —(CH₂)$_c$CONH₂, —SO₂alkyl and —SO₂aryl;
R² is selected from H and alkyl;
R³ is selected from H, alkyl, —(CH₂)$_d$aryl, —(CH₂)$_e$heteroaryl, —(CH₂)$_f$cycloalkyl, —(CH₂)$_g$heterocycloalkyl, —CH(cycloalkyl)₂ and —CH(heterocycloalkyl)₂;
R⁴ and R⁶ are independently selected from H and alkyl;
R⁵ is selected from H, alkyl, alkoxy and OH;
or R⁴ and R⁵, together with the atoms to which they are attached, may join to form a 5- or 6-membered azacycloalkyl structure;
R⁷ and R⁸ are independently selected from H, alkyl, alkoxy, CN and halo;
R⁹ is aryl or heteroaryl;
R¹⁰ is H or alkyl;
a, b, c, d, e, f and g are independently 1, 2 or 3;
*1 and *2 denote chiral centres;
alkyl is a linear saturated hydrocarbon having up to 10 carbon atoms (C₁-C₁₀) or a branched saturated hydrocarbon of between 3 and 10 carbon atoms (C₃-C₁₀); alkyl may optionally be substituted with 1 or 2 substituents independently selected from (C₃-C₁₀)cycloalkyl, (C₁-C₆)alkoxy, OH, CN, CF₃, COOR¹¹, fluoro and NR¹¹R¹²;

cycloalkyl is a mono- or bi-cyclic saturated hydrocarbon of between 3 and 10 carbon atoms; cycloalkyl may optionally be fused to an aryl group;

heterocycloalkyl is a C-linked or N-linked 3 to 10 membered saturated, mono- or bi-cyclic ring, wherein said heterocycloalkyl ring contains, where possible, 1, 2 or 3 heteroatoms independently selected from N, $NR^{11}$ and O;

alkoxy is a linear O-linked hydrocarbon of between 1 and 6 carbon atoms ($C_1$-$C_6$) or a branched O-linked hydrocarbon of between 3 and 6 carbon atoms ($C_3$-$C_6$); alkoxy may optionally be substituted with 1 or 2 substituents independently selected from ($C_3$-$C_{10}$)cycloalkyl, OH, CN, $CF_3$, $COOR^{11}$, fluoro and $NR^{11}R^{12}$;

aryl is phenyl, biphenyl or naphthyl; aryl may be optionally substituted with up to 5 substituents independently selected from alkyl, alkoxy, OH, halo, CN, $COOR^{11}$, $CF_3$ and $NR^{11}R^{12}$;

heteroaryl is a 5, 6, 9 or 10 membered mono- or bi-cyclic aromatic ring, containing, where possible, 1, 2 or 3 ring members independently selected from N, $NR^{11}$, S and O; heteroaryl may be optionally substituted with 1, 2 or 3 substituents independently selected from alkyl, alkoxy, OH, halo, CN, $COOR^{11}$, $CF_3$ and $NR^{11}R^{12}$;

$R^{11}$ and $R^{12}$ are independently selected from H and alkyl; and tautomers, isomers, stereoisomers (including enantiomers, diastereoisomers and racemic and scalemic mixtures thereof), pharmaceutically acceptable salts and solvates thereof.

In another aspect, the invention comprises a subset of the compounds of formula (I) wherein:

$R^1$ is selected from H, alkyl, —COalkyl, —COaryl, —$CO_2$alkyl, —$CH_2CH_2OH$, —$CH_2COOR^{10}$, —$CH_2CONH_2$, —$SO_2$alkyl and —$SO_2$aryl;

$R^2$ is selected from H and alkyl;

$R^3$ is selected from alkyl, —$CH_2$aryl, —$CH_2$cycloalkyl and —CH(cycloalkyl)$_2$;

$R^4$ and $R^6$ are independently selected from H and alkyl;

$R^5$ is selected from H, alkyl, and OH;

or $R^4$ and $R^5$, together with the atoms to which they are attached, may join to form a 5- or 6-membered azacycloalkyl structure;

$R^7$ and $R^8$ are independently selected from H, F, and Cl;

$R^9$ is aryl;

$R^{10}$ is H or alkyl;

*1 and *2 denote chiral centres;

alkyl is a linear saturated hydrocarbon having up to 6 carbon atoms ($C_1$-$C_6$) or a branched saturated hydrocarbon of between 3 and 6 carbon atoms ($C_3$-$C_6$); alkyl may optionally be substituted with 1 or 2 substituents independently selected from ($C_3$-$C_{10}$)cycloalkyl, ($C_1$-$C_6$) alkoxy, OH, CN, $CF_3$, $COOR^{11}$, fluoro and $NR^{11}R^{12}$;

cycloalkyl is a mono- or bi-cyclic saturated hydrocarbon of between 3 and 10 carbon atoms;

alkoxy is a linear O-linked hydrocarbon of between 1 and 6 carbon atoms ($C_1$-$C_6$) or a branched O-linked hydrocarbon of between 3 and 6 carbon atoms ($C_3$-$C_6$); alkoxy may optionally be substituted with 1 or 2 substituents independently selected from ($C_3$-$C_{10}$)cycloalkyl, OH, CN, $CF_3$, $COOR^{11}$, fluoro and $NR^{11}R^{12}$;

aryl is phenyl, biphenyl or naphthyl; aryl may be optionally substituted with up to 5 substituents independently selected from alkyl, alkoxy, OH, halo, CN, $COOR^{11}$, $CF_3$ and $NR^{11}R^{12}$;

$R^{11}$ and $R^{12}$ are independently selected from H and alkyl; and tautomers, isomers, stereoisomers (including enantiomers, diastereoisomers and racemic and scalemic mixtures thereof), pharmaceutically acceptable salts and solvates thereof.

The present invention also comprises the following aspects and combinations thereof:

In an aspect of the invention, $R^1$ is selected from H, alkyl, —COalkyl, —COaryl, —$(CH_2)_a$OH, —$(CH_2)_b$$COOR^{10}$, —$(CH_2)_c$$CONH_2$, —$SO_2$alkyl and —$SO_2$aryl.

In an aspect of the invention, $R^1$ is selected from H, alkyl, —COalkyl, —COaryl, —$(CH_2)_a$OH, —$CH_2COOR^{10}$, —$CH_2CONH_2$, —$SO_2$alkyl and —$SO_2$aryl; wherein a is 1 or 2.

In an aspect of the invention, $R^1$ is selected from H, —COaryl, —COalkyl, —$CH_2$COOH, —$SO_2$Ph and —$SO_2CH_3$.

In an aspect of the invention, $R^1$ is selected from H, —CO-ethyl, methyl, methylsulfonyl, —COphenyl, phenylsulfone, —$CH_2$COOH, —CO-$^i$propyl, propyl, —$CH_2COOCH_3$, —$CH_2CONH_2$, —$CH_2CH_2OH$ and —COnaphthyl.

In an aspect of the invention, $R^1$ is selected from —COalkyl and —COphenyl.

In an aspect of the invention, $R^1$ is selected from H, —COaryl, COheteroaryl, —COalkyl, —$CH_2$COOH, —$SO_2$Ph and —$SO_2CH_3$.

In an aspect of the invention, $R^1$ is selected from —COalkyl, COheteroaryl and —COaryl.

In an aspect of the invention, $R^2$ is selected from H and methyl.

In an aspect of the invention, $R^2$ is H.

In an aspect of the invention, $R^3$ is selected from alkyl, —$(CH_2)_d$aryl, —$(CH_2)_f$cycloalkyl, and —CH(cycloalkyl)$_2$; wherein d and f are, independently, 1 or 2.

In an aspect of the invention, $R^3$ is selected from alkyl, —$CH_2$aryl, —$CH_2$cycloalkyl, and —CH(cycloalkyl)$_2$.

In an aspect of the invention, $R^3$ is selected from —$CH_2$aryl, —$CH_2$cycloalkyl, and —CH(cycloalkyl)$_2$.

In an aspect of the invention, $R^3$ is selected from:

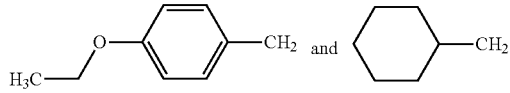

In an aspect of the invention, $R^4$ is selected from H and methyl.

In an aspect of the invention, $R^4$ is H.

In an aspect of the invention, $R^5$ is selected from H, alkyl and OH.

In an aspect of the invention, $R^5$ is selected from H and OH.

In an aspect of the invention, $R^5$ is H.

In an aspect of the invention, $R^4$ and $R^5$, together with the atoms to which they are attached, join to form a pyrrolidine moiety.

In an aspect of the invention, $R^4$ and $R^5$, together with the atoms to which they are attached, join to form a piperidine moiety.

In an aspect of the invention, $R^6$ is selected from H and methyl.

In an aspect of the invention, $R^6$ is H.

In an aspect of the invention, $R^7$ is selected from H, methyl and halo.

In an aspect of the invention, $R^7$ is selected from H, F and Cl.

In an aspect of the invention, $R^7$ is H.

In an aspect of the invention, $R^8$ is selected from H, methyl and halo.

In an aspect of the invention, $R^8$ is selected from H, F and Cl.

In an aspect of the invention, $R^8$ is selected from H and F.

In an aspect of the invention, $R^8$ is H.

In an aspect of the invention, $R^9$ is aryl.

In an aspect of the invention, $R^9$ is selected from phenyl and naphthyl, wherein phenyl may be optionally substituted with up to 3 substituents independently selected from alkyl, alkoxy, OH, halo, CN, $COOR^{11}$, $CF_3$ and $NR^{11}R^{12}$.

In an aspect of the invention, $R^9$ is phenyl, wherein phenyl may be optionally substituted with up to 2 substituents independently selected from alkyl, halo and $CF_3$.

In an aspect of the invention, $R^9$ is selected from phenyl, 1-naphthalene, 2,4-dichlorophenyl, 3,4-dichlorophenyl, 3,4-difluorophenyl, 4-chlorophenyl, 4-trifluoromethylphenyl and 4-ethoxyphenyl.

In an aspect of the invention, $R^9$ is selected from phenyl, heteroaryl and naphthyl, wherein phenyl may be optionally substituted with up to 3 substituents independently selected from alkyl, alkoxy, OH, halo, CN, $COOR^{11}$, $CF_3$ and $NR^{11}R^{12}$.

In an aspect of the invention, $R^9$ is selected from phenyl, 1-naphthalene, 3,4-dichlorophenyl, 3,4-difluorophenyl, 4-chlorophenyl, 4-fluorophenyl, 3-fluorophenyl, 4-trifluoromethylphenyl, pyrid-3-yl, pyrid-2-yl, pyrid-4-yl, benzothiophen-3-yl, thiophen-2-yl, thiophen-3-yl, indol-3-yl, and thiazol-4yl.

In an aspect of the invention, $R^{10}$ is H or methyl.

In an aspect of the invention, the stereochemical configuration about chiral centre *1 is R.

In an aspect of the invention, the stereochemical configuration about chiral centre *2 is S.

In an aspect of the invention, a is 2 and b, c, d, e, f and g are 1.

In an aspect of the invention, a is 2 and b, c, d, e, f, g, h, j, l and m are 1.

In an aspect of the invention, k is 0 or 1.

In an aspect, the invention comprises a compound selected from:

(S)—N-(4-Aminomethyl-benzyl)-2-[(R)-3-(4-ethoxy-phenyl)-2-propionylamino-propionylamino]-3-phenyl-propionamide;

N—[(R)-1-[(S)-1-(4-Aminomethyl-benzylcarbamoyl)-2-phenyl-ethylcarbamoyl]-2-(4-ethoxy-phenyl)-ethyl]-benzamide;

{(R)-1-[(S)-1-(4-Aminomethyl-benzylcarbamoyl)-2-phenyl-ethylcarbamoyl]-2-cyclohexyl-ethylamino}-acetic acid;

(S)—N-(4-Aminomethyl-3-fluoro-benzyl)-2-[(R)-3-(4-ethoxy-phenyl)-2-propionylamino-propionylamino]-3-phenyl-propionamide;

(S)—N-(4-Aminomethyl-2-chloro-benzyl)-2-[(R)-3-(4-ethoxy-phenyl)-2-propionylamino-propionylamino]-3-phenyl-propionamide;

(S)—N-(4-Aminomethyl-benzyl)-3-(3,4-dichloro-phenyl)-2-[(R)-3-(4-ethoxy-phenyl)-2-propionylamino-propionylamino]-propionamide;

(S)—N-(4-Aminomethyl-3-chloro-benzyl)-2-[(R)-3-(4-ethoxy-phenyl)-2-propionylamino-propionylamino]-3-phenyl-propionamide;

(S)—N-(4-Aminomethyl-benzyl)-2-{[(R)-3-(4-ethoxy-phenyl)-2-propionylamino-propionyl]-methyl-amino}-3-phenyl-propionamide;

({(R)-1-[(S)-1-(4-Aminomethyl-benzylcarbamoyl)-2-phenyl-ethylcarbamoyl]-2-cyclohexyl-ethyl}-methyl-amino)-acetic acid;

(S)—N-(4-Aminomethyl-3-fluoro-benzyl)-2-{[(R)-3-(4-ethoxy-phenyl)-2-propionylamino-propionyl]-methyl-amino}-3-phenyl-propionamide;

N—[(R)-1-{[(S)-1-(4-Aminomethyl-benzylcarbamoyl)-2-phenyl-ethyl]-methyl-carbamoyl}-2-(4-ethoxy-phenyl)-ethyl]-benzamide;

N—[(R)-1-{[(S)-1-(4-Aminomethyl-benzylcarbamoyl)-2-phenyl-ethyl]-methyl-carbamoyl}-2-(4-ethoxy-phenyl)-ethyl]-isobutyramide;

Naphthalene-1-carboxylic acid[(R)-1-[(S)-1-(4-aminomethyl-benzylcarbamoyl)-2-phenyl-ethylcarbamoyl]-2-(4-ethoxy-phenyl)-ethyl]-amide;

N—[(R)-1-[(S)-1-(4-Aminomethyl-benzylcarbamoyl)-2-phenyl-ethylcarbamoyl]-2-(4-ethoxy-phenyl)-ethyl]-4-chloro-benzamide;

N—[(R)-1-[(S)-1-(4-Aminomethyl-benzylcarbamoyl)-2-phenyl-ethylcarbamoyl]-2-(4-ethoxy-phenyl)-ethyl]-2,4-dichloro-benzamide;

N—[(R)-1-[(S)-1-(4-Aminomethyl-benzylcarbamoyl)-2-phenyl-ethylcarbamoyl]-2-(4-ethoxy-phenyl)-ethyl]-3,4-difluoro-benzamide;

(R)-2-Amino-N-[(1S,2S)-1-(4-aminomethyl-benzylcarbamoyl)-2-hydroxy-2-phenyl-ethyl]-3-(4-ethoxy-phenyl)-propionamide;

N—[(R)-1-[(S)-1-(4-Aminomethyl-benzylcarbamoyl)-2-phenyl-ethylcarbamoyl]-2-(4-ethoxy-phenyl)-ethyl]-nicotinamide;

(2S,3S)—N-(4-Aminomethyl-benzyl)-2-[(R)-3-(4-ethoxy-phenyl)-2-propionylamino-propionylamino]-3-hydroxy-3-phenyl-propionamide;

N—[(R)-1-[(S)-1-(4-Aminomethyl-benzylcarbamoyl)-2-phenyl-ethylcarbamoyl]-2-(4-ethoxy-phenyl)-ethyl]-isonicotinamide;

Thiophene-3-carboxylic acid-[(R)-1-[(S)-1-(4-aminomethyl-benzylcarbamoyl)-2-phenyl-ethylcarbamoyl]-2-(4-ethoxy-phenyl)-ethyl]-amide;

Thiophene-2-carboxylic acid[(R)-1-[(S)-1-(4-aminomethyl-benzylcarbamoyl)-2-phenyl-ethylcarbamoyl]-2-(4-ethoxy-phenyl)-ethyl]-amide;

Cyclohexanecarboxylic acid[(R)-1-[(S)-1-(4-aminomethyl-benzylcarbamoyl)-2-phenyl-ethylcarbamoyl]-2-(4-ethoxy-phenyl)-ethyl]-amide;

Isoxazole-5-carboxylic acid[(R)-1-[(S)-1-(4-aminomethyl-benzylcarbamoyl)-2-phenyl-ethylcarbamoyl]-2-(4-ethoxy-phenyl)-ethyl]-amide;

Pyridine-2-carboxylic acid[(R)-1-[(S)-1-(4-aminomethyl-benzylcarbamoyl)-2-phenyl-ethylcarbamoyl]-2-(4-ethoxy-phenyl)-ethyl]-amide;

Benzo[b]thiophene-2-carboxylic acid[(R)-1-[(S)-1-(4-aminomethyl-benzylcarbamoyl)-2-phenyl-ethylcarbamoyl]-2-(4-ethoxy-phenyl)-ethyl]-amide;

(R)—N—[(S)-1-(4-Aminomethyl-benzylcarbamoyl)-2-phenyl-ethyl]-2-(4-chloro-benzenesulfonylamino)-3-(4-ethoxy-phenyl)-propionamide;

N—[(R)-1-[(S)-1-(4-Aminomethyl-benzylcarbamoyl)-2-phenyl-ethylcarbamoyl]-2-(4-ethoxy-phenyl)-ethyl]-3-chloro-benzamide;

N—[(R)-1-[(S)-1-(4-Aminomethyl-benzylcarbamoyl)-2-phenyl-ethylcarbamoyl]-2-(4-ethoxy-phenyl)-ethyl]-2-chloro-benzamide N—[(R)-1-[(S)-1-(4-Aminomethyl-benzylcarbamoyl)-2-phenyl-ethylcarbamoyl]-2-(4-ethoxy-phenyl)-ethyl]-3-trifluoromethyl-benzamide;

N—[(R)-1-[(S)-1-(4-Aminomethyl-benzylcarbamoyl)-2-phenyl-ethylcarbamoyl]-2-(4-ethoxy-phenyl)-ethyl]-4-methyl-benzamide;

N—[(R)-1-[(S)-1-(4-Aminomethyl-benzylcarbamoyl)-2-phenyl-ethylcarbamoyl]-2-(4-ethoxy-phenyl)-ethyl]-3,4-dichloro-benzamide;

N—[(R)-1-[(S)-1-(4-Aminomethyl-benzylcarbamoyl)-2-phenyl-ethylcarbamoyl]-2-(4-ethoxy-phenyl)-ethyl]-4-methoxy-benzamide;

(S)—N-(4-Aminomethyl-benzyl)-2-[(R)-3-(4-ethoxy-phenyl)-2-(2-phenylacetylamino-acetylamino)-propionylamino]-3-phenyl-propionamide;

N—[(R)-1-[(S)-1-(4-Aminomethyl-benzylcarbamoyl)-2-phenyl-ethylcarbamoyl]-2-(4-ethoxy-phenyl)-ethyl]-4-fluoro-benzamide;

N—[(R)-1-[(S)-1-(4-Aminomethyl-benzylcarbamoyl)-2-phenyl-ethylcarbamoyl]-2-(4-ethoxy-phenyl)-ethyl]-6-methyl-nicotinamide;

N—[(R)-1-[(S)-1-(4-Aminomethyl-benzylcarbamoyl)-2-phenyl-ethylcarbamoyl]-2-(4-ethoxy-phenyl)-ethyl]-2-methyl-nicotinamide;

N—[(R)-1-[(S)-1-(4-Aminomethyl-benzylcarbamoyl)-2-phenyl-ethylcarbamoyl]-2-(4-ethoxy-phenyl)-ethyl]-2,6-dichloro-nicotinamide;

N—[(R)-1-[(S)-1-(4-Aminomethyl-benzylcarbamoyl)-2-phenyl-ethylcarbamoyl]-2-(4-ethoxy-phenyl)-ethyl]-5,6-dichloro-nicotinamide;

N—[(R)-1-[(S)-1-(4-Aminomethyl-benzylcarbamoyl)-2-phenyl-ethylcarbamoyl]-2-(4-ethoxy-phenyl)-ethyl]-2,3,6-trifluoro-isonicotinamide;

N—[(R)-1-[(S)-1-(4-Aminomethyl-benzylcarbamoyl)-2-phenyl-ethylcarbamoyl]-2-(4-ethoxy-phenyl)-ethyl]-3,3,3-trifluoro-propionamide;

2,4-Dimethyl-thiazole-5-carboxylic acid[(R)-1-[(S)-1-(4-aminomethyl-benzylcarbamoyl)-2-phenyl-ethylcarbamoyl]-2-(4-ethoxy-phenyl)-ethyl]-amide;

2-Methyl-thiazole-5-carboxylic acid[(R)-1-[(S)-1-(4-aminomethyl-benzylcarbamoyl)-2-phenyl-ethylcarbamoyl]-2-(4-ethoxy-phenyl)-ethyl]-amide;

3-Chloro-thiophene-2-carboxylic acid[(R)-1-[(S)-1-(4-aminomethyl-benzylcarbamoyl)-2-phenyl-ethylcarbamoyl]-2-(4-ethoxy-phenyl)-ethyl]-amide;

4-Methyl-thiazole-5-carboxylic acid[(R)-1-[(S)-1-(4-aminomethyl-benzylcarbamoyl)-2-phenyl-ethylcarbamoyl]-2-(4-ethoxy-phenyl)-ethyl]-amide;

Furan-2-carboxylic acid[(R)-1-[(S)-1-(4-aminomethyl-benzylcarbamoyl)-2-phenyl-ethylcarbamoyl]-2-(4-ethoxy-phenyl)-ethyl]-amide;

3-Methyl-thiophene-2-carboxylic acid[(R)-1-[(S)-1-(4-aminomethyl-benzylcarbamoyl)-2-phenyl-ethylcarbamoyl]-2-(4-ethoxy-phenyl)-ethyl]-amide;

N—[(R)-1-[(S)-1-(4-Aminomethyl-benzylcarbamoyl)-2-phenyl-ethylcarbamoyl]-2-(4-ethoxy-phenyl)-ethyl]-2-methoxy-isonicotinamide;

3-Methyl-1H-pyrrole-2-carboxylic acid[(R)-1-[(S)-1-(4-aminomethyl-benzylcarbamoyl)-2-phenyl-ethylcarbamoyl]-2-(4-ethoxy-phenyl)-ethyl]-amide;

3-Amino-thiophene-2-carboxylic acid[(R)-1-[(S)-1-(4-aminomethyl-benzylcarbamoyl)-2-phenyl-ethylcarbamoyl]-2-(4-ethoxy-phenyl)-ethyl]-amide;

N—[(R)-1-[(S)-1-(4-Aminomethyl-benzylcarbamoyl)-2-phenyl-ethylcarbamoyl]-2-(4-propoxy-phenyl)-ethyl]-benzamide;

N—[(R)-1-[(S)-1-(4-Aminomethyl-benzylcarbamoyl)-2-pyridin-2-yl-ethylcarbamoyl]-2-(4-ethoxy-phenyl)-ethyl]-benzamide;

N—[(R)-1-[(S)-1-(4-Aminomethyl-benzylcarbamoyl)-2-(3,4-dichloro-phenyl)-ethylcarbamoyl]-2-(4-ethoxy-phenyl)-ethyl]-benzamide;

N—[(R)-1-[(S)-1-(4-Aminomethyl-benzylcarbamoyl)-2-(4-chloro-phenyl)-ethylcarbamoyl]-2-(4-ethoxy-phenyl)-ethyl]-benzamide;

N—[(R)-1-[(S)-1-(4-Aminomethyl-benzylcarbamoyl)-2-(4-fluoro-phenyl)-ethylcarbamoyl]-2-(4-ethoxy-phenyl)-ethyl]-benzamide;

N—[(R)-1-[(S)-1-(4-Aminomethyl-benzylcarbamoyl)-2-pyridin-3-yl-ethylcarbamoyl]-2-(4-ethoxy-phenyl)-ethyl]-benzamide;

N—[(R)-1-[(S)-1-(4-Aminomethyl-benzylcarbamoyl)-2-(4-methoxy-phenyl)-ethylcarbamoyl]-2-(4-ethoxy-phenyl)-ethyl]-benzamide;

N—[(R)-1-[(S)-1-(4-Aminomethyl-benzylcarbamoyl)-2-pyridin-4-yl-ethylcarbamoyl]-2-(4-ethoxy-phenyl)-ethyl]-benzamide;

N—[(R)-1-[(S)-1-(4-Aminomethyl-benzylcarbamoyl)-2-(3-fluoro-phenyl)-ethylcarbamoyl]-2-(4-ethoxy-phenyl)-ethyl]-benzamide;

N—[(R)-1-[(S)-1-(4-Aminomethyl-benzylcarbamoyl)-2-thiophen-2-yl-ethylcarbamoyl]-2-(4-ethoxy-phenyl)-ethyl]-benzamide;

N—[(R)-1-[(S)-1-(4-Aminomethyl-benzylcarbamoyl)-2-thiophen-3-yl-ethylcarbamoyl]-2-(4-ethoxy-phenyl)-ethyl]-benzamide;

N—[(R)-1-[(S)-1-(4-Aminomethyl-benzylcarbamoyl)-2-thiazol-4-yl-ethylcarbamoyl]-2-(4-ethoxy-phenyl)-ethyl]-benzamide;

N—[(R)-1-[(S)-1-(4-Aminomethyl-benzylcarbamoyl)-2-benzo[b]thiophen-3-yl-ethylcarbamoyl]-2-(4-ethoxy-phenyl)-ethyl]-benzamide;

N—[(R)-1-[(S)-1-(4-Aminomethyl-3-fluoro-benzylcarbamoyl)-2-phenyl-ethylcarbamoyl]-2-(4-ethoxy-phenyl)-ethyl]-benzamide;

N—[(R)-1-[(S)-1-(4-Aminomethyl-3-chloro-benzylcarbamoyl)-2-phenyl-ethylcarbamoyl]-2-(4-ethoxy-phenyl)-ethyl]-benzamide;

Pyridine-2-carboxylic acid[(R)-1-[(S)-1-(4-aminomethyl-benzylcarbamoyl)-2-thiophen-2-yl-ethylcarbamoyl]-2-(4-ethoxy-phenyl)-ethyl]-amide;

N—[(R)-1-[(S)-1-(4-Aminomethyl-benzylcarbamoyl)-2-pyridin-2-yl-ethylcarbamoyl]-2-(4-ethoxy-phenyl)-ethyl]-4-methoxy-benzamide;

Pyridine-2-carboxylic acid[(R)-1-[(S)-1-(4-aminomethyl-3-chloro-benzylcarbamoyl)-2-phenyl-ethylcarbamoyl]-2-(4-ethoxy-phenyl)-ethyl]-amide;

N—[(R)-1-[(S)-1-(4-Aminomethyl-benzylcarbamoyl)-2-pyridin-3-yl-ethylcarbamoyl]-2-(4-ethoxy-phenyl)-ethyl]-4-methoxy-benzamide;

N—[(R)-1-[(S)-1-(4-Aminomethyl-benzylcarbamoyl)-2-(3,4-difluoro-phenyl)-ethylcarbamoyl]-2-(4-ethoxy-phenyl)-ethyl]-isonicotinamide;

Thiophene-2-carboxylic acid[(R)-1-[(S)-1-(4-aminomethyl-benzylcarbamoyl)-2-pyridin-3-yl-ethylcarbamoyl]-2-(4-ethoxy-phenyl)-ethyl]-amide;

N—[(R)-1-[(S)-1-(4-Aminomethyl-benzylcarbamoyl)-2-pyridin-2-yl-ethylcarbamoyl]-2-(4-ethoxy-phenyl)-ethyl]-4-chloro-benzamide;

N—[(R)-1-[(S)-1-(4-Aminomethyl-benzylcarbamoyl)-2-pyridin-2-yl-ethylcarbamoyl]-2-(4-ethoxy-phenyl)-ethyl]-4-methyl-benzamide;

Pyridine-2-carboxylic acid[(R)-1-[(S)-1-(4-aminomethyl-benzylcarbamoyl)-2-(3,4-dichloro-phenyl)-ethylcarbamoyl]-2-(4-ethoxy-phenyl)-ethyl]-amide;

(R)—N—[(S)-1-(4-Aminomethyl-benzylcarbamoyl)-2-pyridin-2-yl-ethyl]-3-(4-ethoxy-phenyl)-2-propionylamino-propionamide;

N—[(R)-1-[(S)-1-(4-Aminomethyl-3-fluoro-benzylcarbamoyl)-2-phenyl-ethylcarbamoyl]-2-(4-ethoxy-phenyl)-ethyl]-isonicotinamide;

Pyridine-2-carboxylic acid[(R)-1-[(S)-1-(4-aminomethyl-3-fluoro-benzylcarbamoyl)-2-phenyl-ethylcarbamoyl]-2-(4-ethoxy-phenyl)-ethyl]-amide;

Thiophene-2-carboxylic acid[(R)-1-[(S)-1-(4-aminomethyl-benzylcarbamoyl)-2-(3,4-dichloro-phenyl)-ethylcarbamoyl]-2-(4-ethoxy-phenyl)-ethyl]-amide;

(R)—N—[(S)-1-(4-Aminomethyl-benzylcarbamoyl)-2-pyridin-3-yl-ethyl]-3-(4-ethoxy-phenyl)-2-propionylamino-propionamide;

N—[(R)-1-[(S)-1-(4-Aminomethyl-benzylcarbamoyl)-2-(3,4-dichloro-phenyl)-ethylcarbamoyl]-2-(4-ethoxy-phenyl)-ethyl]-isonicotinamide;

N—[(R)-1-[(S)-1-(4-Aminomethyl-benzylcarbamoyl)-2-(3,4-dichloro-phenyl)-ethylcarbamoyl]-2-(4-ethoxy-phenyl)-ethyl]-3,3,3-trifluoro-propionamide;

N—[(R)-1-[(S)-1-(4-Aminomethyl-benzylcarbamoyl)-2-pyridin-3-yl-ethylcarbamoyl]-2-(4-ethoxy-phenyl)-ethyl]-4-chloro-benzamide;

Isoxazole-5-carboxylic acid[(R)-1-[(S)-1-(4-aminomethyl-benzylcarbamoyl)-2-pyridin-3-yl-ethylcarbamoyl]-2-(4-ethoxy-phenyl)-ethyl]-amide;

N—[(R)-1-[(S)-1-(4-Aminomethyl-benzylcarbamoyl)-2-pyridin-3-yl-ethylcarbamoyl]-2-(4-ethoxy-phenyl)-ethyl]-4-methyl-benzamide;

N—[(R)-1-[(S)-1-(4-Aminomethyl-benzylcarbamoyl)-2-(3,4-difluoro-phenyl)-ethylcarbamoyl]-2-(4-ethoxy-phenyl)-ethyl]-benzamide;

3-Chloro-thiophene-2-carboxylic acid[(R)-1-[(S)-1-(4-aminomethyl-benzylcarbamoyl)-2-pyridin-3-yl-ethylcarbamoyl]-2-(4-ethoxy-phenyl)-ethyl]-amide;

N—[(R)-1-[(S)-1-(4-Aminomethyl-benzylcarbamoyl)-2-(1H-indol-3-yl)-ethylcarbamoyl]-2-(4-ethoxy-phenyl)-ethyl]-benzamide;

N—[(R)-1-[(S)-1-(4-Aminomethyl-benzylcarbamoyl)-2-benzo[b]thiophen-3-yl-ethylcarbamoyl]-2-(4-ethoxy-phenyl)-ethyl]-isonicotinamide;

3-Acetylamino-thiophene-2-carboxylic acid-[(R)-1-[(S)-1-(4-aminomethyl-benzylcarbamoyl)-2-phenyl-ethylcarbamoyl]-2-(4-ethoxy-phenyl)-ethyl]-amide;

N—[(R)-1-[(S)-1-(4-Aminomethyl-benzylcarbamoyl)-2-(2-fluoro-phenyl)-ethylcarbamoyl]-2-(4-ethoxy-phenyl)-ethyl]-benzamide;

3-Methyl-thiophene-2-carboxylic acid[(R)-1-[(S)-1-(4-aminomethyl-benzylcarbamoyl)-2-pyridin-3-yl-ethylcarbamoyl]-2-(4-ethoxy-phenyl)-ethyl]-amide;

N—[(R)-1-[(S)-1-(4-Aminomethyl-3-methyl-benzylcarbamoyl)-2-phenyl-ethylcarbamoyl]-2-(4-ethoxy-phenyl)-ethyl]-benzamide;

3-Amino-thiophene-2-carboxylic acid[(R)-1-[(S)-1-(4-aminomethyl-benzylcarbamoyl)-2-thiazol-4-yl-ethylcarbamoyl]-2-(4-ethoxy-phenyl)-ethyl]-amide;

3-Chloro-thiophene-2-carboxylic acid[(R)-1-[(S)-1-(4-aminomethyl-benzylcarbamoyl)-2-thiazol-4-yl-ethylcarbamoyl]-2-(4-ethoxy-phenyl)-ethyl]-amide;

N—[(R)-1-[(S)-1-(4-Aminomethyl-benzylcarbamoyl)-2-thiazol-4-yl-ethylcarbamoyl]-2-(4-ethoxy-phenyl)-ethyl]-4-methyl-benzamide;

3-Methyl-1H-pyrrole-2-carboxylic acid[(R)-1-[(S)-1-(4-aminomethyl-benzylcarbamoyl)-2-benzo[b]thiophen-3-yl-ethylcarbamoyl]-2-(4-ethoxy-phenyl)-ethyl]-amide;

3-Amino-thiophene-2-carboxylic acid[(R)-1-[(S)-1-(4-aminomethyl-benzylcarbamoyl)-2-thiazol-4-yl-ethylcarbamoyl]-2-(4-ethoxy-phenyl)-ethyl]-amide;

3-Acetylamino-thiophene-2-carboxylic acid[(R)-1-[(S)-1-(4-aminomethyl-benzylcarbamoyl)-2-benzo[b]thiophen-3-yl-ethylcarbamoyl]-2-(4-ethoxy-phenyl)-ethyl]-amide;

N—[(R)-1-[(S)-1-(4-Aminomethyl-benzylcarbamoyl)-2-pyridin-3-yl-ethylcarbamoyl]-2-(4-ethoxy-phenyl)-ethyl]-3-methyl-benzamide;

N—[(R)-1-[(S)-1-(4-Aminomethyl-benzylcarbamoyl)-2-pyridin-3-yl-ethylcarbamoyl]-2-(4-ethoxy-phenyl)-ethyl]-2-methyl-benzamide;

3,5-Dimethyl-1H-pyrrole-2-carboxylic acid[(R)-1-[(S)-1-(4-aminomethyl-benzylcarbamoyl)-2-phenyl-ethylcarbamoyl]-2-(4-ethoxy-phenyl)-ethyl]-amide;

N—[(R)-1-[(S)-1-(4-Aminomethyl-3-methyl-benzylcarbamoyl)-2-pyridin-3-yl-ethylcarbamoyl]-2-(4-ethoxy-phenyl)-ethyl]-benzamide;

3-Acetylamino-thiophene-2-carboxylic acid[(R)-1-[(S)-1-(4-aminomethyl-benzylcarbamoyl)-2-thiophen-3-yl-ethylcarbamoyl]-2-(4-ethoxy-phenyl)-ethyl]-amide;

3-Amino-thiophene-2-carboxylic acid[(R)-1-[(S)-1-(4-aminomethyl-benzylcarbamoyl)-2-benzo[b]thiophen-3-yl-ethylcarbamoyl]-2-(4-ethoxy-phenyl)-ethyl]-amide;

3-Acetylamino-thiophene-2-carboxylic acid[(R)-1-[(S)-1-(4-aminomethyl-benzylcarbamoyl)-2-benzo[b]thiophen-3-yl-ethylcarbamoyl]-2-(4-ethoxy-phenyl)-ethyl]-amide;

3-Chloro-thiophene-2-carboxylic acid[(R)-1-{[(S)-1-(4-aminomethyl-benzylcarbamoyl)-2-phenyl-ethyl]-methyl-carbamoyl}-2-(4-ethoxy-phenyl)-ethyl]-amide;

N—[(R)-1-[(1S,2R)-1-(4-Aminomethyl-benzylcarbamoyl)-2-hydroxy-2-phenyl-ethylcarbamoyl]-2-(4-ethoxy-phenyl)-ethyl]-benzamide;

3-Chloro-thiophene-2-carboxylic acid[(R)-1-[(1S,2R)-1-(4-aminomethyl-benzylcarbamoyl)-2-hydroxy-2-phenyl-ethylcarbamoyl]-2-(4-ethoxy-phenyl)-ethyl]-amide;

N-{(R,S)-1-[(S)-1-(4-Aminomethyl-benzylcarbamoyl)-2-phenyl-ethylcarbamoyl]-2-[4-(2,2,2-trifluoro-ethoxy)-phenyl]-ethyl}-benzamide;

and pharmaceutically acceptable salts and solvates thereof.

In an aspect, the invention comprises a compound selected from:

N—[(R)-1-[(S)-1-(4-Aminomethyl-benzylcarbamoyl)-2-phenyl-ethylcarbamoyl]-2-(4-ethoxy-phenyl)-ethyl]-benzamide;

Naphthalene-1-carboxylic acid[(R)-1-[(S)-1-(4-aminomethyl-benzylcarbamoyl)-2-phenyl-ethylcarbamoyl]-2-(4-ethoxy-phenyl)-ethyl]-amide;

N—[(R)-1-[(S)-1-(4-Aminomethyl-benzylcarbamoyl)-2-phenyl-ethylcarbamoyl]-2-(4-ethoxy-phenyl)-ethyl]-4-chloro-benzamide;

N—[(R)-1-[(S)-1-(4-Aminomethyl-benzylcarbamoyl)-2-phenyl-ethylcarbamoyl]-2-(4-ethoxy-phenyl)-ethyl]-2,4-dichloro-benzamide;

N—[(R)-1-[(S)-1-(4-Aminomethyl-benzylcarbamoyl)-2-phenyl-ethylcarbamoyl]-2-(4-ethoxy-phenyl)-ethyl]-3,4-difluoro-benzamide;

and pharmaceutically acceptable salts and solvates thereof.

In an aspect, the invention comprises a compound selected from:

N—[(R)-1-[(S)-1-(4-Aminomethyl-benzylcarbamoyl)-2-phenyl-ethylcarbamoyl]-2-(4-ethoxy-phenyl)-ethyl]-benzamide;

Naphthalene-1-carboxylic acid[(R)-1-[(S)-1-(4-aminomethyl-benzylcarbamoyl)-2-phenyl-ethylcarbamoyl]-2-(4-ethoxy-phenyl)-ethyl]-amide;

N—[(R)-1-[(S)-1-(4-Aminomethyl-benzylcarbamoyl)-2-phenyl-ethylcarbamoyl]-2-(4-ethoxy-phenyl)-ethyl]-4-chloro-benzamide;
N—[(R)-1-[(S)-1-(4-Aminomethyl-benzylcarbamoyl)-2-phenyl-ethylcarbamoyl]-2-(4-ethoxy-phenyl)-ethyl]-2,4-dichloro-benzamide;
N—[(R)-1-[(S)-1-(4-Aminomethyl-benzylcarbamoyl)-2-phenyl-ethylcarbamoyl]-2-(4-ethoxy-phenyl)-ethyl]-nicotinamide;
N—[(R)-1-[(S)-1-(4-Aminomethyl-benzylcarbamoyl)-2-phenyl-ethylcarbamoyl]-2-(4-ethoxy-phenyl)-ethyl]-3,4-difluoro-benzamide;
N—[(R)-1-[(S)-1-(4-Aminomethyl-benzylcarbamoyl)-2-phenyl-ethylcarbamoyl]-2-(4-ethoxy-phenyl)-ethyl]-isonicotinamide;
Thiophene-3-carboxylic acid-[(R)-1-[(S)-1-(4-aminomethyl-benzylcarbamoyl)-2-phenyl-ethylcarbamoyl]-2-(4-ethoxy-phenyl)-ethyl]-amide;
Thiophene-2-carboxylic acid[(R)-1-[(S)-1-(4-aminomethyl-benzylcarbamoyl)-2-phenyl-ethylcarbamoyl]-2-(4-ethoxy-phenyl)-ethyl]-amide;
Cyclohexanecarboxylic acid[(R)-1-[(S)-1-(4-aminomethyl-benzylcarbamoyl)-2-phenyl-ethylcarbamoyl]-2-(4-ethoxy-phenyl)-ethyl]-amide;
Isoxazole-5-carboxylic acid[(R)-1-[(S)-1-(4-aminomethyl-benzylcarbamoyl)-2-phenyl-ethylcarbamoyl]-2-(4-ethoxy-phenyl)-ethyl]-amide;
Pyridine-2-carboxylic acid[(R)-1-[(S)-1-(4-aminomethyl-benzylcarbamoyl)-2-phenyl-ethylcarbamoyl]-2-(4-ethoxy-phenyl)-ethyl]-amide;
(R)—N—[(S)-1-(4-Aminomethyl-benzylcarbamoyl)-2-phenyl-ethyl]-2-(4-chloro-benzenesulfonylamino)-3-(4-ethoxy-phenyl)-propionamide;
N—[(R)-1-[(S)-1-(4-Aminomethyl-benzylcarbamoyl)-2-phenyl-ethylcarbamoyl]-2-(4-ethoxy-phenyl)-ethyl]-4-methyl-benzamide;
N—[(R)-1-[(S)-1-(4-Aminomethyl-benzylcarbamoyl)-2-phenyl-ethylcarbamoyl]-2-(4-ethoxy-phenyl)-ethyl]-3,4-dichloro-benzamide;
N—[(R)-1-[(S)-1-(4-Aminomethyl-benzylcarbamoyl)-2-phenyl-ethylcarbamoyl]-2-(4-ethoxy-phenyl)-ethyl]-3-chloro-benzamide;
N—[(R)-1-[(S)-1-(4-Aminomethyl-benzylcarbamoyl)-2-phenyl-ethylcarbamoyl]-2-(4-ethoxy-phenyl)-ethyl]-4-methoxy-benzamide;
N—[(R)-1-[(S)-1-(4-Aminomethyl-benzylcarbamoyl)-2-phenyl-ethylcarbamoyl]-2-(4-ethoxy-phenyl)-ethyl]-4-fluoro-benzamide;
3-Methyl-thiophene-2-carboxylic acid[(R)-1-[(S)-1-(4-aminomethyl-benzylcarbamoyl)-2-phenyl-ethylcarbamoyl]-2-(4-ethoxy-phenyl)-ethyl]-amide;
3-Methyl-1H-pyrrole-2-carboxylic acid[(R)-1-[(S)-1-(4-aminomethyl-benzylcarbamoyl)-2-phenyl-ethylcarbamoyl]-2-(4-ethoxy-phenyl)-ethyl]-amide;
3-Amino-thiophene-2-carboxylic acid[(R)-1-[(S)-1-(4-aminomethyl-benzylcarbamoyl)-2-phenyl-ethylcarbamoyl]-2-(4-ethoxy-phenyl)-ethyl]-amide;
N—[(R)-1-[(S)-1-(4-Aminomethyl-benzylcarbamoyl)-2-phenyl-ethylcarbamoyl]-2-(4-propoxy-phenyl)-ethyl]-benzamide;
N—[(R)-1-[(S)-1-(4-Aminomethyl-benzylcarbamoyl)-2-pyridin-2-yl-ethylcarbamoyl]-2-(4-ethoxy-phenyl)-ethyl]-benzamide;
N—[(R)-1-[(S)-1-(4-Aminomethyl-benzylcarbamoyl)-2-(3,4-dichloro-phenyl)-ethylcarbamoyl]-2-(4-ethoxy-phenyl)-ethyl]-benzamide;
N—[(R)-1-[(S)-1-(4-Aminomethyl-benzylcarbamoyl)-2-(4-fluoro-phenyl)-ethylcarbamoyl]-2-(4-ethoxy-phenyl)-ethyl]-benzamide;
N—[(R)-1-[(S)-1-(4-Aminomethyl-benzylcarbamoyl)-2-pyridin-3-yl-ethylcarbamoyl]-2-(4-ethoxy-phenyl)-ethyl]-benzamide;
N—[(R)-1-[(S)-1-(4-Aminomethyl-benzylcarbamoyl)-2-thiophen-2-yl-ethylcarbamoyl]-2-(4-ethoxy-phenyl)-ethyl]-benzamide;
N—[(R)-1-[(S)-1-(4-Aminomethyl-benzylcarbamoyl)-2-thiophen-3-yl-ethylcarbamoyl-2-(4-ethoxy-phenyl)-ethyl]-benzamide;
N—[(R)-1-[(S)-1-(4-Aminomethyl-benzylcarbamoyl)-2-benzo[b]thiophen-3-yl-ethylcarbamoyl]-2-(4-ethoxy-phenyl)-ethyl]-benzamide;
N—[(R)-1-[(S)-1-(4-Aminomethyl-3-fluoro-benzylcarbamoyl)-2-phenyl-ethylcarbamoyl]-2-(4-ethoxy-phenyl)-ethyl]-benzamide;
N—[(R)-1-[(S)-1-(4-Aminomethyl-3-chloro-benzylcarbamoyl)-2-phenyl-ethylcarbamoyl]-2-(4-ethoxy-phenyl)-ethyl]-benzamide;
Pyridine-2-carboxylic acid[(R)-1-[(S)-1-(4-aminomethyl-benzylcarbamoyl)-2-thiophen-2-yl-ethylcarbamoyl]-2-(4-ethoxy-phenyl)-ethyl]-amide;
N—[(R)-1-[(S)-1-(4-Aminomethyl-benzylcarbamoyl)-2-pyridin-2-yl-ethylcarbamoyl]-2-(4-ethoxy-phenyl)-ethyl]-4-methoxy-benzamide;
Pyridine-2-carboxylic acid[(R)-1-[(S)-1-(4-aminomethyl-3-chloro-benzylcarbamoyl)-2-phenyl-ethylcarbamoyl]-2-(4-ethoxy-phenyl)-ethyl]-amide;
N—[(R)-1-[(S)-1-(4-Aminomethyl-benzylcarbamoyl)-2-pyridin-3-yl-ethylcarbamoyl]-2-(4-ethoxy-phenyl)-ethyl]-4-methoxy-benzamide;
Thiophene-2-carboxylic acid[(R)-1-[(S)-1-(4-aminomethyl-benzylcarbamoyl)-2-pyridin-3-yl-ethylcarbamoyl]-2-(4-ethoxy-phenyl)-ethyl]-amide;
N—[(R)-1-[(S)-1-(4-Aminomethyl-benzylcarbamoyl)-2-pyridin-3-yl-ethylcarbamoyl]-2-(4-ethoxy-phenyl)-ethyl]-4-methyl-benzamide;
N—[(R)-1-[(S)-1-(4-Aminomethyl-benzylcarbamoyl)-2-(3,4-difluoro-phenyl)-ethylcarbamoyl]-2-(4-ethoxy-phenyl)-ethyl]-benzamide;
3-Chloro-thiophene-2-carboxylic acid[(R)-1-[(S)-1-(4-aminomethyl-benzylcarbamoyl)-2-phenyl-ethylcarbamoyl]-2-(4-ethoxy-phenyl)-ethyl]-amide;
3-Chloro-thiophene-2-carboxylic acid[(R)-1-[(S)-1-(4-aminomethyl-benzylcarbamoyl)-2-pyridin-3-yl-ethylcarbamoyl]-2-(4-ethoxy-phenyl)-ethyl]-amide;
N—[(R)-1-[(S)-1-(4-Aminomethyl-benzylcarbamoyl)-2-(1H-indol-3-yl)-ethylcarbamoyl]-2-(4-ethoxy-phenyl)-ethyl]-benzamide;
N—[(R)-1-[(S)-1-(4-Aminomethyl-benzylcarbamoyl)-2-benzo[b]thiophen-3-yl-ethylcarbamoyl]-2-(4-ethoxy-phenyl)-ethyl]-isonicotinamide;
3-Acetylamino-thiophene-2-carboxylic acid-[(R)-1-[(S)-1-(4-aminomethyl-benzylcarbamoyl)-2-phenyl-ethylcarbamoyl]-2-(4-ethoxy-phenyl)-ethyl]-amide;
3-Methyl-thiophene-2-carboxylic acid[(R)-1-[(S)-1-(4-aminomethyl-benzylcarbamoyl)-2-pyridin-3-yl-ethylcarbamoyl]-2-(4-ethoxy-phenyl)-ethyl]-amide;
and pharmaceutically acceptable salts and solvates thereof.

Therapeutic Applications

As previously mentioned, the compounds of the present invention are potent and selective inhibitors of plasma kallikrein. They are therefore useful in the treatment of disease conditions for which over-activity of plasma kallikrein is a causative factor.

Accordingly, the present invention provides a compound of formula (I) for use in medicine.

The present invention also provides for the use of a compound of formula (I) in the manufacture of a medicament for the treatment or prevention of a disease or condition in which plasma kallikrein activity is implicated.

The present invention also provides a compound of formula (I) for use in the treatment or prevention of a disease or condition in which plasma kallikrein activity is implicated.

The present invention also provides a method of treatment of a disease or condition in which plasma kallikrein activity is implicated comprising administration to a subject in need thereof a therapeutically effective amount of a compound of formula (I).

In one aspect, the disease or condition in which plasma kallikrein activity is implicated is selected from Diseases or conditions in which plasma kallikrein activity is implicated include impaired visual acuity, diabetic retinopathy, diabetic macular oedema, hereditary angioedema, diabetes, pancreatitis, cerebral haemorrhage, neuropathy, cardiomyopathy, neuropathy, inflammatory bowel disease, arthritis, inflammation, septic shock, hypotension, cancer, adult respiratory distress syndrome, disseminated intravascular coagulation, cardiopulmonary bypass surgery and bleeding from post operative surgery.

In another aspect, the disease or condition in which plasma kallikrein activity is implicated is retinal vascular permeability associated with diabetic retinopathy and diabetic macular oedema.

Combination Therapy

The compounds of the present invention may be administered in combination with other therapeutic agents. Suitable combination therapies include a compound of formula (I) combined with one or more agents selected from agents that inhibit platelet-derived growth factor (PDGF), endothelial growth factor (VEGF), integrin alpha5beta1, steroids, other agents that inhibit plasma kallikrein and other inhibitors of inflammation. Specific examples of therapeutic agents that may be combined with the compounds of the present invention include those disclosed in EP2281885A and by S. Patel in *Retina,* 2009 June; 29(6 Suppl):S45-8.

When combination therapy is employed, the compounds of the present invention and said combination agents may exist in the same or different pharmaceutical compositions, and may be administered separately, sequentially or simultaneously.

Definitions

The term "alkyl" includes saturated hydrocarbon residues including:

linear groups up to 10 carbon atoms ($C_1$-$C_{10}$), or of up to 6 carbon atoms ($C_1$-$C_6$), or of up to 4 carbon atoms ($C_1$-$C_4$). Examples of such alkyl groups include, but are not limited, to $C_1$-methyl, $C_2$-ethyl, $C_3$-propyl and $C_4$-n-butyl.

branched groups of between 3 and 10 carbon atoms ($C_3$-$C_{10}$), or of up to 7 carbon atoms ($C_3$-$C_7$), or of up to 4 carbon atoms ($C_3$-$C_4$). Examples of such alkyl groups include, but are not limited to, $C_3$-iso-propyl, $C_4$-sec-butyl, $C_4$-iso-butyl, $C_4$-tert-butyl and $C_5$-neo-pentyl.

each optionally substituted as stated above.

The term "alkoxy" includes O-linked hydrocarbon residues including:

linear groups of between 1 and 6 carbon atoms ($C_1$-$C_6$), or of between 1 and 4 carbon atoms ($C_1$-$C_4$). Examples of such alkoxy groups include, but are not limited to, $C_1$-methoxy, $C_2$-ethoxy, $C_3$-n-propoxy and $C_4$-n-butoxy.

branched groups of between 3 and 6 carbon atoms ($C_3$-$C_6$) or of between 3 and 4 carbon atoms ($C_3$-$C_4$). Examples of such alkoxy groups include, but are not limited to, $C_3$-iso-propoxy, and $C_4$-sec-butoxy and tert-butoxy.

each optionally substituted as stated above.

Unless otherwise stated, halo is selected from Cl, F, Br and I.

Cycloalkyl is as defined above. Cycloalkyl groups may contain from 3 to 10 carbon atoms, or from 4 to 10 carbon atoms, or from 5 to 10 carbon atoms, or from 4 to 6 carbon atoms.

Examples of suitable monocyclic cycloalkyl groups include cyclopropyl, cyclobutyl, cyclopentyl, cyclohexyl and cycloheptyl. Examples of suitable bicyclic cycloalkyl groups include decahydronaphthalene and octahydro-1H-indene Examples of suitable cycloalkyl groups, when fused with aryl, include indanyl and 1,2,3,4-tetrahydronaphthyl.

Heterocycloalkyl is as defined above. Examples of suitable heterocycloalkyl groups include oxiranyl, aziridinyl, azetidinyl, tetrahydrofuranyl, pyrrolidinyl, tetrahydropyranyl, piperidinyl, N-methylpiperidinyl, morpholinyl, N-methyl morpholinyl, piperazinyl, N-methylpiperazinyl, azepanyl, oxazepanyl and diazepanyl.

Aryl is as defined above. Typically, aryl will be optionally substituted with 1, 2 or 3 substituents. Optional substituents are selected from those stated above. Examples of suitable aryl groups include phenyl and naphthyl (each optionally substituted as stated above).

Heteroaryl is as defined above. Examples of suitable heteroaryl groups include thienyl, furanyl, pyrrolyl, pyrazolyl, imidazoyl, oxazolyl, isoxazolyl, thiazolyl, isothiazolyl, triazolyl, oxadiazolyl, thiadiazolyl, tetrazolyl, pyridinyl, pyridazinyl, pyrimidinyl, pyrazinyl, indolyl, benzimidazolyl, benzotriazolyl, quinolinyl and isoquinolinyl (optionally substituted as stated above).

The term "C-linked", such as in "C-linked heterocycloalkyl", means that the heterocycloalkyl group is joined to the remainder of the molecule via a ring carbon atom.

The term "N-linked", such as in "N-linked heterocycloalkyl", means that the heterocycloalkyl group is joined to the remainder of the molecule via a ring nitrogen atom.

The term "O-linked", such as in "O-linked hydrocarbon residue", means that the hydrocarbon residue is joined to the remainder of the molecule via an oxygen atom.

In groups such as —COalkyl and —$(CH_2)_b COOR^{10}$, "—" denotes the point of attachment of the substituent group to the remainder of the molecule.

"Pharmaceutically acceptable salt" means a physiologically or toxicologically tolerable salt and includes, when appropriate, pharmaceutically acceptable base addition salts and pharmaceutically acceptable acid addition salts. For example (i) where a compound of the invention contains one or more acidic groups, for example carboxy groups, pharmaceutically acceptable base addition salts that can be formed include sodium, potassium, calcium, magnesium and ammonium salts, or salts with organic amines, such as, diethylamine, N-methyl-glutamine, diethanolamine or amino acids (e.g. lysine) and the like; (ii) where a compound of the invention contains a basic group, such as an amino group, pharmaceutically acceptable acid addition salts that can be formed include hydrochlorides, hydrobromides, sulfates, phosphates, acetates, citrates, lactates, tartrates, mesylates, succinates, oxalates, phosphates, esylates, tosylates, benzenesulfonates, naphthalenedisulphonates, maleates, adipates, fumarates, hippurates, camphorates, xinafoates, p-acetamidobenzoates, dihydroxybenzoates, hydroxynaphthoates, succinates, ascorbates, oleates, bisulfates and the like.

Hemisalts of acids and bases can also be formed, for example, hemisulfate and hemicalcium salts.

For a review of suitable salts, see "Handbook of Pharmaceutical Salts: Properties, Selection and Use" by Stahl and Wermuth (Wiley-VCH, Weinheim, Germany, 2002).

"Prodrug" refers to a compound which is convertible in vivo by metabolic means (e.g. by hydrolysis, reduction or oxidation) to a compound of the invention. Suitable groups for forming pro-drugs are described in 'The Practice of Medicinal Chemistry, $2^{nd}$ Ed. pp 561-585 (2003) and in F. J. Leinweber, Drug Metab. Res., 1987, 18, 379.

The compounds of the invention can exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when the solvent is water.

Where compounds of the invention exist in one or more geometrical, optical, enantiomeric, diastereomeric and tautomeric forms, including but not limited to cis- and trans-forms, E- and Z-forms, R-, S- and meso-forms, keto-, and enol-forms. Unless otherwise stated a reference to a particular compound includes all such isomeric forms, including racemic and other mixtures thereof. Where appropriate such isomers can be separated from their mixtures by the application or adaptation of known methods (e.g. chromatographic techniques and recrystallisation techniques). Where appropriate such isomers can be prepared by the application or adaptation of known methods (e.g. asymmetric synthesis).

In the context of the present invention, references herein to "treatment" include references to curative, palliative and prophylactic treatment.

General Methods

The compounds of formula (I) should be assessed for their biopharmaceutical properties, such as solubility and solution stability (across pH), permeability, etc., in order to select the most appropriate dosage form and route of administration for treatment of the proposed indication. They may be administered alone or in combination with one or more other compounds of the invention or in combination with one or more other drugs (or as any combination thereof). Generally, they will be administered as a formulation in association with one or more pharmaceutically acceptable excipients. The term 'excipient' is used herein to describe any ingredient other than the compound(s) of the invention which may impart either a functional (i.e., drug release rate controlling) and/or a non-functional (i.e., processing aid or diluent) characteristic to the formulations. The choice of excipient will to a large extent depend on factors such as the particular mode of administration, the effect of the excipient on solubility and stability, and the nature of the dosage form.

Compounds of the invention intended for pharmaceutical use may be administered as a solid or liquid, such as a tablet, capsule or solution. Pharmaceutical compositions suitable for the delivery of compounds of the present invention and methods for their preparation will be readily apparent to those skilled in the art. Such compositions and methods for their preparation may be found, for example, in Remington's Pharmaceutical Sciences, 19th Edition (Mack Publishing Company, 1995).

Accordingly, the present invention provides a pharmaceutical composition comprising a compound of formula (I) and a pharmaceutically acceptable carrier, diluent or excipient.

For the treatment of conditions such as retinal vascular permeability associated with diabetic retinopathy and diabetic macular oedema, the compounds of the invention may be administered in a form suitable for injection into the ocular region of a patient, in particular, in a form suitable for intravitreal injection. It is envisaged that formulations suitable for such use will take the form of sterile solutions of a compound of the invention in a suitable aqueous vehicle. The compositions may be administered to the patient under the supervision of the attending physician.

The compounds of the invention may also be administered directly into the blood stream, into subcutaneous tissue, into muscle, or into an internal organ. Suitable means for parenteral administration include intravenous, intraarterial, intraperitoneal, intrathecal, intraventricular, intraurethral, intrasternal, intracranial, intramuscular, intrasynovial and subcutaneous. Suitable devices for parenteral administration include needle (including microneedle) injectors, needle-free injectors and infusion techniques.

Parenteral formulations are typically aqueous or oily solutions. Where the solution is aqueous, excipients such as sugars (including but not restricted to glucose, mannitol, sorbitol, etc.), salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

Parenteral formulations may include implants derived from degradable polymers such as polyesters (i.e., polylactic acid, polylactide, polylactide-co-glycolide, polycapro-lactone, polyhydroxybutyrate), polyorthoesters and polyanhydrides. These formulations may be administered via surgical incision into the subcutaneous tissue, muscular tissue or directly into specific organs.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of co-solvents and/or solubility-enhancing agents such as surfactants, micelle structures and cyclodextrins.

In one embodiment, the compounds of the invention may be administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid plugs, solid microparticulates, semi-solid and liquid (including multiple phases or dispersed systems) such as tablets; soft or hard capsules containing multi- or nano-particulates, liquids, emulsions or powders; lozenges (including liquid-filled); chews; gels; fast dispersing dosage forms; films; ovules; sprays; and buccal/mucoadhesive patches.

Formulations suitable for oral administration may also be designed to deliver the compounds of the invention in an immediate release manner or in a rate-sustaining manner, wherein the release profile can be delayed, pulsed, controlled, sustained, or delayed and sustained or modified in such a manner which optimises the therapeutic efficacy of the said compounds. Means to deliver compounds in a rate-sustaining manner are known in the art and include slow release polymers that can be formulated with the said compounds to control their release.

Examples of rate-sustaining polymers include degradable and non-degradable polymers that can be used to release the said compounds by diffusion or a combination of diffusion and polymer erosion. Examples of rate-sustaining polymers include hydroxypropyl methylcellulose, hydroxypropyl cellulose, methyl cellulose, ethyl cellulose, sodium carboxymethyl cellulose, polyvinyl alcohol, polyvinyl pyrrolidone, xanthum gum, polymethacrylates, polyethylene oxide and polyethylene glycol.

Liquid (including multiple phases and dispersed systems) formulations include emulsions, solutions, syrups and elixirs. Such formulations may be presented as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Liang and Chen, Expert Opinion in Therapeutic Patents, 2001, 11 (6), 981-986.

The formulation of tablets is discussed in Pharmaceutical Dosage Forms: Tablets, Vol. 1, by H. Lieberman and L. Lachman (Marcel Dekker, New York, 1980).

For administration to human patients, the total daily dose of the compounds of the invention is typically in the range 0.01 mg and 1000 mg, or between 0.1 mg and 250 mg, or between 1 mg and 50 mg depending, of course, on the mode of administration. For example, if administered by intra-vitreal injection it is envisaged that the compound of the invention will be dosed infrequently, e.g. once a month. In this circumstance, a dose of between 0.5 mg and 20 mg, such as between 1 mg and 10 mg, is envisaged. If dosed more frequently, e.g. once daily, a much lower dose of between 0.005 mg and 0.02 mg is envisaged.

The total dose may be administered in single or divided doses and may, at the physician's discretion, fall outside of the typical range given herein. These dosages are based on an average human subject having a weight of about 60 kg to 70 kg. The physician will readily be able to determine doses for subjects whose weight falls outside this range, such as infants and the elderly.

Synthetic Methods

The compounds of the present invention can be prepared according to the procedures of the following schemes and examples, using appropriate materials, and are further exemplified by the specific examples provided herein below. Moreover, by utilising the procedures described herein, one of ordinary skill in the art can readily prepare additional compounds that fall within the scope of the present invention claimed herein. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds.

The compounds of the invention may be isolated in the form of their pharmaceutically acceptable salts, such as those described previously herein above.

It may be necessary to protect reactive functional groups (e.g. hydroxy, amino, thio or carboxy) in intermediates used in the preparation of compounds of the invention to avoid their unwanted participation in a reaction leading to the formation of the compounds. Conventional protecting groups, for example those described by T. W. Greene and P. G. M. Wuts in "Protective groups in organic chemistry" John Wiley and Sons, 4$^{th}$ Edition, 2006, may be used. For example, a common amino protecting group suitable for use herein is tert-butoxy carbonyl (Boc), which is readily removed by treatment with an acid such as trifluoroacetic acid or hydrogen chloride in an organic solvent such as dichloromethane. Alternatively the amino protecting group may be a benzyloxycarbonyl (Z) group which can be removed by hydrogenation with a palladium catalyst under a hydrogen atmosphere or 9-fluorenylmethyloxycarbonyl (Fmoc) group which can be removed by solutions of secondary organic amines such as diethylamine or piperidine in an organic solvents. Carboxyl groups are typically protected as esters such as methyl, ethyl, benzyl or tert-butyl which can all be removed by hydrolysis in the presence of bases such as lithium or sodium hydroxide. Benzyl protecting groups can also be removed by hydrogenation with a palladium catalyst under a hydrogen atmosphere whilst tert-butyl groups can also be removed by trifluoroacetic acid. Alternatively a trichloroethyl ester protecting group is removed with zinc in acetic acid. A common hydroxy protecting group suitable for use herein is a methyl ether, deprotection conditions comprise refluxing in 48% aqueous HBr for 1-24 hours, or by stirring with borane tribromide in dichloromethane for 1-24 hours. Alternatively where a hydroxy group is protected as a benzyl ether, deprotection conditions comprise hydrogenation with a palladium catalyst under a hydrogen atmosphere.

The compounds according to general formula I can be prepared using conventional synthetic methods for example, but not limited to, the route outlined in Scheme 1. In a typical first step the amine (2) is coupled using standard peptide coupling conditions to an activated alpha amino acid (1) suitably amino-protected with a standard protecting group such as tert-butyloxycarbonyl (Boc), benzyloxycarbonyl (Z) or 9-fluorenylmethyloxycarbonyl (Fmoc). The activating group (X) may be N-hydroxysuccinimide. The use of such groups is well known in the art. Where $R^5$ or $R^9$ (shown as 'Aryl' in Scheme 1) has a reactive functional group such as an amine or a carboxylic acid, this group will also be protected. Other standard peptide coupling methods include the reaction of acids with amines in the presence of hydroxybenzotriazole and carbodiimide such as water soluble carbodiimide, or 2-(1H-benzotriazole-1-yl)-1,1,3,3-tetramethylaminium hexafluorophosphate or benzotriazole-1-yl-oxy-tris-pyrrolidino-phosphoium hexaffluorophosphate or bromo-trispyrrolidino-phosphoium hexafluorophosphate in the presence of organic bases such as triethylamine, diisopropylethylamine or N-methylmorpholine. In a typical second step the protecting group is removed using standard methods as previously described.

The route exemplified in Scheme 1 then proceeds in the third step via a further standard peptide coupling and in the fourth step via removal of the Boc protecting group using standard conditions as previously described. The amine revealed in 7 may, in a fifth step, then typically be alkylated or acylated with the group R1. Acylation may be carried out by treatment with an acylating agent such as an acyl chloride, for example acetyl chloride or benzoyl chloride, in the presence of a base, typically a tertiary amine base such as triethylamine or diisopropylethylamine. Alkylation may typically be carried by treatment with an alkyl halide or by reductive alkylation. Typically, in a reductive alkylation procedure the amine is allowed to react with an aldehyde or ketone in the presence of a suitable reducing agent such as sodium cyanoborohydride or sodium acetoxyborohydride in a suitable solvent such as methanol, at room temperature. The resulting nitrile compound 8 may then be reduced by hydrogenation. Conversion from 8 to 10 may be achieved in a single step either by direct reduction of the nitrile by hydrogenation in a suitable solvent such as methanol in the presence of a suitable catalyst such as palladium on charcoal in the presence of an acid such as hydrochloric acid or reduction with a suitable borohydride in the presence of a suitable transition metal such as cobalt or nickel chloride in a suitable solvent such as methanol at room temperature. Alternatively, the tert-butoxycarbonyl (Boc) protected amine 9 may be isolated (using, for example, the method as described in S. Caddick et al., *Tetrahedron Lett.*, 2000, 41, 3513) and subsequently deprotected by standard means described previously to give the amine 10.

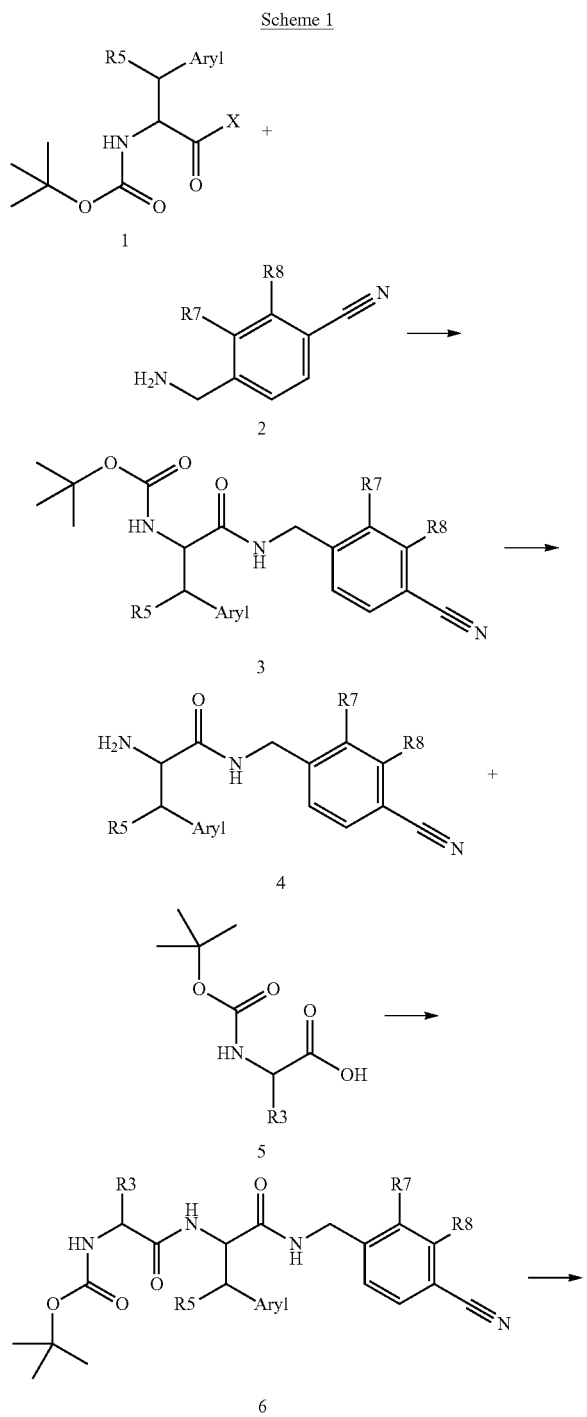

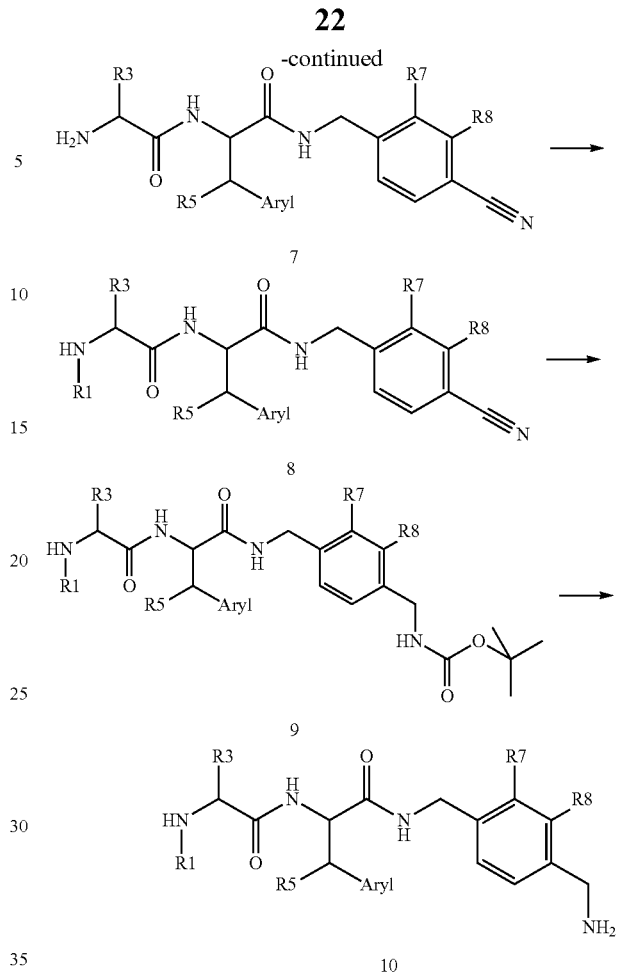

EXAMPLES

Figure 1:
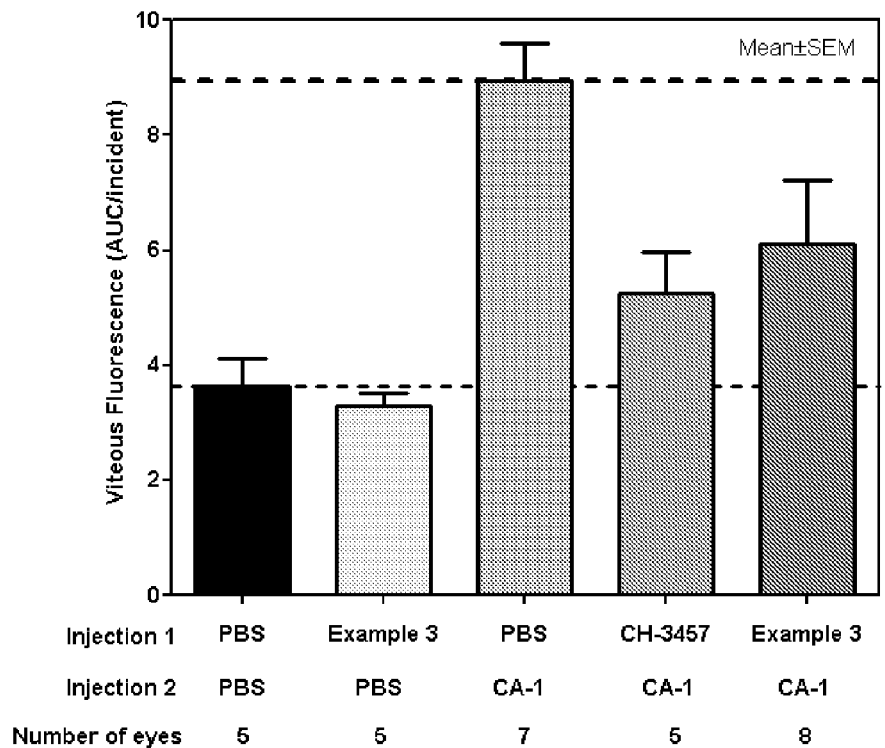
FIG. 1 shows the inhibitory effect of Example 3 and CH-3457 (positive control; plasma kallikrein inhibitor) upon CA-I stimulated RVP in Sprague Dawley rats.

The invention is illustrated by the following non-limiting examples in which the following abbreviations and definitions are used:

| | |
|---|---|
| Cha | 3-Cyclohexylalanine |
| DMF | N,N-Dimethylformamide |
| DMSO | Dimethyl sulfoxide |
| Et | Ethyl |
| EtOAc | Ethyl Acetate |
| hrs | Hours |
| HOBt | Hydroxybenzotriazole |
| LCMS | Liquid chromatography mass spectrometry |
| Me | Methyl |
| MeCN | Acetonitrile |
| MeOH | Methanol |
| min | Minutes |
| MS | Mass spectrum |
| m/z | Mass charge ratio (of parent, MH$^+$, ion unless otherwise stated) |

| | |
|---|---|
| NMR | Nuclear magnetic resonance spectrum - NMR spectra were recorded at a frequency of 400 MHz unless otherwise indicated |
| Pet. Ether | Petroleum ether fraction boiling at 60-80° C. |
| Ph | Phenyl |
| Phe | Phenylalanine |
| n-Pr | n-Propyl |
| THF | Tetrahydrofuran |
| TFA | Trifluoroacetic acid |

All reactions were carried out under an atmosphere of nitrogen unless specified otherwise.

¹H NMR spectra were recorded on a Brucker Avance III (400 MHz) spectrometer with reference to deuterium solvent and at room temperature.

Molecular ions were obtained using LCMS which was carried out using a Chromolith Speedrod RP-18e column, 50×4.6 mm, with a linear gradient 10% to 90% 0.1% $HCO_2H$/MeCN into 0.1% $HCO_2H/H_2O$ over 11 min, flow rate 1.5 mL/min. Data was collected using a Thermofinnigan Surveyor MSQ mass spectrometer with electospray ionisation in conjunction with a Thermofinnigan Surveyor LC system.

Chemical names were generated using the Autonom software provided as part of the ISIS draw package from MDL Information Systems.

Where products were purified by flash chromatography, 'silica' refers to silica gel for chromatography, 0.035 to 0.070 mm (220 to 440 mesh) (e.g. Merck silica gel 60), and an applied pressure of nitrogen up to 10 p.s.i accelerated column elution. Reverse phase preparative HPLC purifications were carried out using a Waters 2525 binary gradient pumping system at flow rates of typically 20 mL/min using a Waters 2996 photodiode array detector.

All solvents and commercial reagents were used as received.

Example 1

(S)—N-(4-Aminomethyl-benzyl)-2-[(R)-3-(4-ethoxy-phenyl)-2-propionylamino-propionylamino]-3-phenyl-propionamide

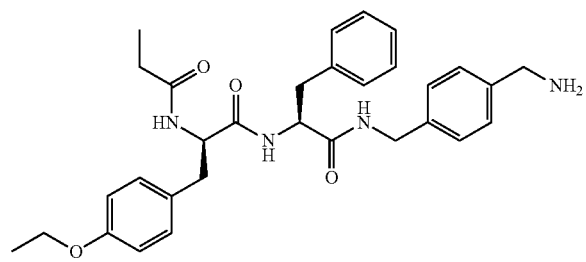 [SMILES: CCOc1ccc(C[C@@H](NC(=O)CC)C(=O)N[C@@H](Cc2ccccc2)C(=O)NCc2ccc(CN)cc2)cc1]

A. (S)-2-[(R)-2-tert-Butoxycarbonylamino-3-(4-ethoxy-phenyl)-propionylamino]-3-phenyl-propionic acid methyl ester H-Phe-OMe.HCl (2.3 g, 10.7 mmol) was dissolved in $CH_2Cl_2$ (100 mL) and DMF (10 mL). This solution was cooled to 0° C. (R)-2-Butoxyloxycarbonylamino-3-(4-ethoxy-phenyl)-propionic acid (3.0 g, 9.7 mmol) was added followed by HOBt (1.57 g, 11.6 mmol) and triethylamine (2.9 g, 29.0 mmol). Water soluble carbodiimide (2.04 g, 10.6 mmol) was then added. After 18 hrs at 0° C. to room temperature reaction mixture was diluted with chloroform (100 mL) and washed with $NaHCO_3$ (1×30 mL), water (1×30 mL), brine (1×30 mL), dried ($Na_2SO_4$) and evaporated in vacuo giving a yellow oil. The residue was purified by flash chromatography (silica), eluent 20% Pet. Ether (60-80° C.), 80% EtOAc, fractions combined and evaporated in vacuo to give a colourless oil identified as (S)-2-[(R)-2-tert-butoxycarbonylamino-3-(4-ethoxy-phenyl)-propionylamino]-3-phenyl-propionic acid methyl ester (4.25 g, 9.03 mmol, 93%).

$[M+H]^+=471.27$.

B. (S)-2-[(R)-2-tert-Butoxycarbonylamino-3-(4-ethoxy-phenyl)-propionylamino]-3-phenyl-propionic acid (S)-2-[(R)-2-tert-Butoxycarbonylamino-3-(4-ethoxy-phenyl)-propionylamino]-3-phenyl-propionic acid methyl ester (2.5 g, 5.3 mmol) was dissolved in THF (100 mL). Lithium hydroxide monohydrate (668 mg, 15.9 mmol) in water (10 mL) was added. The reaction mixture was stirred at room temperature for 18 hrs after which time the reaction mixture was diluted with EtOAc (150 mL). This solution was washed with 0.3M $KHSO_4$ (1×50 mL), water (1×30 mL), brine (1×30 mL), dried ($Na_2SO_4$) and evaporated in vacuo to give a white solid identified as (S)-2-[(R)-2-tert-butoxycarbonylamino-3-(4-ethoxy-phenyl)-propionylamino]-3-phenyl-propionic acid (2.095 g, 4.58 mmol, 86%).

$[M+H]^+=457.25$.

C. [(R)-1-[(S)-1-(4-Cyano-benzylcarbamoyl)-2-phenyl-ethylcarbamoyl]-2-(4-ethoxy-phenyl)-ethyl]-carbamic acid tert-butyl ester 4-(Aminomethyl)benzonitrile hydrochloride (303 mg, 1.80 mmol) was dissolved in $CH_2Cl_2$ (50 mL) and DMF (5 mL). This solution was cooled to 0° C. (S)-2-[(R)-2-tert-butoxycarbonylamino-3-(4-ethoxy-phenyl)-propionylamino]-3-phenyl-propionic acid (745 mg, 1.63 mmol) was added followed by HOBt (265 mg, 1.96 mmol) and triethylamine (495 mg, 4.9 mmol). Water soluble carbodiimide (344 mg, 1.8 mmol) was then added. After 18 hrs at 0° C. to room temperature reaction mixture was diluted with chloroform (100 mL) and washed with $NaHCO_3$ (1×30 mL), water (1×30 mL), brine (1×30 mL), dried ($Na_2SO_4$) and evaporated in vacuo giving a yellow oil. The residue was purified by flash chromatography (silica), eluent 20% Pet. Ether (60-80° C.), 80% EtOAc, fractions combined and evaporated in vacuo to give a colourless oil identified as [(R)-1-[(S)-1-(4-cyano-benzylcarbamoyl)-2-phenyl-ethylcarbamoyl]-2-(4-ethoxy-phenyl)-ethyl]-carbamic acid tert-butyl ester (493 mg, 0.86 mmol, 53%).

$[M+H]^+=571.29$

D. (R)-2-Amino-N—[(S)-1-(4-cyano-benzylcarbamoyl)-2-phenyl-ethyl]-3-(4-ethoxy-phenyl)-propionamide Hydrochloride

[(R)-1-[(S)-1-(4-Cyano-benzylcarbamoyl)-2-phenyl-ethylcarbamoyl]-2-(4-ethoxy-phenyl)-ethyl]-carbamic acid tert-butyl ester (225 mg, 0.39 mmol) was treated with 4M HCl/dioxan (50 mL). After one hour at room temperature the solvent was removed to give a white solid identified as (R)-2-amino-N—[(S)-1-(4-cyano-benzylcarbamoyl)-2-phenyl-ethyl]-3-(4-ethoxy-phenyl)-propionamide hydrochloride (200 mg, 0.39 mmol, 100%).

$[M+H]^+=471.26$

E. (S)—N-(4-Cyano-benzyl)-2-[(R)-3-(4-ethoxy-phenyl)-2-propionylamino-propionylamino]-3-phenyl-propionamide (R)-2-Amino-N—[(S)-1-(4-cyano-benzylcarbamoyl)-2-phenyl-ethyl]-3-(4-ethoxy-phenyl)-propionamide hydrochloride (200 mg, 0.37 mol) was dissolved in dichloromethane (50 mL), this solution was cooled to 0° C. Triethylamine (111 mg, 1.1 mmol) was added followed by propionyl chloride (39 mg, 0.40 mmol). After 18 hrs at 0° C. to room temperature the reaction mixture was diluted with CHCl$_3$ (50 mL), this solution was washed with sat. NaHCO$_3$ (1×20 mL), water (1×20 mL), brine (1×20 mL), dried (Na$_2$SO$_4$) and evaporated in vacuo. The residue was purified by flash chromatography (silica), eluent 2% MeOH, 98% CHCl$_3$, fractions combined and evaporated in vacuo to give a colourless oil identified as (S)—N-(4-cyano-benzyl)-2-[(R)-3-(4-ethoxy-phenyl)-2-propionylamino-propionylamino]-3-phenyl-propionamide (189 mg, 0.36 mmol, 98%).

[M+H]$^+$=527.27

F. [4-({(S)-2-[(R)-3-(4-Ethoxy-phenyl)-2-propionylamino-propionylamino]-3-phenyl-propionylamino}-methyl)-benzyl]-carbamic acid tert-butyl ester (S)—N-(4-Cyano-benzyl)-2-[(R)-3-(4-ethoxy-phenyl)-2-propionylamino-propionylamino]-3-phenyl-propionamide (100 mg, 0.19 mmol) was dissolved in methanol (50 mL). This solution was cooled to 0° C. Nickel (II) chloride hexahydrate (4.5 mg, 0.0192 mmol) and di-tertbutyl dicarbonate (83 mg, 0.38 mmol) were added followed by sodium borohydride (50 mg, 1.33 mmol) portionwise. The reaction mixture was stirred at 0° C. to room temp for 18 hrs. The methanol was removed by evaporation. The residue was dissolved in CHCl$_3$ (70 mL), washed with sat NaHCO$_3$ (1×30 mL), water (1×30 mL), brine (1×30 mL), dried (Na$_2$SO$_4$) and evaporated in vacuo to give a yellow oil. Purified by flash chromatography, eluant 1% MeOH, 99% CHCl$_3$ to give a colourless oil identified as [4-({(S)-2-[(R)-3-(4-ethoxy-phenyl)-2-propionylamino-propionylamino]-3-phenyl-propionylamino}-methyl)-benzyl]-carbamic acid tert-butyl ester (89 mg, 0.14 mmol, 74%).

[M+H]$^+$=631.39

G. (S)—N-(4-Aminomethyl-benzyl)-2-[(R)-3-(4-ethoxy-phenyl)-2-propionylamino-propionylamino]-3-phenyl-propionamide Trifluoroacetate

[4-({(S)-2-[(R)-3-(4-Ethoxy-phenyl)-2-propionylamino-propionylamino]-3-phenyl-propionylamino}-methyl)-benzyl]-carbamic acid tert-butyl ester (89 mg, 0.13 mmol) was dissolved in trifluoroacetic acid (20 mL). This solution was stirred at room temperature for one hour after which time the solvent was removed in vacuo to give a yellow oil. The residue was purified by Prep HPLC (Sunfire prep C18 OBD column. 19×250 mm, 10µ). 10 to 90% 0.1% TFA/MeCN into 0.1% TFA/H$_2$O over 35 min at 20 mL/min. Fractions combined and freeze dried to give a white solid identified as (S)—N-(4-aminomethyl-benzyl)-2-[(R)-3-(4-ethoxy-phenyl)-2-propionylamino-propionylamino]-3-phenyl-propionamide trifluoroacetate (38 mg, 0.056 mmol, 42%)

[M+H]$^+$=531.31

$^1$H NMR: (CD$_3$OD) 1.02 (3H, t, J=7.7 Hz), 1.42 (3H, t, J=7.0 Hz), 2.13-2.21 (2H, m), 2.71-2.77 (1H, m), 2.81-2.92 (2H, m), 3.12-3.16 (1H, m), 4.05 (2H, q, J=6.9 Hz), 4.13 (2H, s), 4.37-4.50 (3H, m), 4.57-4.69 (1H, m), 6.82 (2H, d, J=8.6 Hz), 7.05 (2H, d, J=8.6 Hz), 7.17-7.19 (2H, m), 7.24-7.31 (5H, m), 7.41 (2H, d, J=8.1 Hz).

Example 2

(R)—N—[(S)-1-(4-Aminomethyl-benzylcarbamoyl)-2-phenyl-ethyl]-3-(4-ethoxy-phenyl)-2-methanesulfonylamino-propionamide

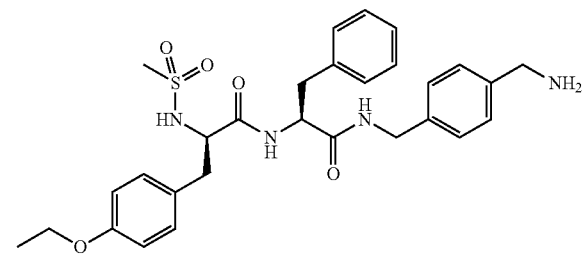 [SMILES: CCOc1ccc(C[C@@H](NS(C)(=O)=O)C(=O)N[C@@H](Cc2ccccc2)C(=O)NCc2ccc(CN)cc2)cc1]

A. (R)—N—[(S)-1-(4-Cyano-benzylcarbamoyl)-2-phenyl-ethyl]-3-(4-ethoxy-phenyl)-2-methanesulfonylamino-propionamide (R)-2-Amino-N—[(S)-1-(4-cyano-benzylcarbamoyl)-2-phenyl-ethyl]-3-(4-ethoxy-phenyl)-propionamide hydrochloride (150 mg, 0.30 mmol) was dissolved in CH$_2$Cl$_2$ (20 mL). This solution was cooled to 0° C. Methanesulfonyl chloride (37 mg, 0.33 mmol) was added followed triethylamine (90 mg, 0.89 mmol). After 18 hrs at 0° C. to room temperature reaction mixture was diluted with chloroform (50 mL) and washed with NaHCO$_3$ (1×20 mL), water (1×20 mL), brine (1×20 mL), dried (Na$_2$SO4) and evaporated in vacuo giving a yellow oil. The residue was purified by flash chromatography (silica), eluant 2% MeOH, 98% CHCl$_3$, fractions combined and evaporated in vacuo to give a white solid identified as (R)—N—[(S)-1-(4-cyano-benzylcarbamoyl)-2-phenyl-ethyl]-3-(4-ethoxy-phenyl)-2-methanesulfonylamino-propionamide (110 mg, 0.20 mmol, 68%).

[M+H]$^+$=549.11

B. [4-({(S)-2-[(R)-3-(4-Ethoxy-phenyl)-2-methanesulfonylamino-propionylamino]-3-phenyl-propionylamino}-methyl)-benzyl]-carbamic acid tert-butyl ester (R)—N—[(S)-1-(4-Cyano-benzylcarbamoyl)-2-phenyl-ethyl]-3-(4-ethoxy-phenyl)-2-methanesulfonylamino-propionamide (110 mg, 0.20 mmol) was dissolved in methanol (50 mL). This solution was cooled to 0° C. Nickel (II) chloride hexahydrate (4.8 mg, 0.02 mmol) and di-tertbutyl dicarbonate (88 mg, 0.4 mmol) were added followed by sodium borohydride (53 mg, 1.4 mmol) portionwise. The reaction mixture was stirred at 0° C. to room temp for 18 hrs. The MeOH was removed by evaporation. The residue was dissolved in CHCl₃ (70 mL), washed with sat NaHCO₃ (1×30 mL), water (1×30 mL), brine (1×30 mL), dried (Na₂SO₄) and evaporated in vacuo to give a yellow oil. Purified by flash chromatography, eluant 2% MeOH, 98% CHCl₃ to give white solid identified as [4-({(S)-2-[(R)-3-(4-ethoxy-phenyl)-2-methanesulfonylamino-propionylamino]-3-phenyl-propionylamino}-methyl)-benzyl]-carbamic acid tert-butyl ester (86 mg, 0.13 mmol, 66%).

[M+H]⁺=653.23, 675.19 (M+Na).

C. (R)—N—[(S)-1-(4-Aminomethyl-benzylcarbamoyl)-2-phenyl-ethyl]-3-(4-ethoxy-phenyl)-2-methanesulfonylamino-propionamide Trifluoroacetate

[4-({(S)-2-[(R)-3-(4-Ethoxy-phenyl)-2-methanesulfonylamino-propionylamino]-3-phenyl-propionylamino}-methyl)-benzyl]-carbamic acid tert-butyl ester (86 mg, 0.13 mmol) was treated with trifluoroacetic acid (20 mL). After one hour at room temp the solvent was evaporated in vacuo. The residue was purified by Prep HPLC (Sunfire prep C18 OBD column. 19×250 mm, 10μ). 10 to 90% 0.1% TFA/MeCN into 0.1% TFA/H₂O over 35 min at 20 mL/min. Fractions combined and freeze dried to give a white solid identified as (R)—N—[(S)-1-(4-aminomethyl-benzylcarbamoyl)-2-phenyl-ethyl]-3-(4-ethoxy-phenyl)-2-methanesulfonylamino-propionamide trifluoroacetate (28 mg, 0.042 mmol, 32%)

[M+H]⁺=553.08

¹H NMR: (CD₃OD) 1.41 (3H, t, J=7.0 Hz), 2.60 (3H, s), 2.69-2.75 (1H, m), 2.81-2.91 (2H, m), 3.09 (1H, dd, J=13.7, 6.5 Hz), 4.04 (2H, q, J=7.0 Hz), 4.13 (3H, m), 4.39 (2H, s), 4.62 (1H, dd, J=8.1, 6.6 Hz), 6.87 (2H, d, J=8.6 Hz), 7.13 (2H, d, J=8.6 Hz), 7.23 (2H, t, J=6.6 Hz), 7.25-7.32 (5H, m), 7.41 (2H, d, J=8.1 Hz).

Example 3

N—[(R)-1-[(S)-1-(4-Aminomethyl-benzylcarbamoyl)-2-phenyl-ethylcarbamoyl]-2-(4-ethoxy-phenyl)-ethyl]-benzamide

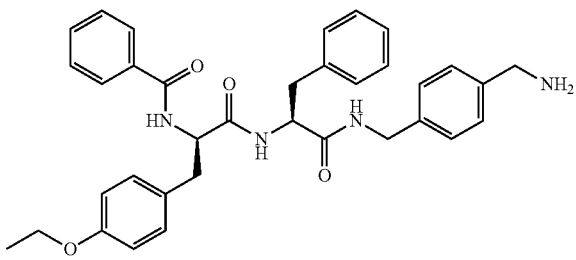 [SMILES: CCOc1ccc(C[C@@H](NC(=O)c2ccccc2)C(=O)N[C@@H](Cc2ccccc2)C(=O)NCc2ccc(CN)cc2)cc1]

A. {(S)-1-[4-(tert-Butoxycarbonylamino-methyl)-benzylcarbamoyl]-2-phenyl-ethyl}-carbamic acid benzyl ester (S)-2-Benzyloxycarbonylamino-3-phenyl-propionic acid 2,5-dioxo-pyrrolidin-1-yl ester (4.25 g, 10.72 mmol) was dissolved in CH₂Cl₂ (100 mL). This solution was cooled to 0° C. 1-(N-Boc-Aminomethyl)-4-(aminomethyl)benzene (2.79 g, 11.79 mmol) was added followed by triethylamine (3.25 g, 32.16 mmol). After 18 hrs at 0° C. to room temperature reaction mixture was diluted with chloroform (100 mL) and washed with NaHCO₃ (1×30 mL), water (1×30 mL), brine (1×30 mL), dried (Na₂SO₄) evaporated in vacuo giving a yellow oil. The residue was triturated with Pet. Ether (60-80° C.) and EtOAc to give a white solid identified as {(S)-1-[4-(tert-butoxycarbonylamino-methyl)-benzylcarbamoyl]-2-phenyl-ethyl}-carbamic acid benzyl ester (3.88 g, 7.49 mmol, 70%).

[M+H]⁺=518.28, 540.32 (M+Na).

B. {4-[((S)-2-Amino-3-phenyl-propionylamino)-methyl]-benzyl}-carbamic acid tert-butyl ester {(S)-1-[4-(tert-Butoxycarbonylamino-methyl)-benzylcarbamoyl]-2-phenyl-ethyl}-carbamic acid benzyl ester (3.66 g, 7.08 mmol) was dissolved in methanol (200 mL). This solution was hydrogenated over 10% Pd/C (500 mg) at atmospheric pressure and room temperature for one hour after which time the catalyst was filtered off through celite and the residue washed with methanol (30 mL), the combined filtrates were evaporated in vacuo to give a white solid identified as {4-[((S)-2-amino-3-phenyl-propionylamino)-methyl]-benzyl}-carbamic acid tert-butyl ester (2.627 g, 6.85 mmol, 97%).

[M+H]⁺=384.37

C. (R)-2-Amino-3-(4-ethoxy-phenyl)-propionic acid (R)-2-Butoxycarbonylamino-3-(4-ethoxy-phenyl)-propionic acid (4.0 g, 12.93 mmol) was dissolved in 4M HCl in dioxan (150 mL). After one hour at room temperature the solvent was removed in vacuo to give a white solid identified as (R)-2-amino-3-(4-ethoxy-phenyl)-propionic acid hydrochloride (3.18 g, 12.9 mmol, 100%).

[M+H]⁺=210.18

D. (R)-2-Benzyloxycarbonylamino-3-(4-ethoxy-phenyl)-propionic acid (R)-2-Amino-3-(4-ethoxy-phenyl)-propionic acid hydrochloride (3.17 g, 12.9 mmol) was dissolved in a solution of sodium hydroxide (1.14 g, 28.38 mmol) in water (100 mL). Benzyl chloroformate (2.64 g, 15.48 mmol) in dioxan (100 mL) was added. The reaction mixture was stirred at room temperature for 18 hrs after which time the dioxan was removed in vacuo. The aqueous residue was washed with diethyl ether (1×100 mL), acidified to pH 2 with 1M HCl and extracted with chloroform (2×200 mL). The combined extracts were washed with water (1×50 mL), brine (1×50 mL), dried (Na₂SO₄) and evaporated in vacuo to give a white solid identified as (R)-2-benzyloxycarbonylamino-3-(4-ethoxy-phenyl)-propionic acid (4.0 g, 11.65 mmol, 90%).

[M+H]⁺=344.20.

E. [(R)-1-{(S)-1-[4-(tert-Butoxycarbonylamino-methyl)-benzylcarbamoyl]-2-phenyl-ethylcarbamoyl}-2-(4-ethoxy-phenyl)-ethyl]-carbamic acid benzyl ester {4-[((S)-2-Amino-3-phenyl-propionylamino)-methyl]-benzyl}-carbamic acid tert-butyl ester (2.63 g, 6.86 mmol) was dissolved in CH₂Cl₂ (100 mL) and DMF (5 mL). This solution was cooled to 0° C. (R)-2-Benzyloxycarbonylamino-3-(4-ethoxy-phenyl)-propionic acid (2.59 g, 7.54 mmol) was added followed by HOBt (1.11 g, 8.23 mmol) and triethylamine (2.08 g, 20.57 mmol). Water soluble carbodiimide (1.45 g, 7.54 mmol) was then added. After 18 hrs at 0°

C. to room temperature reaction mixture was diluted with chloroform (200 mL) and washed with NaHCO$_3$ (1×50 mL), water (1×50 mL), brine (1×50 mL), dried (Na$_2$SO$_4$) and evaporated in vacuo giving a yellow oil. The residue was triturated with ethyl acetate and Pet. Ether (60-80° C.) to give a white solid identified as [(R)-1-{(S)-1-[4-(tert-butoxycarbonylamino-methyl)-benzylcarbamoyl]-2-phenyl-ethylcarbamoyl}-2-(4-ethoxy-phenyl)-ethyl]-carbamic acid benzyl ester (3.55 g, 5.01 mmol, 73%).
[M+H]$^+$=709.34.

F. [4-({(S)-2-[(R)-2-Amino-3-(4-ethoxy-phenyl)-propionylamino]-3-phenyl-propionylamino}-methyl)-benzyl]-carbamic acid tert-butyl ester

[(R)-1-{(S)-1-[4-(tert-Butoxycarbonylamino-methyl)-benzylcarbamoyl]-2-phenyl-ethylcarbamoyl}-2-(4-ethoxy-phenyl)-ethyl]-carbamic acid benzyl ester (3.55 g, 5.00 mmol) was dissolved in methanol (200 mL). This solution was hydrogenated over 10% Pd/C (500 mg) at atmospheric pressure and room temperature for one hour after which time the catalyst was filtered off through Celite and the residue washed with methanol (30 mL), the combined filtrates were evaporated in vacuo to give a white solid identified as [4-({(S)-2-[(R)-2-amino-3-(4-ethoxy-phenyl)-propionylamino]-3-phenyl-propionylamino}-methyl)-benzyl]-carbamic acid tert-butyl ester (2.8 g, 4.87 mmol, 97%).
[M+H]$^+$=575.37.

G. [4-({(S)-2-[(R)-2-Benzoylamino-3-(4-ethoxy-phenyl)-propionylamino]-3-phenyl-propionylamino}-methyl)-benzyl]-carbamic acid tert-butyl ester

[4-({(S)-2-[(R)-2-Amino-3-(4-ethoxy-phenyl)-propionylamino]-3-phenyl-propionylamino}-methyl)-benzyl]-carbamic acid tert-butyl ester (3.45 g, 5.99 mmol) was dissolved in dichloromethane (150 mL). Benzoyl chloride (1.01 g, 7.19 mmol) was added followed by triethylamine (1.82 g, 17.98 mmol). The reaction mixture was stirred at room temperature for 5 hrs and diluted with CHCl$_3$ (150 mL), this solution was washed with 0.3M KHSO$_4$ (1×50 mL), sat. NaHCO$_3$ (1×50 mL), water (1×50 mL), brine (1×50 mL), dried (Na$_2$SO$_4$) and evaporated in vacuo. The residue was triturated with Pet Ether (60-80° C.) and EtOAc to give a white solid identified as [4-({(S)-2-[(R)-2-benzoylamino-3-(4-ethoxy-phenyl)-propionylamino]-3-phenyl-propionylamino}-methyl)-benzyl]-carbamic acid tert-butyl ester (3.06 g, 4.51 mmol, 75%).
[M+H]$^+$=679.34.

H. N—[(R)-1-[(S)-1-(4-Aminomethyl-benzylcarbamoyl)-2-phenyl-ethylcarbamoyl]-2-(4-ethoxy-phenyl)-ethyl]-benzamide hydrochloride

[4-({(S)-2-[(R)-2-Benzoylamino-3-(4-ethoxy-phenyl)-propionylamino]-3-phenyl-propionylamino}-methyl)-benzyl]-carbamic acid tert-butyl ester (2.86 g, 4.21 mmol) was dissolved in 4M HCl in dioxan (150 mL). After one hour at room temperature the solvent was removed in vacuo. The residue was precipitated from ethanol to give a white solid identified as N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride (2.1 g, 3.41 mmol, 81%).
[M+H]$^+$=579.34
$^1$H NMR: (CD$_3$OD), 1.40 (3H, t, J=6.9 Hz), 2.91-2.99 (3H, m), 3.14-3.19 (1H, m), 4.02 (2H, q, J=6.9 Hz), 4.08 (2H, s), 4.41 (1H, d, J=15.5 Hz), 4.51 (1H, d, J=15.5 Hz), 4.66-4.69 (2H, m), 6.82 (2H, d, J=8.4 Hz), 7.10 (2H, d, J=8.2 Hz), 7.18-7.20 (2H, m), 7.25-7.38 (7H, m), 7.44-7.59 (3H, m), 7.72 (2H, d, J=7.8 Hz).

Example 3b

N—[(R)-1-[(S)-1-(4-Aminomethyl-benzylcarbamoyl)-2-phenyl-ethylcarbamoyl]-2-(4-ethoxy-phenyl)-ethyl]-benzamide hydrochloride

[4-({(S)-2-[(R)-2-Benzoylamino-3-(4-ethoxy-phenyl)-propionylamino]-3-phenyl-propionylamino}-methyl)-benzyl]-carbamic acid tert-butyl ester (10.0 g, 14.7 mmol) was stirred in hydrogen chloride/ethyl acetate (3.7M, 250 mL) at room temperature. After two hours the mixture was filtered, washed with ethyl acetate (2×50 mL) and dried to afford a solid (7.9 g). A portion of the solid (0.106 g) was suspended in a mixture of acetonitrile (2.1 mL) and water (0.32 mL), stirred, and heated to 77° C. Additional aliquots of water (0.05 mL) were added successively to the mixture until dissolution was observed. The stirred mixture was then cooled to room temperature overnight. The resulting solid was isolated by filtration and dried in vacuo at 40° C. to afford N—[(R)-1-[(S)-1-(4-aminomethyl-benzylcarbamoyl)-2-phenyl-ethylcarbamoyl]-2-(4-ethoxy-phenyl)-ethyl]-benzamide hydrochloride (0.067 g, 3.41 mmol, 81%). $^1$H NMR (CD$_3$OD) was identical to that of Example 3, Step H.

Example 4

{(R)-1-[(S)-1-(4-Aminomethyl-benzylcarbamoyl)-2-phenyl-ethylcarbamoyl]-2-cyclohexyl-ethylamino}-acetic acid

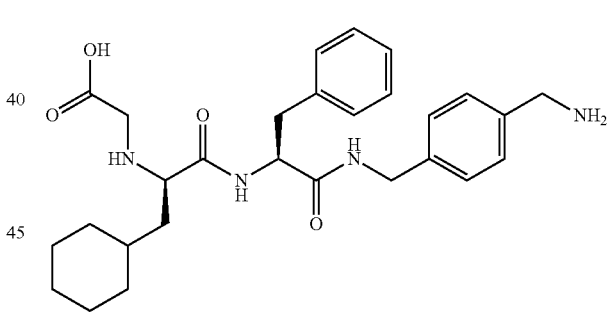

A. [(S)-1-(4-Cyano-benzylcarbamoyl)-2-phenyl-ethyl]-carbamic acid tert-butyl ester 4-Aminomethylbenzonitrile hydrochloride (1.53 g, 9.1 mmol) was dissolved in CH$_2$Cl$_2$ (100 mL). This solution was cooled to 0° C. (S)-2-tert-Butoxycarbonylamino-3-phenyl-propionic acid 2,5-dioxo-pyrrolidin-1-yl ester (3.00 g, 8.3 mmol) was added followed triethylamine (2.51 g, 25 mmol). After 18 hrs at 0° C. to room temperature reaction mixture was diluted with chloroform (100 mL) and washed with NaHCO$_3$ (1×30 mL), water (1×30 mL), brine (1×30 mL), dried (Na$_2$SO$_4$) and evaporated in vacuo giving a yellow oil. The residue was crystallised from EtOAc/Pet. Ether (60-80° C.) to give a white solid identified as [(S)-1-(4-cyano-benzyl-carbamoyl)-2-phenyl-ethyl]-carbamic acid tert-butyl ester (2.71 g, 7.1 mmol, 86%).
[M+H]$^+$=380.13

B. (S)-2-Amino-N-(4-cyano-benzyl)-3-phenyl-propionamide Hydrochloride

[(S)-1-(4-Cyano-benzylcarbamoyl)-2-phenyl-ethyl]-carbamic acid tert-butyl ester (2.71 g, 7.1 mmol) was treated with 4M HCl/dioxan (150 mL). After one hour at room temperature the solvent was removed to give a white solid identified as (S)-2-amino-N-(4-cyano-benzyl)-3-phenyl-propionamide hydrochloride (2.24 g, 7.1 mmol, 99%).
[M+H]$^+$=280.14

C. {(R)-1-[(S)-1-(4-Cyano-benzylcarbamoyl)-2-phenyl-ethylcarbamoyl]-2-cyclohexyl-ethyl}-carbamic acid tert-butyl ester (S)-2-Amino-N-(4-cyano-benzyl)-3-phenyl-propionamide hydrochloride (500 mg, 1.58 mmol) was dissolved in $CH_2Cl_2$ (30 mL) and DMF (3 mL). This solution was cooled to 0° C. Boc-DCha-OH (473 mg, 1.74 mmol) was added followed by HOBt (257 mg, 1.74 mmol) and triethylamine (481 mg, 4.75 mmol). Water soluble carbodiimide (339 mg, 1.74 mmol) was then added. After 18 hrs at 0° C. to room temperature reaction mixture was diluted with chloroform (100 mL) and washed with $NaHCO_3$ (1×30 mL), water (1×30 mL), brine (1×30 mL), dried ($Na_2SO_4$) and evaporated in vacuo giving a yellow oil. The residue was purified by flash chromatography (silica), eluent 60% cyclohexane, 40% EtOAc, fractions combined and evaporated in vacuo to give a foamy white solid identified as {(R)-1-[(S)-1-(4-cyano-benzylcarbamoyl)-2-phenyl-ethylcarbamoyl]-2-cyclohexyl-ethyl}-carbamic acid tert-butyl ester (799 mg, 1.50 mmol, 95%).
[M+H]$^+$=533.18

D. (R)-2-Amino-N—[(S)-1-(4-cyano-benzylcarbamoyl)-2-phenyl-ethyl]-3-cyclohexyl-propionamide Hydrochloride {(R)-1-[(S)-1-(4-Cyano-benzylcarbamoyl)-2-phenyl-ethylcarbamoyl]-2-cyclohexyl-ethyl}-carbamic acid tert-butyl ester (799 mg, 1.5 mmol) was treated with 4M HCl/dioxan (50 mL). After one hour at room temperature the solvent was removed to give a white solid identified as (R)-2-amino-N—[(S)-1-(4-cyano-benzylcarbamoyl)-2-phenyl-ethyl]-3-cyclohexyl-propionamide hydrochloride (703 mg, 1.5 mmol, 100%).
[M+H]$^+$=433.06

E. {(R)-1-[(S)-1-(4-Cyano-benzylcarbamoyl)-2-phenyl-ethylcarbamoyl]-2-cyclohexyl-ethylamino}-acetic acid tert-butyl ester (R)-2-Amino-N—[(S)-1-(4-cyano-benzylcarbamoyl)-2-phenyl-ethyl]-3-cyclohexyl-propionamide hydrochloride (290 mg, 0.62 mmol) was dissolved in acetonitrile (10 mL). tert-Butylbromoacetate (144 mg, 0.74 mmol) was added followed diisopropylethylamine (160 mg, 1.24 mmol). The reaction mixture was stirred at 60° C. for 2 days after which time it was diluted with chloroform (100 mL), washed with water (1×30 mL), brine (1×30 mL), dried ($Na_2SO_4$) and evaporated in vacuo giving a yellow oil. The residue was purified by flash chromatography (silica), eluent 25% Pet. Ether (60-80° C.), 75% EtOAc, fractions combined and evaporated in vacuo to give a colourless oil identified as {(R)-1-[(S)-1-(4-cyano-benzylcarbamoyl)-2-phenyl-ethylcarbamoyl]-2-cyclohexyl-ethylamino}-acetic acid tert-butyl ester (240 mg, 0.44 mmol, 71%). [M+H]$^+$=547.30.

F. ((R)-1-{(S)-1-[4-(tert-Butoxycarbonylamino-methyl)-benzylcarbamoyl]-2-phenyl-ethylcarbamoyl}-2-cyclohexyl-ethylamino)-acetic acid tert-butyl ester {(R)-1-[(S)-1-(4-Cyano-benzylcarbamoyl)-2-phenyl-ethylcarbamoyl]-2-cyclohexyl-ethylamino}-acetic acid tert-butyl ester (240 mg, 0.44 mmol) was dissolved in methanol (25 mL). This solution was cooled to 0° C. Nickel (II) chloride hexahydrate (10.4 mg, 0.44 mmol) and di-tertbutyl dicarbonate (192 mg, 0.88 mmol) were added followed by sodium borohydride (116 mg, 3.1 mmol) portionwise. The reaction mixture was stirred at 0° C. to room temp for 3 days. The MeOH was removed by evaporation. The residue was dissolved in $CHCl_3$ (70 mL), washed with sat $NaHCO_3$ (1×30 mL), water (1×30 mL), brine (1×30 mL), dried ($Na_2SO_4$) and evaporated in vacuo to give a yellow oil. Purified by flash chromatography, eluant 40% Pet. Ether (60-80° C.), 60% EtOAc to give white solid identified as ((R)-1-{(S)-1-[4-(tert-butoxycarbonylamino-methyl)-benzylcarbamoyl]-2-phenyl-ethylcarbamoyl}-2-cyclohexyl-ethylamino)-acetic acid tert-butyl ester (65 mg, 0.10 mmol, 23%).
[M+H]$^+$=651.44.

G. {(R)-1-[(S)-1-(4-Aminomethyl-benzylcarbamoyl)-2-phenyl-ethylcarbamoyl]-2-cyclohexyl-ethylamino}-acetic acid Ditrifluoroacetate ((R)-1-{(S)-1-[4-(tert-Butoxycarbonylamino-methyl)-benzylcarbamoyl]-2-phenyl-ethylcarbamoyl}-2-cyclohexyl-ethylamino)-acetic acid tert-butyl ester (65 mg, 0.1 mmol) was treated with trifluoroacetic acid (4 mL) and $CH_2Cl_2$ (2 mL). After one hour at room temp the solvent was evaporated in vacuo. The residue was purified by Prep HPLC (Sunfire prep C18 OBD column. 19×250 mm, 10μ). 10 to 90% 0.1% TFA/MeCN into 0.1% TFA/$H_2O$ over 35 min at 20 mL/min. Fractions combined and freeze dried to give a white solid identified as {(R)-1-[(S)-1-(4-aminomethyl-benzylcarbamoyl)-2-phenyl-ethylcarbamoyl]-2-cyclohexyl-ethylamino}-acetic acid ditrifluoroacetate (46 mg, 0.064 mmol, 64%).

[M+H]$^+$=495.28

$^1$H NMR: ($CD_3OD$) 0.78-0.98 (2H, m), 1.10-1.25 (4H, m), 1.53-1.70 (7H, m), 2.97 (1H, dd, J=14.0, 10.5 Hz), 3.25 (1H, dd, J=14.1, 5.2 Hz), 3.74 (2H, s), 4.01 (1H, dd, J=8.1, 6.1 Hz), 4.15 (2H, s), 4.47 (2H, s), 4.76 (1H, dd, J=10.5, 5.2 Hz), 7.28-7.38 (7H, m), 7.45 (2H, d, J=8.2 Hz), 8.83 (1H, t, J=5.9 Hz).

Compounds in Tables 1 to 5 were synthesised as described for Examples 1 to 4 (above) and 199 to 201 (below).

TABLE 1

| Ex. No. | R1 | R2 | R3 | R4 | Aryl | R6 | R7 | R8 | m/z |
|---|---|---|---|---|---|---|---|---|---|
| 5 | H | H | CH2-C6H4-O-CH2CH3 (4-ethoxybenzyl) | H | phenyl | H | H | H | 475.3 |
| 6 | H | H | CH2-C6H4-O-CH2CH3 (4-ethoxybenzyl) | H | phenyl | H | H | F | 493.3 |
| 7 | CH3CH2CO | H | CH2-C6H4-O-CH2CH3 (4-ethoxybenzyl) | H | phenyl | H | H | F | 549.3 |
| 8 | H | H | CH2-cyclohexyl | H | phenyl | H | H | H | 315.2 |
| 9 | CH3 | CH3 | CH2-cyclohexyl | H | phenyl | H | H | H | 465.3 |
| 10 | CH3CH2CO | H | CH2-cyclohexyl | H | phenyl | H | H | H | 493.2 |
| 11 | CH3SO2 | H | CH2-cyclohexyl | H | phenyl | H | H | H | 515.2 |

TABLE 1-continued
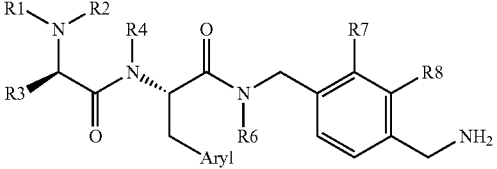
| Ex. No. | R1 | R2 | R3 | R4 | Aryl | R6 | R7 | R8 | m/z |
|---|---|---|---|---|---|---|---|---|---|
| 12 | CH₃CH₂CO | H | 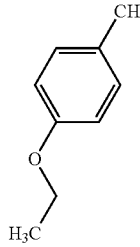 | H | phenyl | H | Cl | H | 565.1 |
| 13 | CH₃ | CH₃ | 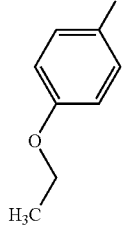 | H | phenyl | H | H | H | 503.2 |
| 14 | H | H | 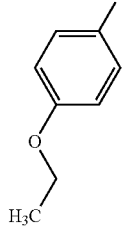 | H | 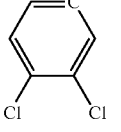 | H | H | H | 543.2 and 545.2 |
| 15 | PhSO₂ | H | 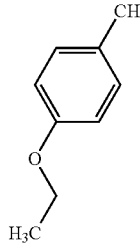 | H | phenyl | H | H | H | 615.2 |
| 16 | CH₃CH₂CO | H | 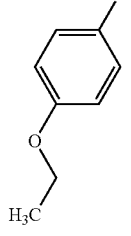 | H | 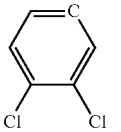 | H | H | H | 599.1 and 601.2 |

TABLE 1-continued
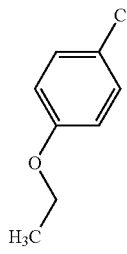
| Ex. No. | R1 | R2 | R3 | R4 | Aryl | R6 | R7 | R8 | m/z |
|---|---|---|---|---|---|---|---|---|---|
| 17 | HOOCCH$_2$ | H | 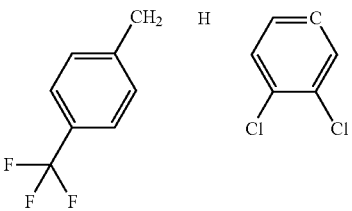 | H | phenyl | H | H | H | 533.2 |
| 18 | H | H | 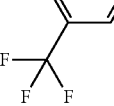 | H | 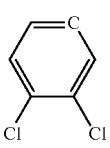 | H | H | H | 567.1 and 569.1 |
| 19 | CH$_3$CH$_2$CO | H | 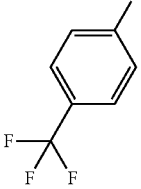 | H | 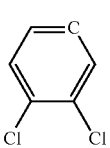 | H | H | H | 623.2 and 625.2 |
| 20 | H | H | 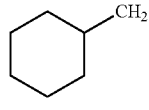 | H | 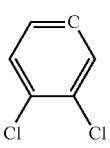 | H | H | H | 505.2 and 507.2 |
| 21 | CH$_3$CH$_2$CO | H | 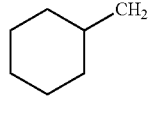 | H | 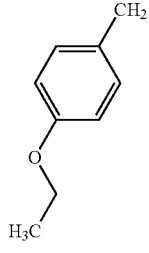 | H | H | H | 561.2 and 563.2 |
| 22 | PhCO | H | CH$_3$ | H | phenyl | H | H | H | 459.2 |
| 23 | CH$_3$CH$_2$CO | H |  | H | phenyl | H | H | Cl | 565.1 |

TABLE 1-continued

| Ex. No. | R1 | R2 | R3 | R4 | Aryl | R6 | R7 | R8 | m/z |
|---|---|---|---|---|---|---|---|---|---|
| 24 | CH₃CH₂CO | H | CH₂-C₆H₄-OCH₂CH₃ (4-ethoxybenzyl) | H | phenyl | CH₃ | H | H | 545.3 |
| 25 | H | H | CH₂-C₆H₄-OCH₂CH₃ (4-ethoxybenzyl) | CH₃ | phenyl | H | H | H | 489.2 |
| 26 | CH₃CH₂CO | H | CH₂-C₆H₄-OCH₂CH₃ (4-ethoxybenzyl) | CH₃ | phenyl | H | H | H | 545.2 |
| 27 | CH₃ | H | CH₂-C₆H₄-OCH₂CH₃ (4-ethoxybenzyl) | H | phenyl | H | H | H | 489.3 |
| 28 | HOOCCH₂ | H | (CH₃)₂CHCH₂ | H | phenyl | H | H | H | 455.3 |
| 29 | HOOCCH₂ | CH₃ | CH₂-cyclohexyl | H | phenyl | H | H | H | 509.3 |
| 30 | HOOCCH₂ | H | CH₂-cyclohexyl | CH₃ | phenyl | H | H | H | 509.3 |

TABLE 1-continued
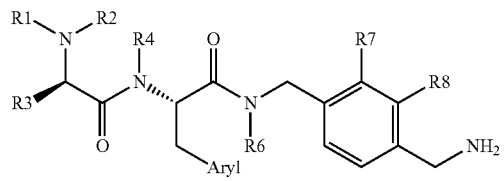
| Ex. No. | R1 | R2 | R3 | R4 | Aryl | R6 | R7 | R8 | m/z |
|---|---|---|---|---|---|---|---|---|---|
| 31 | CH$_3$CH$_2$CO | CH$_3$ | 4-(ethoxy)benzyl | H | phenyl | H | H | H | 545.3 |
| 32 | CH$_3$CH$_2$CO | H | 4-(ethoxy)benzyl | CH$_3$ | phenyl | H | H | F | 563.3 |
| 33 | CH$_3$ | H | cyclohexylmethyl | H | phenyl | H | H | H | 451.4 |
| 34 | HOOCCH$_2$ | H | cyclohexylmethyl | CH$_3$ | phenyl | H | H | F | 527.3 |
| 35 | n-Pr | H | 4-(ethoxy)benzyl | CH$_3$ | phenyl | H | H | H | 531.4 |
| 36 | HOOCCH$_2$ | H | cyclohexylmethyl | H | phenyl | CH$_3$ | H | H | 509.3 |
| 37 | n-Pr | H | cyclohexylmethyl | H | phenyl | H | H | H | 479.4 |

TABLE 1-continued
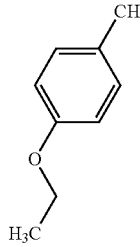
| Ex. No. | R1 | R2 | R3 | R4 | Aryl | R6 | R7 | R8 | m/z |
|---|---|---|---|---|---|---|---|---|---|
| 38 | PhCO | H | 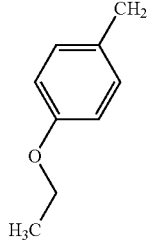 | $CH_3$ | phenyl | H | H | H | 593.3 |
| 39 | $CH_3CO$ | H | 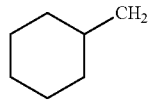 | $CH_3$ | phenyl | H | H | H | 531.3 |
| 40 | $CH_3$ | H | 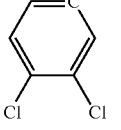 | H | phenyl | H | H | F | 469.3 |
| 41 | $CH_3$ | H | 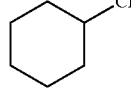 | H | 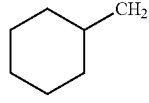 | H | H | F | 537.2 and 539.2 |
| 42 | $HOOCCH_2$ | $CH_3$ | 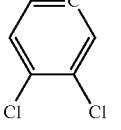 | H | phenyl | H | H | F | 527.3 |
| 43 | $HOOCCH_2$ | $CH_3$ | 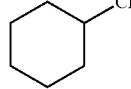 | H | 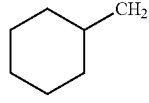 | H | H | F | 595.3 and 597.3 |
| 44 | $(CH_3)_2CHCO$ | H | 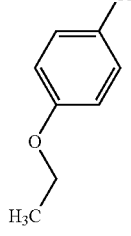 | $CH_3$ | phenyl | H | H | H | 559.3 |

TABLE 1-continued

| Ex. No. | R1 | R2 | R3 | R4 | Aryl | R6 | R7 | R8 | m/z |
|---|---|---|---|---|---|---|---|---|---|
| 45 | n-Pr | $CH_3$ | cyclohexyl-$CH_2$ | H | phenyl | H | H | H | 493.4 |
| 46 | $CH_3OCOCH_2$ | H | cyclohexyl-$CH_2$ | H | phenyl | H | H | H | 509.3 |
| 47 | $CH_3OCOCH_2$ | $CH_3$ | cyclohexyl-$CH_2$ | H | phenyl | H | H | H | 523.3 |
| 48 | $NH_2COCH_2$ | $CH_3$ | cyclohexyl-$CH_2$ | H | phenyl | H | H | H | 508.3 |
| 49 | $HOCH_2CH_2$ | $CH_3$ | cyclohexyl-$CH_2$ | H | phenyl | H | H | H | 495.4 |
| 50 | $NH_2COCH_2$ | H | cyclohexyl-$CH_2$ | H | phenyl | H | H | H | 494.3 |
| 51 | $HOCH_2CH_2$ | H | cyclohexyl-$CH_2$ | H | phenyl | H | H | H | 481.3 |

TABLE 1-continued

[Structure: R1R2N-CH(R3)-C(=O)-N(R4)-CH(CH2-Aryl)-C(=O)-N(R6)-CH2-Ar(R7,R8)-CH2NH2]

| Ex. No. | R1 | R2 | R3 | R4 | Aryl | R6 | R7 | R8 | m/z |
|---|---|---|---|---|---|---|---|---|---|
| 52 | H | H | dicyclohexyl-CH | H | phenyl | H | H | H | 519.3 |
| 53 | n-Pr | n-Pr | cyclohexyl-CH2 | H | phenyl | H | H | H | 521.3 |
| 54 | 1-NaphCO | H | 4-(ethoxy)benzyl (CH2-C6H4-O-CH2CH3) | H | phenyl | H | H | H | 629.3 |
| 55 | 4-Cl—PhCO | H | 4-(ethoxy)benzyl | H | phenyl | H | H | H | 613.3 |
| 56 | 4-CF3—PhCO | H | 4-(ethoxy)benzyl | H | phenyl | H | H | H | 647.3 |
| 57 | 4-Ph—PhCO | H | 4-(ethoxy)benzyl | H | phenyl | H | H | H | 655.3 |

TABLE 1-continued

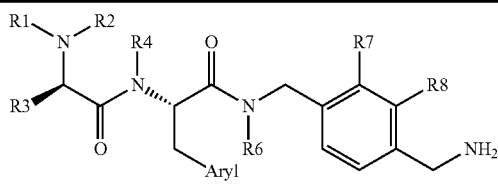

| Ex. No. | R1 | R2 | R3 | R4 | Aryl | R6 | R7 | R8 | m/z |
|---|---|---|---|---|---|---|---|---|---|
| 58 | 2,4-diCl—PhCO | H | 4-ethoxybenzyl (CH$_2$-C$_6$H$_4$-OCH$_2$CH$_3$) | H | phenyl | H | H | H | 647.3 |
| 59 | 3,4-diF—PhCO | H | 4-ethoxybenzyl (CH$_2$-C$_6$H$_4$-OCH$_2$CH$_3$) | H | phenyl | H | H | H | 615.3 |

TABLE 2

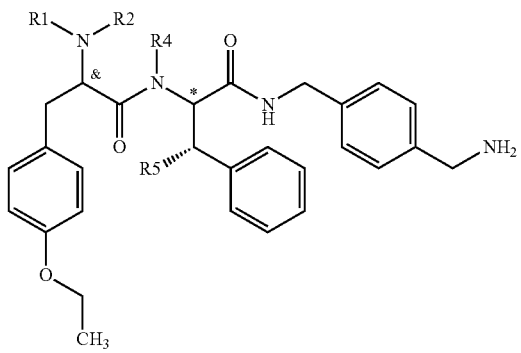

| Example No. | * | & | R1 | R2 | R4 | R5 | m/z |
|---|---|---|---|---|---|---|---|
| 60 | separated | R | H | H | H | OH | 491.2 |
| 61 | but not confirmed | R | H | H | H | OH | 491.2 |
| 62 | separated | R | CH$_3$CH$_2$CO | H | H | OH | 547.2 |
| 63 | but not confirmed | R | CH$_3$CH$_2$CO | H | H | OH | 547.3 |
| 64 | separated | R | CH$_3$CH$_2$CO | H | CH$_3$CH$_2$ | H | 559.3 |

TABLE 2-continued

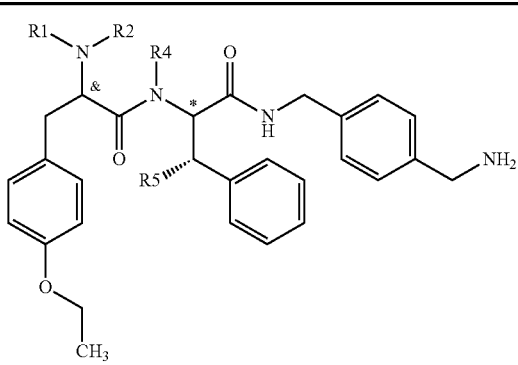

| Example No. | * | & | R1 | R2 | R4 | R5 | m/z |
|---|---|---|---|---|---|---|---|
| 65 | but not confirmed | R | CH$_3$CH$_2$CO | H | CH$_3$CH$_2$ | H | 559.3 |
| 66 | S | S | CH$_3$CH$_2$CO | CH$_3$ | H | H | 545.3 |

TABLE 3

| Example No | | m/z |
|---|---|---|
| 67 | (structure: 4-ethoxybenzyl group on α-carbon with N-propionyl amide, linked to 3-phenylpyrrolidine-2-carboxamide, N-(4-aminomethylbenzyl)) | 557.17 |

TABLE 4

General structure: R1-NH-CH(R3)-C(=O)-N(R4)-CH(CH2-R9)-C(=O)-NH-CH2-(phenyl with R8)-CH2-NH2

| Example No | R1 | R3 | R4 | R8 | R9 | m/z |
|---|---|---|---|---|---|---|
| 68 | benzyl-NH-C(=O)-* | 4-ethoxybenzyl (H3C-O-C6H4-CH2-*) | H | H | phenyl-* | 607.99 |
| 69 | phenyl-NH-C(=O)-* | 4-ethoxybenzyl | H | H | phenyl-* | 594.04 |
| 70 | pyridin-3-yl-C(=O)-* | 4-ethoxybenzyl | H | H | phenyl-* | 580.19 |
| 71 | pyridin-4-yl-C(=O)-* | 4-ethoxybenzyl | H | H | phenyl-* | 580.18 |
| 72 | thiophen-3-yl-C(=O)-* | 4-ethoxybenzyl | H | H | phenyl-* | 585.15 |

TABLE 4-continued

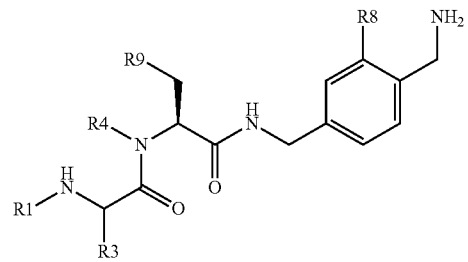

| Example No | R1 | R3 | R4 | R8 | R9 | m/z |
|---|---|---|---|---|---|---|
| 73 | thiophene-2-carbaldehyde* | 4-ethoxybenzyl* | H | H | phenyl* | 585.15 |
| 74 | cyclopropanecarbaldehyde* | 4-ethoxybenzyl* | H | H | phenyl* | 542.95 |
| 75 | cyclohexanecarbaldehyde* | 4-ethoxybenzyl* | H | H | phenyl* | 585 |
| 76 | hexanal* | 4-ethoxybenzyl* | H | H | phenyl* | 572.99 |
| 77 | N-isopropylformamide* | 4-ethoxybenzyl* | H | H | phenyl* | 560.28 |
| 78 | heptanal* | 4-ethoxybenzyl* | H | H | phenyl* | 602.26 |
| 79 | isoxazole-5-carbaldehyde* | 4-ethoxybenzyl* | H | H | phenyl* | 570.13 |
| 80 | 4-(trifluoromethoxy)benzaldehyde* | 4-ethoxybenzyl* | H | H | phenyl* | 663.12 |
| 81 | pyridine-2-carbaldehyde* | 4-ethoxybenzyl* | H | H | phenyl* | 580.18 |

TABLE 4-continued

| Example No | R1 | R3 | R4 | R8 | R9 | m/z |
|---|---|---|---|---|---|---|
| 82 | 1,5-dimethyl-1H-pyrazole-5-carbaldehyde derivative | 4-ethoxybenzyl | H | H | phenyl | 597.2 |
| 83 | benzo[b]thiophene-2-carbaldehyde derivative | 4-ethoxybenzyl | H | H | phenyl | 635.14 |
| 84 | 4-chlorophenylsulfonyl | 4-ethoxybenzyl | H | H | phenyl | 649.13 |
| 85 | phenylacetaldehyde derivative | 4-ethoxybenzyl | H | H | phenyl | 594.10 |
| 86 | 3-phenylpropanal derivative | 4-ethoxybenzyl | H | H | phenyl | 607.18 |
| 87 | 4-phenylbutanal derivative | 4-ethoxybenzyl | H | H | phenyl | 621.2 |
| 88 | 3-chlorobenzaldehyde derivative | 4-ethoxybenzyl | H | H | phenyl | 613.1 |
| 89 | 2-chlorobenzaldehyde derivative | 4-ethoxybenzyl | H | H | phenyl | 613.1 |

TABLE 4-continued
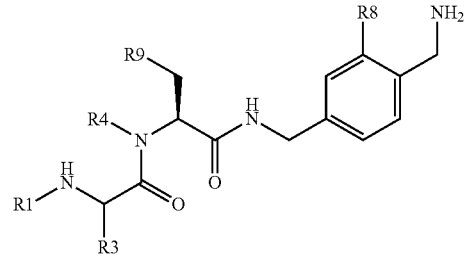
| Example No | R1 | R3 | R4 | R8 | R9 | m/z |
|---|---|---|---|---|---|---|
| 90 | 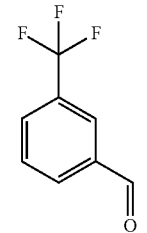 | 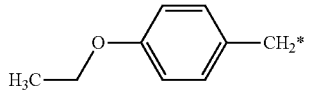 | H | H |  | 647.1 |
| 91 | 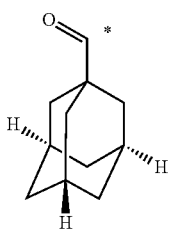 | 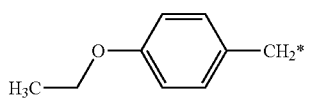 | H | H |  | 637.21 |
| 92 | 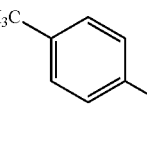 | 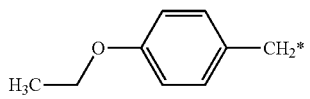 | H | H |  | 594.12 |
| 93 | 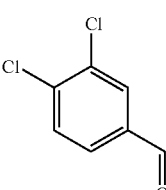 | 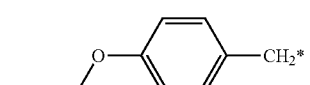 | H | H |  | 647.05 |
| 94 | 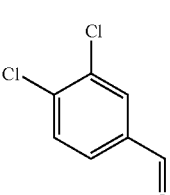 | 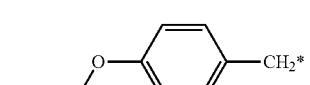 | H | H |  | 647.05 |
| 95 | 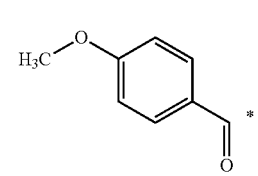 | 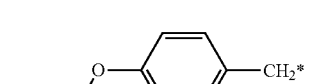 | H | H |  | 610.11 |

TABLE 4-continued

| Example No | R1 | R3 | R4 | R8 | R9 | m/z |
|---|---|---|---|---|---|---|
| 96 | cinnamaldehyde (PhCH=CH-CHO*) | 4-ethoxybenzyl (H₃C-CH₂-O-C₆H₄-CH₂*) | H | H | phenyl* | 605.17 |
| 97 | PhCH₂-C(O)-NH-CH₂-CHO* | 4-ethoxybenzyl | H | H | phenyl* | 650.16 |
| 98 | Ph-C(O)-NH-CH₂-CHO* | 4-ethoxybenzyl | H | H | phenyl* | 636.16 |
| 99 | 4-F-C₆H₄-CHO* | 4-ethoxybenzyl | H | H | phenyl* | 597.14 |
| 100 | PhCH₂-S(O)₂-* | 4-ethoxybenzyl | H | H | phenyl* | 629.15 |
| 101 | 4-CH₃-C₆H₄-S(O)₂-* | 4-ethoxybenzyl | H | H | phenyl* | 686.14 |
| 102 | 4-Cl-C₆H₄-NH-CHO* | 4-ethoxybenzyl | H | H | phenyl* | 628.1 |
| 103 | PhCH₂-N(CH₂CH₃)-CHO* | 4-ethoxybenzyl | H | H | phenyl* | 636.1 |

TABLE 4-continued

| Example No | R1 | R3 | R4 | R8 | R9 | m/z |
|---|---|---|---|---|---|---|
| 104 | 6-methylpyridin-3-yl carbonyl (H3C-pyridine-C(=O)-) | 4-ethoxybenzyl (H3C-CH2-O-C6H4-CH2-) | H | H | phenyl | 594.04 |
| 105 | 2-methylpyridin-3-yl carbonyl | 4-ethoxybenzyl | H | H | phenyl | 594.06 |
| 106 | 2,6-dichloropyridin-3-yl carbonyl | 4-ethoxybenzyl | H | H | phenyl | 648.09 |
| 107 | 2,3-dichloropyridin-5-yl carbonyl | 4-ethoxybenzyl | H | H | phenyl | 648.07 |
| 108 | 2,3,6-trifluoropyridin-4-yl carbonyl | 4-ethoxybenzyl | H | H | phenyl | 633.87 |
| 109 | 3,3,3-trifluoropropanoyl | 4-ethoxybenzyl | H | H | phenyl | 585.12 |
| 110 | 2-chloro-6-methylpyridin-4-yl carbonyl | 4-ethoxybenzyl | H | H | phenyl | 649.92 (M + Na) |

TABLE 4-continued

| Example No | R1 | R3 | R4 | R8 | R9 | m/z |
|---|---|---|---|---|---|---|
| 111 | 2,4-dimethylthiazole-5-carbonyl | 4-ethoxybenzyl | H | H | phenyl | 613.95 |
| 112 | 2-methylthiazole-5-carbonyl | 4-ethoxybenzyl | H | H | phenyl | 599.92 |
| 113 | 2,5-dimethyloxazole-4-carbonyl | 4-ethoxybenzyl | H | H | phenyl | 597.75 |
| 114 | 2-methylquinoline-6-carbonyl | 4-ethoxybenzyl | H | H | phenyl | 644.13 |
| 115 | 7-chloroquinoline-3-carbonyl | 4-ethoxybenzyl | H | H | phenyl | 664.06 |
| 116 | 3-chlorothiophene-2-carbonyl | 4-ethoxybenzyl | H | H | phenyl | 618.97 |
| 117 | 4-methylthiazole-5-carbonyl | 4-ethoxybenzyl | H | H | phenyl | 600.06 |

TABLE 4-continued

| Example No | R1 | R3 | R4 | R8 | R9 | m/z |
|---|---|---|---|---|---|---|
| 118 | furan-2-carbonyl | 4-ethoxybenzyl-O-CH2* | H | H | phenyl | 569.04 |
| 119 | 3-methylthiophene-2-carbonyl | 4-ethoxybenzyl-O-CH2* | H | H | phenyl | 599.04 |
| 120 | 6-methoxypyridine-2-carbonyl | 4-ethoxybenzyl-O-CH2* | H | H | phenyl | 610.01 |
| 121 | 5-methoxypyridine-3-carbonyl | 4-ethoxybenzyl-O-CH2* | H | H | phenyl | 610.06 |
| 122 | 3-methoxythiophene-2-carbonyl | 4-ethoxybenzyl-O-CH2* | H | H | phenyl | 615.05 |
| 123 | 2-methoxypyridine-4-carbonyl | 4-ethoxybenzyl-O-CH2* | H | H | phenyl | 610.07 |
| 124 | 3-methyl-1H-pyrrole-2-carbonyl | 4-ethoxybenzyl-O-CH2* | H | H | phenyl | 582.06 |

TABLE 4-continued

| Example No | R1 | R3 | R4 | R8 | R9 | m/z |
|---|---|---|---|---|---|---|
| 125 | 3-amino-thiophene-2-carbonyl* | 4-ethoxybenzyl* (H₃C-O-C₆H₄-CH₂*) | H | H | phenyl* | 600.57 |
| 126 | benzoyl* | cyclohexyl-CH₂* | H | H | phenyl* | 541.21 |
| 127 | benzoyl* | 4-chlorobenzyl* | H | H | phenyl* | 569.11 |
| 128 | benzoyl* | 4-(4-chlorobenzyloxy)benzyl* | H | H | phenyl* | 675.1 |
| 129 | benzoyl* | 4-hydroxybenzyl* | H | H | phenyl* | 551.15 |
| 130 | benzoyl* | 4-((4-fluorobenzyl)oxy)benzyl* | H | H | phenyl* | 659.12 |
| 131 | benzoyl* | 4-propoxybenzyl* | H | H | phenyl* | 594.05 |
| 132 | thiophene-2-carbonyl* | 4-(benzyloxy)benzyl* | H | H | phenyl* | 642.12 |

TABLE 4-continued

| Example No | R1 | R3 | R4 | R8 | R9 | m/z |
|---|---|---|---|---|---|---|
| 133 | phenyl-C(=O)-* | (CH₃)₂CHCH₂-* | H | H | phenyl* | 501.21 |
| 134 | phenyl-C(=O)-* | 2,6-dichlorophenyl-CH₂-O-C₆H₄-CH₂-* | H | H | phenyl* | 709.12 |
| 135 | phenyl-C(=O)-* | 4-methylphenyl-CH₂-* | H | H | phenyl* | 548.94 |
| 136 | phenyl-C(=O)-* | 3-fluorophenyl-CH₂-O-C₆H₄-CH₂-* | H | H | phenyl* | 659.12 |
| 137 | phenyl-C(=O)-* | 6-methoxypyridin-3-yl-CH₂-* | H | H | phenyl* | 566.09 |
| 138 | phenyl-C(=O)-* | 4-methoxyphenyl-CH₂-* | H | H | phenyl* | 565.1 |
| 139 | phenyl-C(=O)-* | phenyl-CH₂-* | H | H | phenyl* | 535.11 |
| 140 | phenyl-C(=O)-* | 4-ethoxyphenyl-CH₂-* | H | H | pyridinyl* | 580.06 |

TABLE 4-continued

| Example No | R1 | R3 | R4 | R8 | R9 | m/z |
|---|---|---|---|---|---|---|
| 141 | phenyl-CHO* | H3C-O-C6H4-CH2* | H | H | 3,4-dichlorophenyl* | 647.04 and 649.06 |
| 142 | phenyl-CHO* | H3C-O-C6H4-CH2* | H | H | 4-chlorophenyl* | 612.94 |
| 143 | phenyl-CHO* | H3C-O-C6H4-CH2* | H | H | 4-fluorophenyl* | 596.93 |
| 144 | phenyl-CHO* | H3C-O-C6H4-CH2* | H | H | 3-(trifluoromethyl)phenyl* | 646.96 |
| 145 | phenyl-CHO* | H3C-O-C6H4-CH2* | H | H | pyridin-3-yl* | 580.13 |
| 146 | phenyl-CHO* | H3C-O-C6H4-CH2* | H | H | 4-methoxyphenyl* | 608.97 |
| 147 | phenyl-CHO* | H3C-O-C6H4-CH2* | H | H | pyridin-4-yl* | 579.95 |

TABLE 4-continued

| Example No | R1 | R3 | R4 | R8 | R9 | m/z |
|---|---|---|---|---|---|---|
| 148 | phenyl-CHO* | H₃C-O-C₆H₄-CH₂* | H | H | 3-(trifluoromethyl)phenyl* | 646.97 |
| 149 | phenyl-CHO* | H₃C-O-C₆H₄-CH₂* | H | H | 3-fluorophenyl* | 618.93 (M + Na) |
| 150 | phenyl-CHO* | H₃C-O-C₆H₄-CH₂* | H | H | thiophen-2-yl* | 606.88 (M + Na) |
| 151 | phenyl-CHO* | H₃C-O-C₆H₄-CH₂* | H | H | thiophen-3-yl* | 584.98 |
| 152 | phenyl-CHO* | H₃C-O-C₆H₄-CH₂* | H | H | thiazol-5-yl* | 586.03 |
| 153 | phenyl-CHO* | H₃C-O-C₆H₄-CH₂* | H | H | benzothiophen-3-yl* | 635.05 |
| 154 | phenyl-CHO* | H₃C-O-C₆H₄-CH₂* | H | F | phenyl* | 596.93 |
| 155 | phenyl-CHO* | H₃C-O-C₆H₄-CH₂* | H | Cl | phenyl* | 612.92 |

TABLE 4-continued

| Example No | R1 | R3 | R4 | R8 | R9 | m/z |
|---|---|---|---|---|---|---|
| 156 | phenyl-C(=O)-* | 4-ethoxybenzyl (H3C-CH2-O-C6H4-CH2*) | H | CF3 | phenyl* | 646.9 |
| 157 | pyridin-2-yl-C(=O)-* | 4-ethoxybenzyl | H | H | thiophen-2-yl* | 586.26 |
| 158 | 4-methoxyphenyl-C(=O)-* | 4-ethoxybenzyl | H | H | pyridin-2-yl* | 610.02 |
| 159 | pyridin-2-yl-C(=O)-* | 4-ethoxybenzyl | H | Cl | phenyl* | 614.29 |
| 160 | 4-methoxyphenyl-C(=O)-* | 4-ethoxybenzyl | H | H | pyridin-3-yl* | 610.35 |
| 161 | pyridin-4-yl-C(=O)-* | 4-ethoxybenzyl | H | H | 3,4-difluorophenyl* | 616.03 |
| 162 | thiophen-2-yl-C(=O)-* | 4-ethoxybenzyl | H | H | pyrimidin-5-yl* | 585.98 |
| 163 | 4-chlorophenyl-C(=O)-* | 4-ethoxybenzyl | H | H | pyridin-3-yl* | 614.05 |

TABLE 4-continued

| Example No | R1 | R3 | R4 | R8 | R9 | m/z |
|---|---|---|---|---|---|---|
| 164 | 4-methylbenzaldehyde | 4-ethoxybenzyl | H | H | pyridin-3-yl | 616.05 |
| 165 | pyridine-2-carbaldehyde | 4-ethoxybenzyl | H | H | 3,4-dichlorophenyl | 648.04 and 650.04 |
| 166 | propanal | 4-ethoxybenzyl | H | H | pyridin-3-yl | 532.04 |
| 167 | pyridine-4-carbaldehyde | 4-ethoxybenzyl | H | F | phenyl | 598.03 |
| 168 | pyridine-2-carbaldehyde | 4-ethoxybenzyl | H | F | phenyl | 598.04 |
| 169 | thiophene-2-carbaldehyde | 4-ethoxybenzyl | H | H | 3,4-dichlorophenyl | 653.00 and 654.99 |
| 170 | propanal | 4-ethoxybenzyl | H | H | pyridin-3-yl | 532.04 |
| 171 | pyridine-4-carbaldehyde | 4-ethoxybenzyl | H | H | 3,4-dichlorophenyl | 648.02 and 650.04 |

TABLE 4-continued

| Example No | R1 | R3 | R4 | R8 | R9 | m/z |
|---|---|---|---|---|---|---|
| 172 | 3,3,3-trifluoropropanal | 4-ethoxybenzyl | H | H | 3,4-dichlorophenyl | 653.02 |
| 173 | 4-chlorobenzaldehyde | 4-ethoxybenzyl | H | H | pyridin-3-yl | 614.30 |
| 174 | isoxazole-5-carbaldehyde | 4-ethoxybenzyl | H | H | pyridin-3-yl | 571.02 |
| 175 | 3-hydroxythiophene-2-carbaldehyde | 4-ethoxybenzyl | H | H | pyridin-3-yl | 620.26 |
| 176 | benzaldehyde | 4-ethoxybenzyl | H | H | 1H-indol-3-yl | 641.37 (M + Na) |
| 177 | benzaldehyde | 4-ethoxybenzyl | H | H | 1H-imidazol-4-yl | 569.48 |
| 178 | isonicotinaldehyde | 4-ethoxybenzyl | H | H | benzo[b]thiophen-3-yl | 636.36 |

TABLE 4-continued

| Example No | R1 | R3 | R4 | R8 | R9 | m/z |
|---|---|---|---|---|---|---|
| 179 | 3-acetamido-thiophene-2-carbonyl | 4-ethoxybenzyl | H | H | phenyl | 642.38 |
| 180 | benzoyl | 4-ethoxybenzyl | H | H | 2-fluorophenyl | 597.35 |
| 181 | 3-methyl-thiophene-2-carbonyl | 4-ethoxybenzyl | H | H | pyridin-3-yl | 600.32 |
| 182 | benzoyl | 4-ethoxybenzyl | H | Me | phenyl | 593.29 |
| 183 | 3-amino-thiophene-2-carbonyl | 4-ethoxybenzyl | H | H | thiazolyl | 607.26 |
| 184 | 3-chloro-thiophene-2-carbonyl | 4-ethoxybenzyl | H | H | thiazolyl | 625.22 |

TABLE 4-continued

| Example No | R1 | R3 | R4 | R8 | R9 | m/z |
|---|---|---|---|---|---|---|
| 185 | 4-methylphenyl-C(=O)- | 4-ethoxybenzyl | H | H | thiazol-yl | 600.32 |
| 186 | 3-methyl-1H-pyrrole-2-carbonyl | 4-ethoxybenzyl | H | H | benzothiophen-yl | 638.19 |
| 187 | 3-methyl-1H-pyrrole-2-carbonyl | 4-ethoxybenzyl | H | H | thiophen-yl | 588.09 |
| 188 | 3-acetamidothiophene-2-carbonyl | 4-ethoxybenzyl | H | H | benzothiophen-yl | 698.15 |
| 189 | 3-methylphenyl-C(=O)- | 4-ethoxybenzyl | H | H | pyridinyl | 594.02 |
| 190 | 2-methylphenyl-C(=O)- | 4-ethoxybenzyl | H | H | pyridinyl | 594.07 |
| 191 | 3,5-dimethyl-1H-pyrrole-2-carbonyl | 4-ethoxybenzyl | H | H | phenyl | 596.18 |

TABLE 4-continued
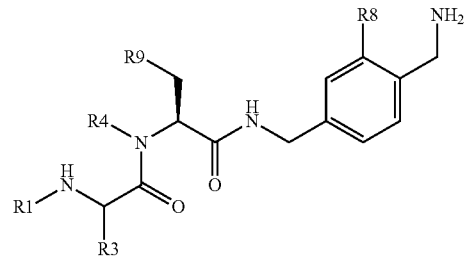
| Example No | R1 | R3 | R4 | R8 | R9 | m/z |
|---|---|---|---|---|---|---|
| 192 | 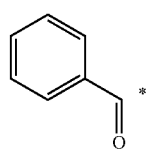 | 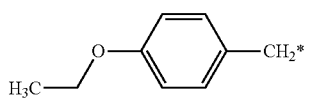 | H | Me | 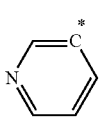 | 594.05 |
| 193 | 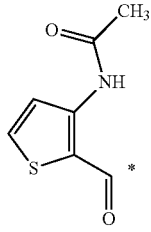 | 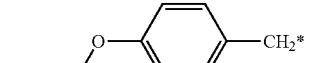 | H | H |  | 648.16 |
| 194 | 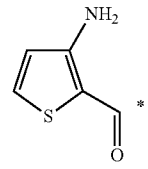 | 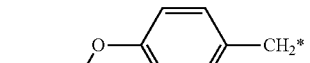 | H | H | 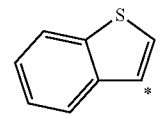 | 656.47 |
| 195 | 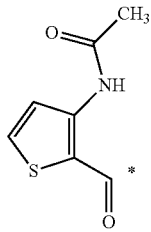 | 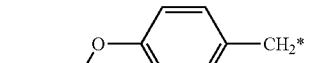 | H | H | 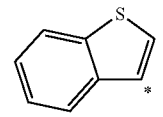 | 605.52 |
| 196 | 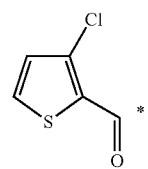 | 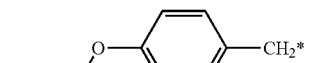 | Me | H | 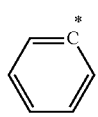 | 633.18 |

TABLE 5

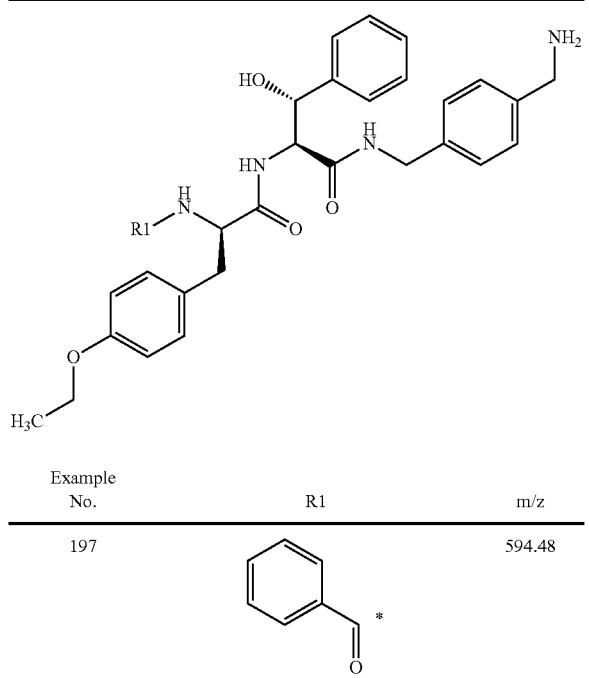

| Example No. | R1 | m/z |
|---|---|---|
| 197 | (benzaldehyde) | 594.48 |

TABLE 5-continued

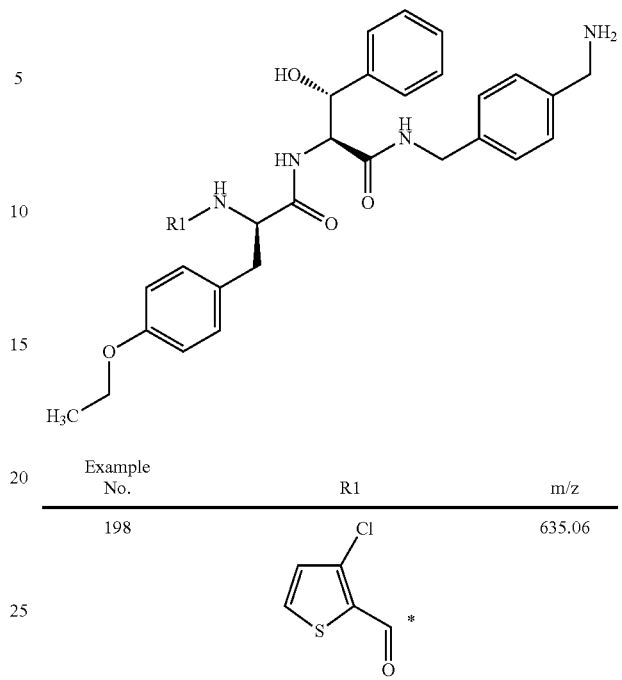

| Example No. | R1 | m/z |
|---|---|---|
| 198 | (3-chloro-thiophene-2-carbaldehyde) | 635.06 |

TABLE 6

| Example No | Name |
|---|---|
| 5 | (R)-2-Amino-N-[(S)-1-(4-aminomethyl-benzylcarbamoyl)-2-phenyl-ethyl]-3-(4-ethoxy-phenyl)-propionamide |
| 6 | (R)-2-Amino-N-[(S)-1-(4-aminomethyl-3-fluoro-benzylcarbamoyl)-2-phenyl-ethyl]-3-(4-ethoxy-phenyl)-propionamide |
| 7 | (S)-N-(4-Aminomethyl-3-fluoro-benzyl)-2-[(R)-3-(4-ethoxy-phenyl)-2-propionylamino-propionylamino]-3-phenyl-propionamide |
| 8 | (R)-2-Amino-N-[(S)-1-(4-aminomethyl-benzylcarbamoyl)-2-phenyl-ethyl]-3-cyclohexyl-propionamide |
| 9 | (R)-N-[(S)-1-(4-Aminomethyl-benzylcarbamoyl)-2-phenyl-ethyl]-3-cyclohexyl-2-dimethylamino-propionamide |
| 10 | (S)-N-(4-Aminomethyl-benzyl)-2-((R)-3-cyclohexyl-2-propionylamino-propionylamino)-3-phenyl-propionamide |
| 11 | (R)-N-[(S)-1-(4-Aminomethyl-benzylcarbamoyl)-2-phenyl-ethyl]-3-cyclohexyl-2-methanesulfonylamino-propionamide |
| 12 | (S)-N-(4-Aminomethyl-2-chloro-benzyl)-2-[(R)-3-(4-ethoxy-phenyl)-2-propionylamino-propionylamino]-3-phenyl-propionamide |
| 13 | (R)-N-[(S)-1-(4-Aminomethyl-benzylcarbamoyl)-2-phenyl-ethyl]-2-dimethylamino-3-(4-ethoxy-phenyl)-propionamide |
| 14 | (R)-2-Amino-N-[(S)-1-(4-aminomethyl-benzylcarbamoyl)-2-(3,4-dichloro-phenyl)-ethyl]-3-(4-ethoxy-phenyl)-propionamide |
| 15 | (R)-N-[(S)-1-(4-Aminomethyl-benzylcarbamoyl)-2-phenyl-ethyl]-2-benzenesulfonylamino-3-(4-ethoxy-phenyl)-propionamide |
| 16 | (S)-N-(4-Aminomethyl-benzyl)-3-(3,4-dichloro-phenyl)-2-[(R)-3-(4-ethoxy-phenyl)-2-propionylamino-propionylamino]-propionamide |
| 17 | [(R)-1-[(S)-1-(4-Aminomethyl-benzylcarbamoyl)-2-phenyl-ethylcarbamoyl]-2-(4-ethoxy-phenyl)-ethylamino]-acetic acid |
| 18 | (R)-2-Amino-N-[(S)-1-(4-aminomethyl-benzylcarbamoyl)-2-(3,4-dichloro-phenyl)-ethyl]-3-(4-trifluoromethyl-phenyl)-propionamide |
| 19 | ((R)-N-[(S)-1-(4-Aminomethyl-benzylcarbamoyl)-2-(3,4-dichloro-phenyl)-ethyl]-2-propionylamino-3-(4-trifluoromethyl-phenyl)-propionamide |
| 20 | (R)-2-Amino-N-[(S)-1-(4-aminomethyl-benzylcarbamoyl)-2-(3,4-dichloro-phenyl)-ethyl]-3-cyclohexyl-propionamide |
| 21 | (R)-N-[(S)-1-(4-Aminomethyl-benzylcarbamoyl)-2-(3,4-dichloro-phenyl)-ethyl]-3-cyclohexyl-2-propionylamino-propionamide |
| 22 | N-{(R)-1-[(S)-1-(4-Aminomethyl-benzylcarbamoyl)-2-phenyl-ethylcarbamoyl]-ethyl}-benzamide |
| 23 | (S)-N-(4-Aminomethyl-3-chloro-benzyl)-2-[(R)-3-(4-ethoxy-phenyl)-2-propionylamino-propionylamino]-3-phenyl-propionamide |
| 24 | (S)-N-(4-Aminomethyl-benzyl)-2-[(R)-3-(4-ethoxy-phenyl)-2-propionylamino-propionylamino]-N-methyl-3-phenyl-propionamide |

TABLE 6-continued

| Example No | Name |
|---|---|
| 25 | (R)-2-Amino-N-[(S)-1-(4-aminomethyl-benzylcarbamoyl)-2-phenyl-ethyl]-3-(4-ethoxy-phenyl)-N-methyl-propionamide |
| 26 | (S)-N-(4-Aminomethyl-benzyl)-2-{[(R)-3-(4-ethoxy-phenyl)-2-propionylamino-propionyl]-methyl-amino}-3-phenyl-propionamide |
| 27 | (R)-N-[(S)-1-(4-Aminomethyl-benzylcarbamoyl)-2-phenyl-ethyl]-3-(4-ethoxy-phenyl)-2-methylamino-propionamide |
| 28 | {(R)-1-[(S)-1-(4-Aminomethyl-benzylcarbamoyl)-2-phenyl-ethylcarbamoyl]-3-methyl-butylamino}-acetic acid |
| 29 | ({(R)-1-[(S)-1-(4-Aminomethyl-benzylcarbamoyl)-2-phenyl-ethylcarbamoyl]-2-cyclohexyl-ethyl}-methyl-amino)-acetic acid |
| 30 | ((R)-1-{[(S)-1-(4-Aminomethyl-benzylcarbamoyl)-2-phenyl-ethyl]-methyl-carbamoyl}-2-cyclohexyl-ethylamino)-acetic acid |
| 31 | (S)-N-(4-Aminomethyl-benzyl)-2-[(R)-3-(4-ethoxy-phenyl)-2-(methyl-propionyl-amino)-propionylamino]-3-phenyl-propionamide |
| 32 | (S)-N-(4-Aminomethyl-3-fluoro-benzyl)-2-{[(R)-3-(4-ethoxy-phenyl)-2-propionylamino-propionyl]-methyl-amino}-3-phenyl-propionamide |
| 33 | (R)-N-[(S)-1-(4-Aminomethyl-benzylcarbamoyl)-2-phenyl-ethyl]-3-cyclohexyl-2-methylamino-propionamide |
| 34 | ((R)-1-{[(S)-1-(4-Aminomethyl-3-fluoro-benzylcarbamoyl)-2-phenyl-ethyl]-methyl-carbamoyl}-2-cyclohexyl-ethylamino)-acetic acid |
| 35 | (R)-N-[(S)-1-(4-Aminomethyl-benzylcarbamoyl)-2-phenyl-ethyl]-3-(4-ethoxy-phenyl)-N-methyl-2-propylamino-propionamide |
| 36 | ((R)-1-{(S)-1-[(4-Aminomethyl-benzyl)-methyl-carbamoyl]-2-phenyl-ethylcarbamoyl}-2-cyclohexyl-ethylamino)-acetic acid |
| 37 | (R)-N-[(S)-1-(4-Aminomethyl-benzylcarbamoyl)-2-phenyl-ethyl]-3-cyclohexyl-2-propylamino-propionamide |
| 38 | N-[(R)-1-{[(S)-1-(4-Aminomethyl-benzylcarbamoyl)-2-phenyl-ethyl]-methyl-carbamoyl}-2-(4-ethoxy-phenyl)-ethyl]-benzamide |
| 39 | (R)-2-Acetylamino-N-[(S)-1-(4-aminomethyl-benzylcarbamoyl)-2-phenyl-ethyl]-3-(4-ethoxy-phenyl)-N-methyl-propionamide |
| 40 | (R)-N-[(S)-1-(4-Aminomethyl-3-fluoro-benzylcarbamoyl)-2-phenyl-ethyl]-3-cyclohexyl-2-methylamino-propionamide |
| 41 | (R)-N-[(S)-1-(4-Aminomethyl-3-fluoro-benzylcarbamoyl)-2-(3,4-dichloro-phenyl)-ethyl]-3-cyclohexyl-2-methylamino-propionamide |
| 42 | ({(R)-1-[(S)-1-(4-Aminomethyl-3-fluoro-benzylcarbamoyl)-2-phenyl-ethylcarbamoyl]-2-cyclohexyl-ethyl}-methyl-amino)-acetic acid |
| 43 | ({(R)-1-[(S)-1-(4-Aminomethyl-3-fluoro-benzylcarbamoyl)-2-(3,4-dichloro-phenyl)-ethylcarbamoyl]-2-cyclohexyl-ethyl}-methyl-amino)-acetic acid |
| 44 | N-[(R)-1-{[(S)-1-(4-Aminomethyl-benzylcarbamoyl)-2-phenyl-ethyl]-methyl-carbamoyl}-2-(4-ethoxy-phenyl)-ethyl]-isobutyramide |
| 45 | (R)-N-[(S)-1-(4-Aminomethyl-benzylcarbamoyl)-2-phenyl-ethyl]-3-cyclohexyl-2-(methyl-propyl-amino)-propionamide |
| 46 | {(R)-1-[(S)-1-(4-Aminomethyl-benzylcarbamoyl)-2-phenyl-ethylcarbamoyl]-2-cyclohexyl-ethylamino}-acetic acid methyl ester |
| 47 | {(R)-1-[(S)-1-(4-Aminomethyl-benzylcarbamoyl)-2-phenyl-ethylcarbamoyl]-2-cyclohexyl-ethylamino}-acetic acid methyl ester |
| 48 | (R)-N-[(S)-1-(4-Aminomethyl-benzylcarbamoyl)-2-phenyl-ethyl]-2-(carbamoylmethyl-methyl-amino)-3-cyclohexyl-propionamide |
| 49 | (R)-N-[(S)-1-(4-Aminomethyl-benzylcarbamoyl)-2-phenyl-ethyl]-3-cyclohexyl-2-[(2-hydroxy-ethyl)-methyl-amino]-propionamide |
| 50 | (R)-N-[(S)-1-(4-Aminomethyl-benzylcarbamoyl)-2-phenyl-ethyl]-2-(carbamoylmethyl-amino)-3-cyclohexyl-propionamide |
| 51 | (R)-N-[(S)-1-(4-Aminomethyl-benzylcarbamoyl)-2-phenyl-ethyl]-3-cyclohexyl-2-(2-hydroxy-ethylamino)-propionamide |
| 52 | (R)-2-Amino-N-[(S)-1-(4-aminomethyl-benzylcarbamoyl)-2-phenyl-ethyl]-3,3-dicyclohexyl-propionamide |
| 53 | (R)-N-[(S)-1-(4-Aminomethyl-benzylcarbamoyl)-2-phenyl-ethyl]-3-cyclohexyl-2-dipropylamino-propionamide |
| 54 | Naphthalene-1-carboxylic acid [(R)-1-[(S)-1-(4-aminomethyl-benzylcarbamoyl)-2-phenyl-ethylcarbamoyl]-2-(4-ethoxy-phenyl)-ethyl]-amide |
| 55 | N-[(R)-1-[(S)-1-(4-Aminomethyl-benzylcarbamoyl)-2-phenyl-ethylcarbamoyl]-2-(4-ethoxy-phenyl)-ethyl]-4-chloro-benzamide |
| 56 | N-[(R)-1-[(S)-1-(4-Aminomethyl-benzylcarbamoyl)-2-phenyl-ethylcarbamoyl]-2-(4-ethoxy-phenyl)-ethyl]-4-trifluoromethyl-benzamide |
| 57 | Biphenyl-4-carboxylic acid [(R)-1-[(S)-1-(4-aminomethyl-benzylcarbamoyl)-2-phenyl-ethylcarbamoyl]-2-(4-ethoxy-phenyl)-ethyl]-amide |
| 58 | N-[(R)-1-[(S)-1-(4-Aminomethyl-benzylcarbamoyl)-2-phenyl-ethylcarbamoyl]-2-(4-ethoxy-phenyl)-ethyl]-2,4-dichloro-benzamide |
| 59 | N-[(R)-1-[(S)-1-(4-Aminomethyl-benzylcarbamoyl)-2-phenyl-ethylcarbamoyl]-2-(4-ethoxy-phenyl)-ethyl]-3,4-difluoro-benzamide |
| 60 | (R)-2-Amino-N-[(1R,2S)-1-(4-aminomethyl-benzylcarbamoyl)-2-hydroxy-2-phenyl-ethyl]-3-(4-ethoxy-phenyl)-propionamide |
| 61 | (R)-2-Amino-N-[(1S,2S)-1-(4-aminomethyl-benzylcarbamoyl)-2-hydroxy-2-phenyl-ethyl]-3-(4-ethoxy-phenyl)-propionamide |
| 62 | (2R,3S)-N-(4-Aminomethyl-benzyl)-2-[(R)-3-(4-ethoxy-phenyl)-2-propionylamino-propionylamino]-3-hydroxy-3-phenyl-propionamide |

TABLE 6-continued

| Example No | Name |
|---|---|
| 63 | (2S,3S)-N-(4-Aminomethyl-benzyl)-2-[(R)-3-(4-ethoxy-phenyl)-2-propionylamino-propionylamino]-3-hydroxy-3-phenyl-propionamide |
| 64 | (R)-N-(4-Aminomethyl-benzyl)-2-{[(R)-3-(4-ethoxy-phenyl)-2-propionylamino-propionyl]-ethyl-amino}-3-phenyl-propionamide |
| 65 | (S)-N-(4-Aminomethyl-benzyl)-2-{[(R)-3-(4-ethoxy-phenyl)-2-propionylamino-propionyl]-ethyl-amino}-3-phenyl-propionamide |
| 66 | (S)-N-(4-Aminomethyl-benzyl)-2-[(S)-3-(4-ethoxy-phenyl)-2-(methyl-propionyl-amino)-propionylamino]-3-phenyl-propionamide |
| 67 | (2S,3R)-1-[(R)-3-(4-Ethoxy-phenyl)-2-propionylamino-propionyl]-3-pheny-pyrrolidine-2-carboxylic acid 4-aminomethyl-benzylamide |
| 68 | (R)-N-[(S)-1-(4-Aminomethyl-benzylcarbamoyl)-2-phenyl-ethyl]-2-(3-benzyl-ureido)-3-(4-ethoxy-phenyl)-propionamide |
| 69 | (R)-N-[(S)-1-(4-Aminomethyl-benzylcarbamoyl)-2-phenyl-ethyl]-3-(4-ethoxy-phenyl)-2-(3-phenyl-ureido)-propionamide |
| 70 | N-[(R)-1-[(S)-1-(4-Aminomethyl-benzylcarbamoyl)-2-phenyl-ethylcarbamoyl]-2-(4-ethoxy-phenyl)-ethyl]-nicotinamide |
| 71 | N-[(R)-1-[(S)-1-(4-Aminomethyl-benzylcarbamoyl)-2-phenyl-ethylcarbamoyl]-2-(4-ethoxy-phenyl)-ethyl]-isonicotinamide |
| 72 | Thiophene-3-carboxylic acid-[(R)-1-[(S)-1-(4-aminomethyl-benzylcarbamoyl)-2-phenyl-ethylcarbamoyl]-2-(4-ethoxy-phenyl)-ethyl]-amide |
| 73 | Thiophene-2-carboxylic acid [(R)-1-[(S)-1-(4-aminomethyl-benzylcarbamoyl)-2-phenyl-ethylcarbamoyl]-2-(4-ethoxy-phenyl)-ethyl]-amide |
| 74 | Cyclopropanecarboxylic acid [(R)-1-[(S)-1-(4-aminomethyl-benzylcarbamoyl)-2-phenyl-ethylcarbamoyl]-2-(4-ethoxy-phenyl)-ethyl]-amide |
| 75 | Cyclohexanecarboxylic acid [(R)-1-[(S)-1-(4-aminomethyl-benzylcarbamoyl)-2-phenyl-ethylcarbamoyl]-2-(4-ethoxy-phenyl)-ethyl]-amide |
| 76 | Hexanoic acid [(R)-1-[(S)-1-(4-aminomethyl-benzylcarbamoyl)-2-phenyl-ethylcarbamoyl]-2-(4-ethoxy-phenyl)-ethyl]-amide |
| 77 | (R)-N-[(S)-1-(4-Aminomethyl-benzylcarbamoyl)-2-phenyl-ethyl]-3-(4-ethoxy-phenyl)-2-(3-isopropyl-ureido)-propionamide |
| 78 | (R)-N-[(S)-1-(4-Aminomethyl-benzylcarbamoyl)-2-phenyl-ethyl]-3-(4-ethoxy-phenyl)-2-(3-hexyl-ureido)-propionamide |
| 79 | Isoxazole-5-carboxylic acid [(R)-1-[(S)-1-(4-aminomethyl-benzylcarbamoyl)-2-phenyl-ethylcarbamoyl]-2-(4-ethoxy-phenyl)-ethyl]-amide |
| 80 | N-[(R)-1-[(S)-1-(4-Aminomethyl-benzylcarbamoyl)-2-phenyl-ethylcarbamoyl]-2-(4-ethoxy-phenyl)-ethyl]-4-trifluoromethoxy-benzamide |
| 81 | Pyridine-2-carboxylic acid [(R)-1-[(S)-1-(4-aminomethyl-benzylcarbamoyl)-2-phenyl-ethylcarbamoyl]-2-(4-ethoxy-phenyl)-ethyl]-amide |
| 82 | 2,5-Dimethyl-2H-pyrazole-3-carboxylic acid [(R)-1-[(S)-1-(4-aminomethyl-benzylcarbamoyl)-2-phenyl-ethylcarbamoyl]-2-(4-ethoxy-phenyl)-ethyl]-amide |
| 83 | Benzo[b]thiophene-2-carboxylic acid[(R)-1-[(S)-1-(4-aminomethyl-benzylcarbamoyl)-2-phenyl-ethylcarbamoyl]-2-(4-ethoxy-phenyl)-ethyl]-amide |
| 84 | (R)-N-[(S)-1-(4-Aminomethyl-benzylcarbamoyl)-2-phenyl-ethyl]-2-(4-chloro-benzenesulfonylamino)-3-(4-ethoxy-phenyl)-propionamide |
| 85 | (S)-N-(4-Aminomethyl-benzyl)-2-[(R)-3-(4-ethoxy-phenyl)-2-phenylacetylamino-propionylamino]-3-phenyl-propionamide |
| 86 | (S)-N-(4-Aminomethyl-benzyl)-2-[(R)-3-(4-ethoxy-phenyl)-2-(3-phenyl-propionylamino)-propionylamino]-3-phenyl-propionamide |
| 87 | N-[(R)-1-[(S)-1-(4-Aminomethyl-benzylcarbamoyl)-2-phenyl-ethylcarbamoyl]-2-(4-ethoxy-phenyl)-ethyl]-4-phenyl-butyramide |
| 88 | N-[(R)-1-[(S)-1-(4-Aminomethyl-benzylcarbamoyl)-2-phenyl-ethylcarbamoyl]-2-(4-ethoxy-phenyl)-ethyl]-3-chloro-benzamide |
| 89 | N-[(R)-1-[(S)-1-(4-Aminomethyl-benzylcarbamoyl)-2-phenyl-ethylcarbamoyl]-2-(4-ethoxy-phenyl)-ethyl]-2-chloro-benzamide |
| 90 | N-[(R)-1-[(S)-1-(4-Aminomethyl-benzylcarbamoyl)-2-phenyl-ethylcarbamoyl]-2-(4-ethoxy-phenyl)-ethyl]-3-trifluoromethyl-benzamide |
| 91 | Adamantane-1-carboxylic acid [(R)-1-[(S)-1-(4-aminomethyl-benzylcarbamoyl)-2-phenyl-ethylcarbamoyl]-2-(4-ethoxy-phenyl)-ethyl]-amide |
| 92 | N-[(R)-1-[(S)-1-(4-Aminomethyl-benzylcarbamoyl)-2-phenyl-ethylcarbamoyl]-2-(4-ethoxy-phenyl)-ethyl]-4-methyl-benzamide |
| 93 | N-[(R)-1-[(S)-1-(4-Aminomethyl-benzylcarbamoyl)-2-phenyl-ethylcarbamoyl]-2-(4-ethoxy-phenyl)-ethyl]-3,4-dichloro-benzamide |
| 94 | N-[(R)-1-[(S)-1-(4-Aminomethyl-benzylcarbamoyl)-2-phenyl-ethylcarbamoy]-2-(4-ethoxy-phenyl)-ethyl]-3,5-dichloro-benzamide |
| 95 | N-[(R)-1-[(S)-1-(4-Aminomethyl-benzylcarbamoyl)-2-phenyl-ethylcarbamoyl]-2-(4-ethoxy-phenyl)-ethyl]-4-methoxy-benzamide |
| 96 | (E)-N-[(R)-1-[(S)-1-(4-Aminomethyl-benzylcarbamoyl)-2-phenyl-ethylcarbamoyl]-2-(4-ethoxy-phenyl)-ethyl]-3-phenyl-acrylamide |
| 97 | (S)-N-(4-Aminomethyl-benzyl)-2-[(R)-3-(4-ethoxy-phenyl)-2-(2-phenylacetylamino-acetylamino)-propionylamino]-3-phenyl-propionamide |
| 98 | N-{[(R)-1-[(S)-1-(4-Aminomethyl-benzylcarbamoyl)-2-phenyl-ethylcarbamoyl]-2-(4-ethoxy-phenyl)-ethylcarbamoyl]-methyl}-benzamide |
| 99 | N-[(R)-1-[(S)-1-(4-Aminomethyl-benzylcarbamoyl)-2-phenyl-ethylcarbamoyl]-2-(4-ethoxy-phenyl)-ethyl]-4-fluoro-benzamide |
| 100 | (R)-N-[(S)-1-(4-Aminomethyl-benzylcarbamoyl)-2-phenyl-ethyl]-3-(4-ethoxy-phenyl)-2-phenylmethanesulfonylamino-propionamide |

TABLE 6-continued

| Example No | Name |
|---|---|
| 101 | (S)-N-(4-Aminomethyl-benzyl)-2-{(R)-3-(4-ethoxy-phenyl)-2-[2-(toluene-4-sulfonylamino)-acetylamino]-propionylamino}-3-phenyl-propionamide |
| 102 | (R)-N-[(S)-1-(4-Aminomethyl-benzylcarbamoyl)-2-phenyl-ethyl]-2-[3-(4-chloro-phenyl)-ureido]-3-(4-ethoxy-phenyl)-propionamide |
| 103 | (R)-N-[(S)-1-(4-Aminomethyl-benzylcarbamoyl)-2-phenyl-ethyl]-2-(3-benzyl-3-ethyl-ureido)-3-(4-ethoxy-phenyl)-propionamide |
| 104 | N-[(R)-1-[(S)-1-(4-Aminomethyl-benzylcarbamoyl)-2-phenyl-ethylcarbamoyl]-2-(4-ethoxy-phenyl)-ethyl]-6-methyl-nicotinamide |
| 105 | N-[(R)-1-[(S)-1-(4-Aminomethyl-benzylcarbamoyl)-2-phenyl-ethylcarbamoyl]-2-(4-ethoxy-phenyl)-ethyl]-2-methyl-nicotinamide |
| 106 | N-[(R)-1-[(S)-1-(4-Aminomethyl-benzylcarbamoyl)-2-phenyl-ethylcarbamoyl]-2-(4-ethoxy-phenyl)-ethyl]-2,6-dichloro-nicotinamide |
| 107 | N-[(R)-1-[(S)-1-(4-Aminomethyl-benzylcarbamoyl)-2-phenyl-ethylcarbamoyl]-2-(4-ethoxy-phenyl)-ethyl]-5,6-dichloro-nicotinamide |
| 108 | N-[(R)-1-[(S)-1-(4-Aminomethyl-benzylcarbamoyl)-2-phenyl-ethylcarbamoyl]-2-(4-ethoxy-phenyl)-ethyl]-2,3,6-trifluoro-isonicotinamide |
| 109 | N-[(R)-1-[(S)-1-(4-Aminomethyl-benzylcarbamoyl)-2-phenyl-ethylcarbamoyl]-2-(4-ethoxy-phenyl)-ethyl]-3,3,3-trifluoro-propionamide |
| 110 | N-[(R)-1-[(S)-1-(4-Aminomethyl-benzylcarbamoyl)-2-phenyl-ethylcarbamoyl]-2-(4-ethoxy-phenyl)-ethyl]-2-chloro-6-methyl-isonicotinamide |
| 111 | 2,4-Dimethyl-thiazole-5-carboxylic acid [(R)-1-[(S)-1-(4-aminomethyl-benzylcarbamoyl)-2-phenyl-ethylcarbamoyl]-2-(4-ethoxy-phenyl)-ethyl]-amide |
| 112 | 2-Methyl-thiazole-5-carboxylic acid [(R)-1-[(S)-1-(4-aminomethyl-benzylcarbamoyl)-2-phenyl-ethylcarbamoyl]-2-(4-ethoxy-phenyl)-ethyl]-amide |
| 113 | 2,5-Dimethyl-oxazole-4-carboxylic acid [(R)-1-[(S)-1-(4-aminomethyl-benzylcarbamoyl)-2-phenyl-ethylcarbamoyl]-2-(4-ethoxy-phenyl)-ethyl]-amide |
| 114 | 2-Methyl-quinoline-6-carboxylic acid [(R)-1-[(S)-1-(4-aminomethyl-benzylcarbamoyl)-2-phenyl-ethylcarbamoyl]-2-(4-ethoxy-phenyl)-ethyl]-amide |
| 115 | 7-Chloro-quinoline-3-carboxylic acid [(R)-1-[(S)-1-(4-aminomethyl-benzylcarbamoyl)-2-phenyl-ethylcarbamoyl]-2-(4-ethoxy-phenyl)-ethyl]-amide |
| 116 | 3-Chloro-thiophene-2-carboxylic acid [(R)-1-[(S)-1-(4-aminomethyl-benzylcarbamoyl)-2-phenyl-ethylcarbamoyl]-2-(4-ethoxy-phenyl)-ethyl]-amide |
| 117 | 4-Methyl-thiazole-5-carboxylic acid[(R)-1-[(S)-1-(4-aminomethyl-benzylcarbamoyl)-2-phenyl-ethylcarbamoyl]-2-(4-ethoxy-phenyl)-ethyl]-amide |
| 118 | Furan-2-carboxylic acid [(R)-1-[(S)-1-(4-aminomethyl-benzylcarbamoyl)-2-phenyl-ethylcarbamoyl]-2-(4-ethoxy-phenyl)-ethyl]-amide |
| 119 | 3-Methyl-thiophene-2-carboxylic acid [(R)-1-[(S)-1-(4-aminomethyl-benzylcarbamoyl)-2-phenyl-ethylcarbamoyl]-2-(4-ethoxy-phenyl)-ethyl]-amide |
| 120 | 6-Methoxy-pyridine-2-carboxylic acid [(R)-1-[(S)-1-(4-aminomethyl-benzylcarbamoyl)-2-phenyl-ethylcarbamoyl]-2-(4-ethoxy-phenyl)-ethyl]-amide |
| 121 | N-[(R)-1-[(S)-1-(4-Aminomethyl-benzylcarbamoyl)-2-phenyl-ethylcarbamoyl]-2-(4-ethoxy-phenyl)-ethyl]-5-methoxy-nicotinamide |
| 122 | 3-Methoxy-thiophene-2-carboxylic acid [(R)-1-[(S)-1-(4-aminomethyl-benzylcarbamoyl)-2-phenyl-ethylcarbamoyl]-2-(4-ethoxy-phenyl)-ethyl]-amide |
| 123 | N-[(R)-1-[(S)-1-(4-Aminomethyl-benzylcarbamoyl)-2-phenyl-ethylcarbamoyl]-2-(4-ethoxy-phenyl)-ethyl]-2-methoxy-isonicotinamide |
| 124 | 3-Methyl-1H-pyrrole-2-carboxylic acid [(R)-1-[(S)-1-(4-aminomethyl-benzylcarbamoyl)-2-phenyl-ethylcarbamoyl]-2-(4-ethoxy-phenyl)-ethyl]-amide |
| 125 | 3-Amino-thiophene-2-carboxylic acid [(R)-1-[(S)-1-(4-aminomethyl-benzylcarbamoyl)-2-phenyl-ethylcarbamoyl]-2-(4-ethoxy-phenyl)-ethyl]-amide |
| 126 | N-{(R)-1-[(S)-1-(4-Aminomethyl-benzylcarbamoyl)-2-phenyl-ethylcarbamoyl]-2-cyclohexyl-ethyl}-benzamide |
| 127 | N-[(R)-1-[(S)-1-(4-Aminomethyl-benzylcarbamoyl)-2-phenyl-ethylcarbamoyl]-2-(4-chloro-phenyl)-ethyl]-benzamide |
| 128 | N-{(R)-1-[(S)-1-(4-Aminomethyl-benzylcarbamoyl)-2-phenyl-ethylcarbamoyl]-2-[4-(4-chloro-benzyloxy)-phenyl]-ethyl}-benzamide |
| 129 | N-[(R)-1-[(S)-1-(4-Aminomethyl-benzylcarbamoyl)-2-phenyl-ethylcarbamoyl]-2-(4-hydroxy-phenyl)-ethyl]-benzamide |
| 130 | N-{(R)-1-[(S)-1-(4-Aminomethyl-benzylcarbamoyl)-2-phenyl-ethylcarbamoyl]-2-[4-(4-fluoro-benzyloxy)-phenyl]-ethyl}-benzamide |
| 131 | N-[(R)-1-[(S)-1-(4-Aminomethyl-benzylcarbamoyl)-2-phenyl-ethylcarbamoyl]-2-(4-propoxy-phenyl)-ethyl]-benzamide |
| 132 | N-[(R)-1-[(S)-1-(4-Aminomethyl-benzylcarbamoyl)-2-phenyl-ethylcarbamoyl]-2-(4-benzyloxy-phenyl)-ethyl]-benzamide |
| 133 | N-{(R)-1-[(S)-1-(4-Aminomethyl-benzylcarbamoyl)-2-phenyl-ethylcarbamoyl]-3-methyl-butyl}-benzamide |
| 134 | N-{(R)-1-[(S)-1-(4-Aminomethyl-benzylcarbamoyl)-2-phenyl-ethylcarbamoyl]-2-[4-(2,6-dichloro-benzyloxy)-phenyl]-ethyl}-benzamide |
| 135 | N-{(R)-1-[(S)-1-(4-Aminomethyl-benzylcarbamoyl)-2-phenyl-ethylcarbamoyl]-2-p-tolyl-ethyl}-benzamide |
| 136 | N-{(R)-1-[(S)-1-(4-Aminomethyl-benzylcarbamoyl)-2-phenyl-ethylcarbamoyl]-2-[4-(3-fluoro-benzyloxy)-phenyl]-ethyl}-benzamide |
| 137 | N-[(R)-1-[(S)-1-(4-Aminomethyl-benzylcarbamoyl)-2-phenyl-ethylcarbamoyl]-2-(6-methoxy-pyridin-3-yl)-ethyl]-benzamide |
| 138 | N-[(R)-1-[(S)-1-(4-Aminomethyl-benzylcarbamoyl)-2-phenyl-ethylcarbamoyl]-2-(4-methoxy-phenyl)-ethyl]-benzamide |

TABLE 6-continued

| Example No | Name |
|---|---|
| 139 | N-{(R)-1-[(S)-1-(4-Aminomethyl-benzylcarbamoyl)-2-phenyl-ethylcarbamoyl]-2-phenyl-ethyl}-benzamide |
| 140 | N-[(R)-1-[(S)-1-(4-Aminomethyl-benzylcarbamoyl)-2-pyridin-2-yl-ethylcarbamoyl]-2-(4-ethoxy-phenyl)-ethyl]-benzamide |
| 141 | N-[(R)-1-[(S)-1-(4-Aminomethyl-benzylcarbamoyl)-2-(3,4-dichloro-phenyl)-ethylcarbamoyl]-2-(4-ethoxy-phenyl)-ethyl]-benzamide |
| 142 | N-[(R)-1-[(S)-1-(4-Aminomethyl-benzylcarbamoyl)-2-(4-chloro-phenyl)-ethylcarbamoyl]-2-(4-ethoxy-phenyl)-ethyl]-benzamide |
| 143 | N-[(R)-1-[(S)-1-(4-Aminomethyl-benzylcarbamoyl)-2-(4-fluoro-phenyl)-ethylcarbamoyl]-2-(4-ethoxy-phenyl)-ethyl]-benzamide |
| 144 | N-[(R)-1-[(S)-1-(4-Aminomethyl-benzylcarbamoyl)-2-(3-trifluoromethyl-phenyl)-ethylcarbamoyl]-2-(4-ethoxy-phenyl)-ethyl]-benzamide |
| 145 | N-[(R)-1-[(S)-1-(4-Aminomethyl-benzylcarbamoyl)-2-pyridin-3-yl-ethylcarbamoyl]-2-(4-ethoxy-phenyl)-ethyl]-benzamide |
| 146 | N-[(R)-1-[(S)-1-(4-Aminomethyl-benzylcarbamoyl)-2-(4-methoxy-phenyl)-ethylcarbamoyl]-2-(4-ethoxy-phenyl)-ethyl]-benzamide |
| 147 | N-[(R)-1-[(S)-1-(4-Aminomethyl-benzylcarbamoyl)-2-pyridin-4-yl-ethylcarbamoyl]-2-(4-ethoxy-phenyl)-ethyl]-benzamide |
| 148 | N-[(R)-1-[(S)-1-(4-Aminomethyl-benzylcarbamoyl)-2-(4-trifluoromethyl-phenyl)-ethylcarbamoyl]-2-(4-ethoxy-phenyl)-ethyl]-benzamide |
| 149 | N-[(R)-1-[(S)-1-(4-Aminomethyl-benzylcarbamoyl)-2-(3-fluoro-phenyl)-ethylcarbamoyl]-2-(4-ethoxy-phenyl)-ethyl]-benzamide |
| 150 | N-[(R)-1-[(S)-1-(4-Aminomethyl-benzylcarbamoyl)-2-thiophen-2-yl-ethylcarbamoyl]-2-(4-ethoxy-phenyl)-ethyl]-benzamide |
| 151 | N-[(R)-1-[(S)-1-(4-Aminomethyl-benzylcarbamoyl)-2-thiophen-3-yl-ethylcarbamoyl-2-(4-ethoxy-phenyl)-ethyl]-benzamide |
| 152 | N-[(R)-1-[(S)-1-(4-Aminomethyl-benzylcarbamoyl)-2-thiazol-4-yl-ethylcarbamoyl]-2-(4-ethoxy-phenyl)-ethyl]-benzamide |
| 153 | N-[(R)-1-[(S)-1-(4-Aminomethyl-benzylcarbamoyl)-2-benzo[b]thiophen-3-yl-ethylcarbamoyl]-2-(4-ethoxy-phenyl)-ethyl]-benzamide |
| 154 | N-[(R)-1-[(S)-1-(4-Aminomethyl-3-fluoro-benzylcarbamoyl)-2-phenyl-ethylcarbamoyl]-2-(4-ethoxy-phenyl)-ethyl]-benzamide |
| 155 | N-[(R)-1-[(S)-1-(4-Aminomethyl-3-chloro-benzylcarbamoyl)-2-phenyl-ethylcarbamoyl]-2-(4-ethoxy-phenyl)-ethyl]-benzamide |
| 156 | N-[(R)-1-[(S)-1-(4-Aminomethyl-3-trifluoromethyl-benzylcarbamoyl)-2-phenyl-ethylcarbamoyl]-2-(4-ethoxy-phenyl)-ethyl]-benzamide |
| 157 | Pyridine-2-carboxylic acid [(R)-1-[(S)-1-(4-aminomethyl-benzylcarbamoyl)-2-thiophen-2-yl-ethylcarbamoyl]-2-(4-ethoxy-phenyl)-ethyl]-amide |
| 158 | N-[(R)-1-[(S)-1-(4-Aminomethyl-benzylcarbamoyl)-2-pyridin-2-yl-ethylcarbamoyl]-2-(4-ethoxy-phenyl)-ethyl]-4-methoxy-benzamide |
| 159 | Pyridine-2-carboxylic acid [(R)-1-[(S)-1-(4-aminomethyl-3-chloro-benzylcarbamoyl)-2-phenyl-ethylcarbamoyl]-2-(4-ethoxy-phenyl)-ethyl]-amide |
| 160 | N-[(R)-1-[(S)-1-(4-Aminomethyl-benzylcarbamoyl)-2-pyridin-3-yl-ethylcarbamoyl]-2-(4-ethoxy-phenyl)-ethyl]-4-methoxy-benzamide |
| 161 | N-[(R)-1-[(S)-1-(4-Aminomethyl-benzylcarbamoyl)-2-(3,4-difluoro-phenyl)-ethylcarbamoyl]-2-(4-ethoxy-phenyl)-ethyl]-isonicotinamide |
| 162 | Thiophene-2-carboxylic acid [(R)-1-[(S)-1-(4-aminomethyl-benzylcarbamoyl)-2-pyridin-3-yl-ethylcarbamoyl]-2-(4-ethoxy-phenyl)-ethyl]-amide |
| 163 | N-[(R)-1-[(S)-1-(4-Aminomethyl-benzylcarbamoyl)-2-pyridin-2-yl-ethylcarbamoyl]-2-(4-ethoxy-phenyl)-ethyl]-4-chloro-benzamide |
| 164 | N-[(R)-1-[(S)-1-(4-Aminomethyl-benzylcarbamoyl)-2-pyridin-2-yl-ethylcarbamoyl]-2-(4-ethoxy-phenyl)-ethyl]-4-methyl-benzamide |
| 165 | Pyridine-2-carboxylic acid [(R)-1-[(S)-1-(4-aminomethyl-benzylcarbamoyl)-2-(3,4-dichloro-phenyl)-ethylcarbamoyl]-2-(4-ethoxy-phenyl)-ethyl]-amide |
| 166 | (R)-N-[(S)-1-(4-Aminomethyl-benzylcarbamoyl)-2-pyridin-2-yl-ethyl]-3-(4-ethoxy-phenyl)-2-propionylamino-propionamide |
| 167 | N-[(R)-1-[(S)-1-(4-Aminomethyl-3-fluoro-benzylcarbamoyl)-2-phenyl-ethylcarbamoyl]-2-(4-ethoxy-phenyl)-ethyl]-isonicotinamide |
| 168 | Pyridine-2-carboxylic acid [(R)-1-[(S)-1-(4-aminomethyl-3-fluoro-benzylcarbamoyl)-2-phenyl-ethylcarbamoyl]-2-(4-ethoxy-phenyl)-ethyl]-amide |
| 169 | Thiophene-2-carboxylic acid [(R)-1-[(S)-1-(4-aminomethyl-benzylcarbamoyl)-2-(3,4-dichloro-phenyl)-ethylcarbamoyl]-2-(4-ethoxy-phenyl)-ethyl]-amide |
| 170 | (R)-N-[(S)-1-(4-Aminomethyl-benzylcarbamoyl)-2-pyridin-3-yl-ethyl]-3-(4-ethoxy-phenyl)-2-propionylamino-propionamide |
| 171 | N-[(R)-1-[(S)-1-(4-Aminomethyl-benzylcarbamoyl)-2-(3,4-dichloro-phenyl)-ethylcarbamoyl]-2-(4-ethoxy-phenyl)-ethyl]-isonicotinamide |
| 172 | N-[(R)-1-[(S)-1-(4-Aminomethyl-benzylcarbamoyl)-2-(3,4-dichloro-phenyl)-ethylcarbamoyl]-2-(4-ethoxy-phenyl)-ethyl]-3,3,3-trifluoro-propionamide |
| 173 | N-[(R)-1-[(S)-1-(4-Aminomethyl-benzylcarbamoyl)-2-pyridin-3-yl-ethylcarbamoyl]-2-(4-ethoxy-phenyl)-ethyl]-4-chloro-benzamide |
| 174 | Isoxazole-5-carboxylic acid [(R)-1-[(S)-1-(4-aminomethyl-benzylcarbamoyl)-2-pyridin-3-yl-ethylcarbamoyl]-2-(4-ethoxy-phenyl)-ethyl]-amide |
| 175 | 3-Chloro-thiophene-2-carboxylic acid [(R)-1-[(S)-1-(4-aminomethyl-benzylcarbamoyl)-2-pyridin-3-yl-ethylcarbamoyl]-2-(4-ethoxy-phenyl)-ethyl]-amide |
| 176 | N-[(R)-1-[(S)-1-(4-Aminomethyl-benzylcarbamoyl)-2-(1H-indol-3-yl)-ethylcarbamoyl]-2-(4-ethoxy-phenyl)-ethyl]-benzamide |

TABLE 6-continued

| Example No | Name |
|---|---|
| 177 | N-[(R)-1-[(S)-1-(4-Aminomethyl-benzylcarbamoyl)-2-(1H-imidazol-4-yl)-ethylcarbamoyl]-2-(4-ethoxy-phenyl)-ethyl]-benzamide |
| 178 | N-[(R)-1-[(S)-1-(4-Aminomethyl-benzylcarbamoyl)-2-benzo[b]thiophen-3-yl-ethylcarbamoyl]-2-(4-ethoxy-phenyl)-ethyl]-isonicotinamide |
| 179 | 3-Acetylamino-thiophene-2-carboxylic acid-[(R)-1-[(S)-1-(4-aminomethyl-benzylcarbamoyl)-2-phenyl-ethylcarbamoyl]-2-(4-ethoxy-phenyl)-ethyl]-amide |
| 180 | N-[(R)-1-[(S)-1-(4-Aminomethyl-benzylcarbamoyl)-2-(2-fluoro-phenyl)-ethylcarbamoyl]-2-(4-ethoxy-phenyl)-ethyl]-benzamide |
| 181 | 3-Methyl-thiophene-2-carboxylic acid [(R)-1-[(S)-1-(4-aminomethyl-benzylcarbamoyl)-2-pyridin-3-yl-ethylcarbamoyl]-2-(4-ethoxy-phenyl)-ethyl]-amide |
| 182 | N-[(R)-1-[(S)-1-(4-Aminomethyl-3-methyl-benzylcarbamoyl)-2-phenyl-ethylcarbamoyl]-2-(4-ethoxy-phenyl)-ethyl]-benzamide |
| 183 | 3-Amino-thiophene-2-carboxylic acid [(R)-1-[(S)-1-(4-aminomethyl-benzylcarbamoyl)-2-thiazol-4-yl-ethylcarbamoyl]-2-(4-ethoxy-phenyl)-ethyl]-amide |
| 184 | 3-Chloro-thiophene-2-carboxylic acid [(R)-1-[(S)-1-(4-aminomethyl-benzylcarbamoyl)-2-thiazol-4-yl-ethylcarbamoyl]-2-(4-ethoxy-phenyl)-ethyl]-amide |
| 185 | N-[(R)-1-[(S)-1-(4-Aminomethyl-benzylcarbamoyl)-2-thiazol-4-yl-ethylcarbamoyl]-2-(4-ethoxy-phenyl)-ethyl]-4-methyl-benzamide |
| 186 | 3-Methyl-1H-pyrrole-2-carboxylic acid [(R)-1-[(S)-1-(4-aminomethyl-benzylcarbamoyl)-2-benzo[b]thiophen-3-yl-ethylcarbamoyl]-2-(4-ethoxy-phenyl)-ethyl]-amide |
| 187 | 3-Amino-thiophene-2-carboxylic acid [(R)-1-[(S)-1-(4-aminomethyl-benzylcarbamoyl)-2-thiazol-4-yl-ethylcarbamoyl]-2-(4-ethoxy-phenyl)-ethyl]-amide |
| 188 | 3-Acetylamino-thiophene-2-carboxylic acid [(R)-1-[(S)-1-(4-aminomethyl-benzylcarbamoyl)-2-benzo[b]thiophen-3-yl-ethylcarbamoyl]-2-(4-ethoxy-phenyl)-ethyl]-amide |
| 189 | N-[(R)-1-[(S)-1-(4-Aminomethyl-benzylcarbamoyl)-2-pyridin-3-yl-ethylcarbamoyl]-2-(4-ethoxy-phenyl)-ethyl]-3-methyl-benzamide |
| 190 | N-[(R)-1-[(S)-1-(4-Aminomethyl-benzylcarbamoyl)-2-pyridin-3-yl-ethylcarbamoyl]-2-(4-ethoxy-phenyl)-ethyl]-2-methyl-benzamide |
| 191 | 3,5-Dimethyl-1H-pyrrole-2-carboxylic acid [(R)-1-[(S)-1-(4-aminomethyl-benzylcarbamoyl)-2-phenyl-ethylcarbamoyl]-2-(4-ethoxy-phenyl)-ethyl]-amide |
| 192 | N-[(R)-1-[(S)-1-(4-Aminomethyl-3-methyl-benzylcarbamoyl)-2-pyridin-3-yl-ethylcarbamoyl]-2-(4-ethoxy-phenyl)-ethyl]-benzamide |
| 193 | 3-Acetylamino-thiophene-2-carboxylic acid [(R)-1-[(S)-1-(4-aminomethyl-benzylcarbamoyl)-2-thiophen-3-yl-ethylcarbamoyl]-2-(4-ethoxy-phenyl)-ethyl]-amide |
| 194 | 3-Amino-thiophene-2-carboxylic acid [(R)-1-[(S)-1-(4-aminomethyl-benzylcarbamoyl)-2-benzo[b]thiophen-3-yl-ethylcarbamoyl]-2-(4-ethoxy-phenyl)-ethyl]-amide |
| 195 | 3-Acetylamino-thiophene-2-carboxylic acid [(R)-1-[(S)-1-(4-aminomethyl-benzylcarbamoyl)-2-benzo[b]thiophen-3-yl-ethylcarbamoyl]-2-(4-ethoxy-phenyl)-ethyl]-amide |
| 196 | 3-Chloro-thiophene-2-carboxylic acid [(R)-1-{[(S)-1-(4-aminomethyl-benzylcarbamoyl)-2-phenyl-ethyl]-methyl-carbamoyl}-2-(4-ethoxy-phenyl)-ethyl]-amide |
| 197 | N-[(R)-1-[(1S,2R)-1-(4-Aminomethyl-benzylcarbamoyl)-2-hydroxy-2-phenyl-ethylcarbamoyl]-2-(4-ethoxy-phenyl)-ethyl]-benzamide |
| 198 | 3-Chloro-thiophene-2-carboxylic acid [(R)-1-[(1S,2R)-1-(4-aminomethyl-benzylcarbamoyl)-2-hydroxy-2-phenyl-ethylcarbamoyl]-2-(4-ethoxy-phenyl)-ethyl]-amide |

TABLE 7

NMR data of examples

| Example No | Solvent | NMR (ppm) |
|---|---|---|
| 5 | CD$_3$OD | δ 1.42 (3H, t, J = 7.0 Hz), 2.80-2.91 (2H, m), 2.94-2.99 (1H, m), 3.08-3.13 (1H, m), 3.96-4.10 (3H, m), 4.14 (2H, s), 4.31-4.36 (1H, m), 4.47-4.52 (1H, m), 4.66-4.70 (1H, m), 6.88 (2H, d, J = 8.6 Hz), 7.02 (2H, d, J = 8.6 Hz), 7.25-7.40 (7H, m), 7.42 (2H, d, J = 8.1 Hz), 8.73-8.76 (1H, m) |
| 6 | CD$_3$OD | δ1.42 (3H, t, J = 7.0 Hz), 2.80-2.89 (2H, m), 2.95-3.00 (1H, m), 3.08-3.13 (1H, m), 4.03-4.13 (3H, m), 4.21 (2H, s), 4.32-4.38 (1H, m), 4.46-4.51 (1H, m), 4.65-4.69 (1H, m), 6.88 (2H, d, J = 8.6 Hz), 7.03 (2H, d, J = 8.6 Hz), 7.05-7.09 (2H, m), 7.26-7.37 (5H, m), 7.41-7.47 (1H, m), 8.78-8.80 (1H, m) |
| 7 | CD$_3$OD | δ 1.02 (3H, t, J = 7.7 Hz), 1.42 (3H, t, J = 7.0 Hz), 2.13-2.21 (2H, m), 2.71-2.77 (1H, m), 2.81-2.92 (3H, m), 3.12-3.16 (1H, m), 4.05 (2H, q, |

TABLE 7-continued

NMR data of examples

| Example No | Solvent | NMR (ppm) |
|---|---|---|
| | | J = 6.9 Hz), 4.13 (2H, s), 4.37-4.50 (3H, m), 4.57-4.69 (1H, m), 6.82 (2H, d, J = 8.6 Hz), 7.05 (2H, d, J = 8.6 Hz), 7.17-7.27 (4H, m), 7.30-7.35 (3H, m), 7.46-7.49 (1H, m) |
| 8 | CD$_3$OD | δ 0.82-0.94 (2H, m), 1.19-1.28 (4H, m), 1.42-1.48 (2H, m), 1.64-1.71 (5H, m), 2.92-2.98 (1H, m), 3.23-3.28 (1H, m), 3.88 (1H, q, J = 7.6 Hz), 4.15 (2H, s), 4.39 (1H, d, J = 15.3 Hz), 4.52 (1H, d, J = 15.3 Hz), 4.76-4.79 (1H, m), 7.33-7.37 (7H, m), 7.44 (2H, d, J = 8.1 Hz) |
| 9 | CD$_3$OD | δ 0.84-1.03 (4H, m), 1.13-1.23 (2H, m), 1.52-1.77 (7H, m), 2.93 (6H, s), 2.96-3.02 (1H, m), 3.20-3.30 (1H, m), 3.81 (1H, q, J = 3.9 Hz), 4.15 (2H, s), 4.47 (2H, q, J = 15.4 Hz), 4.76 (1H, dd, J = 5.3, 10.5 Hz), 7.29-7.40 (7H, m), 7.45 (2H, d, J = 8.2 Hz) |
| 10 | CD$_3$OD | δ 0.84-0.92 (2H, m), 1.03 (3H, t, J = 7.7 Hz), 1.11-1.20 (4H, m), 1.35-1.39 (2H, m), 1.64-1.67 (5H, m), 2.15-2.26 (2H, m), 2.87-2.93 (1H, m), 3.39-3.42 (1H, m), 4.14 (2H, s), 4.21-4.26 (1H, m), 4.41-4.42 (1H, m), 4.44-4.57 (1H, m), 4.69-4.75 (1H, m), 7.27-7.44 (9H, m), 8.08 (1H, d, J = 5.8 Hz), 8.49 (1H, d, J = 8.3 Hz), 8.63-8.70 (1H, m) |
| 11 | CD$_3$OD | δ 0.85-0.95 (2H, m), 1.21-1.40 (6H, m), 1.70-1.79 (5H, m), 2.85 (3H, s), 2.95 (1H, dd, J = 10.0, 14.0 Hz), 3.29 (1H, dd, J = 5.5, 14.0 Hz), 3.98 (1H, dd, J = 5.6, 8.8 Hz), 4.14 (2H, s), 4.43 (2H, s), 4.71 (1H, dd, J = 5.4, 10.0 Hz), 7.27-7.35 (7H, m), 7.42 (2H, d, J = 8.1 Hz) |
| 12 | CD$_3$OD | δ 1.04 (3H, t, J = 7.5 Hz), 1.40 (3H, t, J = 7.0 Hz), 2.15-2.23 (2H, m), 2.74-2.90 (3H, m), 2.97-3.21 (2H, m), 3.98-4.13 (2H, m), 4.14 (2H, s), 4.35-4.58 (3H, m), 4.61-4.68 (1H, m), 6.82 (2H, d, J = 8.6 Hz), 7.04-7.08 (1H, m), 7.12-7.42 (9H, m), 7.55 (1H, d, J = 1.6 Hz) |
| 13 | CD$_3$OD | δ 1.42 (3H, t, J = 7.0 Hz), 2.61-2.66 (1H, m), 2.83-2.88 (1H, m), 3.00 (6H, s), 3.02-3.08 (1H, m), 3.29 (1H, dd, J = 12.9, 4.9 Hz), 3.98-4.06 (3H, m), 4.14 (2H, s), 4.19-4.21 (1H, m), 4.33-4.45 (2H, m), 6.87 (2H, d, J = 8.6 Hz), 6.89-7.05 (2H, m), 7.12 (2H, d, J = 8.6 Hz), 7.22-7.27 (5H, m), 7.40 (2H, d, J = 8.2 Hz), 8.61-8.64 (1H, m) |
| 14 | CD$_3$OD | δ 1.42 (3H, t, J = 7.0 Hz), 2.82-2.92 (2H, m), 3.03-3.09 (2H, m), 4.04-4.13 (3H, m), 4.15 (2H, s), 4.30-4.35 (1H, m), 4.48-4.53 (1H, m), 4.65-4.69 (1H, m), 6.87-6.91 (2H, m), 7.02-7.06 (2H, m), 7.15 (1H, dd, J = 8.3, 2.0 Hz), 7.29 (2H, d, J = 8.1 Hz), 7.43-7.46 (4H, m), 8.74 (1H, t, J = 5.8 Hz) |
| 15 | CD$_3$OD | δ 1.42 (3H, t, J = 7.0 Hz), 2.54-2.60 (1H, m), 2.67-2.72 (1H, m), 2.78-2.83 (1H, m), 3.06-3.11 (1H, m), 3.91-3.95 (1H, m), 3.98-4.04 (2H, m), 4.14 (2H, s), 4.36-4.49 (2H, m), 4.54-4.58 (1H, m), 6.69-6.72 (1H, m), 6.91 (2H, d, J = 8.6 Hz), 7.19-7.21 (2H, m), 7.24-7.32 (5H, m), 7.41-7.45 (4H, m), 7.55-7.59 (1H, m), 7.64-7.66 (2H, m). |
| 16 | CD$_3$OD | δ 1.03 (3H, t, J = 7.6 Hz), 1.42 (3H, t, J = 7.0 Hz), 2.14-2.24 (2H, m), 2.75-2.94 (3H, m), 3.07-3.12 (1H, m), 4.04 (2H, q, J = 7.0 Hz), 4.14 (2H, s), 4.36-4.51 (3H, m), 4.61-4.65 (1H, m), 6.81-6.84 (2H, m), 7.03-7.09 (3H, m), 7.33 (2H, d, J = 8.1 Hz), 7.38-7.43 (4H, m) |
| 17 | CD$_3$OD | δ 1.17 (3H, t, J = 7.0 Hz), 2.49-2.54 (1H, m), 2.74-2.83 (3H, m), 3.32 (2H, s), 3.81 (1H, q, J = 7.0 Hz), 3.88 (2H, s), 3.90-3.94 (1H, m), 4.08-4.21 (2H, m), 4.30-4.34 (2H, m), 6.60-6.65 (2H, m), 6.77-6.82 (2H, m), 6.94-6.96 (2H, m), 7.01-7.11 (5H, m), 7.17 (2H, d, J = 8.2 Hz), 8.43 (1H, t, J = 6.0 Hz) |
| 18 | CD$_3$OD | δ 2.82-2.88 (1H, m), 3.02-3.09 (2H, m), 3.20-3.26 (1H, m), 4.15 (2H, s), 4.21-4.34 (2H, m), 4.49-4.54 (1H, m), 4.68-4.72 (1H, m), 7.19 (1H, dd, J = 8.2, 2.0 Hz), 7.29 (2H, d, J = 8.1 Hz), 7.34 (2H, d, J = 8.0 Hz), 7.43-7.48 (4H, m), 7.68 (2H, d, J = 8.2 Hz), 8.76 (1H, t, J = 5.8 Hz) |
| 19 | CD$_3$OD | δ 1.02 (3H, t, J = 7.6 Hz), 2.19 (2H, q, J = 7.6 Hz), 2.86-2.94 (2H, m), 3.06-3.16 (2H, m), 4.14 (2H, s), 4.37-4.50 (2H, m), 4.61-4.70 (2H, m), 7.13 (1H, dd, J = 8.3, 2.0 Hz), 7.32-7.37 (4H, m), 7.42-7.45 (4H, m), 7.60 (2H, d, J = 8.2 Hz) |
| 20 | CD$_3$OD | δ 0.82-0.99 (2H, m), 1.15-1.30 (4H, m), 1.44-1.54 (2H, m), 1.62-1.73 (5H, m), 2.91-2.97 (1H, m), 3.22-3.27 (1H, m), 3.90 (1H, t, J = 7.1 Hz), 4.16 (2H, s), 4.38-4.55 (2H, m), 4.77-4.81 (1H, m), 7.26 (1H, dd, J = 8.2, 2.0 Hz), 7.37 (2H, d, J = 8.1 Hz), 7.43-7.52 (4H, m) |
| 21 | CD$_3$OD | δ 0.85-0.94 (2H, m), 1.02-1.22 (7H, m), 1.34-1.42 (2H, m), 1.62-1.69 (5H, m), 2.16-2.27 (2H, m), 2.85-2.92 (1H, m), 3.39-3.44 (1H, m), 4.14 (2H, s), 4.18-4.24 (1H, m), 4.40-4.45 (1H, m), 4.53-4.58 (1H, m), 4.73-4.79 (1H, m), 7.24 (1H, dd, J = 8.2, 2.0 Hz), 7.38-7.51 (6H, m), 8.11 (1H, d, J = 5.6 Hz), 8.59 (1H, d, J = 8.5 Hz), 8.69 (1H, t, J = 6.0 Hz) |
| 22 | CD$_3$OD | δ 1.30 (3H, d, J = 7.1 Hz), 2.92-2.98 (1H, m), 3.40 (1H, d, J = 4.9 Hz), 4.09 (2H, s), 4.41-4.48 (2H, m), 4.54-4.60 (1H, m), 4.68-4.74 (1H, m), 7.24-7.34 (5H, m), 7.38 (4H, s), 7.43-7.49 (2H, m), 7.56-7.60 (1H, m), 7.80-7.82 (2H, m), 8.51 (1H, d, J = 8.2 Hz), 8.56 (1H, d, J = 5.3 Hz), 8.66 (1H, t, J = 6.0 Hz) |
| 23 | CD$_3$OD | δ 1.03 (3H, t, J = 7.6 Hz), 1.42 (3H, t, J = 7.0 Hz), 2.16-2.22 (2H, m), 2.73-2.93 (3H, m), 3.11-3.16 (1H, m), 4.05 (2H, q, J = 6.9 Hz),), 4.28 (2H, s), 4.37-4.48 (3H, m), 4.60-4.64 (1H, m), 6.82 (2H, d, J = 8.6 Hz), 7.05 (2H, d, J = 8.7 Hz), 7.17 (2H, t, J = 6.6 Hz), 7.29-7.33 (4H, m), 7.46 (2H, dd, J = 9.6, 1.4 Hz) |

TABLE 7-continued

NMR data of examples

| Example No | Solvent | NMR (ppm) |
|---|---|---|
| 24 | CD$_3$OD | δ 1.08 (3H, t, J = 7.7 Hz), 1.38-1.42 (3H, m), 2.18-2.25 (2H, m), 2.71-3.07 (7H, m), 4.00-4.07 (2H, m), 4.14 (2H, s), 4.54-4.58 (2H, m), 4.62-4.66 (1H, m), 5.09-5.15 (1H, m), 6.83-6.88 (2H, m), 7.08-7.21 (4H, m), 7.26-7.38 (4H, m), 7.42 (2H, d, J = 8.1 Hz), 8.29 (1H, d, J = 7.8 Hz), 8.35 (1H, d, J = 8.3 Hz) |
| 25 | CD$_3$OD | δ 1.41 (3H, t, J = 7.0 Hz), 2.56-2.68 (2H, m), 2.94-2.98 (1H, m), 3.01 (3H, s), 3.39-3.41 (1H, m), 4.05 (2H, q, J = 7.0 Hz), 4.14 (2H, s), 4.33-4.38 (1H, m), 4.49-4.55 (2H, m), 5.52-5.56 (1H, m), 6.86-6.89 (2H, m), 7.02 (2H, d, J = 8.6 Hz), 7.28-7.39 (7H, m), 7.43 (2H, d, J = 8.1 Hz), 8.53 (1H, t, J = 5.8 Hz) |
| 26 | CD$_3$OD | δ 1.05 (3H, t, J = 7.6 Hz), 1.39 (3H, t, J = 7.0 Hz), 2.15-2.23 (2H, m), 2.51-2.63 (2H, m), 2.83-2.90 (1H, m), 2.96 (3H, s), 3.39-3.41 (1H, m), 4.01 (2H, q, J = 7.0 Hz), 4.13 (2H, s), 4.38-4.50 (2H, m), 4.83-4.87 (1H, m), 5.47-5.51 (1H, m), 6.78-6.82 (2H, m), 7.01 (2H, d, J = 8.6 Hz), 7.22-7.40 (7H, m), 7.43 (2H, d, J = 8.1 Hz), 8.19 (1H, d, J = 6.8 Hz), 8.34 (1H, t, J = 6.0 Hz) |
| 27 | CD$_3$OD | δ 1.42 (3H, t, J = 7.0 Hz), 2.66 (3H, s), 2.78-2.90 (1H, m), 3.01-3.15 (3H, m), 4.02-4.10 (3H, m), 4.14 (2H, s), 4.34-4.47 (2H, m), 4.59-4.70 (1H, m), 6.83-6.88 (2H, m), 6.97-7.02 (2H, m), 7.20-7.22 (2H, m), 7.26-7.34 (5H, m), 7.42 (2H, d, J = 8.1 Hz), 8.69 (1H, t, J = 5.8 Hz) |
| 28 | CD$_3$OD | δ 0.81-0.83 (6H, m), 1.10-1.18 (1H, m), 1.48-1.55 (1H, m), 1.58-1.65 (1H, m), 2.92-2.98 (1H, m), 3.25-3.30 (1H, m), 3.75 (2H, s), 3.92-3.96 (1H, m), 4.15 (2H, s), 4.48-4.53 (2H, m), 4.75-4.79 (1H, m), 7.27-7.40 (7H, m), 7.46 (2H, d, J = 8.2 Hz), 8.83 (1H, t, J = 5.9 Hz) |
| 29 | CD$_3$OD | δ 0.70-1.03 (6H, m), 1.37-1.69 (7H, m), 2.81-2.87 (4H, m), 3.06-3.11 (1H, m), 3.72-3.96 (3H, m), 3.99 (2H, s), 4.26-4.37 (2H, m), 4.58-4.62 (1H, m), 7.13-7.24 (7H, m), 7.30 (2H, d, J = 8.1 Hz), 8.72 (1H, t, J = 5.9 Hz) |
| 30 | CD$_3$OD | δ 0.75-0.93 (3H, m), 1.20-1.31 (5H, m), 1.54-1.81 (5H, m), 3.02 (3H, s), 3.08-3.17 (1H, m), 3.43-3.48 (1H, m), 3.81 (2H, s), 4.15 (2H, s), 4.45-4.53 (3H, m), 5.65-5.71 (1H, m), 7.27-7.39 (5H, m), 7.41 (2H, d, J = 8.1 Hz), 7.48 (2H, d, J = 8.2 Hz), 8.67 (1H, t, J = 5.9 Hz) |
| 31 | CD$_3$OD | δ 0.67-0.71 and 0.77-0.80 (3H, m), 1.19-1.24 (3H, m), 1.99-2.11 (2H, m), 2.65-2.83 (5H, m), 2.91-3.09 (2H, m), 3.81-3.88 (2H, m), 3.95 (2H, s), 4.17-4.32 (2H, m), 4.43-4.54 (1H, m), 4.77-4.82 (1H, m), 6.62-6.69 (2H, m), 6.90-6.94 (2H, m), 6.98-7.20 (7H, m), 7.21-7.26 (2H, m), 7.69 (1H, d, J = 7.9 Hz), 8.26-8.29 and 8.40-8.43 (1H, m) |
| 32 | CD$_3$OD | δ 1.02-1.10 (3H, m), 1.40 (3H, t, J = 7.0 Hz), 2.11-2.24 (2H, m), 2.51-2.63 (2H, m), 2.82-2.90 (1H, m), 2.95 (3H, s), 3.36-3.41 (1H, m), 3.98-4.03 (2H, m), 4.20 (2H, s), 4.38-4.51 (2H, m), 4.85 (1H, t, J = 7.3 Hz), 5.46-5.50 (1H, m), 6.77-6.85 (2H, m), 7.00-7.08 (2H, m), 7.11-7.18 (2H, m), 7.21-7.36 (5H, m), 7.42-7.48 (1H, m), 8.43 (1H, t, J = 6.1 Hz) |
| 33 | CD$_3$OD | δ 0.63-0.80 (2H, m), 0.87-1.08 (4H, m), 1.32-1.54 (7H, m), 2.50 (3H, s), 2.79-2.85 (1H, m), 3.08-3.13 (1H, m), 3.66-3.70 (1H, m), 3.99 (2H, s), 4.27-4.36 (2H, m), 4.59-4.65 (1H, m), 7.13-7.24 (7H, m), 7.30 (2H, d, J = 8.2 Hz), 8.71 (1H, t, J = 5.9 Hz), 8.80 (1H, d, J = 7.6 Hz) |
| 34 | CD$_3$OD | δ 0.75-0.91 (3H, m), 1.20-1.33 (5H, m), 1.55 (1H, d, J = 12.3 Hz), 1.62-1.71 (3H, m), 1.80 (1H, d, J = 12.5 Hz), 3.02 (3H, s), 3.08-3.18 (1H, m), 3.45-3.50 (1H, m), 3.83-3.87 (2H, m), 4.23 (2H, s), 4.46-4.52 (3H, m), 5.66-5.72 (1H, m), 7.21-7.41 (7H, m), 7.52 (1H, t, J = 7.8 Hz), 8.77 (1H, t, J = 6.0 Hz) |
| 35 | CD$_3$OD | δ 0.83 (3H, t, J = 7.4 Hz), 1.24-1.30 (3H, m), 1.51-1.62 (2H, m), 2.64 (3H, s), 2.65-2.89 (5H, m), 3.09-3.14 (1H, m), 3.85-3.96 (2H, m), 3.98 (2H, s), 4.16-4.22 (1H, m), 4.28-4.37 (1H, m), 4.47-4.50 (1H, m), 5.29 (1H, t, J = 8.1 Hz), 6.67-6.75 (2H, m), 6.87-6.90 (2H, m), 7.09 (2H, d, J = 8.2 Hz), 7.15-7.29 (7H, m), 8.42 (1H, t, J = 6.0 Hz) |
| 36 | CD$_3$OD | δ 1.15-1.30 (6H, m), 1.52-1.76 (7H, m), 2.89-3.02 (4H, m), 3.10-3.19 (1H, m), 3.73-3.80 (2H, m), 3.99-4.05 (1H, m), 4.12-4.14 (2H, m), 4.48-4.59 (1H, m), 4.71-4.80 (1H, m), 5.08-5.16 (1H, m), 7.19-7.49 (9H, m) |
| 37 | CD$_3$OD | δ 0.62-1.08 (9H, m), 1.34-1.66 (9H, m), 2.71-2.86 (3H, m), 3.07-3.11 (1H, m), 3.69-3.73 (1H, m), 4.00 (2H, s), 4.27-4.37 (2H, m), 4.59-4.63 (1H, m), 7.13-7.27 (7H, m), 7.30 (2H, d, J = 8.1 Hz), 8.68 (1H, t, J = 5.9 Hz) |
| 38 | CD$_3$OD | δ 1.39 (3H, t, J = 7.0 Hz), 2.66-2.71 (1H, m), 2.79-2.94 (2H, m), 3.01 (3H, s), 3.38-3.43 (1H, m), 3.97-4.03 (2H, m), 4.07-4.14 (2H, m), 4.40-4.50 (2H, m), 5.03-5.09 (1H, m), 5.52-5.56 (1H, m), 6.78-6.86 (2H, m), 7.05-7.18 (2H, m), 7.20-7.71 (12H, m), 7.73-7.81 (2H, m), 8.37 (1H, t, J = 6.0 Hz), 8.58 (1H, d, J = 6.7 Hz) |
| 39 | CD$_3$OD | δ 1.39 (3H, t, J = 7.0 Hz), 1.93 (3H, s), 2.50-2.63 (2H, m), 2.81-2.90 (1H, m), 2.95 (3H, s), 3.34-3.41 (1H, m), 3.95-4.05 (2H, m), 4.13 (2H, s), 4.33-4.51 (2H, m), 4.82-4.89 (1H, m), 5.46-5.50 (1H, m), 6.78-6.85 (2H, m), 7.00-7.05 (2H, m), 7.09-7.36 (7H, m), 7.39-7.43 (2H, m), 8.29 (1H, t, J = 6.0 Hz) |
| 40 | CD$_3$OD | δ 0.61-0.81 (2H, m), 0.88-1.05 (4H, m), 1.34-1.54 (7H, m), 2.51 (3H, s), 2.80-2.86 (1H, m), 3.08-3.13 (1H, m), 3.67-3.70 (1H, m), 4.07 (2H, |

TABLE 7-continued

NMR data of examples

| Example No | Solvent | NMR (ppm) |
|---|---|---|
| | | s), 4.27-4.37 (2H, m), 4.59-4.63 (1H, m), 6.99-7.04 (2H, m), 7.13-7.24 (5H, m), 7.34 (1H, t, J = 7.9 Hz), 8.73 (1H, t, J = 6.0 Hz) |
| 41 | CD$_3$OD | δ 0.73-1.25 (6H, m), 1.50-1.69 (7H, m), 2.67 (3H, s), 2.94-3.00 (1H, m), 3.24-3.29 (1H, m), 3.81-3.85 (1H, m), 4.23 (2H, s), 4.44-4.54 (2H, m), 4.76-4.80 (1H, m), 7.18-7.23 (2H, m), 7.31 (1H, dd, J = 8.3, 2.0 Hz), 7.45-7.56 (3H, m), 8.91 (1H, t, J = 5.9 Hz), 8.97 (1H, d, J = 7.7 Hz) |
| 42 | CD$_3$OD | δ 0.83-1.19 (6H, m), 1.53-1.85 (7H, m), 2.94-3.08 (4H, m), 3.21-3.26 (1H, m), 3.87-4.08 (3H, m), 4.22 (2H, s), 4.38-4.55 (2H, m), 4.72-4.76 (1H, m), 7.18-7.22 (2H, m), 7.28-7.39 (5H, m), 7.47-7.51 (1H, m), 8.93 (1H, t, J = 6.0 Hz), 9.05 (1H, d, J = 7.2 Hz) |
| 43 | CD$_3$OD | δ 0.78-0.97 (4H, m), 1.03-1.20 (2H, m), 1.47-1.50 (1H, m), 1.54-1.63 (5H, m), 1.75-1.82 (1H, m), 2.92-2.95 (1H, m), 2.98 (3H, s), 3.19-3.24 (1H, m), 3.98-4.13 (3H, m), 4.19 (2H, s), 4.38-4.52 (2H, m), 4.70-4.74 (1H, m), 7.17-7.20 (2H, m), 7.27 (1H, dd, J = 8.3, 2.0 Hz), 7.37-7.52 (3H, m), 8.92 (1H, t, J = 5.9 Hz), 9.08 (1H, d, J = 7.3 Hz) |
| 44 | CD$_3$OD | δ 1.01-1.05 (6H, m), 1.40 (3H, t, J = 7.0 Hz), 2.36-2.62 (3H, m), 2.85-2.91 (1H, m), 2.96 (3H, s), 3.37-3.42 (1H,, m), 3.98-4.04 (2H, m), 4.13 (2H, s), 4.39-4.50 (2H, m), 4.82-4.86 (1H,, m), 5.48-5.52 (1H, m), 6.77-6.85 (2H, m), 6.99-7.04 (2H, m), 7.22-7.36 (7H, m), 7.39-7.44 (2H, m), 8.37 (1H, t, J = 6.0 Hz) |
| 45 | CD$_3$OD | δ 0.71-1.03 (9H, m), 1.36-1.63 (9H, m), 2.75 (3H, s), 2.81-3.11 (4H, m), 3.71-3.74 (1H, m), 4.00 (2H, s), 4.31-4.33 (2H, m), 4.59-4.63 (1H, m), 7.14-7.24 (7H, m), 7.30 (2H, d, J = 8.2 Hz), 8.71 (1H, t, J = 5.8 Hz) |
| 46 | CD$_3$OD | δ 0.78-0.97 (2H, m), 1.09-1.25 (4H, m), 1.54-1.69 (7H, m), 2.93-2.99 (1H, m), 3.24-3.29 (1H, m), 3.87 (3H, m), 3.94 (2H, d, J = 2.5 Hz), 3.99-4.04 (1H, m), 4.15 (2H, s), 4.43-4.53 (2H, m), 4.73-4.77 (1H, m), 7.25-7.38 (7H, m), 7.46 (2H, d, J = 8.1 Hz), 8.83 (1H, t, J = 5.9 Hz) |
| 47 | CD$_3$OD | δ 0.72-1.14 (6H, m), 1.40-1.73 (7H, m), 2.85-2.91 (4H, m), 3.11-3.16 (1H, m), 3.77 (3H, m), 3.93-3.96 (1H, m), 4.04 (2H, s), 4.07-4.18 (2H, m), 4.36 (2H, s), 4.63-4.67 (1H, m), 7.17-7.27 (7H, m), 7.35 (2H, d, J = 8.1 Hz), 8.73 (1H, t, J = 5.9 Hz), 8.92 (1H, d, J = 7.3 Hz) |
| 48 | CD$_3$OD | δ 0.87-1.17 (6H, m), 1.54-1.79 (7H, m), 2.89 (3H, s), 2.95-3.02 (1H, m), 3.21-3.27 (1H, m), 3.79-3.99 (3H, m), 4.15 (2H, s), 4.47 (2H, s), 4.74-4.78 (1H, m), 7.29-7.39 (7H, m), 7.46 (2H, d, J = 8.1 Hz), 8.84 (1H, t, J = 5.8 Hz) |
| 49 | CD$_3$OD | δ 0.75-1.08 (6H, m), 1.41-1.76 (7H, m), 2.85-2.91 (4H, m), 3.11-3.36 (3H, m), 3.78-3.90 (3H, m), 4.04 (2H, s), 4.31-4.41 (2H, m), 4.63-4.67 (1H, m), 7.18-7.29 (7H, m), 7.35 (2H, d, J = 8.2 Hz), 8.76 (1H, t, J = 5.9 Hz) |
| 52 | CD$_3$OD | δ, 0.74-0.88 (4H 0.78-2.10 (23H, m), 2.92-3.08 (1H, m), 3.12-3.30 (1H, m), 4.07 (1H, d, 4.2 Hz), 4.15 (2H, s), 4.42 (1H, dd, J = 15.3, 5.5 Hz), 4.52 (1H, dd, J = 15.3, 6.0 Hz), 4.66 (1H, dd, J = 10.2, 5.2 Hz), 7.20-7.48 (9H, m), 8.87 (1H, t, J = 6.0 Hz) |
| 53 | CD$_3$OD | δ 0.83-1.19 (12H, m), 1.50 (1H, d, J = 12.2 Hz), 1.60-1.79 (10H, m), 2.98 (1H, dd, J = 10.6, 14.2 Hz), 3.14-3.28 (5H, m), 3.91 (1H, dd, J = 3.4, 11.7 Hz), 4.15 (2H, s), 4.47-4.49 (2H, m), 4.77 (1H, dd, J = 5.2, 10.5 Hz), H, s7.36-7.41 (6H (7H, m), 7.45 (2H, d, J = 8.1 Hz), 8.89-8.92 (1H, m) |
| 54 | CD$_3$OD | δ 1.44 (3H, t, J = 7.0 Hz), 2.81-2.87 (1H, m), 2.95-3.02 (2H, m), 3.19-3.24 (1H, m), 4.03-4.09 (4H, m), 4.46 (2H, d, J = 6.0 Hz), 4.84-4.89 (1H, m), 6.88 (2H, d, J = 8.5 Hz), 7.04 (2H, d, J = 8.5 Hz), 7.17-7.51 (13H, m), 7.85 (1H, d, J = 8.5 Hz), 7.93 (1H, d, J = 8.5 Hz), 7.90 and 8.00 (total 1H, each dd, J = each 7.2 Hz), 8.43 (1H, d, J = 8.1 Hz), 8.63 (1H, d, J = 5.9 Hz), 8.75 (1H, t, J = 7.0 Hz) |
| 55 | CD$_3$OD | δ 1.25 (3H, t, J = 7.0 Hz), 2.77-2.83 (H3H, m), 2.96-3.02 (1H, m), 3.85-3.97 (4H, m), 4.22-4.26 (1H, m), 4.27-4.39 (1H, m), 4.48-4.54 (2H, m), 6.66-6.68 (2H, m), 6.94 (2H, d, J = 8.6 Hz), 7.01-7.03 (2H, m), 7.11-7.29 (9H, m), 7.31 (1H, d, J = 1.8 Hz), 7.53 (1H, d, J = 8.6 Hz), 8.22 (1H, d, J = 8.0 Hz), 8.36-8.44 (2H, m) |
| 56 | CD$_3$OD | δ 1.25 (3H, t, J = 7.0 Hz), 2.75-2.83 (4H, m), 2.87-2.99 (1H, m), 3.85-3.89 (2H, m), 3.97 (2H, s), 4.22-4.39 (2H, m), 4.53-4.57 (H1H, m), 6.67 (2H, d, J = 8.5 Hz), 6.95 (2H, d, J = 8.5 Hz), 7.02-7.04 (2H, m), 7.11-7.22 (7H, m), 7.60 (2H, d, J = 8.3 Hz), 7.71 (2H, d, J = 8.2 Hz), 8.25 (1H, d, J = 8.0 Hz), 8.42 (1H, t, J = 5.8 Hz) |
| 57 | CD$_3$OD | δ 1.41 (3H, t, J = 7.0 Hz), 2.91-3.04 (4H, m), 3.15-3.20 (1H, m), 4.01-4.07 (4H, m), 4.40 (1H, d, J = 15.4 Hz), 4.53 (1H, d, J = 15.4 Hz), 4.67-4.71 (1H, m), 6.84 (2H, d, J = 8.7 Hz), 7.11 (2H, d, J = 8.6 Hz), 7.19-7.24 (2H, m), 7.27-7.37 (9H, m), 7.44-7.54 (2H, m), 7.70-7.73 (4H, m), 7.80-7.82 (1H, m) |
| 58 | CD$_3$OD | δ 1.42 (3H, t, J = 7.0 Hz), 2.80-2.98 (4H, m), 3.02-3.06 (1H, m), 4.05 (2H, d, J = 7.0 Hz), 4.12 (2H, s), 4.39-4.46 (2H, m), 4.68-4.76 (2H, m), 6.85 (2H, d, J = 8.6 Hz), 7.12 (2H, d, J = 8.6 Hz), 7.20-7.22 (2H, m), 7.26-7.32 (6H, m), 7.39-7.41 (3H, m), 7.54 (1H, d, J = 1.9 Hz), 8.54 (1H, t, J = 5.9 Hz) |
| 59 | CD$_3$OD | δ 1.25 (3H, t, J = 7.0 Hz), 2.77-2.81 (4H, m), 2.97-3.02 (1H, m), 3.87 (2H, q, J = 7.0 Hz), 3.93 (2H, s), 4.26-4.30 (1H, m), 4.35-4.40 (1H, m), |

TABLE 7-continued

NMR data of examples

| Example No | Solvent | NMR (ppm) |
|---|---|---|
| | | 4.48-4.55 (2H, m), 6.68 (2H, d, J = 8.6 Hz), 6.94 (2H, d, J = 8.6 Hz), 7.01-7.03 (2H, m), 7.09-7.22 (8H, m), 7.42-7.45 (2H, m), 8.22 (1H, d, J = 8.1 Hz), 8.41 (1H, t, J = 5.8 Hz) |
| 60 | CD$_3$OD | δ 1.23 (3H, t, J = 7.0 Hz), 2.81-2.87 (1H, m), 3.01-3.06 (1H, m), 3.85-3.91 (2H, m), 3.94 (2H, s), 3.96-4.04 (2H, m), 4.18-4.24 (1H, m), 4.53 (1H, d, J = 7.0 Hz), 4.84 (1H, d, J = 7.1 Hz), 6.70-6.74 (2H, m), 6.88 (2H, d, J = 8.0 Hz), 7.01-7.04 (2H, m), 7.13-7.23 (5H, m), 7.27-7.31 (2H, m) |
| 61 | CD$_3$OD | δ 1.43 (3H, t, J = 7.0 Hz), 2.68-2.74 (1H, m), 2.98-3.03 (1H, m), 4.06 (2H, q, J = 7.0 Hz), 4.14 (2H, s), 4.21-4.24 (1H, m), 4.42-4.50 (2H, m), 4.75 (1H, d, J = 4.4 Hz), 5.28 (1H, d, J = 4.4 Hz), 6.85-6.89 (2H, m), 6.97-7.00 (2H, m), 7.30-7.35 (4H, m), 7.38-7.43 (3H, m), 7.5 (2H, d, J = 7.3 Hz) |
| 62 | CD$_3$OD | δ 0.93 (3H, t, J = 7.7 Hz), 1.25 (3H, t, J = 7.0 Hz), 2.01-2.11 (2H, m), 2.60-2.66 (1H, m), 2.79-2.84 (1H, m), 3.86 (2H, q, J = 7.0 Hz), 3.99 (2H, s), 4.22-4.32 (2H, m), 4.41-4.43 (1H, m), 4.46 (1H, d, J = 4.0 Hz), 5.13 (1H, d, J = 4.0 Hz), 6.64-6.67 (2H, m), 6.91-6.95 (2H, m), 7.14-7.33 (9H, m) |
| 63 | CD$_3$OD | δ 1.00 (3H, t, J = 7.6 Hz), 1.43 (3H, t, J = 7.0 Hz), 2.13-2.19 (2H,, m), 2.61-2.66 (1H, m), 2.78-2.83 (1H, m), 4.04 (2H, q, J = 7.0 Hz), 4.14 (2H, s), 4.45-4.65 (4H, m), 5.37 (1H, d, J = 3.0 Hz), 6.77-6.81 (2H, m), 7.01 (2H, d, J = 8.6 Hz), 7.28-7.45 (9H,, m), 8.00 (1H, d, J = 6.9 Hz), 8.23 (1H, d, J = 8.4 Hz), 8.51 (1H, t, J = 6.0 Hz) |
| 64 | CD$_3$OD | δ 0.98 (3H, t, J = 7.2 Hz), 1.06-1.13 (3H, m), 1.40 (3H, t, J = 7.0 Hz), 2.19-2.24 (2H, m), 2.71-2.82 (1H,, m), 2.98-3.05 (1H, m), 3.14-3.22 (1H, m), 3.29-3.35 (1H,, m), 3.51-3.60 (1H, m), 3.98-4.04 (2H, m), 4.13 (2H, s), 4.35-4.48 (2H, m), 4.78-4.89 (1H, m), 5.12-5.21 (1H, m), 6.79-6.83 (2H, m), 7.07-7.16 (2H, m), 7.26-7.38 (7H, m), 7.41 (2H, d, J = 8.1 Hz), 8.21 (1H, t, J = 6.1 Hz) |
| 65 | CD$_3$OD | δ 0.96-1.10 (6H, m), 1.33-1.44 (3H, m), 2.10-2.27 and 2.41-2.46 (total 3H, m), 2.74-2.97 (2H, m), 3.12-3.23 (1H, m), 3.28-3.34 (1H, m), 3.41-3.50 (1H, m), 3.92-4.08 (2H, m), 4.12 (2H, s), 4.34-4.50 (2H, m), 4.60-4.64 and 4.78-4.82 (1H, m), 4.94-4.98 and 5.08-5.12 (total 1H, m), 6.80-6.89 (2H, m), 7.09-7.42 (11H, m), 8.11 (1H, t, J = 6.0 Hz), 8.20 (1H, d, J = 6.5 Hz), 8.45 (1H, d, J = 7.2 Hz), 8.77 (1H, t, J = 5.8 Hz) |
| 66 | CD$_3$OD | δ 0.82-0.86 and 0.96-1.00 (total 3H, m), 1.38-1.43 (3H, m), 2.18-2.30 (2H, m), 2.63 (3H, s), 2.84-3.02 (2H, m), 3.11-3.28 (2H, m), 3.99-4.06 (2H, m), 4.15 (2H, s), 4.39-4.51 (2H, m), 4.64-4.79 (1H, m), 5.22-5.26 (1H, m), 6.81-6.87 (2H, m), 7.09-7.13 (2H, m), 7.22-7.37 (7H, m), 7.42-7.46 (2H, m), 7.76 (1H, d, J = 7.9 Hz), 8.45-8.47 and 8.59-8.62 (total 1H, m) |
| 67 | CD$_3$OD | δ 1.00 (3H, t, J = 7.7 Hz), 1.44 (3H, t, J = 7.0 Hz), 1.64-1.72 (1H, m), 2.08-2.31 (3H, m), 2.98-3.09 (2H, m), 3.30-3.36 (1H, m), 3.39-3.44 (1H, m), 3.91-3.97 (1H, m), 4.03-4.07 (2H, m), 4.14 (2H, s), 4.10-4.16 (1H, m), 4.31-4.34 (1H, m), 4.37 (1H, d, J = 4.9 Hz), 4.51-4.57 (1H, m), 4.82-4.86 (1H, m), H, s6.91-6.97 (4H, m), 7.25-7.36 (7H, m), 7.42 (2H, d, J = 8.2 Hz), 8.35-8.50 (1H, m) |
| 68 | d$^6$-DMSO | δ: 1.29 (3H, t, J = 7.0 Hz), 2.43 (1H, dd, J = 13.7, 8.0 Hz), 2.63 (1H, dd, J = 13.8, 4.7 Hz), 2.77 (1H, dd, J = 13.6, 10.4 Hz), 3.06 (1H, dd, J = 13.7, 4.4 Hz), 3.91-3.96 (4H, m), 4.07 (1H, dd, J = 15.4, 5.8 Hz), 4.15 (1H, dd, J = 15.4, 6.0 Hz), 4.23-4.26 (2H, m), 4.32-4.37 (1H, m), 4.44-4.50 (1H, m), 6.09 (1H, d, J = 7.7 Hz), 6.58 (1H, t, J = 6.0 Hz), 6.67 (2H, d, J = 8.7 Hz), 6.76 (2H, d, J = 8.6 Hz), 7.08-7.38 (11H, m), 7.45 (2H, d, J = 7.5 Hz), 8.28 (3H, br s), 8.48 (1H, d, J = 8.5 Hz), 8.62 (1H, t, J = 6.0 Hz). |
| 69 | d$^6$-DMSO | δ: 1.28 (3H, t, J = 7.0 Hz), 2.47-2.50 (1H, m), 2.67 (1H, dd, J = 13.9, 4.6 Hz), 2.79 (1H, dd, J = 13.6, 10.5 Hz), 3.07 (1H, dd, J = 13.7, 4.3 Hz), 3.90-3.97 (4H, m), 4.23-4.33 (2H, m), 4.43-4.53 (2H, m), 6.24 (1H, d, J = 7.7 Hz), 6.66 (2H, d, J = 8.7 Hz), 6.72 (2H, d, J = 8.7 Hz), 6.86 (1H, t, J = 7.4 Hz), 7.13-7.32 (11H, m), 7.36 (2H, d, J = 8.1 Hz), 8.23 (2H, br s), 8.58-8.63 (2H, m), 8.77 (1H, s). |
| 70 | d$^6$-DMSO | δ: 1.26 (3H, t, J = 7.0 Hz), 2.66 (1H, dd, J = 13.5, 10.6 Hz), 2.73 (1H, dd, J = 13.8, 4.0 Hz), 2.82 (1H, dd, J = 13.5, 10.2 Hz), 3.05 (1H, dd, J = 13.6, 4.9 Hz), 3.89-4.01 (4H, m), 4.27 (1H, dd, J = 15.4, 5.8 Hz), 4.34 (1H, dd, J = 15.4, 6.1 Hz), 4.55-4.68 (2H, m), 6.75 (2H, d, J = 8.6 Hz), 7.07-7.32 (8H, m), 7.39 (2H, d, J = 8.1 Hz), 7.73 (1H, dd, J = 7.9, 5.2 Hz), 8.13-8.59 (4H, m), 8.63 (2H, m), 8.81 (1H, dd, J = 5.1, 1.3 Hz), 8.99-9.01 (2H, m). |
| 71 | d$^6$-DMSO | δ: 1.26 (3H, t, J = 6.9 Hz), 2.64 (1H, dd, J = 13.5, 10.8 Hz), 2.72 (1H, dd, J = 13.6, 3.8 Hz), 2.82 (1H, dd, J = 13.5, 10.2 Hz), 3.05 (1H, dd, J = 13.6, 4.7 Hz), 3.80-4.01 (4H, m), 4.27 (1H, dd, J = 15.4, 5.8 Hz), 4.34 (1H, dd, J = 15.4, 6.0 Hz), 4.58-4.68 (2H, m), 6.75 (2H, d, J = 8.6 Hz), 7.14 (2H, d, J = 8.7 Hz), 7.17-7.27 (6H, m), 7.38 (2H, d, J = 8.1 Hz), 7.85 (2H, d, J = 5.9 Hz), 8.14-8.50 (3H, m), 8.64 (1H, d, J = 6.2 Hz), 8.67 (1H, d, J = 8.6 Hz), 8.80 (2H, d, J = 6.0 Hz), 9.03 (1H, d, J = 8.3 Hz). |

TABLE 7-continued

NMR data of examples

| Example No | Solvent | NMR (ppm) |
|---|---|---|
| 72 | d⁶-DMSO | δ: 1.26 (3H, t, J = 7.0 Hz), 2.62-2.64 (2H, m), 2.81 (1H, dd, J = 13.6, 10.0 Hz), 3.03 (1H, dd, J = 13.4, 4.5 Hz), 3.92 (2H, q, J = 7.0 Hz), 3.96 (2H, s), 4.25-4.35 (2H, m), 4.54-4.61 (2H, m), 6.74 (2H, d, J = 8.6 Hz), 7.13 (2H, d, J = 8.7 Hz), 7.16-7.25 (7H, m), 7.35 (2H, d, J = 8.1 Hz), 7.43 (1H, dd, J = 5.0, 1.3 Hz), 7.53 (1H, dd, J = 5.0, 3.0 Hz), 8.11 (1H, dd, J = 2.8, 1.0), 8.20 (2H, br s), 8.33 (1H, d, J = 8.2 Hz), 8.54 (1H, d, J = 8.7 Hz), 8.60 (1H, t, J = 6.0 Hz). |
| 73 | d⁶-DMSO | δ: 1.26 (3H, t, J = 7.0 Hz), 2.48-2.68 (2H, m), 2.81 (1H, dd, J = 13.6, 10.1 Hz), 3.03 (1H, dd, J = 13.6, 4.7 Hz), 3.89-3.96 (4H, m), 4.24-4.34 (2H, m), 4.53-4.62 (2H, m), 6.74 (2H, d, J = 8.6 Hz), 7.10-7.27 (9H, m), 7.37 (2H, d, J = 8.1 Hz), 7.71 (1H, dd, J = 4.9, 0.9 Hz), 7.82 (1H, dd, J = 3.6, 2.8 Hz), 8.20 (3H, br s), 8.56 (2H, dd, J = 10.5, 9.1 Hz), 8.62 (1H, t, J = 6.0 Hz). |
| 74 | d⁶-DMSO | δ: 0.48-0.57 (4H, m), 1.29 (3H, t, J = 7.0 Hz), 1.56-1.62 (1H, m), 2.43-2.49 (1H, m), 2.54-2.59 (1H, m), 2.73-2.79 (1H, m), 3.00-3.05 (1H, m), 3.92-3.97 (4H, m), 4.20-4.33 (2H, m), 4.38-4.43 (1H, m), 4.47-4.53 (1H, m), 6.73 (2H, d, J = 8.6 Hz), 6.98 (2H, d, J = 8.6 Hz), 7.16-7.26 (7H, m), 7.38 (2H, d, J = 8.1 Hz), 8.23 (1H, d, J = 7.7 Hz), 8.28 (2H, s), 8.48 (1H, d, J = 8.6 Hz), 8.54 (1H, t, J = 6.0 Hz). |
| 75 | d⁶-DMSO | δ: 0.96-1.15 (5H, m), 1.20 (3H, t, J = 7.0 Hz), 1.36-1.55 (5H, m), 1.96-2.01 (1H, m), 2.34-2.41 (1H, m), 2.51-2.56 (1H, m), 2.67-2.73 (1H, m), 2.92-2.97 (1H, m), 3.86 (2H, q, J = 7.0 Hz), 3.90 (2H, s), 4.15-4.24 (2H, m), 4.27-4.32 (1H, m), 4.41-4.47 (1H, m), 6.64 (2H, d, J = 8.6 Hz), 6.88 (2H, d, J = 8.6 Hz), 7.08-7.18 (7H, m), 7.30 (2H, d, J = 8.1 Hz), 7.66 (1H, d, J = 8.0 Hz), 8.17 (2H, s), 8.29 (1H, d, J = 8.5 Hz), 8.51 (1H, t, J = 6.0 Hz). |
| 76 | d⁶-DMSO | δ: 0.78 (3H, t, J = 7.3 Hz), 0.99-1.05 (2H, m), 1.12-1.21 (2H, m), 1.26-1.36 (5H, m), 1.91-2.03 (2H, m), 2.38-2.44 (1H, m), 2.56-2.61 (1H, m), 2.74-2.80 (1H, m), 2.99-3.04 (1H, m), 3.93 (2H, q, J = 7.0 Hz), 3.97 (2H, s), 4.23-4.33 (2H, m), 4.39-4.44 (1H, m), 4.50-4.56 (1H, m), 6.72 (2H, d, J = 8.6 Hz), 6.98 (2H, d, J = 8.6 Hz), 7.15-7.26 (7H, m), 7.38 (2H, d, J = 8.1 Hz), 7.88 (1H, d, J = 8.0 Hz), 8.22 (2H, s), 8.42 (1H, d, J = 8.6 Hz), 8.58 (1H, t, J = 6.0 Hz). |
| 77 | d⁶-DMSO | δ: 0.93 (3H, d, J = 4.2 Hz), 0.95 (3H, d, J = 4.1 Hz), 1.28 (3H, t, J = 7.0 Hz), 2.41 (1H, dd, J = 13.7, 8.0 Hz), 2.58 (1H, dd, J = 13.8, 4.7 Hz), 2.77 (1H, dd, J = 13.6, 10.5 Hz), 3.06 (1H, dd, J = 13.7, 4.2 Hz), 3.50-3.58 (1H, m), 3.70-4.01 (4H, m), 4.25-4.30 (3H, m), 4.41-4.47 (1H, m), 5.82 (1H, d, J = 7.6 Hz), 5.99 (1H, d, J = 7.6 Hz), 6.67 (2H, d, J = 8.6 Hz), 6.76 (2H, d, J = 8.6 Hz), 7.16-7.26 (7H, m), 7.39 (2H, d, J = 8.1 Hz), 8.37 (2H, br s), 8.46 (1H, d, J = 8.5 Hz), 8.65 (1H, t, J = 6.0 Hz). |
| 78 | d⁶-DMSO | δ: 0.83 (3H, t, J = 7.0 Hz), 1.16-1.30 (11H, m), 2.41 (1H, dd, J = 13.8, 8.0 Hz), 2.59 (1H, dd, J = 13.6, 4.6 Hz), 2.77 (1H, dd, J = 13.7, 10.5 Hz), 2.83-2.90 (2H, m), 3.05 (1H, dd, J = 13.7, 4.2 Hz), 3.93 (2H, q, J = 7.0 Hz), 3.95 (2H, m), 4.26-4.32 (3H, m), 4.42-4.46 (1H, m), 5.91 (1H, d, J = 7.6 Hz), 6.09 (1H, t, J = 5.6 Hz), 6.67 (2H, d, J = 8.7 Hz), 6.76 (2H, d, J = 8.6 Hz), 7.16-7.26 (7H, m), 7.39 (2H, d, J = 8.1 Hz), 8.35 (2H, br s), 8.45 (1H, d, J = 8.5 Hz), 8.65 (1H, t, J = 6.0 Hz). |
| 79 | d⁶-DMSO | δ: 1.34 (3H, t, J = 7.0 Hz), 2.65-2.79 (2H, m), 2.85-2.91 (1H, m), 3.09-3.13 (1H, m), 3.99 (2H, q, J = 7.0 Hz), 4.04 (2H, s), 4.32-4.42 (2H, m), 4.65-4.73 (2H, m), 6.80 (2H, d, J = 8.6 Hz), 7.15 (2H, d, J = 1.9 Hz), 7.16 (1H, s), 7.22-7.34 (7H, m), 7.44 (2H, d, J = 8.1 Hz), 8.29 (2H, s), 8.68-8.72 (2H, m), 8.77 (1H, d, J = 1.8 Hz), 8.96 (1H, d, J = 8.6 Hz). |
| 80 | d⁶-DMSO | δ: 1.26 (3H, t, J = 7.0 Hz), 2.61-2.72 (2H, m), 2.79-2.84 (1H, m), 3.02-3.07 (1H, m), 3.92 (2H, q, J = 7.0 Hz), 3.96 (2H, s), 4.25-4.37 (2H, m), 4.56-4.63 (2H, m), 6.75 (2H, d, J = 8.6 Hz), 7.14 (2H, d, J = 8.6 Hz), 7.16-7.25 (7H, m), 7.37 (2H, d, J = 8.1 Hz), 7.42 (2H, d, J = 8.2 Hz), 7.85-7.88 (2H, m), 8.21 (2H, s), 8.56-8.64 (3H, m). |
| 81 | d⁶-DMSO | δ: 1.25 (3H, t, J = 7.0 Hz), 2.68 (1H, m), 2.78-2.85 (2H, m), 3.06 (1H, dd, J = 13.6, 4.4 Hz), 3.86-4.01 (4H, m), 4.28 (2H, d, J = 6.0 Hz), 4.50-4.56 (1H, m), 4.74-4.79 (1H, m), 6.59 (2H, d, J = 8.7 Hz), 6.65 (2H, d, J = 8.8 Hz), 7.17-7.38 (8H, m), 7.59-7.61 (1H, m), 7.96-7.99 (2H, m), 8.33 (3H, br s), 8.48 (1H, d, J = 8.2 Hz), 8.61 (1H, dt, J = 4.7, 1.2 Hz), 8.66 (1H, t, J = 6.0 Hz), 8.71 (1H, d, J = 8.5 Hz). |
| 82 | d⁶-DMSO | δ: 1.27 (3H, t, J = 6.9 Hz), 2.13 (3H, s), 2.57-2.69 (2H, m), 2.82 (1H, dd, J = 13.6, 10.0 Hz), 3.05 (1H, dd, J = 13.6, 4.7 Hz), 3.78 (3H, s), 3.91 (2H, q, J = 7.0 Hz), 3.92-3.99 (2H, m), 4.25-4.36 (2H, m), 4.50-4.62 (2H, m), 6.63 (1H, s), 6.74 (2H, d, J = 8.6 Hz), 7.11 (2H, d, J = 8.7 Hz), 7.17-7.25 (7H, m), 7.37 (2H, d, J = 8.2 Hz), 8.25 (2H, br s), 8.35 (1H, d, J = 8.4 Hz), 8.55 (1H, d, J = 8.6 Hz), 8.60 (1H, t, J = 6.0 Hz). |
| 83 | d⁶-DMSO | δ: 1.25 (3H, t, J = 7.0 Hz), 2.61-2.70 (2H, m), 2.82 (1H, dd, J = 13.5, 10.1 Hz), 3.05 (1H, dd, J = 13.6, 4.7 Hz), 3.91 (2H, q, J = 7.0 Hz), 3.94 (2H, s), 4.25-4.35 (2H, m), 4.58-4.64 (2H, m), 6.75 (2H, d, J = 8.6 Hz), 7.14-7.25 (9H, m), 7.38 (2H, d, J = 8.2 Hz), 7.42-7.45 (2H, m), 7.93-7.99 (2H, m), 8.18 (1H, s), 8.27 (2H, br s), 8.63-8.67 (2H, m), 8.84 (1H, d, J = 8.4 Hz). |
| 84 | d⁶-DMSO | δ: 1.31 (3H, t, J = 7.0 Hz), 2.21-2.27 (1H, m), 2.35-2.39 (1H, m), 2.67-2.72 (1H, m), 2.90-2.95 (1H, m), 3.94 (2H, q, J = 7.0 Hz), 3.99 (3H, s), 4.22-4.27 (1H, m), 4.38-4.44 (1H, m), 4.49-4.55 (1H, m), 6.63 (2H, d, J = 8.6 Hz), |

TABLE 7-continued

NMR data of examples

| Example No | Solvent | NMR (ppm) |
|---|---|---|
| | | 6.93 (2H, d, J = 8.6 Hz), 7.13-7.25 (7H, m), 7.31-7.34 (2H, m), 7.38-7.42 (4H, m), 8.10 (1H, s), 8.20 (2H, s), 8.48 (1H, d, J = 8.8 Hz), 8.56 (1H, t, J = 6.0 Hz). |
| 85 | d$^6$-DMSO | δ: 1.30 (3H, t, J = 6.96 Hz), 2.38-2.42 (1H, m), 2.58-2.62 (1H, m), 2.73-2.79 (1H, m), 2.99-3.03 (1H, m), 3.91-3.95 (4H, m), 4.24-4.25 (2H, m), 4.41-4.46 (1H, m), 4.51-4.57 (1H, m), 6.67 (2H, d, J = 8.69 Hz), 6.89 (2H, d, J = 8.64 Hz), 7.07 (2H, d, J = 1.8 Hz), 7.17-7.25 (10H, m), 7.37 (2H, t, J = 8.08 Hz), 8.14 (1H, t, J = 8.12 Hz), 8.26 (3H, s, br), 8.49 (1H, d, J = 8.57 Hz), 8.56-8.59 (1H, m). |
| 86 | d$^6$-DMSO | δ: 1.28 (3H, t, J = 6.92 Hz), 2.26-2.35 (2H, m), 2.39-2.45 (1H, m), 2.49 (2H, s), 2.56-2.65 (2H, m), 2.74-2.80 (1H, m), 3.00-3.05 (1H, m), 3.93-3.96 (3H, m), 4.25-4.32 (2H, m), 4.41-4.46 (1H, m), 4.49-4.55 (1H, m), 6.70 (2H, d, J = 8.48 Hz), 6.92 (2H, d, J = 8.48 Hz), 7.08 (2H, d, J = 7.16 Hz), 7.18-7.24 (10H, m), 7.38 (2H, t, J = 8.0 Hz), 8.00 (1H, d, J = 8.00 Hz), 8.28 (3H, s, br), 8.46 (1H, d, J = 8.48 Hz), 8.57 (1H, t, J = 5.92 Hz). |
| 87 | d$^6$-DMSO | δ: 1.28 (3H, t, J = 6.92 Hz), 1.51-1.58 (2H, m), 1.73-1.86 (2H, m), 2.39-2.45 (2H, m), 2.49 (2H, s), 2.56-2.65 (2H, m), 2.95-3.03 (1H, m), 3.86-3.97 (4H, m), 4.29-4.34 (3H, m), 4.47-4.53 (1H, m), 6.66 (2H, d, J = 8.21 Hz), 6.96 (2H, d, J = 8.17 Hz), 7.17-7.34 (10H, m), 7.36-7.40 (2H, m), 8.02-8.11 (1H, m), 8.26 (3H, s, br), 8.34-8.56 (2H, m). |
| 88 | d$^6$-DMSO | δ: 1.33 (3H, t, J = 6.93 Hz), 2.71-2.75 (2H, m), 2.86-2.92 (1H, m), 3.09-3.14 (1H, m), 3.98-4.03 (4H, m), 4.32-4.43 (2H, m), 4.63-4.69 (2H, m), 6.82 (2H, d, J = 8.52 Hz), 7.21 (2H, d, J = 8.68 Hz), 7.27-7.31 (7H, m), 7.44 (2H, d, J = 8.07 Hz), 7.51-7.54 (1H, m), 7.63-7.65 (1H, m), 7.77 (1H, d, J = 7.84 Hz), 7.86 (1H, d, J = 1.68 Hz), 8.35 (3H, s, br), 8.63-8.74 (3H, m). |
| 89 | d$^6$-DMSO | δ: 1.29 (3H, t, J = 6.88 Hz), 2.52-2.58 (1H, m), 2.71-2.79 (1H, m), 2.81-2.84 (1H, m), 3.02-3.07 (1H, m), 3.95-3.98 (4H, m), 4.24-4.36 (2H, m), 4.58-4.63 (2H, m), 6.76 (2H, d, J = 8.56 Hz), 7.08 (2H, d, J = 8.56 Hz), 7.14-7.25 (9H, m), 7.33-7.43 (4H, m), 8.285 (3H, s, br), 8.47 (2H, t, J = 7.84 Hz), 8.62 (1H, t, J = 5.764 Hz). |
| 90 | d$^6$-DMSO | δ: 1.26 (3H, t, J = 6.89 Hz), 2.61-2.74 (2H, m), 2.79-2.85 (1H, m), 3.02-3.07 (1H, m), 3.91-3.96 (4H, m), 4.25-4.36 (2H, m), 4.58-4.67 (2H, m), 6.74 (2H, d, J = 8.56 Hz), 7.15-7.24 (9H, m), 7.37 (2H, d, J = 8.12 Hz), 7.68 (1H, t, J = 7.80 Hz), 7.87 (1H, d, J = 7.89 Hz), 8.03 (1H, d, J = 7.89 Hz), 8.09 (1H, s) 8.28 (3H, s, br), 8.48-8.65 (2H, m), 8.82 (1H, d, J = 8.28 Hz). |
| 91 | d$^6$-DMSO | δ: 1.27 (3H, t, J = 6.88 Hz), 1.55-1.61 (11H, m), 1.89 (2H, s), 2.49 (2H, s), 2.62-2.72 (2H, m), 2.79-2.84 (1H, m), 3.01-3.05 (1H, m), 3.91-3.96 (4H, m), 4.23-4.39 (3H, m), 4.49-4.54 (1H, m), 6.69 (2H, d, J = 8.36 Hz), 6.88 (2H, d, J = 8.37 Hz), 7.19-7.25 (8H, m), 7.39 (2H, d, J = 7.84 Hz), 8.32-8.38 (3H, m), 8.65-8.68 (1H, m). |
| 92 | d$^6$-DMSO | δ: 1.26 (3H, t, J = 6.93 Hz), 2.32 (3H, s), 2.67 (2H, d, J = 7.20 Hz), 2.78-2.84 (1H, m), 3.02-3.07 (1H, m), 3.91-3.97 (4H, m), 4.27-4.36 (2H, m), 4.57-4.60 (2H, m), 6.73 (2H, d, J = 8.57 Hz), 7.12 (2H, d, J = 8.57 Hz), 7.21-7.24 (9H, m), 7.36 (2H, t, J = 8.08 Hz), 7.65 (2H, t, J = 8.17 Hz), 8.25 (3H, s, br), 8.37 (1H, d, J = 8.08 Hz), 8.54 (1H, d, J = 8.60 Hz), 8.59-8.62 (1H, m). |
| 93 | d$^6$-DMSO | δ: 1.33 (3H, t, J = 6.97 Hz), 2.67-2.79 (2H, m), 2.86-2.91 (1H, m), 3.093-3.14 (1H, m), 3.98-4.04 (4H, m), 4.32-4.44 (2H, m), 4.63-4.70 (2H, m), 6.81 (2H, d, J = 8.57 Hz), 7.21 (2H, d, J = 8.60 Hz), 7.27-7.32 (8H, m), 7.44 (2H, d, J = 8.08 Hz), 7.79 (2H, s), 8.06 (1H, s), 8.38 (3H, s, br), 8.63-8.70 (1H, m), 8.83 (1H, d, J = 8.28 Hz). |
| 94 | d$^6$-DMSO | δ: 1.26 (3H, t, J = 6.93 Hz), 2.61-2.71 (2H, m), 2.71-2.84 (1H, m), 3.02-3.06 (1H, m), 3.92-3.96 (4H, m), 4.25-4.35 (2H, m), 4.57-4.64 (2H, m), 6.75 (2H, d, J = 8.64 Hz), 7.14 (2H, d, J = 8.56 Hz), 7.21-7.25 (8H, m), 7.36 (2H, d, J = 8.08 Hz), 7.76-7.79 (3H, m), 8.24 (3H, s, br), 8.59 (1H, t, J = 6.32 Hz), 8.78 (1H, d, J = 8.24 Hz). |
| 95 | d$^6$-DMSO | δ: 1.26 (3H, t, J = 6.97 Hz), 2.65-2.69 (2H, m), 2.79-2.84 (1H, m), 3.03-3.07 (1H, m), 3.797 (3H, s), 3.91-3.95 (4H, m), 4.25-4.34 (2H, m), 4.53-4.59 (2H, m), 6.73 (2H, d, J = 8.57 Hz), 6.95 (2H, d, J = 8.88 Hz), 7.13 (2H, d, J = 8.64 Hz), 7.18-7.24 (7H, m), 7.37 (2H, d, J = 8.12Hz), 7.74 (2H, t, J = 8.85 Hz), 8.29 (3H, s, br), 8.34 (1H, d, J = 8.60 Hz), 8.54 (1H, d, J = 8.60 Hz), 8.61 (1H, t, J = 5.96 Hz). |
| 96 | d$^6$-DMSO | δ: 1.27 (3H, t, J = 6.92 Hz), 2.61-2.66 (2H, m), 2.76-2.82 (1H, m), 3.01-3.06 (1H, m), 3.90-3.95 (4H, m), 4.28-4.31 (2H, m), 4.52-4.62 (2H, m), 6.67-6.73 (3H, m), 6.97 (2H, d, J = 8.53 Hz), 7.18-7.27 (10H, m), 7.35-7.41 (3H, m), 7.50 (2H, d, J = 6.73 Hz), 8.21 (4H, d, J = 8.00 Hz), 8.59 (2H, t, J = 7.24 Hz). |
| 97 | d$^6$-DMSO | δ: 1.28 (3H, t, J = 6.88 Hz), 2.40-2.46 (1H, m), 2.59-2.64 (1H, m), 2.73-2.79 (1H, m), 2.98-3.03 (1H, m), 3.43 (2H, s), 3.51-3.57 (1H, m), 3.67-3.73 (1H, m), 3.92-3.97 (4H, m), 4.24-4.33 (2H, m), 4.43-4.54 (2H, m), 6.68 (2H, d, J = 8.56 Hz), 6.88 (2H, d, J = 8.57 Hz), 7.20-7.26 (12H, m), 7.37 (2H, d, J = 8.08 Hz), 7.96 (1H, d, J = 8.21 Hz), 8.20-8.27 (4H, m), 8.47 (1H, d, J = 8.50 Hz), 8.57 (1H, t, J = 5.97 Hz). |

TABLE 7-continued

NMR data of examples

| Example No | Solvent | NMR (ppm) |
|---|---|---|
| 98 | d⁶-DMSO | δ: 1.27 (3H, t, J = 6.93 Hz), 2.47-2.49 (1H, m), 2.62-2.66 (1H, m), 2.76-2.82 (1H, m), 3.01-3.06 (1H, m), 3.72-3.77 (1H, m), 3.85-3.91 (3H, m), 3.94-3.98 (2H, m), 4.26-4.30 (2H, m), 4.44-4.54 (2H, m), 6.61 (2H, d, J = 8.64 Hz), 6.83 (2H, d, J = 8.60 Hz), 7.18 (2H, d, J = 8.05 Hz), 7.26-7.27 (5H, m), 7.36 (2H, d, J = 8.12 Hz), 7.46 (2H, d, J = 7.68 Hz), 7.51-7.55 (1H, m), 7.84 (2H, t, J = 7.126 Hz), 7.92 (1H, d, J = 8.08 Hz), 8.30 (3H, s, br), 8.50 (1H, d, J = 8.53 Hz), 8.57 (1H, t, J = 5.93 Hz), 8.73 (1H, t, J = 5.84). |
| 99 | d⁶-DMSO | δ: 1.26 (3H, t, J = 6.93 Hz), 2.65-2.67 (2H, m), 2.78-2.84 (1H, m), 3.03-3.07 (1H, m), 3.91-3.96 (4H, m), 4.25-4.36 (2H, m), 4.55-4.61 (2H, m), 6.74 (2H, d, J = 8.60 Hz), 7.14 (2H, d, J = 8.64 Hz), 7.21-7.28 (9H, m), 7.36 (2H, d, J = 8.12 Hz), 7.80-7.83 (2H, m), 8.23 (3H, s, br), 8.53-8.583 (3H, m). |
| 100 | d⁶-DMSO | δ: 1.36 (3H, t, J = 7.0 Hz), 2.50-2.56 (1H, m), 2.59-2.63 (1H, m), 2.82-2.88 (1H, m), 3.02-3.07 (1H, m), 3.79-3.85 (1H, m), 3.97 (2H, s), 4.03 (2H, q, J = 7.0 Hz), 4.16-4.21 (2H, m), 4.32 (2H, d, J = 5.8 Hz), 4.63-4.69 (1H, m), 6.87 (2H, d, J = 8.6 Hz), 7.15 (2H, d, J = 8.6 Hz), 7.20-7.35 (14H, m), 7.47-7.57 (1H, m), 7.73-7.81 (2H, m), 8.61-8.66 (2H, m). |
| 101 | d⁶-DMSO | δ: 1.28 (3H, t, J = 6.92 Hz), 2.36 (3H, s), 2.38-2.42 (1H, m), 2.56-2.60 (1H, m), 2.73-2.78 (1H, m), 2.98-3.03 (1H, m), 3.23-3.28 (1H, m), 3.92-3.98 (4H, m), 4.27-4.32 (2H, m), 4.41-4.46 (1H, m), 4.49-4.55 (1H, m), 6.66 (2H, d, J = 8.61 Hz), 6.79 (2H, d, J = 8.60 Hz), 7.20 (2H, d, J = 6.21 Hz), 7.26-7.29 (6H, m), 7.32-7.40 (4H, m) 7.62 (2H, d, J = 8.28 Hz), 7..80-7.88 (2H, m), 8.29 (3H, s, br), 8.52 (1H, d, J = 8.52 Hz), 8.59-8.62 (1H, m). |
| 102 | d⁶-DMSO | δ: 1.27 (3H, t, J = 7.0 Hz), 2.42-2.47 (1H, m), 2.64-2.69 (1H, m), 2.75-2.81 (1H, m), 3.04-3.08 (1H, m), 3.92 (2H, q, J = 7.0 Hz), 3.96 (2H, s), 4.28 (2H, d, J = 5.8 Hz), 4.43-4.53 (2H, m), 6.23 (1H, d, J = 7.7 Hz), 6.65 (4H, s), 7.17-7.23 (5H, m), 7.26-7.36 (8H, m), 8.19 (2H, s), 8.63-8.65 (1H, m), 8.91 (1H, s). |
| 103 | d⁶-DMSO | δ: 1.26 (3H, t, J = 6.93 Hz), 1.31-1.43 (7H, m), 2.68 (2H, d, J = 7.47 Hz), 2.79-2.84 (1H, m), 3.02-3.07 (1H, m), 3.90-3.95 (2H, m), 4.06 (2H, d, J = 6.40 Hz), 4.25-4.32 (2H, m), 4.56-4.63 (2H, m), 6.75 (2H, d, J = 8.52 Hz), 7.13-7.22 (12H, m), 7.32-7.35 (1H, m), 7.40-7.43 (2H, m), 7.59-7.63 (1H, m), 7.74 (2H, d, J = 7.90 Hz), 8.45-8.52 (3H, m). |
| 104 | d⁶-DMSO | δ: 1.26 (3H, t, J = 6.93 Hz), 2.65-2.75 (2H, m + 3H, s), 2.82-2.86 (1H, m), 3.04-3.08 (1H, m), 3.91-3.96 (4H, m), 4.24-4.36 (2H, m), 4.57-4.69 (2H, m), 6.73 (2H, d, J = 8.52 Hz), 7.14 (2H, d, J = 8.68 Hz), 7.17-7.24 (6H, m), 7.39 (2H, d, J = 8.07 Hz), 7.79 (1H, d, J = 7.84 Hz), 8.44 (3H, s, br), 8.49-8.52 (1H, m), 8.65-8.69 (2H, m), 9.00 (1H, d, J = 1.68 Hz), 9.14 (1H, d, J = 1.68 Hz). |
| 105 | d⁶-DMSO | δ: 1.29 (3H, t, J = 6.93 Hz), 2.42 (3H, s), 2.75-2.86 (3H, m), 3.05-3.09 (1H, m), 3.95-3.97 (4H, m), 4.25-4.37 (2H, m), 4.61-4.74 (2H, m), 6.78 (2H, d, J = 8.52 Hz), 7.09 (2H, d, J = 8.68 Hz), 7.21-7.27 (6H, m), 7.40 (2H, d, J = 8.07 Hz), 7.76-7.80 (1H, m), 8.07-8.13 (1H, m), 8.42 (3H, s, br), 8.67-8.73 (3H, m), 8.94 (1H, d, J = 1.68 Hz). |
| 106 | d⁶-DMSO | δ: 1.13 (3H, t, J = 6.93 Hz), 2.70-2.84 (3H, m), 3.01-3.06 (1H, m), 3.95-3.98 (4H, m), 4.24-4.36 (2H, m), 4.59-4.69 (2H, m), 6.76 (2H, d, J = 8.52 Hz), 7.04 (2H, d, J = 8.68 Hz), 7.16-7.26 (6H, m), 7.38 (2H, d, J = 8.07 Hz), 7.61 (1H, s), 8.33 (3H, s, br), 8.58-8.60 (1H, m), 8.64-8.67 (1H, m), 8.78 (1H, d, J = 1.68 Hz). |
| 107 | d⁶-DMSO | δ: 1.24 (3H, t, J = 6.93 Hz), 2.56-2.62 (1H, m), 2.69-2.73 (1H, m), 2.78-2.84 (1H, m), 3.02-3.07 (1H, m), 3.89-3.95 (4H, m), 4.24-4.37 (2H, m), 4.58-4.67 (2H, m), 6.75 (2H, d, J = 8.52 Hz), 7.13 (2H, d, J = 8.68 Hz), 7.16-7.25 (8H, m), 7.36 (2H, d, J = 8.07 Hz), 8.26 (3H, s, br), 8.59-8.64 (1H, m), 8.65 (1H, d, J = 1.68 Hz), 8.94 (1H, d, J = 1.68 Hz). |
| 108 | d⁶-DMSO | δ: 1.28 (3H, t, J = 6.93 Hz), 2.69-2.82 (2H, m), 3.02-3.09 (2H, m), 3.92-3.98 (4H, m), 4.26-4.33 (2H, m), 4.59-4.62 (2H, m), 6.74 (2H, d, J = 8.52 Hz), 6.98 (2H, d, J = 8.68 Hz), 7.23-7.29 (7H, m), 7.37-7.40 (2H, m), 8.05 (1H, s, br), 8.23 (3H, s, br), 8.65-8.69 (1H, m), 8.85 (1H, d, J = 1.68 Hz). |
| 109 | d⁶-DMSO | δ: 1.28 (3H, t, J = 6.93 Hz), 2.36-2.40 (1H, m), 2.59-2.63 (1H, m), 2.73-2.79 (1H, m), 3.00-3.03 (1H, m), 3.19-3.27 (1H, m), 3.91-3.97 (4H, m), 4.28-4.36 (2H, m), 4.52-4.54 (2H, m), 6.68 (2H, d, J = 8.52 Hz), 6.84 (2H, d, J = 8.68 Hz), 7.19-7.24 (7H, m), 7.38 (2H, d, J = 8.07 Hz), 8.35 (3H, s, br), 8.59-8.63 (2H, m). |
| 110 | d⁶-DMSO | δ: 1.26 (3H, t, J = 6.93 Hz), 2.47 (3H, s), 2.49-2.50 (1H, m), 2.59-2.63 (1H, m), 2.69-2.74 (1H, m), 3.02-3.07 (1H, m), 3.91-3.95 (4H, m), 4.28-4.37 (2H, m), 4.57-4.66 (2H, m), 4.79-4.80 (2H, m), 6.74 (2H, d, J = 8.52 Hz), 7.14 (2H, d, J = 8.68 Hz), 7.16-7.23 (6H, m), 7.38 (2H, d, J = 8.07 Hz), 7.55 (2H, d, J = 7.84 Hz), 8.40 (2H, s, br), 8.63-8.67 (1H, m), 8.91 (1H, d, J = 1.68 Hz). |
| 111 | d⁶-DMSO | δ: 1.27 (3H, t, J = 6.93 Hz), 2.30 (3H, s), 2.59 (3H, s), 2.61-2.72 (2H, m), 2.79-2.84 (1H, m), 3.04-3.09 (1H, m), 3.91-3.96 (4H, m), 4.29-4.35 (2H, m), 4.50-4.60 (2H, m), 6.73 (2H, d, J = 8.52 Hz), 7.03 (2H, d, J = 8.68 Hz), 7.15-7.27 (7H, m), 7.39 (2H, d, J = 8.07 Hz), 8.07 (1H, d, J = 7.84 Hz), 8.42 (2H, s, br), 8.62-8.66 (2H, m). |

TABLE 7-continued

NMR data of examples

| Example No | Solvent | NMR (ppm) |
|---|---|---|
| 112 | d$^6$-DMSO | δ: 1.26 (3H, t, J = 6.93 Hz), 2.66 (3H, s), 2.77-2.84 (3H, m), 3.03-3.08 (1H, m), 3.87-3.97 (4H, m), 4.28 (2H, d), 4.49-4.55 (1H, m), 4.70-4.75 (1H, m), 6.61 (2H, d, J = 8.52 Hz), 6.67 (2H, d, J = 8.68 Hz), 7.19-7.30 (7H, m), 7.38 (2H, d, J = 8.07 Hz), 7.89 (1H, d, J = 7.84 Hz), 8.06 (1H, s), 8.41 (2H, s, br), 8.65-8.70 (2H, m). |
| 113 | d$^6$-DMSO | δ: 1.27 (3H, t, J = 6.93 Hz), 2.36 (3H, s), 2.45 (3H, s), 2.63-2.68 (1H, m), 2.75-2.84 (2H, m), 3.04-3.08 (1H, m), 3.88-3.96 (4H, m), 4.29 (2H, d), 4.48-4.54 (1H, m), 4.64-4.69 (1H, m), 6.62 (2H, d, J = 8.52 Hz), 6.65 (2H, d, J = 8.68 Hz), 7.17-7.24 (6H, m), 7.39 (2H, d, J = 8.07 Hz), 7.54 (1H, d, J = 7.84 Hz), 8.40 (3H, s, br), 8.64-8.66 (2H, m). |
| 114 | d$^6$-DMSO | δ: 1.26 (3H, t, J = 7.07 Hz), 2.09 (3H, s), 2.67-2.77 (2H, m), 2.78-2.88 (1H, m), 3.05-3.09 (1H, m), 3.92-3.97 (4H, m), 4.31-4.40 (2H, m), 4.59-4.63 (1H, m), 4.64-4.74 (1H, m), 6.77 (2H, d, J = 8.34 Hz), 7.17-7.29 (10H, m), 7.39 (2H, d, J = 8.36 Hz), 7.87 (1H, d, J = 8.55 Hz), 8.26-8.36 (4H, m), 8.62 (1H, s), 8.68-8.71 (2H, m), 8.88-8.95 (1H, m). |
| 115 | d$^6$-DMSO | δ: 1.26 (3H, t, J = 6.36 Hz), 2.66-2.87 (3H, m), 3.05-3.10 (1H, m), 3.92-3.97 (4H, m), 4.31-4.38 (2H, m), 4.38-4.40 (2H, m), 4.59-4.63 (1H, m), 4.69-4.75 (1H, m), 6.77 (2H, d, J = 7.95 Hz), 7.14 (2H, d, J = 7.95 Hz), 7.16-7.23 (6H, m), 7.38 (2H, d, J = 7.82 Hz), 7.55 (2H, d, J = 7.95 Hz), 7.74 (1H, d, J = 11.13 Hz), 8.40 (3H, s, br), 8.63-8.67 (1H, m), 8.91 (1H, d, J = 2.69 Hz), 9.05 (1H, J = 8.68 Hz), 9.20 (1H, d, J = 2.2 Hz). |
| 116 | d$^6$-DMSO | δ: 1.28 (3H, t, J = 6.57 Hz), 2.61-2.67 (1H, m), 2.79-2.85 (2H, m), 3.08-3.12 (1H, m), 3.92-3.98 (4H, m), 4.31 (2H, d, J = 6.57 Hz), 4.53-4.58 (1H, m), 4.67-4.71 (1H, m), 6.66 (2H, d, J = 8.09 Hz), 6.74 (2H, d, J = 8.23 Hz), 7.14 (1H, d, J = 5.47 Hz), 7.22-7.25 (2H, m), 7.30-7.35 (4H, m), 7.39 (2H, d, J = 8.09 Hz), 7.82 (1H, d, J = 7.66 Hz), 7.86 (1H, d, J = 5.47 Hz), 8.35 (3H, s, br), 8.69 (1H, t, J = 6.57 Hz), 8.76 (1H, d, J = 8.21 Hz). |
| 117 | d$^6$-DMSO | δ: 1.28 (3H, t, J = 7.0 Hz), 2.38 (3H, s), 2.62 (1H, d, J = 10.3 Hz), 2.70 (1H, dd, J = 14.3 Hz, 4.2 Hz), 2.82 (1H, dd, J = 13.5 Hz, 10.1 Hz), 3.07 (1H, dd, J = 13.6 Hz, 4.5 Hz), 3.95 (2H, q, J = 7.0 Hz), 3.98 (2H, d, J = 4.8 Hz), 4.26-4.37 (2H, m), 4.52-4.62 (2H, m), 6.75 (2H, d, J = 8.7 Hz), 7.07 (2H, d, J = 8.6 Hz), 7.18-7.12 (1H, m), 7.23-7.28 (6H, m), 7.38 (2H, d, J = 8.1 Hz), 8.21 (1H, d, J = 8.3 Hz), 8.26 (2H, br.s), 8.62 (2H, d, J = 7.6 Hz), 9.01 (1H, s) |
| 118 | d$^6$-DMSO | δ: 1.27 (3H, t, J = 7.0 Hz), 2.64-2.67 (2H, m), 2.81 (1H, dd, J = 13.5 Hz, 10.1 Hz), 3.04 (1H, dd, J = 13.5 Hz, 4.6 Hz), 3.93 (2H, q, J = 7.0 Hz), 3.97 (2H, d, J = 5.4 Hz), 4.30 (2H, dd, J = 5.5 Hz, 3.5 Hz), 4.54-4.63 (2H, m), 6.60 (1H, dd, J = 3.5 Hz, 1.9 Hz), 6.7 (2H, d, J = 8.6 Hz), 7.01 (2H, d, J = 8.6 Hz), 7.11 (1H, d, J = 3.5 Hz), 7.16-7.28 (7H, m), 7.38 (2H, d, J = 8.1 Hz), 7.81 (1H, d, J = 1.1 Hz), 8.18 (1H, d, J = 8.4 Hz), 8.28 (2H, br.s), 8.60 (1H, d, J = 8.6 Hz), 8.64 (1H, t, J = 6.0 Hz) |
| 119 | d$^6$-DMSO | δ: 1.28 (3H, t, J = 6.9 Hz), 2.22 (3H, s), 2.65 (1H, dd, J = 13.6 Hz, 9.3 Hz), 2.72 (1H, dd, J = 13.8 Hz, 4.2 Hz), 2.82 (1H, dd, J = 13.5 Hz, 10.2 Hz), 3.08 (1H, dd, J = 13.5 Hz, 4.5 Hz), 3.94 (2H, q, J = 7.0 Hz), 3.98 (2H, br.s), 4.31 (2H, d, J = 5.8 Hz), 4.52-4.59 (2H, m), 6.73 (2H, d, J = 8.6 Hz), 6.91 (1H, d, J = 5.0 Hz), 6.98 (2H, d, J = 8.6 Hz), 7.18-7.21 (1H, m), 7.23-7.30 (6H, m), 7.38 (2H, d, J = 7.9 Hz), 7.55 (1H, d, J = 5.0 Hz), 7.72 (1H, d, J = 7.8 Hz), 8.23 (2H, br.s), 8.62 (2H, d, J = 9.6 Hz) |
| 120 | d$^6$-DMSO | δ: 1.27 (3H, t, J = 7.0 Hz), 2.70-2.75 (1H, m), 2.80-2.86 (2H, m), 3.07-3.11 (1H, m), 3.88 (3H, s), 3.92 (2H, q, J = 6.9 Hz), 3.97 (2H, q, J = 5.7 Hz), 4.31 (2H, d, J = 6.1 Hz), 4.52-4.58 (1H, m), 4.67-4.72 (1H, m), 6.65 (2H, d, J = 8.6 Hz), 6.76 (2H, d, J = 8.4 Hz), 7.02-7.04 (1H, m), 7.21-7.34 (7H, m), 7.37 (2H, d, J = 8.1 Hz), 7.53-7.55 (1H, m), 7.85-7.88 (1H, m), 8.23 (2H, s), 8.27 (1H, d, J = 8.1 Hz), 8.67 (1H, t, J = 5.9 Hz), 8.71 (1H, d, J = 8.4 Hz). |
| 121 | d$^6$-DMSO | δ: 1.28 (3H, t, J = 6.9 Hz), 2.66-2.75 (2H, m), 2.80-2.86 (1H, m), 3.03-3.08 (1H, m), 3.87 (3H, s), 3.91-4.00 (4H, m), 4.30-4.38 (2H, m), 4.59-4.68 (2H, m), 6.77 (2H, d, J = 8.6 Hz), 7.16 (1H, s), 7.18-7.21 (2H, m), 7.23-7.27 (6H, m), 7.38 (2H, d, J = 8.2 Hz), 7.70 (1H, t, J = 4.2 Hz), 8.24 (2H, s), 8.44 (1H, d, J = 2.9 Hz), 8.51 (1H, d, J = 1.6 Hz),, 8.62-8.64 (2H, m), 8.79 (1H, d, J = 8.4 Hz). |
| 122 | d$^6$-DMSO | δ: 1.29 (3H, t, J = 7.0 Hz), 2.56-2.62 (1H, m), 2.73-2.84 (2H, m), 3.07-3.11 (1H, m), 3.89 (3H, s), 3.94 (2H, q, J = 7.0 Hz), 3.98 (2H, s), 4.30 (2H, d, J = 6.0 Hz), 4.49-4.55 (1H, m), 4.65-4.70 (1H, m), 6.67 (4H, s), 7.11 (1H, d, J = 5.4 Hz), 7.20-7.25 (3H, m), 7.29-7.35 (4H, m), 7.37 (2H, d, J = 8.1 Hz), 7.47 (1H, d, J = 7.4 Hz), 7.72 (1H, d, J = 5.5 Hz), 8.18 (2H, s), 8.63 (1H, t, J = 6.0 Hz), 8.67 (1H, d, J = 8.5 Hz). |
| 123 | d$^6$-DMSO | δ: 1.28 (3H, t, J = 7.0 Hz), 2.58-2.70 (2H, m), 2.79-2.85 (1H, m), 3.03-3.08 (1H, m), 3.87 (3H, s), 3.93 (2H, q, J = 7.0 Hz), 3.99 (2H, q, J = 5.5 Hz), 4.26-4.38 (2H, m), 4.59-4.65 (2H, m), 6.76 (2H, d, J = 8.6 Hz), 7.08 (1H, s), 7.15 (2H, d, J = 8.3 Hz), 7.18-7.27 (8H, m), 7.36 (2H, d, J = 8.0 Hz), 8.19 (2H, s), 8.25 (1H, d, J = 5.2 Hz), 8.59-8.62 (2H, m), 8.72 (1H, d, J = 8.1 Hz). |
| 124 | d$^6$-DMSO | δ: 1.28 (3H, t, J = 6.84 Hz), 2.13 (3H, s), 2.56-2.59 (1H, m), 2.69-2.74 (1H, m), 2.78-2.84 (1H, m), 3.05-3.10 (1H, m), 3.91-4.00 (4H, m), 4.30 (2H, d, J = 5.82 Hz), 4.52-4.64 (2H, m), 5.91 (1H, s) 6.71 (2H, d, J = 8.66 Hz), |

TABLE 7-continued

NMR data of examples

| Example No | Solvent | NMR (ppm) |
|---|---|---|
| | | 6.77 (1H, t, J = 2.36 Hz), 6.92 (2H, d, J = 7.78 Hz), 7.18-7.28 (8H, m), 7.34 (2H, d, J = 8.49 Hz), 8.09 (3H, s, br), 8.60-8.64 (2H, m). |
| 125 | d$^6$-DMSO | δ: 1.28 (3H, t, J = 7.0 Hz), 2.67-2.69 (2H, m), 2.82 (1H, dd, J = 13.5 Hz, 10.0 Hz), 3.05 (1H, dd, J = 13.6 Hz, 6.4 Hz), 3.93 (2H, q, J = 7.0 Hz), 3.97 (2H, d, J = 5.6 Hz), 4.31 (2H, d, J = 5.8 Hz), 4.47-4.57 (2H, m), 6.57 (1H, d, J = 5.4 Hz), 6.71 (2H, d, J = 8.6 Hz), 6.97 (2H, d, J = 8.6 Hz), 7.18-7.27 (10H m), 7.38 (2H, d, J = 6.0 Hz), 7.40 (1H, d, J = 3.1 Hz), 8.28 (2H, br.s), 8.51 (1H, d, J = 8.5 Hz), 8.61 (1H, t, J = 6.0 Hz) |
| 126 | d$^6$-DMSO | δ: 0.80-0.85 (2H, m), 1.02-1.12 (4H, m), 1.22-1.32 (1H, m), 1.41-1.48 (1H, m), 1.53-1.62 (5H, m), 2.76-2.82 (1H, m), 3.09-3.13 (1H, m), 3.95 (2H, s), 4.28-4.35 (2H, m), 4.37-4.43 (1H, m), 4.46-4.52 (1H, m), 7.15-7.27 (7H, m), 7.34-7.37 (2H, m), 7.39-7.46 (2H, m), 7.48-7.54 (1H, m), 7.80-7.83 (2H, m), 8.21 (2H, s), 8.51 (2H, d, J = 7.8 Hz), 8.59 (1H, t, J = 6.1 Hz). |
| 127 | d$^6$-DMSO | δ: 2.62-2.69 (2H, m), 2.71-2.77 (1H, m), 2.96-3.01 (1H, m), 3.87 (2H, d, J = 4.56 Hz), 4.22-4.25 (2H, m), 4.49-4.61 (2H, m), 7.10-7.22 (10H, m), 7.30-7.36 (4H, m), 7.40-7.48 (1H, m), 7.67 (2H, d, J = 6.61 Hz), 8.30 (3H, s, br), 8.47 (1H, d, J = 8.82 Hz), 8.56-8.62 (2H, m). |
| 128 | d$^6$-DMSO | δ: 2.70 (2H, d, J = 7.21 Hz), 2.78-2.85 (1H, m), 3.03-3.07 (1H, m), 3.95 (2H, d, J = 8.78 Hz), 4.27-4.36 (2H, m), 4.55-4.63 (2H, m), 6.84 (2H, d, J = 8.52 Hz), 7.05-7.29 (12H, m), 7.37-7.44 (6H, m), 7.74 (2H, d, J = 7.52 Hz), 8.34 (3H, s, br), 8.50 (1H, d, J = 7.57 Hz), 8.58 (1H, d, J = 8.77 Hz), 8.63-8.66 (2H, m). |
| 129 | d$^6$-DMSO | δ: 2.61-2.63 (2H, m), 2.70-2.77 (1H, m), 2.95-3.00 (1H, m), 3.88 (2H, d, J = 6.26 Hz), 4.18-4.29 (2H, m), 4.47-4.54 (2H, m), 4.91 (1H, s), 6.76 (2H, d, J = 8.18 Hz), 7.07-7.18 (9H, m), 7.26-7.36 (4H, m), 7.66-7.68 (2H, m), 8.24 (3H, s, br), 8.42 (1H, d, J = 8.17 Hz), 8.50 (1H, d, J = 8.02 Hz), 8.53-8.58 (1H, m). |
| 130 | d$^6$-DMSO | δ: 2.65 (2H, d, J = 5.97 Hz), 2.79-2.85 (1H, m), 3.03-3.06 (1H, m), 3.95 (2H, s), 4.31 (2H, s), 4.55 (2H, s, br), 6.58 (2H, d, J = 7.55 Hz), 7.01 (2H, d, J = 7.12 Hz), 7.18-7.24 (10H, m), 7.37-7.50 (7H, m), 7.74 (2H, d, J = 7.10 Hz), 8.32 (3H, s, br), 8.46 (1H, d, J = 9.60 Hz), 8.53 (1H, d, J = 9.60 Hz), 8.61 (1H, s). |
| 131 | d$^6$-DMSO | δ: 1.43 (3H, t, J = 6.97 Hz), 2.88 (2H, d, J = 6.67 Hz), 2.95-3.06 (2H, m), 3.14-3.23 (2H, m), 4.06-4.12 (2H, m), 4.39-4.49 (2H, m), 4.75-4.78 (2H, m), 6.91 (2H, d, J = 8.95 Hz), 7.31 (2H, m), 7.37-7.46 (9H, m), 7.54-7.67 (5H, m), 7.89-7.98 (2H, m), 8.46 (2H, s, br), 8.65-8.81 (3H, m). |
| 132 | d$^6$-DMSO | δ: 2.68 (2H, d, J = 7.36 Hz), 2.79-2.98 (1H, m), 3.03-3.06 (1H, m), 3.96 (2H, s), 4.21-4.32 (2H, m), 4.59-4.61 (2H, m), 5.00 (2H, s), 6.84 (2H, d, J = 8.15 Hz), 7.14-7.24 (12H, m), 7.35-7.40 (5H, m), 7.67-7.76 (2H, m), 7.82-7.88 (2H, m), 8.24 (1H, s, br), 8.47-8.64 (4H, m). |
| 133 | d$^6$-DMSO | δ: 0.81 (3H, d, J = 6.3 Hz), 0.87 (3H, d, J = 6.3 Hz), 1.27-1.39 (2H, m), 1.45-1.52 (1H, m), 2.81-2.87 (1H, m), 3.20-3.24 (1H, m), 4.02 (2H, s), 4.35-4.44 (3H, m), 4.52-4.58 (1H, m), 7.22-7.35 (7H, m), 7.43 (2H, d, J = 8.1 Hz), 7.48-7.52 (2H, m), 7.58-7.64 (1H, m), 7.87-7.89 (2H, m), 8.30 (2H, s), 8.59-8.69 (3H, m). |
| 134 | d$^6$-DMSO | δ: 2.70 (2H, d, J = 7.36 Hz), 2.78-2.84 (1H, m), 3.03-3.06 (1H, m), 3.97 (2H, s), 4.11-4.34 (2H, m), 4.59-4.63 (2H, m), 5.14 (2H, s), 6.90 (2H, d, J = 8.21 Hz), 7.11-7.30 (11H, m), 7.36-7.54 (5H, m), 7.67-7.75 (2H, m), 7.80-7.88 (2H, m), 8.47-8.58 (4H, m). |
| 135 | d$^6$-DMSO | δ: 2.20 (3H, s), 2.71 (2H, d, J = 7.81 Hz), 2.79-2.85 (1H, m), 3.03-3.07 (1H, m), 3.93-3.96 (2H, m), 4.25-4.36 (2H, m), 4.55-4.65 (2H, m), 7.00 (2H, d, J = 9.01 Hz), 7.12 (2H, d, J = 7.78 Hz), 7.18 (2H, d, J = 7.79 Hz), 7.22-7.24 (4H, m), 7.38 (2H, d, J = 6.49 Hz), 7.42 (2H, d, J = 7.79 Hz), 7.48-7.50 (1H, m), 7.74-7.76 (2H, m), 8.33 (3H, s, br), 8.51 (1H, d, J = 7.79 Hz), 8.58 (1H, d, J = 7.79 Hz), 8.62-8.65 (1H, m). |
| 136 | d$^6$-DMSO | δ: 2.70 (2H, d, J = 7.28 Hz), 2.74-2.85 (1H, m), 3.04-3.08 (1H, m), 3.95 (2H, s), 4.27-4.36 (2H, m), 4.58-4.62 (2H, m), 5.03 (2H, d, J = 8.21 Hz), 7.15-7.24 (11H, m), 7.37-7.52 (5H, m), 7.56-7.61 (1H, m), 7.75 (2H, d, J = 8.22 Hz), 8.34 (3H, s, br), 8.50 (1H, d, J = 7.02 Hz), 8.58 (1H, d, J = 9.38 Hz), 8.62-8.65 (1H, m). |
| 137 | d$^6$-DMSO | δ: 2.66-2.69 (2H, m), 2.81 (1H, dd, J = 13.5, 10.0 Hz), 3.05 (1H, dd, J = 13.6, 4.7 Hz), 3.69 (2H, s), 3.77 (3H, s), 4.23-4.33 (2H, m), 4.58-4.67 (2H, m), 6.68 (1H, d, J = 8.5 Hz), 7.07-7.25 (11H, m), 7.43 (2H, t, J = 7.3 Hz), 7.49-7.55 (2H, m), 7.75 (2H, d, J = 7.2 Hz), 8.00 (1H, d, J = 1.8 Hz), 8.49-8.57 (3H, m). |
| 138 | d$^6$-DMSO | δ: 2.69-2.71 (1H, m), 2.79-2.85 (1H, m), 3.03-3.07 (1H, m), 3.67 (3H, s), 3.96 (2H, s), 4.26-4.32 (2H, m), 4.55-4.63 (2H, m), 6.76 (2H, d, J = 8.52 Hz), 7.14-7.25 (9H, m), 7.36-7.44 (4H, m), 7.48-7.52 (1H, m), 7.74-7.76 (2H, m), 8.29 (3H, s, br), 8.56 (1H, d, J = 1.68 Hz), 8.613-8.64 (2H, m). |
| 139 | d$^6$-DMSO | δ: 2.82-2.85 (3H, m), 3.03-3.08 (1H, m), 3.93-3.98 (2H, m), 4.26-4.31 (2H, m), 4.56-4.69 (2H, m), 7.11-7.26 (12H, m), 7.37-7.43 (4H, m), 7.48-7.51 (1H, m), 7.73-7.75 (2H, m), 8.32 (3H, s, br), 8.53-8.65 (2H, m). |

TABLE 7-continued

NMR data of examples

| Example No | Solvent | NMR (ppm) |
|---|---|---|
| 140 | d6-DMSO | δ: 1.09 (3H, t, J = 7.0 Hz), 2.50-2.66 (2H, m), 3.05 (1H, dd, J = 13.4, 10.4 Hz), 3.26-3.32 (1H, m), 3.45-3.54 (2H, m), 3.74 (2H, q, J = 7.0 Hz), 4.09-4.15 (2H, m), 4.33-4.38 (1H, m), 4.65-4.71 (1H, m), 6.57 (2H, d, J = 8.6 Hz), 7.00 (2H, d, J = 8.5 Hz), 7.09 (2H, d, J = 8.0 Hz), 7.16-7.35 (5H, m), 7.53-7.58 (4H, m), 7.95-8.20 (3H, br m), 8.48-8.56 (3H, m), 8.64 (1H, d, J = 8.5 Hz). |
| 141 | d6-DMSO | δ: 1.26 (3H, t, J = 7.0 Hz), 2.65-2.84 (3H, m), 3.03-3.08 (1H, m), 3.92 (2H, q, J = 7.0 Hz), 3.96 (2H, s), 4.27-4.35 (2H, m), 4.57-4.63 (2H, m), 6.75 (2H, d, J = 8.7 Hz), 7.16 (2H, d, J = 8.6 Hz), 7.23 (1H, dd, J = 8.3, 1.7 Hz), 7.27 (2H, d, J = 8.1 Hz), 7.37-7.51 (6H, m), 7.55 (1H, d, J = 1.8 Hz), 7.73-7.75 (2H, m), 8.24 (2H, s), 8.50 (1H, d, J = 8.1 Hz), 8.67-8.71 (2H, m). |
| 142 | d6-DMSO | δ: 1.26 (3H, t, J = 6.9 Hz), 2.67-2.83 (3H, m), 3.01-3.05 (1H, m), 3.89-3.95 (4H, m), 4.27-4.35 (2H, m), 4.53-4.63 (2H, m), 6.75 (2H, d, J = 8.5 Hz), 7.14 (2H, d, J = 8.5 Hz), 7.20-7.26 (5H, m), 7.37-7.44 (4H, m), 7.50 (1H, t, J = 7.3 Hz), 7.66-7.72 (1H, m), 7.75 (2H, d, J = 7.4 Hz), 8.31 (2H, s), 8.53 (1H, d, J = 8.1 Hz), 8.62 (1H, d, J = 8.7 Hz), 8.69 (1H, t, J = 5.9 Hz). |
| 143 | d6-DMSO | δ: 1.26 (3H, t, J = 6.93 Hz), 2.70 (2H, d, J = 7.52 Hz), 2.89-2.95 (1H, m), 3.12-3.17 (1H, m), 3.89-3.94 (2H, m), 3.95 (2H, s), 4.31 (2H, d,, J = 5.38 Hz), 4.56-4.66 (2H, m), 6.74 (2H, d, J = 8.52 Hz), 7.12 (2H, d, J = 6.93 Hz), 7.26 (2H, d, J = 9.72 Hz), 7.38-7.44 (5H, m), 7.50-7.54 (3H, m), 7.75 (2H, d, J = 8.31 Hz), 8.34 (3H, s, br), 8.51 (1H, d, J = 8.32 Hz), 8.62 (1H, d, J = 8.32 Hz), 8.68-8.71 (1H, m). |
| 144 | d6-DMSO | δ: 1.26 (3H, t, J = 6.93 Hz), 2.65 (2H, d, J = 6.98 Hz), 2.89-2.95 (1H, m), 3.16-3.21 (1H, m), 3.91-3.96 (2H, m), 4.32 (2H, J = 5.82 Hz), 4.57-4.66 (2H, m), 6.73 (2H, d, J = 8.54 Hz), 7.13 (2H, d, J = 9.08 Hz), 7.27 (2H, d, J = 8.01 Hz), 7.39-7.44 (8H, m), 7.50-7.57 (1H, m), 7.68-7.71 (1H, m), 7.73-7.75 (2H, m), 8.44-8.50 (4H, m), 8.72-8.76 (2H, m). |
| 145 | d6-DMSO | δ: 1.26 (3H, t, J = 7.0 Hz), 2.64 (2H, d, J = 7.2 Hz), 2.82 (1H, dd, J = 13.5, 10.3 Hz), 3.07 (1H, dd, J = 13.6, 4.2 Hz), 3.81 (2H, s), 3.92 (2H, q, J = 7.0 Hz), 4.26-4.35 (2H, m), 4.55-4.65 (2H, m), 5.70-6.60 (2H, br s), 6.75 (2H, d, J = 8.6 Hz), 7.14-7.34 (7H, m), 7.39-7.51 (3H, m), 7.62 (1H, d, J = 7.7 Hz), 7.73 (2H, d, J = 7.2 Hz), 8.39 (1H, dd, J = 4.8, 1.4 Hz), 8.46 (1H, d, J = 1.6 Hz), 8.52 (1H, d, J = 8.0 Hz), 8.62 (1H, t, J = 6.0 Hz), 8.68 (1H, d, J = 8.8 Hz). |
| 146 | d6-DMSO | δ: 1.26 (3H, t, J = 7.0 Hz), 2.69-2.77 (3H, m), 2.94-2.99 (1H, m), 3.65 (3H, s), 3.92 (2H, q, J = 7.0 Hz), 3.96 (2H, s), 4.25-4.35 (2H, m), 4.49-4.54 (1H, m), 4.57-4.63 (1H, m), 6.75 (4H, dd, J = 8.6, 1.7 Hz), 7.13-7.18 (4H, m), 7.25 (2H, d, J = 8.1 Hz), 7.36 (2H, d, J = 8.1 Hz), 7.40-7.44 (2H, m), 7.48-7.52 (1H, m), 7.72-7.75 (2H, m), 8.19 (2H, s), 8.48-8.53 (2H, m), 8.62 (1H, t, J = 6.0 Hz). |
| 147 | d6-DMSO | δ: 1.26 (3H, t, J = 7.0 Hz), 2.69 (2H, d, J = 7.2 Hz), 2.83 (1H, dd J = 13.6, 10.0 Hz), 3.06 (1H, dd, J = 13.7, 4.5 Hz), 3.87 (2H, s), 3.92 (2H, q, J = 7.0 Hz), 4.26-4.31 (2H, m), 4.55-4.60 (1H, m), 4.62-4.67 (1H, m), 6.51-6.79 (1H, m), 6.75 (2H, d, J = 8.6 Hz), 7.13-7.19 (3H, m), 7.20-7.22 (4H, m), 7.31 (1H, d, J = 8.1 Hz), 7.40-7.44 (3H, m), 7.45-7.52 (1H, m), 7.71-7.75 (2H, m), 8.36-8.39 (2H, m), 8.50-8.61 (3H, m). |
| 148 | d6-DMSO | δ: 1.26 (3H, t, J = 6.93 Hz), 2.70 (2H, d, J = 7.09 Hz), 2.89-2.95 (1H, m), 3.12-3.17 (1H, m), 3.89-3.94 (2H, m), 3.95 (2H, s), 4.31-4.32 (2H, m), 4.56-4.66 (2H, m), 6.74 (2H, d, J = 7.19 Hz), 7.12 (2H, d, J = 8.40 Hz), 7.26 (2H, d, J = 8.40 Hz), 7.38-7.44 (5H, m), 7.50-7.54 (3H, m), 7.74-7.76 (2H, m), 8.35 (3H, s, br), 8.51 (1H, d, J = 7.2 Hz), 8.62 (1H, d, J = 8.40 Hz), 8.68-8.71 (1H, m). |
| 149 | d6-DMSO | δ: 1.26 (3H, t, J = 6.93 Hz), 2.67-2.69 (2H, m), 2.81-2.87 (1H, m), 3.06-3.10 (1H, m), 3.59 (2H, s, br), 3.89-3.98 (4H, m), 4.22-4.33 (2H, m), 4.57-4.62 (2H, m), 6.74 (2H, d, J = 8.52 Hz), 7.13-7.16 (7H, m), 7.22-7.27 (2H, m), 7.35-7.41 (3H, m), 7.43-7.51 (1H, m), 7.72-7.81 (2H, m), 8.29-8.32 (1H, m), 8.48-8.53 (1H, m), 8.54-8.64 (1H, m). |
| 150 | d6-DMSO | δ: 1.28 (3H, t, J = 7.0 Hz), 2.80-2.87 (2H, m), 3.07 (1H, dd, J = 14.7, 9.4 Hz), 3.27 (2H, dd, J = 14.8, 4.3 Hz), 3.32 (2H, br.s), 3.69 (1H, s), 3.94 (2H, q, J = 6.9 Hz), 4.27-4.30 (2H, m), 4.53-4.58 (1H, m), 4.60-4.66 (1H, m), 6.78 (2H, d, J = 8.6 Hz), 6.86-6.90 (2H, m), 7.12-7.24 (6H, m), 7.31 (1H, d, J = 5.0 Hz), 7.42 (2H, t, J = 7.4 Hz), 7.50 (1H, q, J = 7.3 Hz), 7.73 (2H, d, J = 7.1 Hz), 8.51 (1H, t, J = 5.5 Hz), 8.57 (2H, m) |
| 151 | d6-DMSO | δ: 1.28 (3H, t, J = 6.9 Hz), 2.77 (2H, br.s), 2.89 (1H, dd, J = 14.1, 9.8 Hz), 3.07 (1H, dd, J = 14.1, 4.4 Hz), 3.33 (3H, br.s), 3.65 (1H, br.s), 3.94 (2H, q, J = 6.9 Hz), 4.28 (2H, t, J = 5.8 Hz), 4.52-4.58 (1H, m), 4.60-4.65 (1H, m), 6.78 (2H, d, J = 8.5 Hz), 6.98 (1H, d, J = 4.6 Hz), 7.15 (3H, br.s), 7.18-7.23 (4H, m), 7.38-7.41 (1H, m), 7.44 (2H, d, J = 7.6 Hz), 7.51 (1H, t, J = 7.2 Hz), 7.75 (2H, d, J = 7.2 Hz), 8.50 (1H, br.s), 8.57 (2H, d, J = 6.2 Hz) |
| 152 | d6-DMSO | δ: 1.28 (3H, t, J = 7.0 Hz), 2.67 (1H, t, J = 1.6 Hz), 2.77 (1H, d, J = 7.3 Hz), 3.06 (1H, dd, J = 14.5 Hz, 9.7 Hz), 3.23 (1H, dd, J = 14.6 Hz, 4.7 Hz), 3.94 (2H, q, J = 7.0 Hz), 3.96-3.99 (2H, m), 4.31 (2H, t, J = 5.7 Hz), 4.58 (1H, q, J = 7.5 Hz), 4.70 (1H, td, J = 9.1 Hz, 4.6 Hz), |

TABLE 7-continued

NMR data of examples

| Example No | Solvent | NMR (ppm) |
|---|---|---|
| | | 6.77 (2H, d, J = 8.6 Hz), 7.16 (2H, d, J = 8.6 Hz), 7.23 (2H, d, J = 8.1 Hz), 7.26 (1H, d, J = 1.5 Hz), 7.33 (2H, d, J = 8.2 Hz), 7.43 (2H, t, J = 7.5 Hz), 7.52 (1H, t, J = 7.4 Hz), 7.42 (2H, d, J = 7.1 Hz), 8.05 (2H, br.s), 8.55 (2H, d, J = 7.6 Hz), 8.59 (1H, d, J = 8.6 Hz), 8.95 (1H, d, J = 1.8 Hz) |
| 153 | d$^6$-DMSO | δ: 1.27 (3H, t, J = 7.0 Hz), 2.66-2.72 (3H, m), 3.10 (1H, dd, J = 14.4 Hz, 9.8 Hz), 3.91 (2H, q, J = 7.0 Hz), 3.98 (2H, d, J = 5.2 Hz), 4.33 (2H, qd, J = 14.5 Hz, 6.0 Hz), 4.61 (1H, td, J = 8.7 Hz, 4.9 Hz), 4.72 (1H, td, J = 9.1 Hz, 4.7 Hz), 6.71 (2H, d, J = 8.6 Hz), 7.12 (2H, d, J = .6 Hz), 7.26 (2H, d, J = 8.2 Hz), 7.35 (3H, d, J = 7.7 Hz), 7.38-7.40 (2H, m), 7.42 (2H, d, J = 7.8 Hz), 7.49 (1H, d, J = 7.4 Hz), 7.73 (2H, d, J = 7.2 Hz), 7.97 (2H, d, J = 8.0 Hz), 8.06 (2H, br.s), 8.45 (1H, d, J = 7.8 Hz), 8.66-8.72 (2H, m) |
| 154 | d$^6$-DMSO | δ: 1.26 (3H, t, J = 7.0 Hz), 2.70 (2H, d, J = 7.3 Hz), 2.79-2.85 (1H, m), 3.03-3.08 (1H, m), 3.94 (2H, q, J = 7.0 Hz), 4.00 (2H, s), 4.27-4.39 (2H, m), 4.54-4.62 (2H, m), 6.75 (2H, d, J = 8.6 Hz), 7.07-7.25 (9H, m), 7.41-7.52 (4H, m), 7.70-7.74 (2H, m), 8.26 (2H, s), 8.49 (1H, d, J = 8.1 Hz), 8.58 (1H, d, J = 8.6 Hz), 8.66 (1H, t, J = 6.0 Hz). |
| 155 | d$^6$-DMSO | δ: 1.26 (3H, t, J = 6.9 Hz), 2.72 (2H, d, J = 7.2 Hz), 2.80-2.86 (1H, m), 3.03-3.08 (1H, m), 3.92 (2H, q, J = 6.9 Hz), 4.06 (2H, s), 4.26-4.37 (2H, m), 4.53-4.62 (2H, m), 6.74 (2H, d, J = 8.5 Hz), 7.13 (2H, d, J = 8.5 Hz), 7.15-7.23 (6H, m), 7.38-7.43 (3H, m), 7.48-7.53 (2H, m), 7.75 (2H, d, J = 7.3 Hz), 8.49 (2H, s), 8.52 (1H, d, J = 8.2 Hz), 8.59 (1H, d, J = 8.5 Hz), 8.71 (1H, t, J = 5.9 Hz). |
| 156 | d$^6$-DMSO | δ: 1.26 (3H, t, J = 7.0 Hz), 2.70 (2H, d, J = 7.2 Hz), 2.79-2.85 (1H, m), 3.03-3.07 (1H, m), 3.92 (2H, q, J = 7.0 Hz), 4.11 (2H, s), 4.33-4.46 (2H, m), 4.54-4.62 (2H, m), 6.74 (2H, d, J = 8.6 Hz), 7.12 (2H, d, J = 8.6 Hz), 7.16-7.25 (7H, m), 7.39-7.43 (2H, m), 7.47-7.56 (2H, m), 7.67-7.74 (4H, m), 8.48 (1H, d, J = 8.0 Hz), 8.59 (1H, d, J = 8.5 Hz), 8.75 (1H, t, J = 6.0 Hz). |
| 157 | d$^6$-DMSO | δ: 1.27 (3H, t, J = 7.0 Hz), 2.81-2.86 (1H, m), 2.93-2.97 (1H, m), 3.06-3.12 (1H, m), 3.24-3.29 (1H, m), 3.90-3.99 (4H, m), 4.30 (2H, d, J = 5.8 Hz), 4.50-4.56 (2H, m), 4.78-4.83 (2H, m), 6.69 (2H, d, J = 8.6 Hz), 6.86 (2H, d, J = 8.6 Hz), 6.91-6.94 (2H, m), 7.23 (2H, d, J = 8.1 Hz), 7.35-7.38 (3H, m), 7.60-7.63 (1H, m), 7.96-8.00 (2H, m), 8.20 (2H, s), 8.56 (1H, d, J = 8.3 Hz), 8.63 (1H, d, J = 4.8 Hz), 8.67 (1H, d, J = 6.0 Hz), 8.74 (1H, d, J = 8.3 Hz). |
| 158 | d$^6$-DMSO | δ: 1.28 (3H, t, J = 6.9 Hz), 2.74 (2H, d, J = 7.2 Hz), 3.02 (2H, dd, J = 13.9 Hz, 9.4 Hz), 3.18 (1H, d, J = 13.9 Hz, 4.6 Hz), 3.66 (1H, s), 3.80 (3H, s), 3.93 (2H, q, J = 6.9 Hz), 4.27 (2H, d, J = 6.0 Hz), 4.52 (1H, q, J = 7.4 Hz), 4.73-4.79 (1H, m), 6.74 (2H, d, J = 8.6 Hz), 6.96 (2H, d, J = 8.8 Hz), 7.09 (2H, d, J = 8.2 Hz), 7.13 (2H, d, J = 8.6 Hz), 7.17-7.21 (3H, m), 7.34 (1H, d, J = 7.8 Hz), 7.63 (1H, td, J = 7.6 Hz, 1.7 Hz), 7.7 (2H, d, J = 8.8 Hz), 8.36 (1H, d, J = 4.0 Hz), 8.41 (2H, d, J = 6.6 Hz), 8.60 (1H, d, J = 8.4 Hz) |
| 159 | d$^6$-DMSO | δ: 1.27 (3H, t, J = 7.0 Hz), 2.68-2.74 (1H, m), 2.82-2.88 (2H, m), 3.05-3.10 (1H, m), 3.90 (2H, q, J = 7.0 Hz), 4.06 (2H, q, J = 5.7 Hz), 4.31 (2H, d, J = 5.9 Hz), 4.50-4.55 (1H, m), 4.76-4.81 (1H, m), 6.59-6.65 (4H, m), 7.19-7.23 (2H, m), 7.28 (2H, t, J = 7.4 Hz), 7.33 (2H, d, J = 7.2 Hz), 7.37 (1H, d, J = 1.0 Hz), 7.50 (1H, d, J = 8.0 Hz), 7.59-7.63 (1H, m), 7.98-8.02 (2H, m), 8.38 (2H, s), 8.51 (1H, d, J = 8.2 Hz), 8.61 (1H, d, J = 4.7 Hz), 8.71-8.74 (2H, m). |
| 160 | d$^6$-DMSO | δ: 1.28 (3H, t, J = 7.66 Hz), 2.70 (2H, d, J = 7.60 Hz), 2.94-3.00 (1H, m), 3.21-3.24 (1H, m), 3.80 (3H, s), 3.92-4.00 (4H, m), 4.33 (2H, d, J = 6.69 Hz), 4.52 (1H, q, J = 7.45 Hz), 4.66-4.69 (2H, m), 6.75 (2H, d, J = 7.79 Hz), 6.96 (2H, d, J = 8.68 Hz), 7.17 (2H, d, J = 8.45 Hz), 7.27 (2H, d, J = 7.82 Hz), 7.38 (2H, d, J = 7.82 Hz), 7.67 (1H, s, br), 7.74 (1H, d, J = 9.03 Hz), 8.11 (1H, s, br), 8.22 (2H, s, br), 8.45 (1H, d, J = 8.34 Hz), 8.68-8.69 (4H, m). |
| 161 | d$^6$-DMSO | δ: 1.28 (3H, t, J = 6.94 Hz), 2.62-2.84 (3H, m), 2.96-3.07 (1H, m), 3.90-4.02 (4H, m), 4.32 (2H, d, J = 5.8 Hz), 4.60-4.67 (2H, m), 6.77 (2H, d, J = 8.88 Hz), 7.16-7.22 (1H, m), 7.26 (2H, d, J = 8.32 Hz), 7.29-7.35 (5H, m), 7.36 (2H, d, J = 8.32 Hz), 7.64 (1H, d, J = 6.53 Hz), 8.08 (3H, s, br), 8.58-8.71 (3H, m), 8.82 (1H, d, J = 7.71 Hz). |
| 162 | d$^6$-DMSO | δ: 1.27 (3H, t, J = 7.0 Hz), 2.61 (2H, dd, J = 14.0 Hz, 4.3 Hz), 2.86 (1H, dd, J = 13.7 Hz, 10.3 Hz), 3.10 (1H, dd, J = 13.7 Hz, 4.5 Hz), 3.93 (2H, q, J = 7.0 Hz), 3.98-4.00 (2H, m), 4.3 (2H, d, J = 5.8 Hz), 4.56 (1H, td, J = 9.0 Hz, 5.0 Hz), 4.66 (1H, td, J = 9.0 Hz, 4.8 Hz), 6.75 (2H, d, J = 8.6 Hz), 7.12 (1H, dd J = 4.9, 3.7 Hz), 7.16 (2H, d, J = 8.6 Hz), 7.26 (2H, d, J = 8.3 Hz), 7.36 (3H, d, J = 8.1 Hz), 7.72 (1H, dd, J = 5.0 Hz, 0.7 Hz), 7.76 (1H, br.s), 7.81 (1H, d, J = 3.2 Hz), 8.07 (2H, br.s), 8.47-8.55 (3H, m), 8.64 (2H, t, J = 9.0 Hz) |
| 163 | d$^6$-DMSO | δ: 1.28 (3H, t, J = 7.0 Hz), 2.67-2.75 (2H, m), 3.03 (2H, dd, J = 13.8 Hz, 9.5 Hz), 3.21 (2H, dd, J = 14.0 Hz, 4.7 Hz), 3.93 (2H, q, J = 7.0 Hz), 3.99 (2H, q, J = 5.8 Hz), 4.20-4.40 (3H, m), 4.53-4.58 (1H, m), 4.77-4.83 (1H, m), 6.75 (2H, d, J = 8.6 Hz), 7.14 (2H, d, J = 8.6 Hz), 7.23 (2H, d, J = 8.1 Hz), 7.34 (2H, d, J = 8.2 Hz), 7.52 (2H, d, J = 8.6 Hz), |

TABLE 7-continued

NMR data of examples

| Example No | Solvent | NMR (ppm) |
|---|---|---|
| | | 7.76 (2H, d, J = 8.6 Hz), 8.07 (2H, br.s), 8.44 (1H, d, J = 4.5 Hz), 8.53 (1H, br.s), 8.66 (2H, d, J = 7.6 Hz) |
| 164 | d$^6$-DMSO | δ: 1.28 (3H, t, J = 7.0 Hz), 2.34 (3H, s), 2.74 (2H, d, J = 8.2 Hz), 3.05 (1H, dd, J = 13.9, 9.5 Hz), 3.23 (1H, dd, J = 14.0, 4.7 Hz), 3.93 (2H, q, J = 7.0 Hz), 3.99 (2H, q, J = 5.8 Hz), 4.26-4.36 (2H, m), 4.54 (1H, dd, J = 14.5, 7.7 Hz), 4.79 (1H, td, J = 8.9 Hz, 4.8 Hz), 6.75 (2H, d, J = 8.6 Hz), 7.13 (2H, d, J = 8.6 Hz), 7.24 (4H, d, J = 8.0 Hz), 7.30 (1H, br.s), 7.34 (3H, d, J = 8.0 Hz), 7.66 (2H, d, J = 8.1 Hz), 7.76 (1H, br.s), 8.09 (2H, br.s), 8.45 (2H, t, J = 6.0 Hz), 8.54 (1H, t, J = 6.0 Hz), 8.64 (1H, d, J = 8.3 Hz) |
| 165 | d$^6$-DMSO | δ: 1.28 (3H, t, J = 6.9 Hz), 2.71-2.92 (3H, m), 3.06-3.10 (1H, m), 3.92 (2H, q, J = 6.9 Hz), 3.96-4.01 (2H, m), 4.31 (2H, d, J = 5.8 Hz), 4.53-4.59 (1H, m), 4.75-4.80 (1H, m), 6.57-6.72 (4H, m), 7.27 (2H, d, J = 8.0 Hz), 7.30-7.33 (1H, m), 7.37 (2H, d, J = 8.0 Hz), 7.55 (1H, d, J = 8.2 Hz), 7.59-7.63 (1H, m), 7.64 (1H, s), 7.98-8.01 (2H, m), 8.13 (2H, s), 8.47 (1H, d, J = 8.2 Hz), 8.62 (1H, d, J = 4.7 Hz), 8.65-8.67 (1H, m), 8.77 (1H, d, J = 8.2 Hz) |
| 166 | d$^6$-DMSO | δ: 0.85 (3H, t, J = 7.6 Hz), 1.30 (3H, t, J = 7.0 Hz), 2.02 (2H, q, J = 7.6 Hz), 2.63-2.68 (1H, m), 2.99 (2H, dd, J = 14.0, 9.6 Hz), 3.20 (1H, dd, J = 13.9, 4.8 Hz), 3.95 (2H, q, J = 7.0 Hz), 4.00 (2H, q, J = 6.0 Hz), 4.28 (2H, t, J = 7.2 Hz), 4.32-4.35 (1H, m), 4.74 (1H, td, J = 8.9 Hz, 4.8 Hz), 6.73 (2H, d, J = 8.6 Hz), 7.00 (2H, d, J = 8.6 Hz), 7.23 (2H, d, J = 8.1 Hz), 7.29 (2H, d, J = 7.24 Hz), 7.36 (2H, d, J = 8.12 Hz), 7.74 (1H, br.s), 7.97 (1H, d, J = 5.2 Hz), 8.08 (2H, br.s), 8.51 (3H, d, J = 4.2 Hz) |
| 167 | d$^6$-DMSO | δ: 1.27 (3H, t, J = 6.9 Hz), 2.65-2.89 (3H, m), 3.05-3.10 (1H, m), 3.93 (2H, q, J = 6.9 Hz), 4.00 (2H, q, J = 5.4 Hz), 4.27-4.40 (2H, m), 4.58-4.70 (2H, m), 6.76 (2H, d, J = 8.5 Hz), 7.08 (1H, s), 7.11 (1H, d, J = 2.8 Hz), 7.16-7.29 (7H, m), 7.51 (1H, t, J = 8.0 Hz), 7.95 (2H, s), 8.47 (2H, s), 8.72-8.78 (2H, m), 8.87 (2H, s), 9.19 (1H, d, J = 7.7 Hz). |
| 168 | d$^6$-DMSO | δ: 1.27 (3H, t, J = 7.0 Hz), 2.69-2.74 (1H, m), 2.82-2.93 (2H, m), 3.05-3.10 (1H, m), 3.90 (2H, q, J = 7.0 Hz), 4.01 (2H, q, J = 5.7 Hz), 4.32 (2H, d, J = 6.0 Hz), 4.51-4.56 (1H, m), 4.76-4.79 (1H, m), 6.60-6.67 (3H, m), 7.06-7.09 (2H, m), 7.18-7.22 (2H, m), 7.28 (2H, t, J = 7.4 Hz), 7.33 (2H, d, J = 3.8 Hz), 7.46 (1H, t, J = 7.8 Hz), 7.59-7.63 (1H, m), 7.96-7.99 (2H, m), 8.31 (2H, s), 8.50 (1H, d, J = 8.2 Hz), 8.60-8.62 (1H, m), 8.71-8.74 (2H, m). |
| 169 | d$^6$-DMSO | δ: 1.26-1.30 (3H, m), 2.60-2.84 (3H, m), 3.03-3.07 (1H, m), 3.93 (2H, q, J = 7.0 Hz), 4.00 (2H, q, J = 5.4 Hz), 4.32 (2H, d, J = 5.8 Hz), 4.56-4.66 (2H, m), 6.76 (2H, d, J = 8.6 Hz), 7.11-7.13 (1H, m), 7.16 (2H, d, J = 8.5 Hz), 7.23 (1H, dd, J = 8.3, 1.8 Hz), 7.28 (2H, d, J = 8.0 Hz), 7.38 (2H, d, J = 8.0 Hz), 7.48 (1H, d, J = 8.2 Hz) 7.55 (1H, d, J = 1.7 Hz), 7.73 (1H, dd, J = 5.0, 0.7 Hz), 7.81 (1H, d, J = 3.2 Hz), 8.17 (2H, s), 8.53 (1H, d, J = 8.3 Hz), 8.63-8.66 (2H, m). |
| 170 | d$^6$-DMSO | δ: 0.84 (3H, t, J = 7.6 Hz), 1.30 (3H, t, J = 7.0 Hz), 2.00 (2H, q, J = 7.6 Hz), 2.43-2.47 (1H, m), 2.61 (1H, dd, J = 13.7 Hz, 4.8 Hz), 2.94 (1H, dd, J = 13.6 Hz, 10.2 Hz), 3.20 (1H, dd, J = 13.8 Hz, 4.4 Hz), 3.97 (2H, q, J = 7.0 Hz), 3.99 (2H, q, J = 5.5 Hz), 4.30 (2H, d, J = 5.6 Hz), 4.35 (1H, td, J = 8.4, 5.2 Hz), 4.62 (1H, td, J = 9.3, 4.6 Hz), 6.73 (2H, d, J = 8.6 Hz), 7.02 (2H, d, J = 8.6 Hz), 7.26 (2H, d, J = 8.0 Hz), 7.40 (2H, d, J = 8.1 Hz), 7.71 (1H, br.s), 8.00 (1H, d, J = 7.6 Hz), 8.12 (1H, d, J = 6.4 Hz), 8.27 (2H, br.s), 8.58 (1H, d, J = 8.4 Hz), 8.65 (1H, br.s), 8.66 (2H, br.s) |
| 171 | d$^6$-DMSO | δ: 1.28 (3H, t, J = 7.0 Hz), 2.62-2.68 (1H, m), 2.75-2.85 (2H, m), 3.03-3.08 (1H, m), 3.94 (2H, q, J = 7.0 Hz), 3.97-4.02 (2H, m), 4.28-4.38 (2H, m), 4.63-4.67 (2H, m), 6.77 (2H, d, J = 8.6 Hz), 7.17 (2H, d, J = 8.5 Hz), 7.22-7.25 (1H, m), 7.28 (2H, d, J = 8.1 Hz), 7.38 (2H, d, J = 8.0 Hz), 7.50 (1H, d, J = 8.2 Hz), 7.55 (1H, d, J = 1.4 Hz), 7.65 (2H, d, J = 5.8 Hz), 7.71-7.78 (1H, m), 8.12 (2H, s), 8.62-8.73 (3H, m), 8.81 (1H, d, J = 8.4 Hz). |
| 173 | d$^6$-DMSO | δ: 1.28 (3H, t, J = 6.82 Hz), 2.61-2.71 (2H, m), 2.85-2.91 (1H, m), 3.02-3.14 (1H, m), 3.93-4.01 (4H, m), 4.32-4.34 (2H, m), 4.56-4.69 (2H, m), 6.76 (2H, d, J = 8.67 Hz), 7.16 (2H, d, J = 8.67 Hz), 7.26 (2H, d, J = 8.67 Hz), 7.36 (2H, d, J = 7.51 Hz), 7.40-7.47 (1H, m), 7.51 (2H, d, J = 8.48 Hz), 7.56 (1H, d, J = 7.51 Hz), 7.76 (2H, d, J = 8.09 Hz), 8.12 (2H, s, br), 8.48-8.58 (2H, m), 8.62-8.68 (3H, m). |
| 174 | d$^6$-DMSO | δ: 1.28 (3H, t, J = 7.05 Hz), 2.65-2.71 (1H, m), 2.79-2.82 (1H, m), 3.04-3.07 (1H, m), 3.28-3.31 (1H, m), 3.91-3.99 (4H, m), 4.31 (2H, s), 4.58-4.60 (1H, m), 4.74-4.75 (1H, m), 6.75 (2H, d, J = 8.13 Hz), 7.14 (2H, d, J = 9.73 Hz), 7.27 (2H, d, J = 8.41 Hz), 7.41 (2H, d, J = 8.41 Hz), 7.85-7.88 (1H, m), 8.34-8.42 (4H, m), 8.72-8.83 (5H, m), 9.08 (1H, d, J = 8.41 Hz). |
| 175 | d$^6$-DMSO | δ: 1.29 (3H, t, J = 6.75 Hz), 2.61-2.64 (1H, m), 2.78-2.83 (1H, m), 2.87-2.93 (1H, m), 3.14-3.19 (1H, m), 3.92-4.00 (4H, m), 4.32 (2H, d, J = 5.78 Hz), 4.60-4.65 (2H, m), 6.71 (2H, d, J = 8.18 Hz), 6.87 (2H, d J = 8.56 Hz), 7.14 (1H, d, J = 5.45 Hz), 7.26 (2H, d, J = 8.56 Hz), 7.37 (2H, d, J = 7.78 Hz), 7.49-7.52 (1H, m), 7.83-7.90 (2H, m), 8.10 (3H, s, br), 8.54 (1H, d, J = 4.69 Hz), 8.60-8.66 (2H, m), 8.77 (1H, d, J = 8.63 Hz). |

TABLE 7-continued

NMR data of examples

| Example No | Solvent | NMR (ppm) |
|---|---|---|
| 176 | d⁶-DMSO | δ: 1.27 (3H, t, J = 7.0 Hz), 2.66-2.77 (2H, m), 2.98 (1H, dd, J = 14.5 Hz, 9.6 Hz), 3.19 (1H, dd, J = 14.5 Hz, 4.6 Hz), 3.91 (2H, q, J = 7.0 Hz), 3.98 (2H, q, J = 5.7 Hz), 4.32 (2H, d, J = 5.9 Hz), 4.62 (2H, qd, J = 9.3 Hz, 4.6 Hz), 6.69 (2H, d, J = 8.6 Hz), 6.99 (1H, t, J = 6.9 Hz), 7.08 (3H, d, J = 8.7 Hz), 7.16 (1H, d, J = 2.1 Hz), 7.26 (2H, d, J = 8.0 Hz), 7.33 (3H, dd, J = 8.0 Hz, 6.1 Hz), 7.42 (2H, t, J = 7.5 Hz), 7.51 (1H, t, J = 7.4 Hz), 7.66 (1H, d, J = 7.8 Hz), 7.73 (2H, d, J = 7.2 Hz), 8.06 (2H, br.s), 8.39 (1H, d, J = 7.8 Hz), 8.52 (1H, d, J = 6.5 Hz), 8.61 (1H, t, J = 4.9 Hz), 10.82 (1H, br.s) |
| 177 | d⁶-DMSO | δ: 1.28 (3H, t, J = 7.0 Hz), 2.32-2.34 (1H, m), 2.66 (2H, t, J = 1.7 Hz), 2.85 (1H, d, J = 7.44 Hz), 2.91-3.03 (1H, m), 3.17 (1H, dd, J = 15.2 Hz, 5.0 Hz), 3.94 (2H, q, J = 7.0 Hz), 3.98-4.00 (1H, br.m), 4.20 (1H, d, J = 6.2 Hz), 4.55 (1H, q, J = 7.4 Hz), 4.62-4.68 (1H, m), 6.78 (2H, d, J = 8.5 Hz), 7.19 (2H, d, J = 8.5 Hz), 7.28 (2H, d, J = 8.4 Hz), 7.34-7.38 (2H, m), 7.44 (2H, q, J = 8.0 Hz), 7.51-7.56 (1H, m), 7.72-7.78 (2H, m), 8.08 (2H, br.s), 8.52 (1H, t, J = 6.6 Hz), 8.59-8.66 (2H, m), 8.97 (1H, br.s), 14.02 (1H, br.s), 14.18 (1H, br.s) |
| 178 | d⁶-DMSO | δ: 1.28 (3H, t, J = 7.0 Hz), 2.66 (1H, d, J = 11.0 Hz), 2.73 (1H, dd, J = 13.5, 3.6 Hz), 3.10 (1H, dd, J = 14.4, 9.8 Hz), 3.29 (1H, d, J = 4.9 Hz), 3.66 (2H, s), 3.92 (2H, q, J = 7.0 Hz), 4.30 (2H, qd, J = 15.2, 5.7 Hz), 4.66 (1H, td, J = 9.1, 4.4 Hz), 4.75 (1H, td, J = 9.0, 5.0 Hz), 6.73 (2H, d, J = 8.6 Hz), 7.14 (5H, dd, J = 8.3, 5.1 Hz), 7.22 (2H, d, J = 8.1 Hz), 7.35-7.44 (4H, m), 7.61 (2H, dd, J = 4.5, 1.5 Hz), 7.97 (2H, t, J = 9.4 Hz), 8.62 (1H, br, s), 8.67 (2H, dd, J = 4.5, 1.5 Hz), 8.71 (1H, br, s), 8.80 (1H, br, s) |
| 179 | d⁶-DMSO | δ: 1.28 (3H, t, J = 7.0 Hz), 2.02 (3H, s), 2.68-2.74 (2H, m), 2.83 (1H, dd, J = 13.6, 10.0 Hz), 3.05 (1H, dd, J = 13.5, 4.6 Hz), 3.93 (2H, q, J = 7.0 Hz), 3.98 (2H, d, J = 5.8 Hz), 4.32 (2H, qd, J = 15.3, 6.0 Hz), 4.55-4.64 (2H, m), 6.73 (2H, d, J = 8.5 Hz), 7.06 (2H, d, J = 8.5 Hz), 7.19-7.27 (7H, m), 7.38 (2H, d, J = 8.1 Hz), 7.69 (1H, d, J = 5.4 Hz), 7.85 (1H, d, J = 5.4 Hz), 8.11 (1H, d, J = 8.1 Hz), 8.22 (2H, br.s), 8.58 (1H, d, J = 8.5 Hz), 8.65 (1H, t, J = 5.7 Hz), 10.70 (1H, s) |
| 180 | d⁶-DMSO | δ: 1.27 (3H, t, J = 7.09 Hz), 2.72-2.74 (2H, m), 2.84-2.90 (1H, m), 3.09-3.16 (1H, m), 3.59 (2H, s, br), 3.91-3.98 (4H, m), 4.29-4.33 (2H, m), 4.57-4.67 (2H, m), 6.76 (2H, d, J = 8.79 Hz), 7.01-7.16 (7H, m), 7.22-7.27 (2H, m), 7.35-7.41 (3H, m), 7.43-7.51 (1H, m), 7.76 (2H, d, J = 7.19 Hz), 8.37 (3H, s, br), 8.57 (1H, d, J = 7.97 Hz), 8.64-8.69 (1H, m). |
| 181 | d⁶-DMSO | δ: 1.30 (3H, t, J = 7.21 Hz), 2.22 (3H, s), 2.56-2.78 (2H, m), 2.96-3.08 (1H, m), 3.23-3.28 (1H, m), 3.95-4.00 (4H, m), 4.32 (2H, d, J = 5.60 Hz), 4.49-4.54 (1H, m), 4.66-4.72 (1H, m), 6.76 (2H, d, J = 8.32 Hz), 6.91 (1H, d J = 5.14 Hz), 7.05 (2H, d, J = 8.69 Hz), 7.27 (2H, d, J = 7.90 Hz), 7.39 (2H, d, J = 8.30 Hz), 7.56 (1H, d, J = 5.14 Hz), 7.72 (1H, s, br), 7.88 (1H, d, J = 7.61?Hz), 8.16 (1H, d, J = 7.61 Hz), 8.27 (3H, s, br), 8.67-8.74 (3H, m). |
| 182 | d⁶-DMSO | δ: 1.28 (3H, t, J = 7.0 Hz), 2.29 (3H, s), 2.69 (2H, d, J = 7.2 Hz), 2.80-2.86 (1H, m), 3.04-3.09 (1H, m), 3.91-3.97 (4H, m), 4.24-4.34 (2H, m), 4.56-4.63 (2H, m), 6.76 (2H, d, J = 8.7 Hz), 7.08-7.31 (10H, m), 7.41-7.45 (2H, m), 7.50-7.53 (1H, m), 7.74-7.76 (2H, m), 8.15 (2H, s), 8.48 (1H, d, J = 8.0 Hz), 8.57-8.61 (2H, m) |
| 183 | d⁶-DMSO | δ: 1.28 (3H, t, J = 7.0 Hz), 2.76 (2H, d, J = 5.8 Hz), 3.06 (2H, dd, J = 14.5, 9.5 Hz), 3.22 (1H, dd, J = 14.5, 4.5 Hz), 3.94 (2H, q, J = 7.0 Hz), 3.98 (1H, d, J = 5.7 Hz), 4.29 (2H, d, J = 6.0 Hz), 4.44-4.50 (1H, m), 4.65 (1H, td, J = 8.8, 4.9 Hz), 6.33 (2H, br.s), 6.55 (1H, d, J = 5.3 Hz), 6.74 (2H, d, J = 8.6 Hz), 7.04 (2H, d, J = 8.5 Hz), 7.22 (2H, d, J = 8.0 Hz), 7.27 (1H, d, J = 1.4 Hz), 7.29 (1H, s), 7.34 (2H, d, J = 8.0 Hz), 7.39 (1H, d, J = 5.4 Hz), 8.07 (2H, br.s), 8.52 (1H, s), 8.53 (1H, s), 8.97 (1H, d, J = 1.8 Hz) |
| 184 | d⁶-DMSO | δ: 1.28 (3H, t, J = 7.0 Hz), 1.35 (1H, s), 1.89 (3H, s), 2.72 (1H, dd, J = 14.7, 7.9 Hz), 2.86 (1H, dd, J = 13.7, 4.7 Hz), 3.05 (1H, dd, J = 14.4, 9.8 Hz), 3.24 (1H, dd, J = 14.7, 4.6 Hz), 3.67 (2H, s), 3.94 (2H, q, J = 7.0 Hz), 4.25 (2H, d, J = 5.2 Hz), 4.65-4.70 (2H, m), 6.72 (2H, d, J = 8.6 Hz), 6.88 (2H, d, J = 8.7 Hz), 7.11 (2H, d, J = 7.9 Hz), 7.14 (1H, d, J = 5.2 Hz), 7.22 (2H, d, J = 7.8 Hz), 7.34 (1H, d, J = 1.7 Hz), 7.85 (1H, d, J = 5.2 Hz), 7.89 (2H, d, J = 7.5 Hz), 8.51 (1H, t, J = 6.0 Hz), 8.68 (1H, d, J = 8.6 Hz), 9.04 (1H, d, J = 1.9 Hz) |
| 185 | d⁶-DMSO | δ: 1.28 (3H, t, J = 6.9 Hz), 2.34 (3H, s), 2.77 (2H, d, J = 7.3 Hz), 3.05 (1H, dd, J = 14.6, 9.6 Hz), 3.22 (1H, dd, J = 14.6, 4.7 Hz), 3.93 (2H, q, J = 7.0 Hz), 3.97 (2H, m), 4.3 (2H, dd, J = 5.0, 4.9 Hz), 4.56 (1H, dd, J = 14.8, 7.6), 4.66-4.71 (1H, m), 6.76 (2H, d, J = 8.7 Hz), 7.15 (2H, d, J = 8.6 Hz), 7.22-7.26 (4H, m), 7.34 (2H, d, J = 8.2 Hz), 7.66 (2H, d, J = 8.2 Hz), 8.08 (3H, br s), 8.47 (1H, d, J = 7.8 Hz), 8.54 (1H, d, J = 6.0), 8.58 (1H, d, J = 8.3 Hz), 8.95 (1H, d, J = 2.0 Hz). |
| 186 | d⁶-DMSO | δ: 1.26 (3H, t, J = 7.0 Hz), 2.12 (3H, s), 2.26-2.67 (1H, m), 2.74 (1H, dd, J = 13.7, 4.7 Hz), 3.09 (1H, dd, J = 14.5, 10.1 Hz), 3.35 (1H, d, J = 5.6 Hz), 3.65 (2H, s), 3.89 (2H, q, J = 7.0 Hz), 4.27 (2H, d, J = 6.0 Hz), |

TABLE 7-continued

NMR data of examples

| Example No | Solvent | NMR (ppm) |
|---|---|---|
| | | 4.64 (2H, dd, J = 7.5, 4.7 Hz), 5.90 (1H, br.s), 6.59 (2H, d, J = 8.6 Hz), 6.76 (1H, t, J = 2.5 Hz), 6.86 (2H, d, J = 8.5 Hz), 7.13 (2H, d, J = 7.3 Hz), 7.20 (2H, d, J = 8.1 Hz), 7.24 (1H, br.s), 7.36-7.45 (3H, m). 7.97 (2H, d, J = 8.2 Hz), 8.64 (1H, br.s), 8.68 (1H, d, J = 7.2 Hz), 11.12 (1H, br.s) |
| 187 | d⁶-DMSO | δ: 1.29 (3H, t, J = 7.0 Hz), 2.14 (3H, s), 2.66 (1H, dd, J = 13.1, 9.0 Hz), 2.78 (1H, dd, J = 13.7, 4.5 Hz), 2.86 (1H, dd, J = 14.2, 10.0 Hz), 3.07 (1H, dd, J = 14.2, 4.4 Hz), 3.66 (2H, s), 3.95 (2H, q, J = 7.0 Hz), 4.26 (2H, d, J = 4.6 Hz), 4.51 (1H, td, J = 9.0, 4.8 Hz), 4.61-4.67 (1H, m), 5.91 (1H, s), 6.75 (2H, d, J = 8.6 Hz), 6.77 (1H, d, J = 2.7 Hz), 7.02 (3H, d, J = 8.5 Hz), 7.12 (2H, d, J = 7.6 Hz), 7.15 (2H, br.s), 7.21 (2H, d, J = 8.3 Hz), 7.29 (1H, d, J = 7.4 Hz), 7.42 (1H, dd, J = 4.8, 2.9 Hz), 8.32 (1H, s), 8.49 (1H, br.s), 8.57 (1H, d, J = 7.0 Hz), 11.11 (1H, s) |
| 188 | d⁶-DMSO | δ: 1.26 (3H, t, J = 7.0 Hz), 2.01 (3H, s), 2.08 (1H, s), 2.66-2.72 (1H, m), 2.76-2.80 (1H, m), 3.12 (1H, dd, J = 14.4, 9.6), 3.67 (1H, s), 3.90 (2H, q, J = 7.0 Hz), 4.10 (1H, dd, J = 17.3, 6.1 Hz), 4.28-4.31 (2H, m), 4.35 (1H, dd, J = 13.5, 6.8 Hz), 4.59 (1H, br.s), 4.71-4.76 (1H, m), 6.66 (2H, d, J = 8.6 Hz), 7.02 (2H, d, J = 8.5 Hz), 7.14 (3H, d, J = 7.6 Hz), 7.22 (1H, d, J = 8.2 Hz), 7.31-7.42 (4H, m), 7.67 (1H, d, J = 5.2 Hz), 7.84 (1H, d, J = 5.4 Hz), 7.97 (2H, dd, J = 12.2, 8.0 Hz), 8.05 (br.s, 1H), 8.60 (2H, br.d, J = 7.1 Hz), 10.66 (1H, br.s) |
| 189 | d⁶-DMSO | δ: 1.28 (3H, t, J = 6.70 Hz), 2.33 (3H, s), 2.69 (2H, d, J = 7.51 Hz), 2.91-2.99 (1H, m), 3.13-3.18 (1H, m), 3.92-4.00 (4H, m), 4.33 (2H, d, J = 5.94 Hz), 4.52-4.61 (1H, m), 4.63-4.69 (1H, m), 6.76 (2H, d, J = 8.67 Hz), 7.15 (2H, d, J = 7.86 Hz), 7.27 (2H, d, J = 8.096 Hz), 7.31 (2H, d, J = 6.36 Hz), 7.36 (2H, d, J = 7.51 Hz), 7.47-7.53 (1H, m), 7.56 (1H, d, J = 7.51 Hz), 7.87 (1H, d, J = 7.341 Hz), 8.11 (3H, s, br), 8.45 (1H, d, J = 7.86 Hz), 8.53 (2H, d, J = 4.72 Hz), 8.57-8.65 (2H, m). |
| 190 | d⁶-DMSO | δ: 1.31 (3H, t, J = 6.88 Hz), 2.08 (3H, s), 2.70-2.71 (1H, m), 2.74-2.75 (1H, m), 2.88-2.94 (1H, m), 3.13-3.18 (1H, m), 3.90-4.01 (4H, m), 4.33 (2H, d, J = 6.21?Hz), 4.57-4.62 (1H, m), 4.66-4.71 (1H, m), 6.80 (2H, d, J = 8.06 Hz), 7.09-7.11 (5H, m), 7.14-7.31 (2H, m), 7.36 (2H, d, J = 8.056 Hz), 7.45-7.48 (1H, m), 7.84 (1H, d, J = 7.051 Hz), 8.11 (3H, s, br), 8.34 (1H, d, J = 8.06 Hz), 8.52-8.53 (1H, m), 8.56 (1H, d, J = 5.021 Hz), 8.63-8.65 (2H, m). |
| 191 | d⁶-DMSO | δ: 1.29 (3H, t, J = 6.84 Hz), 2.07 (3H, s), 2.14 (3H, s), 2.53-2.59 (1H, m), 2.69-2.74 (1H, m), 2.77-2.83 (1H, m), 3.05-3.09 (1H, m), 3.91-4.01 (4H, m), 4.30 (2H, d, J = 5.98 Hz), 4.51-4.65 (2H, m), 5.63 (1H, d, J = 1.50 Hz) 6.71 (2H, d, J = 8.88 Hz), 6.90 (2H, t, J = 8.88 Hz), 7.04 (1H, d, J = 8.17 Hz), 7.18-7.28 (8H, m), 7.34 (2H, d, J = 7.35 Hz), 8.10 (2H, s, br), 8.57-8.64 (2H, m). |
| 192 | d⁶-DMSO | δ: 1.28 (3H, t, J = 6.82 Hz), 2.30 (3H, s), 2.71-2.74 (2H, m), 2.80-2.86 (1H, m), 3.04-3.09 (1H, m), 3.91-3.95 (4H, m), 4.25-4.30 (2H, m), 4.54-4.59 (1H, m), 4.69-4.74 (1H, m), 6.76 (2H, d, J = 7.887 Hz), 7.08-7.31 (10H, m), 7.41-7.45 (2H, m), 7.50-7.53 (1H, m), 7.74-7.76 (2H, m), 8.31-8.39 (3H, m), 8.63 (1H, d, J = 7.88 Hz), 8.75-8.78 (3H, m). |
| 193 | d⁶-DMSO | δ: 1.27 (3H, t, J = 7.0 Hz), 2.01 (3H, s), 2.32-2.34 (1H, m), 2.67 (1H, t, J = 1.7 Hz), 2.76-2.78 (2H, m), 2.88 (2H, dd, J = 14.1, 9.6 Hz), 3.04 (2H, dd, J = 14.2, 4.6 Hz), 3.67 (1H, s), 3.93 (2H, q, J = 7.0 Hz), 4.28 (2H, t, J = 6.4 Hz), 4.56-4.62 (2H, m), 6.75 (2H, d, J = 8.6 Hz), 6.99 (1H, d, J = 5.8 Hz), 7.12 (3H, t, J = 8.3 Hz), 7.15 (1H, d, J = 3.5 Hz), 7.22 (2H, d, J = 8.0 Hz), 7.39 (1H, dd, J = 4.8, 3.0 Hz), 7.69 (1H, d, J = 5.4 Hz), 7.85 (1H, d, J = 5.4 Hz), 8.15 (1H, d, J = 8.3 Hz), 8.50 (2H, t, J = 8.0 Hz), 10.69 (1H, br.s) |
| 194 | d⁶-DMSO | (DMSO) δ: 1.27 (3H, t, J = 7.0 Hz), 7.00 (2H, d, J = 7.0 Hz), 3.10 (2H, dd, J = 14.5, 10.0 Hz), 3.90 (2H, q, J = 7.0 Hz), 4.00 (2H, q, J = 5.5 Hz), 4.33 (2H, d, J = 6.1 Hz), 4.52 (1H, q, J = 6.6 Hz), 4.67 (1H, td, J = 9.6 Hz, 4.1 Hz), 6.35 (1H, br.s), 6.56 (1H, d, J = 5.4 Hz), 6.61 (2H, d, J = 8.6 Hz), 6.91 (2H, d, J = 8.6 Hz), 7.14 (1H, d, J = 7.7 Hz), 7.26 (2H, d, J = 7.5 Hz), 7.36 (2H, d, J = 8.1 Hz), 7.38 (2H, d, J = 5.3 Hz), 7.46-7.41 (3H, m), 7.98 (2H, d, J = 8.8 Hz), 8.06 (2H, br.s), 8.60 (1H, d, J = 8.12 Hz), 8.70 (1H, br.s) |
| 195 | d⁶-DMSO | δ: 1.28 (3H, t, J = 7.0 Hz), 2.76 (2H, d, J = 5.8 Hz), 3.06 (2H, dd, J = 14.5, 9.5 Hz), 3.22 (1H, dd, J = 14.5, 4.5 Hz), 3.94 (2H, q, J = 7.0 Hz), 3.98 (1H, d, J = 5.7 Hz), 4.29 (2H, d, J = 6.0 Hz), 4.44-4.50 (1H, m), 4.65 (1H, td, J = 8.8, 4.9 Hz), 6.33 (2H, br.s), 6.55 (1H, d, J = 5.3 Hz), 6.74 (2H, d, J = 8.6 Hz), 7.04 (2H, d, J = 8.5 Hz), 7.22 (2H, d, J = 8.0 Hz), 7.27 (1H, d, J = 1.4 Hz), 7.29 (1H, s), 7.34 (2H, d, J = 8.0 Hz), 7.39 (1H, d, J = 5.4 Hz), 8.07 (2H, br.s), 8.52 (1H, s), 8.53 (1H, s), 8.97 (1H, d, J = 1.8 Hz) |
| 196 | d⁶-DMSO | δ: 1.29 (3H, t, J = 6.91 Hz), 2.42-2.46 (1H, m), 2.76-3.00 (3H, m), 3.05 (3H, s), 3.27-3.31 (1H, m), 3.93-4.00 (4H, m), 4.29 (2H, d, J = 6.28 Hz), 4.89-4.99 (1H, m), 5.34-5.38 (1H, m), 6.67 (2H, d, J = 8.78 Hz), 6.74 (2H, d, J = 8.21 Hz), 6.98-7.01 (1H, m), 7.14 (1H, d, J = 5.67 Hz), |

TABLE 7-continued

NMR data of examples

| Example No | Solvent | NMR (ppm) |
|---|---|---|
| | | 7.19-7.38 (7H, m), 7.86 (1H, d, J = 5.67 Hz), 7.88 (1H, d, J = 7.09 Hz), 8.09 (3H, s, br), 8.41-8.48 (1H, m). |
| 197 | d⁶-DMSO | δ: 1.28 (3H, t, J = 7.15 Hz), 2.72-2.74 (2H, m), 3.92-3.99 (4H, m), 4.36 (2H, d, J = 6.40 Hz), 4.47-4.50 (1H, m), 4.67-4.73 (1H, m), 5.22 (1H, s, br), 5.83 (1H, s, br), 6.76 (2H, d, J = 8.51 Hz), 7.17-7.30 (6H, m), 7.37-7.45 (5H, m), 7.52-7.53 (1H, m), 8.30 (4H, s, br), 8.38-8.44 (2H, m), 8.60 (1H, d, J = 7.64 Hz). |
| 198 | d⁶-DMSO | δ: 1.28 (3H, t, J = 6.70 Hz), 2.61-2.64 (1H, m), 2.79-2.83 (1H, m),, 3.91-4.00 (4H, m), 4.34-4.36 (2H, m), 4.45-4.48 (1H, m), 4.82-4.85 (1H, m), 5.26-5.28 (1H, m), 5.85-5.86 (1H, m), 6.54 (1H, s, br), 6.65 (2H, d, J = 8.21 Hz), 6.71 (2H, d, J = 8.213 Hz), 7.13 (1H, d, J = 5.47 Hz), 7.23-7.36 (4H, m), 7.49 (2H, d, J = 7.11 Hz), 7.82-7.86 (3H, m), 8.07 (3H, s, br), 8.36 (1H, t, J = 5.81 Hz), 8.53 (1H, d, J = 8.92 Hz). |

Example 199

N—[(R)-1-[(S)-1-(4-Aminomethyl-benzylcarbamoyl)-2-pyridin-3-yl-ethylcarbamoyl]-2-(4-ethoxyphenyl)-ethyl]-4-methyl-benzamide

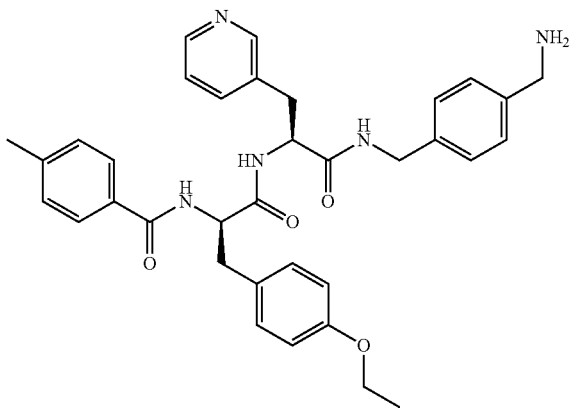 [SMILES: CCOc1ccc(C[C@@H](NC(=O)c2ccc(C)cc2)C(=O)N[C@@H](Cc2cccnc2)C(=O)NCc2ccc(CN)cc2)cc1]

A. [4-(tert-Butoxycarbonylamino-methyl)-benzyl]-carbamic acid benzyl ester tert-Butyl 4-(Aminomethyl)benzylcarbamate (7.5 g, 31.74 mmol) was dissolved in dichloromethane (250 mL). This solution was cooled to 0° C. and triethylamine (9.63 g, 93.2 mmol) was added followed by carbonic acid benzyl ester 2,5-dioxo-pyrrolidin-1-yl ester (9.5 g, 38.09 mmol). The reaction mixture was stirred at 0° C. to room temperature for 18 hours and diluted with CHCl₃ (200 mL) the filtrate was washed with 0.3M KHSO₄ (1×50 mL), sat. NaHCO₃ (1×50 mL), water (1×50 mL), brine (1×50 mL), dried (Na₂SO₄) and evaporated in vacuo to give a white solid. The solid were triturated with EtOAc/Pet Ether 60-80° C. to give a white solid identified as [4-(tert-butoxycarbonylamino-methyl)-benzyl]-carbamic acid benzyl ester (11.3 g, 30.5 mmol, 96%).
[M+H]⁺=392.98 (M+Na)

B. (4-Aminomethyl-benzyl)-carbamic acid benzyl ester hydrochloride

[4-(tert-Butoxycarbonylamino-methyl)-benzyl]-carbamic acid benzyl ester (10.8 g, 29.15 mmol) was dissolved in 4M HCl in dioxan (400 mL). After one hour at room temperature the solvent was removed in vacuo. The residue was slurried with acetone and the solid was filtered off to give a white solid identified as (4-aminomethyl-benzyl)-carbamic acid benzyl ester hydrochloride (11.9 g, 30.135 mmol, 99%).
[M+H]⁺=359.15

C. {(S)-1-[4-(Benzyloxycarbonylamino-methyl)-benzylcarbamoyl]-2-pyridin-3-yl-ethyl}-carbamic acid tert-butylester (S)-2-tert-Butoxycarbonylamino-3-pyridin-3-yl-propionic acid (2.12 g, 7.96 mmol) was dissolved in CH₂Cl₂ (100 mL), HBTU (3.29 g, 8.68 mmol) and triethylamine (2.20 g, 21.71 mmol) were added. After 20 mins at room temperature the reaction mixture was cooled to 0° C. and (4-aminomethyl-benzyl)-carbamic acid benzyl ester hydrochloride (1.96 g, 7.24 mmol) was added. After 2 hours at 0° C. the reaction mixture was diluted with CHCl₃ (200 mL), this solution was washed with 0.3M KHSO₄ (1×50 mL), sat NaHCO₃ (1×50 mL), water (1×50 mL), brine (1×50 mL), dried (Na₂SO₄) and evaporated in vacuo to give a white solid. The solid was triturated with EtOAc/Pet Ether 60-80° C. to give a white solid identified as {(S)-1-[4-(benzyloxycarbonylamino-methyl)-benzylcarbamoyl]-2-pyridin-3-yl-ethyl}-carbamic acid tert-butylester (2.53 g, 4.88 mmol, 67%).
[M+H]⁺=519.16

D. {4-[((S)-2-Amino-3-pyridin-3-yl-propionylamino)-methyl]-benzyl}-carbamic acid benzyl ester Dihydrochloride {(S)-1-[4-(Benzyloxycarbonylamino-methyl)-benzylcarbamoyl]-2-pyridin-3-yl-ethyl}-carbamic acid tert-butylester (2.52 g, 4.89 mmol) was treated with 4M HCl/dioxan (50 mL). After one hour at room temperature the solvent was removed to give a white solid identified as {4-[((S)-2-amino-3-pyridin-3-yl-propionylamino)-methyl]-benzyl}-carbamic acid benzyl ester dihydrochloride (2.31 g, 4.71 mmol, 97%).
[M+H]+=419.18
¹H NMR: (d⁶-DMSO) δ: 9.38 (1H, t, J=5.7 Hz), 8.87 (1H, s), 8.81 (1H, d, J=5.4 Hz), 8.42-8.49 (2H, br s), 8.41 (1H, d, J=8.0 Hz), 7.93 (1H, dd, J=7.9, 5.8 Hz), 7.87 (1H, t, J=6.2 Hz), 7.28-7.38 (4H, m), 7.16-7.25 (4H, m), 5.03 (2H, s), 4.22-4.43 (4H, m), 4.18 (2H, d, J=6.1 Hz), 3.39 (1H, dd, J=14, 5.6 Hz), 3.26 (1H, dd, J=14.0, 8.2 Hz).

E. [(R)-1-{(S)-1-[4-(Benzyloxycarbonylamino-methyl)-benzylcarbamoyl]-2-pyridin-3-yl-ethylcarbamoyl}-2-(4-ethoxy-phenyl)-ethyl]-carbamic acid tert-butyl ester (R)-2-Benzyloxycarbonylamino-3-(4-ethoxy-phenyl)-propionic acid (870 mg, 2.80 mmol) was dissolved in CH$_2$Cl$_2$ (100 mL), HBTU (1.21 g, 3.20 mmol) and triethylamine (1.35 g, 13.33 mmol) were added. After 20 mins at room temperature the reaction mixture was cooled to 0° C. and {4-[((S)-2-amino-3-pyridin-3-yl-propionylamino)-methyl]-benzyl}-carbamic acid benzyl ester dihydrochloride (1.31 g, 2.67 mmol) was added. After 2 hours at 0° C. the reaction mixture was diluted with CHCl$_3$ (200 mL), this solution was washed with 0.3M KHSO$_4$ (1×50 mL), sat NaHCO$_3$ (1×50 mL), water (1×50 mL), brine (1×50 mL), dried (Na$_2$SO$_4$) and evaporated in vacuo to give a white solid. The solid was triturated with EtOAc/Pet Ether 60-80° C. to give a white solid identified as [(R)-1-{(S)-1-[4-(benzyloxycarbonylamino-methyl)-benzylcarbamoyl]-2-pyridin-3-yl-ethylcarbamoyl}-2-(4-ethoxy-phenyl)-ethyl]-carbamic acid tert-butyl ester (2.40 g, 1.70 mmol, 90%).
[M+H]$^+$=710.18

F. [4-({(S)-2-[(R)-2-Amino-3-(4-ethoxy-phenyl)-propionylamino]-3-pyridin-3-yl-propionylamino}-methyl)-benzyl]carbamic acid benzyl ester Dihydrochloride

[(R)-1-{(S)-1-[4-(Benzyloxycarbonylamino-methyl)-benzylcarbamoyl]-2-pyridin-3-yl-ethylcarbamoyl}-2-(4-ethoxy-phenyl)-ethyl]-carbamic acid tert-butyl ester (1.70, 2.42 mmol) was treated with 4M HCl/dioxan (100 mL). After one hour at room temperature the solvent was removed to give a white solid identified as [4-({(S)-2-[(R)-2-amino-3-(4-ethoxy-phenyl)-propionylamino]-3-pyridin-3-yl-propionylamino}-methyl)-benzyl]-carbamic acid benzyl ester dihydrochloride (1.50 g, 2.32 mmol, 97%).
[M+H]+=609.99
$^1$H NMR: (d$^6$-DMSO) δ: 9.29 (1H, d, J=8.4 Hz), 8.96 (1H, t, J=5.8 Hz), 8.83 (1H, s), 8.77 (1H, d, J=5.4 Hz), 8.39 (1H, d, J=8.2 Hz), 8.28-7.98 (2H, br s), 7.92 (1H, dd, J=8.0, 5.7 Hz), 7.86 (1H, t, J=6.2 Hz), 7.28-7.38 (4H, m), 7.11-7.20 (4H, m), 6.95 (2H, d, J=8.6 Hz), 6.79 (2H, d, J=8.6 Hz), 5.02 (2H, s), 4.68-4.75 (1H, m), 4.23-4.25 (2H, m), 4.16 (2H, d, J=6.1 Hz), 3.83-4.13 (4H, m), 3.22 (1H, dd, J=14.0, 4.4 Hz), 3.03 (1H, dd, J=13.7, 9.7 Hz), 2.84 (1H, dd, J=14.0, 5.9 Hz), 2.63 (1H, dd, J=13.8, 6.1 Hz), 1.29 (3H, t, J=7.0 Hz).

G. [4-({(S)-2-[(R)-3-(4-Ethoxy-phenyl)-2-(4-methyl-benzoylamino)-propionylamino]-3-pyridin-3-yl-propionylamino}-methyl)-benzyl]-carbamic acid benzyl ester

[4-({(S)-2-[(R)-2-Amino-3-(4-ethoxy-phenyl)-propionylamino]-3-pyridin-3-yl-propionylamino}-methyl)-benzyl]-carbamic acid benzyl ester dihydrochloride (150 mg, 0.23 mol) was dissolved in dichloromethane (50 mL), this solution was cooled to 0° C. Triethylamine (70 mg, 0.70 mmol) was added followed by p-toluoyl chloride (39 mg, 0.26 mmol). After 18 hrs at 0° C. to room temperature the reaction mixture was diluted with CHCl$_3$ (50 mL), this solution was washed with sat. NaHCO$_3$ (1×20 mL), water (1×20 mL), brine (1×20 mL), dried (Na$_2$SO$_4$) and evaporated in vacuo. The residue was purified by flash chromatography (silica), eluent 2% MeOH, 98% CHCl$_3$, fractions combined and evaporated in vacuo to give a colourless oil identified as [4-({(S)-2-[(R)-3-(4-ethoxy-phenyl)-2-(4-methyl-benzoylamino)-propionylamino]-3-pyridin-3-yl-propionylamino}-methyl)-benzyl]-carbamic acid benzyl ester (130 mg, 0.18 mmol, 77%).
[M+H]$^+$=728.14

H. N—[(R)-1-[(S)-1-(4-Aminomethyl-benzylcarbamoyl)-2-pyridin-3-yl-ethylcarbamoyl]-2-(4-ethoxy-phenyl)-ethyl]-4-methyl-benzamide Dihydrochloride

[4-({(S)-2-[(R)-3-(4-ethoxy-phenyl)-2-(4-methyl-benzoylamino)-propionylamino]-3-pyridin-3-yl-propionylamino}-methyl)-benzyl]-carbamic acid benzyl ester (98 mg, 0.13 mmol) was dissolved in methanol (100 mL), 1M hydrochloric acid (0.263 mL, 0.263 mmol) was added and the reaction mixture was hydrogenated over 10% Pd/C (50 mg) at atmospheric pressure for 2 hours after which time the catalyst was filtered off and washed with methanol (100 mL), the combined filtrates were evaporated in vacuo to give a white solid which was recrystallised from ethanol to give a white solid identified as N—[(R)-1-[(S)-1-(4-aminomethyl-benzylcarbamoyl)-2-pyridin-3-yl-ethylcarbamoyl]-2-(4-ethoxy-phenyl)-ethyl]-4-methyl-benzamide dihydrochloride.
Yield=340 mg, 0.498 mmol, 57%
[M+H]$^+$=593.99
$^1$H NMR: (d$^6$-DMSO) δ: 1.28 (3H, t, J=7.05 Hz), 2.34 (3H, s), 2.72 (2H, d, J=8.16 Hz), 3.01-3.06 (1H, m), 3.25-3.28 (1H, m), 3.91-3.98 (4H, m), 4.32-4.38 (2H, m), 4.54-4.57 (1H, m), 4.70-4.73 (1H, m), 6.75 (2H, d, J=6.83 Hz), 7.18 (2H, d, J=8.56 Hz), 7.24 (2H, d, J=7.56 Hz), 7.25-7.27 (1H, m), 7.28 (2H, d, J=6.78 Hz), 7.39 (2H, d, J=7.51 Hz), 7.67 (1H, d, J=7.51 Hz), 7.76 (1H, s, br), 8.22 (1H, d, J=7.56 Hz), 8.33 (3H, s, br), 8.71-8.77 (4H, m).

Example 200

N—[(R)-1-[(S)-1-(4-Aminomethyl-benzylcarbamoyl)-2-(3,4-difluoro-phenyl)-ethylcarbamoyl]-2-(4-ethoxy-phenyl)-ethyl]-benzamide

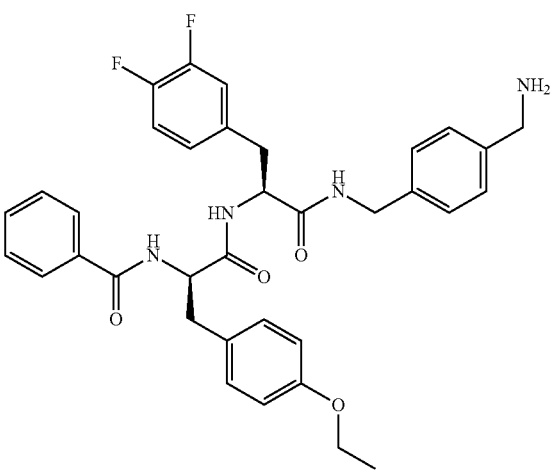 [SMILES: CCOc1ccc(C[C@@H](NC(=O)c2ccccc2)C(=O)N[C@@H](Cc2ccc(F)c(F)c2)C(=O)NCc2ccc(CN)cc2)cc1]

A. [4-(tert-Butoxycarbonylamino-methyl)-benzyl]-carbamic acid 9H-fluoren-9-ylmethyl ester tert-Butyl 4-(Aminomethyl)benzylcarbamate (7.5 g, 31.74 mmol) was dissolved in dichloromethane (250 mL). This solution was cooled to 0° C. and triethylamine (9.63 g, 93.2 mmol) was added followed by carbonic acid 2,5-dioxo-pyrrolidin-1-yl ester 9H-fluoren-9-ylmethyl ester (12.85 g, 38.09 mmol). The reaction mixture was stirred at 0° C. to room temperature for 3 hours and diluted with CHCl$_3$ (200 mL) the filtrate was washed with 0.3M KHSO$_4$ (1×50 mL), sat. NaHCO$_3$ (1×50 mL), water (1×50 mL), brine (1×50 mL), dried (Na$_2$SO$_4$) and evaporated in vacuo to give a white solid. The solid was triturated with EtOAc/Pet Ether 60-80° C. to give a white solid identified as [4-(tert-butoxycarbonylamino-methyl)-benzyl]-carbamic acid 9H-fluoren-9-ylmethyl ester (13.96 g, 30.44 mmol, 96%).

[M+H]$^+$=359.14 (M-Boc)

B. (4-Aminomethyl-benzyl)-carbamic acid 9H-fluoren-9-ylmethyl ester Hydrochloride

[4-(tert-Butoxycarbonylamino-methyl)-benzyl]-carbamic acid 9H-fluoren-9-ylmethyl ester (13.9 g, 31.41 mmol) was dissolved in 4M HCl in dioxan (400 mL). After one hour at room temperature the solvent was removed in vacuo. The residue was triturated with acetone, the solid was filtered off to give a white solid identified as (4-aminomethyl-benzyl)-carbamic acid 9H-fluoren-9-ylmethyl ester hydrochloride (11.9 g, 30.135 mmol, 99%)

[M+H]$^+$=359.15

C. ((S)-2-(3,4-Difluoro-phenyl)-1-{4-[(9H-fluoren-9-ylmethoxycarbonylamino)-methyl]-benzylcarbamoyl}-ethyl)-carbamic acid tert-butyl ester (S)-2-tert-Butoxycarbonylamino-3-(3,4-difluoro-phenyl)-propionic acid (2.1 g, 6.96 mmol) was dissolved in CH$_2$Cl$_2$ (250 mL) and DMF (25 mL). This solution was cooled to 0° C. (4-Aminomethyl-benzyl)-carbamic acid 9H-fluoren-9-ylmethyl ester hydrochloride (2.5 g, 6.33 mmol) was added followed by HOBt (940 mg, 6.96 mmol) and triethylamine (1.92 g, 18.99 mmol). Water soluble carbodiimide (1.45 g, 7.6 mmol) was then added. After 18 hours at 0° C. to room temperature reaction mixture was diluted with chloroform (400 mL) washed with 0.3MKHSO$_4$ (1×30 mL), NaHCO$_3$ (1×30 mL), water (1×30 mL), brine (1×30 mL) and evaporated in vacuo giving a white solid. The residue was triturated with ethyl acetate/pet ether 60-80° C. to give a white solid identified as ((S)-2-(3,4-difluoro-phenyl)-1-{4-[(9H-fluoren-9-ylmethoxycarbonylamino)-methyl]-benzylcarbamoyl}-ethyl)-carbamic acid tert-butyl ester (2.60 g, 4.05 mmol, 64%).

[M+H]$^+$=641.9, 664.07 (M+Na)

D. (4-{[(S)-2-Amino-3-(3,4-difluoro-phenyl)-propionylamino]methyl}-benzyl)-carbamic acid 9H-fluoren-9-ylmethyl ester hydrochloride ((S)-2-(3,4-Difluoro-phenyl)-1-{4-[(9H-fluoren-9-ylmethoxycarbonylamino)-methyl]-benzylcarbamoyl}-ethyl)-carbamic acid tert-butyl ester (2.5 g, 3.90 mmol) was dissolved in 4M HCl in dioxan (150 mL). After one hour at room temperature the solvent was removed in vacuo to give a white solid identified as (4-{[(S)-2-amino-3-(3,4-difluoro-phenyl)-propionylamino]-methyl}-benzyl)-carbamic acid 9H-fluoren-9-ylmethyl ester hydrochloride (2.25 g, 3.89 mmol, 100%).

[M+H]$^+$=542.12

E. [(R)-1-((S)-2-(3,4-Difluoro-phenyl)-1-{4-[(9H-fluoren-9-ylmethoxycarbonylamino)-methyl]-benzylcarbamoyl}-ethylcarbamoyl)-2-(4-ethoxy-phenyl)-ethyl]-carbamic acid tert-butyl ester (R)-2-tert-Butoxycarbonylamino-3-(4-ethoxy-phenyl)-propionic acid (895 mg, 2.90 mmol) was dissolved in CH$_2$Cl$_2$ (250 mL) and DMF (25 mL). This solution was cooled to 0° C. (4-{[(S)-2-Amino-3-(3,4-difluoro-phenyl)-propionylamino]-methyl}-benzyl)-carbamic acid 9H-fluoren-9-ylmethyl ester hydrochloride (1.5 g, 2.63 mmol) was added followed by HOBt (391 mg, 2.90 mmol) and triethylamine (800 mg, 7.89 mmol). Water soluble carbodiimide (605 mg, 3.16 mmol) was then added. After 18 hours at 0° C. to room temperature reaction mixture was diluted with chloroform (200 mL) washed with 0.3MKHSO$_4$ (1×30 mL), NaHCO$_3$ (1×30 mL), water (1×30 mL), brine (1×30 mL) and evaporated in vacuo giving a white solid. The residue was triturated with ethyl acetate/pet ether 60-80° C. to give a white solid identified [(R)-1-((S)-2-(3,4-difluoro-phenyl)-1-{4-[(9H-fluoren-9-ylmethoxycarbonylamino)-methyl]-benzylcarbamoyl}-ethylcarbamoyl)-2-(4-ethoxy-phenyl)-ethyl]-carbamic acid tert-butyl ester (2.1 g, 2.52 mmol, 96%).

[M+H]$^+$=733.15 (M-Boc)

F. (4-{[(S)-2-[(R)-2-Amino-3-(4-ethoxy-phenyl)-propionylamino]-3-(3,4-difluoro-phenyl)-propionylamino]-methyl}-benzyl)-carbamic acid 9H-fluoren-9-ylmethyl ester Hydrochloride

[(R)-1-((S)-2-(3,4-Difluoro-phenyl)-1-{4-[(9H-fluoren-9-ylmethoxycarbonylamino)-methyl]-benzylcarbamoyl}-ethylcarbamoyl)-2-(4-ethoxy-phenyl)-ethyl]-carbamic acid tert-butyl ester (2.1 g, 2.52 mmol) was dissolved in 4M HCl in dioxan (150 mL). After one hour at room temperature the solvent was removed in vacuo and the residue triturated with acetone to give a white solid identified as (4-{[(S)-2-[(R)-2-amino-3-(4-ethoxy-phenyl)-propionylamino]-3-(3,4-difluoro-phenyl)-propionylamino]-methyl}-benzyl)-carbamic acid 9H-fluoren-9-ylmethyl ester hydrochloride (1.9 g, 2.47 mmol, 98%).

[M+H]$^+$=73.12

G. (4-{[(S)-2-[(R)-2-Benzoylamino-3-(4-ethoxy-phenyl)-propionylamino]-3-(3,4-difluoro-phenyl)-propionylamino]-methyl}-benzyl)-carbamic acid 9H-fluoren-9-ylmethyl ester (4-{[(S)-2-[(R)-2-Amino-3-(4-ethoxy-phenyl)-propionylamino]-3-(3,4-difluoro-phenyl)-propionylamino]-methyl}-benzyl)-carbamic acid 9H-fluoren-9-ylmethyl ester hydrochloride (410 mg, 0.53 mmol) was dissolved in dichloromethane (50 mL). This solution was cooled to 0° C. and triethylamine (162 mg, 1.60 mmol) was added followed by benzoyl chloride (82 mg, 0.59 mmol). The reaction mixture was stirred at 0° C. to room temperature for 3 hours and diluted with CHCl$_3$ (100 mL) the filtrate was washed with 0.3M KHSO$_4$ (1×30 mL), sat. NaHCO$_3$ (1×30 mL), water (1×30 mL), brine (1×30 mL), dried (Na$_2$SO$_4$) and evaporated in vacuo to give a white solid. The solid were triturated with hot ethanol, the cooled suspension was filtered to give a white solid identified as (4-{[(S)-2-[(R)-2-benzoylamino-3-(4-ethoxy-phenyl)-propionylamino]-3-(3,4-difluoro-phenyl)-propionylamino]-methyl}-benzyl)-carbamic acid 9H-fluoren-9-ylmethyl ester (240 mg, 0.34 mmol, 99%).

[M+H]$^+$=697.18

H. N—[(R)-1-[(S)-1-(4-Aminomethyl-benzylcarbamoyl)-2-(3,4-difluoro-phenyl)-ethylcarbamoyl]-2-(4-ethoxy-phenyl)-ethyl]-benzamide Hydrochloride (4-{[(S)-2-[(R)-2-Benzoylamino-3-(4-ethoxy-phenyl)-propionylamino]-3-(3,4-difluoro-phenyl)-propionylamino]-methyl}-benzyl)-carbamic acid 9H-fluoren-9-ylmethyl ester (180 mg, 0.215 mmol) was dissolved in diethylamine/THF (1:1, 100 mL) the reaction mixture was stirred at room temperature for 3 hours after which time the solvent was removed in vacuo and the residue was triturated with ethyl acetate/pet ether 60-80° C. to give a white solid identified which was treated with 4M HCl in dioxan (20 mL), the solvent was removed in vacuo and the residue recrystallised from EtOH to give a white solid identified as N—[(R)-1-[(S)-1-(4-aminomethyl-benzylcarbamoyl)-2-(3,4-difluoro-phenyl)-ethylcarbamoyl]-2-(4-ethoxy-phenyl)-ethyl]-benzamide hydrochloride (62 mg, 0.095 mmol, 44%).

[M+H]$^+$=614.68

$^1$H NMR: (d$^6$-DMSO) δ: 1.26 (3H, t, J=6.79 Hz), 2.65-2.84 (3H, m), 3.03-3.08 (1H, m), 3.92 (2H, q, J=6.11 Hz), 3.96 (2H, s), 4.27-4.35 (2H, m), 4.57-4.63 (2H, m), 6.75 (2H, d, J=8.03 Hz), 7.16 (2H, d, J=8.76 Hz), 7.23-7.25 (1H, m), 7.26-7.27 (2H, m), 7.37-7.51 (6H, m), 7.43 (1H, d, J=7.3 Hz), 7.73-7.75 (2H, m), 8.24 (2H, s), 8.50 (1H, d, J=7.40 Hz), 8.67-8.71 (2H, m).

Example 201

N-{(R,S)-1-[(S)-1-(4-Aminomethyl-benzylcarbamoyl)-2-phenyl-ethylcarbamoyl]-2-[4-(2,2,2-trifluoro-ethoxy)-phenyl]-ethyl}-benzamide

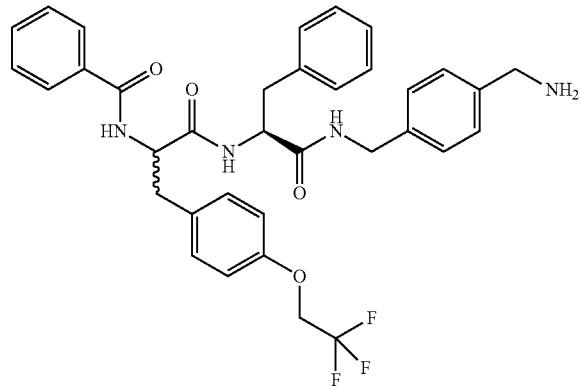 [SMILES: NCc1ccc(CNC(=O)[C@H](Cc2ccccc2)NC(=O)C(Cc2ccc(OCC(F)(F)F)cc2)NC(=O)c2ccccc2)cc1]

A. (R,S)-2-Benzyloxycarbonylamino-3-[4-(2,2,2-trifluoro-ethoxy)-phenyl]-propionic acid (R)-2-Benzyloxycarbonylamino-3-(4-hydroxy-phenyl)-propionic acid (1.0 g, 3.17 mmol) was dissolved in THF (70 mL), 2,22-trifluoroethyl trifluoromethanesulfonate (883 mg, 3.81 mmol) and cesium carbonate (3.1 g, 9.5 mmol) were added. The reaction mixture was stirred at 65° C. for 18 hours after which time the solvent was removed in vacuo and the residue taken up in EtOAc (100 mls), this solution was washed with 1M HCl (1×30 mL), water (1×30 mL), brine (1×30 mL), dried (Na$_2$SO$_4$) and evaporated in vacuo. The residue was purified by flash chromatography (silica), eluent 1% AcOH, 5% MeOH, 94% CHCl$_3$, fractions combined and evaporated in vacuo to give a colourless oil identified as (R,S)-2-benzyloxycarbonylamino-3-[4-(2,2,2-trifluoro-ethoxy)-phenyl]-propionic acid (380 mg, 0.96 mmol, 30%).

[M+H]$^+$=395.11

B. {(R,S)-1-{(S)-1-[4-(tert-Butoxycarbonylamino-methyl)-benzylcarbamoyl]-2-phenyl-ethylcarbamoyl}-2-[4-(2,2,2-trifluoro-ethoxy)-phenyl]-ethyl}-carbamic acid benzyl ester (R,S)-2-Benzyloxycarbonylamino-3-[4-(2,2,2-trifluoro-ethoxy)-phenyl]-propionic acid (200 mg, 0.50 mmol) was dissolved in CH$_2$Cl$_2$ (50 mL) and DMF (2.5 mL). This solution was cooled to 0° C. {4-[((S)-2-amino-3-phenyl-propionylamino)-methyl]-benzyl}-carbamic acid tert-butyl ester (231 mg, 0.60 mmol) was added followed by HOBt (75 mg, 0.55 mmol) and triethylamine (153 mg, 1.51 mmol). Water soluble carbodiimide (116 mg, 0.60 mmol) was then added. After 18 hours at 0° C. to room temperature reaction mixture was diluted with chloroform (400 mL) washed with 0.3M KHSO4 (1×30 mL), NaHCO$_3$ (1×30 mL), water (1×30 mL), brine (1×30 mL), dried (Na$_2$SO$_4$) and evaporated in vacuo giving a yellow oil. The residue was purified by flash chromatography (silica), eluent 3% MeOH, 97% CHCl$_3$, fractions combined and evaporated in vacuo to give a white solid identified as {(R,S)-1-{(S)-1-[4-(tert-butoxycarbonylamino-methyl)-benzylcarbamoyl]-2-phenyl-ethylcarbamoyl}-2-[4-(2,2,2-trifluoro-ethoxy)-phenyl]-ethyl}-carbamic acid benzyl ester (350 mg, 0.46 mmol, 92%).

[M+H]$^+$=663.43 (M-Boc), 785.44 (M+Na)

C. {4-[((S)-2-{(R,S)-2-Amino-3-[4-(2,2,2-trifluoro-ethoxy)-phenyl]-propionylamino}-3-phenyl-propionylamino)-methyl]-benzyl}-carbamic acid tert-butyl ester {(R,S)-1-{(S)-1-[4-(tert-butoxycarbonylamino-methyl)-benzylcarbamoyl]-2-phenyl-ethylcarbamoyl}-2-[4-(2,2,2-trifluoro-ethoxy)-phenyl]-ethyl}-carbamic acid benzyl ester (350 mg, 0.46 mmol) was dissolved in methanol (100 mL) This solution was hydrogenated over 10% Pd/C (50 mg) at atmospheric for 2 hours after which time the catalyst was filtered off and washed with methanol (100 mls), the combined filtrates were evaporated in vacuo to give a white solid identified as {4-[((S)-2-{(R,S)-2-amino-3-[4-(2,2,2-trifluoro-ethoxy)-phenyl]-propionylamino}-3-phenyl-propionylamino)-methyl]-benzyl}-carbamic acid tert-butyl ester (270 mg, 0.43 mmol, 94%).

[M+H]$^+$=629.40

D. {4-[((S)-2-{(R,S)-2-Benzoylamino-3-[4-(2,2,2-trifluoro-ethoxy)-phenyl]-propionylamino}-3-phenyl-propionylamino)-methyl]-benzyl}-carbamic acid tert-butyl ester {4-[((S)-2-{(R,S)-2-Amino-3-[4-(2,2,2-trifluoro-ethoxy)-phenyl]-propionylamino}-3-phenyl-propionylamino)-methyl]-benzyl}-carbamic acid tert-butyl ester (250 mg, 0.40 mmol) was dissolved in dichloromethane (50 mL). This solution was cooled to 0° C. and triethylamine (121 mg, 1.19 mmol) was added followed by benzoyl chloride (61 mg, 0.44 mmol). The reaction mixture was stirred at 0° C. to room temperature for 18 hours and diluted with CHCl$_3$ (100 mls) the filtrate was washed with 0.3M KHSO$_4$ (1×30 mL), sat. NaHCO$_3$ (1×30 mL), water (1×30 mL), brine (1×30 mL), dried (Na$_2$SO$_4$) and evaporated in vacuo to give a white solid. The solid was triturated with ethyl acetate/pet ether 60-80° C. to give a white solid identified as {4-[((S)-2-{(R,S)-2-benzo ylamino-3-[4-(2,2,2-trifluoro-ethoxy)-phenyl]-propionylamino}-3-phenyl-propionylamino)-methyl]-benzyl}-carbamic acid tert-butyl ester (190 mg, 0.26 mmol, 65%).
[M+H]+=733.357, 755.49 (M+Na)

E. N-{(R,S)-1-[(S)-1-(4-Aminomethyl-benzylcarbamoyl)-2-phenyl-ethylcarbamoyl]-2-[4-(2,2,2-trifluoro-ethoxy)-phenyl]-ethyl}-benzamide Ditrifluoroacetate {4-[((S)-2-{(R,S)-2-Benzoylamino-3-[4-(2,2,2-trifluoro-ethoxy)-phenyl]-propionylamino}-3-phenyl-propionylamino)-methyl]-benzyl}-carbamic acid tert-butyl ester (190 mg, 0.26 mmol) was treated with 4M HCl/dioxan (50 mL). After one hour at room temperature the solvent was removed. The residue was purified by Prep HPLC (Sunfire prep C18 OBD column. 19×250 mm, 10μ). 10 to 90% 0.1% TFA/MeCN into 0.1% TFA/H$_2$O over 35 min at 20 ml/min. Fractions were combined and freeze dried to give a white solid identified N-{(R,S)-1-[(S)-1-(4-aminomethyl-benzylcarbamoyl)-2-phenyl-ethylcarbamoyl]-2-[4-(2,2,2-trifluoro-ethoxy)-phenyl]-ethyl}-benzamide ditrifluoroacetate (56 mg, 0.075 mmol, 29%).
[M+H]+=632.51
$^1$H NMR (d6-DMSO) δ: 2.68 (1H, d, J=7.44 Hz), 2.82-3.08 (5H, m), 3.98 (2H, d, J=5.92 Hz), 4.31-4.34 (2H, m), 4.60-4.70 (4H, m), 6.90-6.94 (2H, m), 7.16-7.28 (6H, m), 7.34-7.37 (2H, m), 7.43-7.52 (3H, m), 7.74-7.79 (2H, m), 8.09 (3H, s, br), 8.47 (1H, d, J=8.45 Hz), 8.58-8.62 (2H, m).

Determination of the Kinetic Solubility in Phosphate Buffer

The solubility was determined turbidimetrically using standard published methods (Lipinski et. al. Advanced Drug Delivery Reviews 23 (1997) 3-25). A 10 mM compound stock was prepared in DMSO, which was added to 25 mM pH 7.0 sodium phosphate buffer to produce concentrations ranging from 12 to 235 μM. After shaking for approximately 30 seconds the reduction in light transmission of these samples, at 650 nm, was measured (Molecular Devices Spectromax UV/visible spectrophotometer). A second measurement was taken at approximately 30 seconds later. Absorbance of greater than 0.005 is taken to indicate that some precipitation of compound has occurred and therefore the compound is not soluble at that concentration.

Data acquired from these determinations are shown in Table 8 below:

TABLE 8

| Example No | solubility in PO$_4$ buffer (μM) |
|---|---|
| 1 | 235 |
| 2 | 235 |
| 3 | 12 |
| 4 | 235 |
| 5 | 235 |
| 6 | 235 |
| 8 | 235 |
| 9 | 235 |
| 10 | 235 |
| 11 | 235 |
| 12 | 235 |
| 14 | 235 |
| 15 | 235 |
| 17 | 235 |
| 18 | 235 |
| 20 | 235 |
| 21 | 12 |

TABLE 8-continued

| Example No | solubility in PO$_4$ buffer (μM) |
|---|---|
| 24 | 235 |
| 25 | 235 |
| 26 | 235 |
| 27 | 235 |
| 29 | 235 |
| 30 | 235 |
| 31 | 235 |
| 32 | 235 |
| 33 | 235 |
| 34 | 235 |
| 35 | 235 |
| 36 | 235 |
| 37 | 235 |
| 38 | 235 |
| 39 | 235 |
| 40 | 235 |
| 41 | 235 |
| 42 | 235 |
| 43 | 235 |
| 44 | 235 |
| 45 | 235 |
| 51 | 235 |
| 52 | 235 |
| 53 | 235 |
| 54 | 12 |
| 55 | 36 |
| 56 | 36 |
| 57 | 36 |
| 58 | 36 |
| 59 | 36 |
| 61 | 235 |
| 63 | 235 |
| 64 | 235 |
| 67 | 235 |

Determination of Thermodynamic Solubility in Phosphate Buffer

The thermodynamic solubility of compound was determined in Ammonium Phosphate Buffer (pH7.4, 290 mOsm). Compounds were made up at a nominal concentration of 1 mg/mL, vortexed then placed on a shaker for 1 h, 37° C. at approximately 950 rpm. Following incubation samples were transferred to eppendorf tubes and centrifuged at 15,000 g (r.c.f.) for 10 minutes at 37° C. The concentration of compound in the supernatant was determined by LC-MS/MS analysis using a calibration line prepared from a DMSO stock.

Data acquired from these determinations are shown in Table 9 below:

TABLE 9

| Example No | Solubility in PO$_4$ buffer (μg/ml) |
|---|---|
| 3 | 10 |
| 38 | 14.55 |
| 54 | 0.8 |
| 55 | 1.5 |
| 56 | 0.9 |
| 58 | 4.1 |
| 59 | 7.7 |
| 70 | 11.53 |
| 71 | 22.1 |
| 72 | 6.9 |
| 73 | 5.1 |
| 75 | 1.06 |
| 79 | 2.4 |
| 81 | 1.3 |
| 84 | 0.5 |

TABLE 9-continued

| Example No | Solubility in PO$_4$ buffer (µg/ml) |
|---|---|
| 88 | 0.2 |
| 92 | 0.2 |
| 93 | 0.01 |
| 95 | 2.05 |
| 99 | 2.88 |
| 116 | 1.39 |
| 119 | 1.61 |
| 124 | 64.45 |
| 125 | 43.60 |
| 131 | 0.56 |
| 140 | 79.63 |
| 141 | 0.15 |
| 143 | 2.86 |
| 145 | 68.91 |
| 150 | 0.12 |
| 151 | 4.31 |
| 152 | 122.19 |
| 153 | 0.19 |
| 154 | 3.14 |
| 155 | 0.44 |
| 157 | 4.77 |
| 158 | 70.56 |
| 159 | 1.15 |
| 160 | 20.4 |
| 162 | 69.69 |
| 173 | 2.38 |
| 174 | 232.69 |
| 175 | 23.4 |
| 176 | 2.28 |
| 178 | 1.54 |
| 179 | 17.72 |
| 181 | 61.65 |
| 199 | 15.88 |
| 200 | 0.22 |

Biological Methods

The ability of the compounds of formula (I) to inhibit plasma kallikrein may be determined using the following biological assay:

Determination of the IC$_{50}$ for Plasma Kallikrein

Plasma kallikrein inhibitory activity in vitro was determined using standard published methods (see e.g. Johansen et al., Int. J. Tiss. Reac. 1986, 8, 185; Shori et al., Biochem. Pharmacol., 1992, 43, 1209; Stürzebecher et al., Biol. Chem. Hoppe-Seyler, 1992, 373, 1025). Human plasma kallikrein (Protogen) was incubated at 37° C. with the fluorogenic substrate H-DPro-Phe-Arg-AFC and various concentrations of the test compound. Residual enzyme activity (initial rate of reaction) was determined by measuring the change in optical absorbance at 410 nm and the IC$_{50}$ value for the test compound was determined.

Data acquired from this assay are shown in Tables 10 and 11 below:

TABLE 10

| Example No | IC50 (human PKal) µM |
|---|---|
| 1 | 0.089 |
| 2 | 0.82 |
| 3 | 0.022 |
| 4 | 0.23 |
| 5 | 0.46 |
| 6 | 1.0 |
| 7 | 0.074 |
| 8 | 0.74 |
| 9 | 2.0 |
| 10 | 7.2 |
| 11 | 1.7 |
| 12 | 0.29 |
| 13 | 10 |
| 14 | 0.40 |
| 15 | 0.47 |
| 16 | 0.053 |
| 17 | 5.8 |
| 18 | 8.8 |
| 19 | 10 |
| 20 | 0.73 |
| 21 | 5.1 |
| 22 | 10 |
| 23 | 0.031 |
| 24 | 0.45 |
| 25 | 0.34 |
| 26 | 0.081 |
| 27 | 1.3 |
| 28 | 8.9 |
| 29 | 0.30 |
| 30 | 0.58 |
| 31 | 4.3 |
| 32 | 0.20 |
| 33 | 1.1 |
| 34 | 1.4 |
| 35 | 2.0 |
| 36 | 8.2 |
| 37 | 0.91 |
| 38 | 0.047 |
| 39 | 0.31 |
| 40 | 1.8 |
| 41 | 1.3 |
| 42 | 0.53 |
| 43 | 1.3 |
| 44 | 0.18 |
| 45 | 0.79 |
| 46 | 1.2 |
| 47 | 2.1 |
| 48 | 4.7 |
| 49 | 2.2 |
| 50 | 4.3 |
| 51 | 1.0 |
| 52 | 0.86 |
| 53 | 0.65 |
| 54 | 0.083 |
| 55 | 0.031 |
| 56 | 0.50 |
| 57 | 10 |
| 58 | 0.17 |
| 59 | 0.078 |
| 60 | 10 |
| 61 | 0.22 |
| 62 | 10 |
| 63 | 0.052 |
| 64 | 3.4 |
| 65 | 10 |
| 66 | 10 |
| 67 | 1.6 |

TABLE 11

| Example No | IC$_{50}$ (human PKal) (µM) |
|---|---|
| 68 | 0.861 |
| 69 | 0.621 |
| 70 | 0.126 |
| 71 | 0.077 |
| 72 | 0.046 |
| 73 | 0.025 |
| 74 | 0.545 |
| 75 | 0.270 |
| 76 | 0.452 |
| 77 | 1.959 |

TABLE 11-continued

| Example No | IC$_{50}$ (human PKal) (μM) |
|---|---|
| 78 | 10.000 |
| 79 | 0.038 |
| 80 | 0.398 |
| 81 | 0.040 |
| 82 | 0.539 |
| 83 | 0.254 |
| 84 | 0.219 |
| 85 | 0.485 |
| 86 | 0.423 |
| 87 | 0.755 |
| 88 | 0.090 |
| 89 | 0.099 |
| 90 | 0.276 |
| 91 | 2.083 |
| 92 | 0.032 |
| 93 | 0.175 |
| 94 | 1.080 |
| 95 | 0.046 |
| 96 | 0.764 |
| 97 | 0.241 |
| 98 | 0.576 |
| 99 | 0.095 |
| 100 | 0.474 |
| 101 | 1.113 |
| 102 | 10.000 |
| 103 | 10.000 |
| 104 | 0.159 |
| 105 | 0.185 |
| 106 | 0.256 |
| 107 | 0.133 |
| 108 | 0.232 |
| 109 | 0.155 |
| 110 | 0.598 |
| 111 | 0.058 |
| 112 | 0.298 |
| 113 | 0.455 |
| 114 | 0.427 |
| 115 | 0.417 |
| 116 | 0.018 |
| 117 | 0.048 |
| 118 | 0.061 |
| 119 | 0.015 |
| 120 | 0.540 |
| 121 | 0.310 |
| 122 | 0.519 |
| 123 | 0.214 |
| 124 | 0.020 |
| 125 | 0.010 |
| 126 | 4.013 |
| 127 | 0.521 |
| 128 | 2.009 |
| 129 | 10.000 |
| 130 | 2.491 |
| 131 | 0.040 |
| 132 | 1.209 |
| 133 | 10.000 |
| 134 | 10.000 |
| 135 | 0.424 |
| 136 | 1.017 |
| 137 | 7.540 |
| 138 | 0.310 |
| 139 | 1.141 |
| 140 | 0.045 |
| 141 | 0.055 |
| 142 | 0.096 |
| 143 | 0.083 |
| 144 | 0.340 |
| 145 | 0.025 |
| 146 | 0.232 |
| 147 | 0.284 |
| 148 | 0.934 |
| 149 | 0.091 |
| 150 | 0.051 |
| 151 | 0.009 |
| 152 | 0.023 |
| 153 | 0.010 |
| 154 | 0.021 |
| 155 | 0.022 |
| 156 | 1.083 |
| 157 | 0.036 |
| 158 | 0.047 |
| 159 | 0.015 |
| 160 | 0.010 |
| 161 | 0.049 |
| 162 | 0.010 |
| 163 | 0.064 |
| 164 | 0.050 |
| 165 | 0.070 |
| 166 | 0.262 |
| 167 | 0.080 |
| 168 | 0.076 |
| 169 | 0.044 |
| 170 | 0.051 |
| 171 | 0.123 |
| 172 | 0.881 |
| 173 | 0.213 |
| 174 | 0.045 |
| 175 | 0.003 |
| 176 | 0.028 |
| 177 | 0.457 |
| 178 | 0.042 |
| 179 | 0.022 |
| 180 | 0.073 |
| 181 | 0.010 |
| 182 | 0.015 |
| 183 | 0.016 |
| 184 | 0.010 |
| 185 | 0.049 |
| 186 | 0.014 |
| 187 | 0.007 |
| 188 | 0.036 |
| 189 | 0.023 |
| 190 | 0.028 |
| 191 | 0.020 |
| 192 | 0.012 |
| 193 | 0.025 |
| 194 | 0.013 |
| 195 | 0.014 |
| 196 | 0.032 |
| 197 | 0.012 |
| 198 | 0.007 |
| 199 | 0.010 |
| 200 | 0.045 |
| 201 | 0.012 |

Selected compounds were further screened for inhibitory activity against the related enzyme KLK1. The ability of the compounds of formula (I) to inhibit KLK1 may be determined using the following biological assay:

Determination of the IC$_{50}$ for KLK1

KLK1 inhibitory activity in vitro was determined using standard published methods (see e.g. Johansen et al., Int. J. Tiss. Reac. 1986, 8, 185; Shori et al., Biochem. Pharmacol., 1992, 43, 1209; Stürzebecher et al., Biol. Chem. Hoppe-Seyler, 1992, 373, 1025). Human KLK1 (Callbiochem) was incubated at 37° C. with the fluorogenic substrate H-DVal-Leu-Arg-AFC and various concentrations of the test compound. Residual enzyme activity (initial rate of reaction) was determined by measuring the change in optical absorbance at 410 nm and the IC$_{50}$ value for the test compound was determined.

Data acquired from this assay are shown in Tables 12 and 13 below:

TABLE 12

| Example No | IC50 (human KLK1) μM |
|---|---|
| 1 | >1 |
| 3 | >10 |
| 4 | >10 |
| 5 | 0.16 |
| 6 | >1 |
| 7 | >1 |
| 8 | >1 |
| 9 | >1 |
| 14 | 3.7 |
| 15 | 2.2 |
| 16 | 4.9 |
| 17 | >10 |
| 18 | 1.6 |
| 19 | >10 |
| 20 | 3.7 |
| 21 | 10 |
| 22 | 9.6 |
| 23 | 5.6 |
| 24 | >10 |
| 25 | 6.3 |
| 26 | >10 |
| 27 | 4.0 |
| 28 | >10 |
| 29 | >10 |
| 30 | >10 |
| 31 | 9.6 |
| 32 | >10 |
| 33 | >10 |
| 34 | 7.7 |
| 35 | >10 |
| 36 | >10 |
| 37 | >10 |
| 38 | >10 |
| 39 | >10 |
| 40 | >10 |
| 41 | 2.5 |
| 42 | >10 |
| 43 | >10 |
| 44 | >10 |
| 45 | >10 |
| 46 | >10 |
| 47 | >10 |
| 48 | >10 |
| 49 | >10 |
| 50 | 5 |
| 51 | >10 |
| 52 | 9.5 |
| 53 | >10 |
| 66 | 8.4 |
| 67 | >10 |

TABLE 13

| Example No | $IC_{50}$ (human KLK1) (μM) |
|---|---|
| 68 | >10 |
| 69 | >10 |
| 70 | 7.5 |
| 71 | >10 |
| 72 | 9.1 |
| 73 | 9.3 |
| 74 | >10 |
| 75 | >10 |
| 76 | 3.6 |
| 77 | >10 |
| 78 | >10 |
| 79 | 8.6 |
| 80 | >10 |
| 81 | >10 |
| 82 | >10 |
| 83 | >10 |
| 84 | 1.2 |
| 85 | 2.9 |
| 86 | >10 |
| 87 | 3.4 |
| 88 | >10 |
| 89 | 3.7 |
| 90 | >10 |
| 91 | >10 |
| 92 | >10 |
| 93 | >10 |
| 94 | >10 |
| 95 | >10 |
| 96 | >10 |
| 97 | 4.7 |
| 98 | 5.1 |
| 99 | >10 |
| 100 | 2.9 |
| 101 | >10 |
| 102 | 9.0 |
| 103 | >10 |
| 104 | >10 |
| 105 | >10 |
| 106 | 8.4 |
| 107 | 7.5 |
| 108 | >10 |
| 109 | >10 |
| 110 | >10 |
| 111 | >10 |
| 112 | >10 |
| 113 | >10 |
| 114 | >10 |
| 115 | 9.0 |
| 116 | 6.3 |
| 117 | 6.1 |
| 118 | >10 |
| 119 | 6.1 |
| 120 | >10 |
| 121 | >10 |
| 122 | 4.8 |
| 123 | >10 |
| 124 | 8.4 |
| 125 | 7.0 |
| 126 | >10 |
| 127 | >10 |
| 128 | >10 |
| 129 | >10 |
| 130 | >10 |
| 131 | 9.5 |
| 132 | >10 |
| 133 | >10 |
| 134 | >10 |
| 135 | >10 |
| 136 | >10 |
| 137 | >10 |
| 138 | >10 |
| 139 | >10 |
| 140 | >10 |
| 141 | >10 |
| 142 | >10 |
| 143 | >10 |
| 144 | >10 |
| 145 | >10 |
| 146 | >10 |
| 147 | >10 |
| 148 | >10 |
| 149 | >10 |
| 150 | >10 |
| 151 | >10 |
| 152 | >10 |
| 153 | >10 |
| 154 | >10 |
| 155 | >10 |
| 156 | >10 |

TABLE 13-continued

| Example No | IC$_{50}$ (human KLK1) (µM) |
|---|---|
| 157 | >10 |
| 158 | >10 |
| 159 | >10 |
| 160 | >10 |
| 161 | 6.9 |
| 162 | >10 |
| 163 | >10 |
| 164 | >10 |
| 165 | >10 |
| 166 | >10 |
| 167 | >10 |
| 168 | >10 |
| 169 | 9.9 |
| 170 | >10 |
| 171 | 9.4 |
| 172 | >10 |
| 173 | >10 |
| 174 | >10 |
| 175 | >10 |
| 176 | >10 |
| 177 | >10 |
| 178 | >10 |
| 179 | 7.2 |
| 180 | >10 |
| 181 | >10 |
| 182 | >10 |
| 183 | >10 |
| 184 | >10 |
| 185 | >10 |
| 186 | 3.8 |
| 187 | >10 |
| 188 | >10 |
| 189 | >10 |
| 190 | >10 |
| 191 | >10 |
| 192 | >10 |
| 193 | >10 |
| 194 | 7.1 |
| 195 | >10 |
| 196 | 9.9 |
| 197 | >10 |
| 198 | 9.1 |
| 199 | >10 |
| 200 | 7.6 |
| 201 | >10 |

Selected compounds were further screened for inhibitory activity against the related enzymes plasmin, thrombin, trypsin, Factor Xa and Factor XIIa. The ability of the compounds of formula (I) to these enzymes may be determined using the following biological assays:

Determination of Enzyme Selectivity

Human serine protease enzymes plasmin, thrombin, trypsin, Factor Xa and Factor XIIa were assayed for enzymatic activity using an appropriate fluorogenic substrate. Protease activity was measured by monitoring the accumulation of liberated fluorescence from the substrate over 5 minutes. The linear rate of fluorescence increase per minute was expressed as percentage (%) activity. The Km for the cleavage of each substrate was determined by standard transformation of the Michaelis-Menten equation. The compound inhibitor assays were performed at substrate Km concentration and activities were calculated as the concentration of inhibitor giving 50% inhibition (IC$_{50}$) of the uninhibited enzyme activity (100%).

Data acquired from these assays are shown in Table 14 below:

TABLE 14

(Selectivity data)

| Example No | IC50 (µM) | | | |
|---|---|---|---|---|
| | Thrombin | Trypsin | Plasmin | Factor Xa |
| 3 | >40 | 10.8 | 3.5 | >10 |

TABLE 15

(Selectivity data: Factor XIIa)

| Example No | IC$_{50}$ (Factor XIIa) (µM) |
|---|---|
| 3 | >10 |
| 85 | >10 |
| 91 | >10 |
| 92 | >10 |
| 93 | >10 |
| 94 | >10 |
| 95 | >10 |
| 96 | >10 |
| 157 | >10 |
| 182 | >10 |
| 183 | >10 |
| 184 | >10 |
| 185 | >10 |
| 186 | >10 |
| 187 | >10 |
| 188 | >10 |
| 189 | >10 |
| 190 | >10 |
| 191 | >10 |
| 192 | >10 |
| 193 | >10 |
| 194 | >10 |
| 195 | >10 |
| 196 | >10 |
| 197 | >10 |
| 198 | >10 |
| 199 | >10 |
| 201 | >10 |

Carbonic Anhydrase I Induced Retinal Vascular Permeability Model

The activity of Example 3 has been established using this in vivo model in the rat. Rats received an intravitreal injection (5 µL) of phosphate buffered saline (PBS), CH-3457 (a plasma kallikrein inhibitor positive control) (10 µM) or Example 3 (1 µM) at time 0. After 30 mins, a second intravitreal injection (5 µL) of PBS or CA-I (200 ng/eye) was given. After 15 minutes, 10% sodium fluorescein was infused and retinal vascular permeability (RVP) was measured by vitreous fluorophotometry 75 minutes following the initial IVT injections. Data for Example 3 are presented in FIG. 1, in which the lower dashed line indicates basal RVP following PBS/PBS and upper dashed line indicates maximal stimulation. Intravitreal injection of 1 µM Example 3 alone had no effect upon basal RVP compared to PBS alone (3.29±0.21 vs. 3.64±0.48). Intravitreal injection of Example 3 reduced RVP (stimulated by CA-I injection) by 53±21%.

Pharmacokinetics

A pharmacokinetic study of Example 3 was performed to assess the ocular and systemic pharmacokinetics following a single IVT dose in pigmented (Dutch-belted) rabbits. Six rabbits per dose level were given a single, bilateral, IVT injection of 50 µL of a 4.2 µg/mL (210 ng per eye) Example 3 formulated in phosphate buffered saline. One rabbit was euthanized at each time point (4, 8, 24, 48, 96 and 168 hours after IVT administration) and ocular tissue concentrations of Example 3 in the vitreous, retina/choroid and aqueous humour were measured. Serial blood samples were collected in surviving rabbits.

Figure 2:
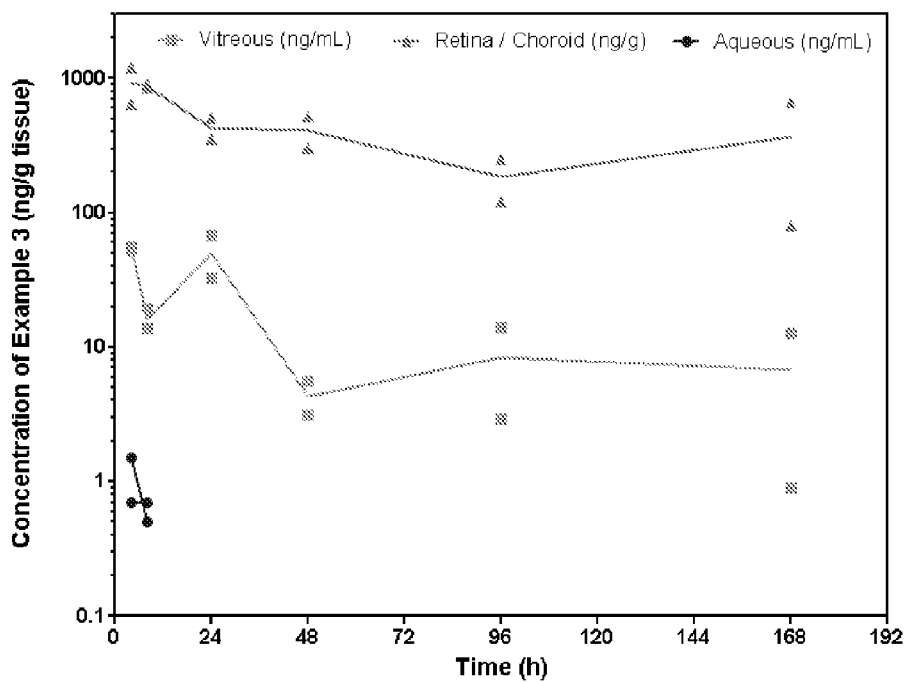
FIG. 2 shows the ocular tissue concentrations of Example 3 following IVT administration of 4.2 µg/mL (210 ng/eye).

Ocular tissue concentration data are presented in FIG. 2, in which the solid line for each ocular tissue concentration is the average of the left and right eye of each rabbit. The decline in ocular tissue concentrations of Example 3 was minimal over 7 days. Plasma concentrations of Example 3 following IVT administration were below 1 ng/mL at all time points.

The invention claimed is:
1. A compound of formula I

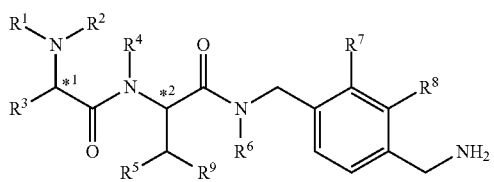

wherein:
- $R^1$ is H, alkyl, —COalkyl, —COaryl, —COheteroaryl, —CO$_2$alkyl, —(CH$_2$)$_a$OH, —(CH$_2$)$_b$COOR$^{10}$, —(CH$_2$)$_c$CONH$_2$, —SO$_2$alkyl, —SO$_2$aryl, —SO$_2$(CH$_2$)$_h$R$^{13}$, —CO(CH$_2$)$_i$R$^{14}$, —COcycloalkyl, —COCH=CHR$^{15}$, —CO(CH$_2$)$_j$NHCO(CH$_2$)$_k$R$^{16}$, or —CONR$^{17}$R$^{18}$;
- $R^2$ is H, or alkyl;
- $R^3$ is H, alkyl, —(CH$_2$)$_d$aryl, —(CH$_2$)$_e$heteroaryl, —(CH$_2$)$_f$cycloalkyl, —(CH$_2$)$_g$heterocycloalkyl, —CH(cycloalkyl)$_2$, —CH(heterocycloalkyl)$_2$, or —(CH$_2$)$_l$aryl-O—(CH$_2$)$_m$-aryl;
- $R^4$ and $R^6$ are independently H or alkyl;
- $R^5$ is H, alkyl, alkoxy, or OH;
- or $R^4$ and $R^5$, together with the atoms to which they are attached, may join to form a 5- or 6-membered azacycloalkyl structure;
- $R^7$ and $R^8$ are independently H, alkyl, alkoxy, CN, halo, or CF$_3$;
- $R^9$ is aryl or heteroaryl;
- $R^{10}$ is H or alkyl;
- a, b, c, d, e, f, g, h, i, j, l and m are independently 1, 2 or 3;
- k is 0, 1, 2 or 3;
- *1 and *2 denote chiral centres;
- alkyl is a linear saturated hydrocarbon having up to 10 carbon atoms (C$_1$-C$_{10}$) or a branched saturated hydrocarbon of between 3 and 10 carbon atoms (C$_3$-C$_{10}$); alkyl may optionally be substituted with 1 or 2 substituents independently selected from (C$_3$-C$_{10}$)cycloalkyl, (C$_1$-C$_6$)alkoxy, OH, CN, CF$_3$, COOR$^{11}$, fluoro and NR$^{11}$R$^{12}$;
- cycloalkyl is a mono- or bi-cyclic saturated hydrocarbon of between 3 and 10 carbon atoms optionally fused to an aryl group;
- heterocycloalkyl is a C-linked or N-linked 3 to 10 membered saturated, mono- or bi-cyclic ring, wherein said heterocycloalkyl ring contains, where possible, 1, 2 or 3 heteroatoms independently selected from N, NR$^{11}$ and O;
- alkoxy is a linear O-linked hydrocarbon of between 1 and 6 carbon atoms (C$_1$-C$_6$) or a branched O-linked hydrocarbon of between 3 and 6 carbon atoms (C$_3$-C$_6$) in either case optionally be substituted with 1 or 2 substituents independently selected from (C$_3$-C$_{10}$)cycloalkyl, OH, CN, CF$_3$, COOR$^{11}$, fluoro and NR$^{11}$R$^{12}$;
- aryl is phenyl, biphenyl or naphthyl optionally substituted with up to 5 substituents independently selected from alkyl, alkoxy, OH, halo, CN, COOR$^{11}$, CF$_3$ and NR$^{11}$R$^{12}$;
- heteroaryl is a 5, 6, 9 or 10 membered mono- or bi-cyclic aromatic ring, containing, where possible, 1, 2 or 3 ring members independently selected from N, NR$^{11}$, S and O; optionally substituted with 1, 2 or 3 substituents independently selected from alkyl, alkoxy, OH, halo, CN, COOR$^{11}$, CF$_3$, NR$^{11}$R$^{12}$ and NHR$^{19}$;
- $R^{11}$ and $R^{12}$ are independently H, or alkyl;
- $R^{13}$ is aryl or heteroaryl;
- $R^{14}$ is aryl, heteroaryl, cycloalkyl or heterocycloalkyl;
- $R^{15}$ is H, alkyl, aryl, heteroaryl, cycloalkyl or heterocycloalkyl;
- $R^{16}$ is H, aryl or heteroaryl;
- $R^{17}$ is H, alkyl, aryl, heteroaryl or heterocycloalkyl;
- $R^{18}$ is —(CH$_2$)$_m$R$^{21}$, where m is 0, 1, 2 or 3 and R$^{21}$ is H, aryl or heteroaryl;
- $R^{19}$ —COalkyl, —COaryl or —COheteroaryl;

or a tautomer, isomer, stereoisomer, enantiomer, diastereoisomer, or racemic and scalemic mixture thereof, a pharmaceutically acceptable salt or solvate thereof.

2. A compound of claim 1, wherein $R^9$ is phenyl or naphthyl, wherein phenyl may be optionally substituted with up to 3 substituents independently selected from alkyl, alkoxy, OH, halo, CN, COOR$^{11}$, CF$_3$ and NR$^{11}$R$^{12}$.

3. A compound of claim 1, wherein $R^9$ is phenyl, 1-naphthalene, 2,4-dichlorophenyl, 3,4-dichlorophenyl, 3,4-difluorophenyl, 4-chlorophenyl, 4-trifluoromethylphenyl, or 4-ethoxyphenyl.

4. A compound of claim 1, wherein $R^1$ is H, —COaryl, —COalkyl, —CH$_2$COOH, —SO$_2$Ph, or —SO$_2$CH$_3$.

5. A compound of claim 1, wherein $R^1$ is —COalkyl or —COaryl.

6. A compound of claim 1, wherein $R^3$ is:

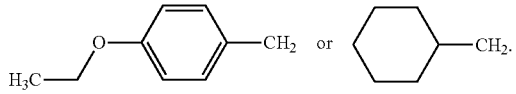

7. A compound of claim 1, wherein $R^4$ and $R^6$ are independently H or CH$_3$.

8. A compound of claim 1, wherein the stereochemical configuration about chiral centre *1 is R.

9. A compound of claim 1, wherein the stereochemical configuration about chiral centre *2 is S.

10. A compound of claim 1, wherein a is 2 and b, c, d, e, f, g, h, j, l and m are each 1.

11. A compound as claimed in claim 1, the compound being:
- (S)—N-(4-Aminomethyl-benzyl)-2-[(R)-3-(4-ethoxy-phenyl)-2-propionylamino-propionylamino]-3-phenyl-propionamide;
- N—[(R)-1-[(S)-1-(4-Aminomethyl-benzylcarbamoyl)-2-phenyl-ethylcarbamoyl]-2-(4-ethoxy-phenyl)-ethyl]-benzamide;
- {(R)-1-[(S)-1-(4-Aminomethyl-benzylcarbamoyl)-2-phenyl-ethylcarbamoyl]-2-cyclohexyl-ethylamino}-acetic acid;

(S)—N-(4-Aminomethyl-3-fluoro-benzyl)-2-[(R)-3-(4-ethoxy-phenyl)-2-propionylamino-propionylamino]-3-phenyl-propionamide;
(S)—N-(4-Aminomethyl-2-chloro-benzyl)-2-[(R)-3-(4-ethoxy-phenyl)-2-propionylamino-propionylamino]-3-phenyl-propionamide;
(S)—N-(4-Aminomethyl-benzyl)-3-(3,4-dichloro-phenyl)-2-[(R)-3-(4-ethoxy-phenyl)-2-propionylamino-propionylamino]-propionamide;
(S)—N-(4-Aminomethyl-3-chloro-benzyl)-2-[(R)-3-(4-ethoxy-phenyl)-2-propionylamino-propionylamino]-3-phenyl-propionamide;
(S)—N-(4-Aminomethyl-benzyl)-2-{[(R)-3-(4-ethoxy-phenyl)-2-propionylamino-propionyl]-methyl-amino}-3-phenyl-propionamide;
({(R)-1-[(S)-1-(4-Aminomethyl-benzylcarbamoyl)-2-phenyl-ethylcarbamoyl]-2-cyclohexyl-ethyl}-methyl-amino)-acetic acid;
(S)—N-(4-Aminomethyl-3-fluoro-benzyl)-2-{[(R)-3-(4-ethoxy-phenyl)-2-propionylamino-propionyl]-methyl-amino}-3-phenyl-propionamide;
N—[(R)-1-{[(S)-1-(4-Aminomethyl-benzylcarbamoyl)-2-phenyl-ethyl]-methyl-carbamoyl}-2-(4-ethoxy-phenyl)-ethyl]-benzamide;
N—[(R)-1-{[(S)-1-(4-Aminomethyl-benzylcarbamoyl)-2-phenyl-ethyl]-methyl-carbamoyl}-2-(4-ethoxy-phenyl)-ethyl]-isobutyramide;
Naphthalene-1-carboxylic acid [(R)-1-[(S)-1-(4-aminomethyl-benzylcarbamoyl)-2-phenyl-ethylcarbamoyl]-2-(4-ethoxy-phenyl)-ethyl]-amide;
N—[(R)-1-[(S)-1-(4-Aminomethyl-benzylcarbamoyl)-2-phenyl-ethylcarbamoyl]-2-(4-ethoxy-phenyl)-ethyl]-4-chloro-benzamide;
N—[(R)-1-[(S)-1-(4-Aminomethyl-benzylcarbamoyl)-2-phenyl-ethylcarbamoyl]-2-(4-ethoxy-phenyl)-ethyl]-2,4-dichloro-benzamide;
N—[(R)-1-[(S)-1-(4-Aminomethyl-benzylcarbamoyl)-2-phenyl-ethylcarbamoyl]-2-(4-ethoxy-phenyl)-ethyl]-3,4-difluoro-benzamide;
(R)-2-Amino-N-[(1S,2S)-1-(4-aminomethyl-benzylcarbamoyl)-2-hydroxy-2-phenyl-ethyl]-3-(4-ethoxy-phenyl)-propionamide;
N—[(R)-1-[(S)-1-(4-Aminomethyl-benzylcarbamoyl)-2-phenyl-ethylcarbamoyl]-2-(4-ethoxy-phenyl)-ethyl]-nicotinamide;
(2S,3S)—N-(4-Aminomethyl-benzyl)-2-[(R)-3-(4-ethoxy-phenyl)-2-propionylamino-propionylamino]-3-hydroxy-3-phenyl-propionamide;
N—[(R)-1-[(S)-1-(4-Aminomethyl-benzylcarbamoyl)-2-phenyl-ethylcarbamoyl]-2-(4-ethoxy-phenyl)-ethyl]-isonicotinamide;
Thiophene-3-carboxylic acid-[(R)-1-[(S)-1-(4-aminomethyl-benzylcarbamoyl)-2-phenyl-ethylcarbamoyl]-2-(4-ethoxy-phenyl)-ethyl]-amide;
Thiophene-2-carboxylic acid [(R)-1-[(S)-1-(4-aminomethyl-benzylcarbamoyl)-2-phenyl-ethylcarbamoyl]-2-(4-ethoxy-phenyl)-ethyl]-amide;
Cyclohexanecarboxylic acid [(R)-1-[(S)-1-(4-aminomethyl-benzylcarbamoyl)-2-phenyl-ethylcarbamoyl]-2-(4-ethoxy-phenyl)-ethyl]-amide;
Isoxazole-5-carboxylic acid [(R)-1-[(S)-1-(4-aminomethyl-benzylcarbamoyl)-2-phenyl-ethylcarbamoyl]-2-(4-ethoxy-phenyl)-ethyl]-amide;
Pyridine-2-carboxylic acid [(R)-1-[(S)-1-(4-aminomethyl-benzylcarbamoyl)-2-phenyl-ethylcarbamoyl]-2-(4-ethoxy-phenyl)-ethyl]-amide;
Benzo[b]thiophene-2-carboxylic acid[(R)-1-[(S)-1-(4-aminomethyl-benzylcarbamoyl)-2-phenyl-ethylcarbamoyl]-2-(4-ethoxy-phenyl)-ethyl]-amide;
(R)—N—[(S)-1-(4-Aminomethyl-benzylcarbamoyl)-2-phenyl-ethyl]-2-(4-chloro-benzenesulfonylamino)-3-(4-ethoxy-phenyl)-propionamide;
N—[(R)-1-[(S)-1-(4-Aminomethyl-benzylcarbamoyl)-2-phenyl-ethylcarbamoyl]-2-(4-ethoxy-phenyl)-ethyl]-3-chloro-benzamide;
N—[(R)-1-[(S)-1-(4-Aminomethyl-benzylcarbamoyl)-2-phenyl-ethylcarbamoyl]-2-(4-ethoxy-phenyl)-ethyl]-2-chloro-benzamide
N—[(R)-1-[(S)-1-(4-Aminomethyl-benzylcarbamoyl)-2-phenyl-ethylcarbamoyl]-2-(4-ethoxy-phenyl)-ethyl]-3-trifluoromethyl-benzamide;
N—[(R)-1-[(S)-1-(4-Aminomethyl-benzylcarbamoyl)-2-phenyl-ethylcarbamoyl]-2-(4-ethoxy-phenyl)-ethyl]-4-methyl-benzamide;
N—[(R)-1-[(S)-1-(4-Aminomethyl-benzylcarbamoyl)-2-phenyl-ethylcarbamoyl]-2-(4-ethoxy-phenyl)-ethyl]-3,4-dichloro-benzamide;
N—[(R)-1-[(S)-1-(4-Aminomethyl-benzylcarbamoyl)-2-phenyl-ethylcarbamoyl]-2-(4-ethoxy-phenyl)-ethyl]-4-methoxy-benzamide;
(S)—N-(4-Aminomethyl-benzyl)-2-[(R)-3-(4-ethoxy-phenyl)-2-(2-phenylacetylamino-acetylamino)-propionylamino]-3-phenyl-propionamide;
N—[(R)-1-[(S)-1-(4-Aminomethyl-benzylcarbamoyl)-2-phenyl-ethylcarbamoyl]-2-(4-ethoxy-phenyl)-ethyl]-4-fluoro-benzamide;
N—[(R)-1-[(S)-1-(4-Aminomethyl-benzylcarbamoyl)-2-phenyl-ethylcarbamoyl]-2-(4-ethoxy-phenyl)-ethyl]-6-methyl-nicotinamide;
N—[(R)-1-[(S)-1-(4-Aminomethyl-benzylcarbamoyl)-2-phenyl-ethylcarbamoyl]-2-(4-ethoxy-phenyl)-ethyl]-2-methyl-nicotinamide;
N—[(R)-1-[(S)-1-(4-Aminomethyl-benzylcarbamoyl)-2-phenyl-ethylcarbamoyl]-2-(4-ethoxy-phenyl)-ethyl]-2,6-dichloro-nicotinamide;
N—[(R)-1-[(S)-1-(4-Aminomethyl-benzylcarbamoyl)-2-phenyl-ethylcarbamoyl]-2-(4-ethoxy-phenyl)-ethyl]-5,6-dichloro-nicotinamide;
N—[(R)-1-[(S)-1-(4-Aminomethyl-benzylcarbamoyl)-2-phenyl-ethylcarbamoyl]-2-(4-ethoxy-phenyl)-ethyl]-2,3,6-trifluoro-isonicotinamide;
N—[(R)-1-[(S)-1-(4-Aminomethyl-benzylcarbamoyl)-2-phenyl-ethylcarbamoyl]-2-(4-ethoxy-phenyl)-ethyl]-3,3,3-trifluoro-propionamide;
2,4-Dimethyl-thiazole-5-carboxylic acid [(R)-1-[(S)-1-(4-aminomethyl-benzylcarbamoyl)-2-phenyl-ethylcarbamoyl]-2-(4-ethoxy-phenyl)-ethyl]-amide;
2-Methyl-thiazole-5-carboxylic acid [(R)-1-[(S)-1-(4-aminomethyl-benzylcarbamoyl)-2-phenyl-ethylcarbamoyl]-2-(4-ethoxy-phenyl)-ethyl]-amide;
3-Chloro-thiophene-2-carboxylic acid [(R)-1-[(S)-1-(4-aminomethyl-benzylcarbamoyl)-2-phenyl-ethylcarbamoyl]-2-(4-ethoxy-phenyl)-ethyl]-amide;
4-Methyl-thiazole-5-carboxylic acid[(R)-1-[(S)-1-(4-aminomethyl-benzylcarbamoyl)-2-phenyl-ethylcarbamoyl]-2-(4-ethoxy-phenyl)-ethyl]-amide;
Furan-2-carboxylic acid [(R)-1-[(S)-1-(4-aminomethyl-benzylcarbamoyl)-2-phenyl-ethylcarbamoyl]-2-(4-ethoxy-phenyl)-ethyl]-amide;
3-Methyl-thiophene-2-carboxylic acid [(R)-1-[(S)-1-(4-aminomethyl-benzylcarbamoyl)-2-phenyl-ethylcarbamoyl]-2-(4-ethoxy-phenyl)-ethyl]-amide;

N—[(R)-1-[(S)-1-(4-Aminomethyl-benzylcarbamoyl)-2-phenyl-ethylcarbamoyl]-2-(4-ethoxy-phenyl)-ethyl]-2-methoxy-isonicotinamide;
3-Methyl-1H-pyrrole-2-carboxylic acid [(R)-1-[(S)-1-(4-aminomethyl-benzylcarbamoyl)-2-phenyl-ethylcarbamoyl]-2-(4-ethoxy-phenyl)-ethyl]-amide;
3-Amino-thiophene-2-carboxylic acid [(R)-1-[(S)-1-(4-aminomethyl-benzylcarbamoyl)-2-phenyl-ethylcarbamoyl]-2-(4-ethoxy-phenyl)-ethyl]-amide;
N—[(R)-1-[(S)-1-(4-Aminomethyl-benzylcarbamoyl)-2-phenyl-ethylcarbamoyl]-2-(4-propoxy-phenyl)-ethyl]-benzamide;
N—[(R)-1-[(S)-1-(4-Aminomethyl-benzylcarbamoyl)-2-pyridin-2-yl-ethylcarbamoyl]-2-(4-ethoxy-phenyl)-ethyl]-benzamide;
N—[(R)-1-[(S)-1-(4-Aminomethyl-benzylcarbamoyl)-2-(3,4-dichloro-phenyl)-ethylcarbamoyl]-2-(4-ethoxy-phenyl)-ethyl]-benzamide;
N—[(R)-1-[(S)-1-(4-Aminomethyl-benzylcarbamoyl)-2-(4-chloro-phenyl)-ethylcarbamoyl]-2-(4-ethoxy-phenyl)-ethyl]-benzamide;
N—[(R)-1-[(S)-1-(4-Aminomethyl-benzylcarbamoyl)-2-(4-fluoro-phenyl)-ethylcarbamoyl]-2-(4-ethoxy-phenyl)-ethyl]-benzamide;
N—[(R)-1-[(S)-1-(4-Aminomethyl-benzylcarbamoyl)-2-pyridin-3-yl-ethylcarbamoyl]-2-(4-ethoxy-phenyl)-ethyl]-benzamide;
N—[(R)-1-[(S)-1-(4-Aminomethyl-benzylcarbamoyl)-2-(4-methoxy-phenyl)-ethylcarbamoyl]-2-(4-ethoxy-phenyl)-ethyl]-benzamide;
N—[(R)-1-[(S)-1-(4-Aminomethyl-benzylcarbamoyl)-2-pyridin-4-yl-ethylcarbamoyl]-2-(4-ethoxy-phenyl)-ethyl]-benzamide;
N—[(R)-1-[(S)-1-(4-Aminomethyl-benzylcarbamoyl)-2-(3-fluoro-phenyl)-ethylcarbamoyl]-2-(4-ethoxy-phenyl)-ethyl]-benzamide;
N—[(R)-1-[(S)-1-(4-Aminomethyl-benzylcarbamoyl)-2-thiophen-2-yl-ethylcarbamoyl]-2-(4-ethoxy-phenyl)-ethyl]-benzamide;
N—[(R)-1-[(S)-1-(4-Aminomethyl-benzylcarbamoyl)-2-thiophen-3-yl-ethylcarbamoyl-2-(4-ethoxy-phenyl)-ethyl]-benzamide;
N—[(R)-1-[(S)-1-(4-Aminomethyl-benzylcarbamoyl)-2-thiazol-4-yl-ethylcarbamoyl]-2-(4-ethoxy-phenyl)-ethyl]-benzamide;
N—[(R)-1-[(S)-1-(4-Aminomethyl-benzylcarbamoyl)-2-benzo[b]thiophen-3-yl-ethylcarbamoyl]-2-(4-ethoxy-phenyl)-ethyl]-benzamide;
N—[(R)-1-[(S)-1-(4-Aminomethyl-3-fluoro-benzylcarbamoyl)-2-phenyl-ethylcarbamoyl]-2-(4-ethoxy-phenyl)-ethyl]-benzamide;
N—[(R)-1-[(S)-1-(4-Aminomethyl-3-chloro-benzylcarbamoyl)-2-phenyl-ethylcarbamoyl]-2-(4-ethoxy-phenyl)-ethyl]-benzamide;
Pyridine-2-carboxylic acid [(R)-1-[(S)-1-(4-aminomethyl-benzylcarbamoyl)-2-thiophen-2-yl-ethylcarbamoyl]-2-(4-ethoxy-phenyl)-ethyl]-amide;
N—[(R)-1-[(S)-1-(4-Aminomethyl-benzylcarbamoyl)-2-pyridin-2-yl-ethylcarbamoyl]-2-(4-ethoxy-phenyl)-ethyl]-4-methoxy-benzamide;
Pyridine-2-carboxylic acid [(R)-1-[(S)-1-(4-aminomethyl-3-chloro-benzylcarbamoyl)-2-phenyl-ethylcarbamoyl]-2-(4-ethoxy-phenyl)-ethyl]-amide;
N—[(R)-1-[(S)-1-(4-Aminomethyl-benzylcarbamoyl)-2-pyridin-3-yl-ethylcarbamoyl]-2-(4-ethoxy-phenyl)-ethyl]-4-methoxy-benzamide;
N—[(R)-1-[(S)-1-(4-Aminomethyl-benzylcarbamoyl)-2-(3,4-difluoro-phenyl)-ethylcarbamoyl]-2-(4-ethoxy-phenyl)-ethyl]-isonicotinamide;
Thiophene-2-carboxylic acid [(R)-1-[(S)-1-(4-aminomethyl-benzylcarbamoyl)-2-pyridin-3-yl-ethylcarbamoyl]-2-(4-ethoxy-phenyl)-ethyl]-amide;
N—[(R)-1-[(S)-1-(4-Aminomethyl-benzylcarbamoyl)-2-pyridin-2-yl-ethylcarbamoyl]-2-(4-ethoxy-phenyl)-ethyl]-4-chloro-benzamide;
N—[(R)-1-[(S)-1-(4-Aminomethyl-benzylcarbamoyl)-2-pyridin-2-yl-ethylcarbamoyl]-2-(4-ethoxy-phenyl)-ethyl]-4-methyl-benzamide;
Pyridine-2-carboxylic acid [(R)-1-[(S)-1-(4-aminomethyl-benzylcarbamoyl)-2-(3,4-dichloro-phenyl)-ethylcarbamoyl]-2-(4-ethoxy-phenyl)-ethyl]-amide;
(R)—N—[(S)-1-(4-Aminomethyl-benzylcarbamoyl)-2-pyridin-2-yl-ethyl]-3-(4-ethoxy-phenyl)-2-propionylamino-propionamide;
N—[(R)-1-[(S)-1-(4-Aminomethyl-3-fluoro-benzylcarbamoyl)-2-phenyl-ethylcarbamoyl]-2-(4-ethoxy-phenyl)-ethyl]-isonicotinamide;
Pyridine-2-carboxylic acid [(R)-1-[(S)-1-(4-aminomethyl-3-fluoro-benzylcarbamoyl)-2-phenyl-ethylcarbamoyl]-2-(4-ethoxy-phenyl)-ethyl]-amide;
Thiophene-2-carboxylic acid [(R)-1-[(S)-1-(4-aminomethyl-benzylcarbamoyl)-2-(3,4-dichloro-phenyl)-ethylcarbamoyl]-2-(4-ethoxy-phenyl)-ethyl]-amide;
(R)—N—[(S)-1-(4-Aminomethyl-benzylcarbamoyl)-2-pyridin-3-yl-ethyl]-3-(4-ethoxy-phenyl)-2-propionylamino-propionamide;
N—[(R)-1-[(S)-1-(4-Aminomethyl-benzylcarbamoyl)-2-(3,4-dichloro-phenyl)-ethylcarbamoyl]-2-(4-ethoxy-phenyl)-ethyl]-isonicotinamide;
N—[(R)-1-[(S)-1-(4-Aminomethyl-benzylcarbamoyl)-2-(3,4-dichloro-phenyl)-ethylcarbamoyl]-2-(4-ethoxy-phenyl)-ethyl]-3,3,3-trifluoro-propionamide;
N—[(R)-1-[(S)-1-(4-Aminomethyl-benzylcarbamoyl)-2-pyridin-3-yl-ethylcarbamoyl]-2-(4-ethoxy-phenyl)-ethyl]-4-chloro-benzamide;
Isoxazole-5-carboxylic acid [(R)-1-[(S)-1-(4-aminomethyl-benzylcarbamoyl)-2-pyridin-3-yl-ethylcarbamoyl]-2-(4-ethoxy-phenyl)-ethyl]-amide;
N—[(R)-1-[(S)-1-(4-Aminomethyl-benzylcarbamoyl)-2-pyridin-3-yl-ethylcarbamoyl]-2-(4-ethoxy-phenyl)-ethyl]-4-methyl-benzamide;
N—[(R)-1-[(S)-1-(4-Aminomethyl-benzylcarbamoyl)-2-(3,4-difluoro-phenyl)-ethylcarbamoyl]-2-(4-ethoxy-phenyl)-ethyl]-benzamide;
3-Chloro-thiophene-2-carboxylic acid [(R)-1-[(S)-1-(4-aminomethyl-benzylcarbamoyl)-2-pyridin-3-yl-ethylcarbamoyl]-2-(4-ethoxy-phenyl)-ethyl]-amide;
N—[(R)-1-[(S)-1-(4-Aminomethyl-benzylcarbamoyl)-2-(1H-indol-3-yl)-ethylcarbamoyl]-2-(4-ethoxy-phenyl)-ethyl]-benzamide;
N—[(R)-1-[(S)-1-(4-Aminomethyl-benzylcarbamoyl)-2-benzo[b]thiophen-3-yl-ethylcarbamoyl]-2-(4-ethoxy-phenyl)-ethyl]-isonicotinamide;
3-Acetylamino-thiophene-2-carboxylic acid-[(R)-1-[(S)-1-(4-aminomethyl-benzylcarbamoyl)-2-phenyl-ethylcarbamoyl]-2-(4-ethoxy-phenyl)-ethyl]-amide;
N—[(R)-1-[(S)-1-(4-Aminomethyl-benzylcarbamoyl)-2-(2-fluoro-phenyl)-ethylcarbamoyl]-2-(4-ethoxy-phenyl)-ethyl]-benzamide;
3-Methyl-thiophene-2-carboxylic acid [(R)-1-[(S)-1-(4-aminomethyl-benzylcarbamoyl)-2-pyridin-3-yl-ethylcarbamoyl]-2-(4-ethoxy-phenyl)-ethyl]-amide;

N—[(R)-1-[(S)-1-(4-Aminomethyl-3-methyl-benzylcarbamoyl)-2-phenyl-ethylcarbamoyl]-2-(4-ethoxy-phenyl)-ethyl]-benzamide;

3-Amino-thiophene-2-carboxylic acid [(R)-1-[(S)-1-(4-aminomethyl-benzylcarbamoyl)-2-thiazol-4-yl-ethylcarbamoyl]-2-(4-ethoxy-phenyl)-ethyl]-amide;

3-Chloro-thiophene-2-carboxylic acid [(R)-1-[(S)-1-(4-aminomethyl-benzylcarbamoyl)-2-thiazol-4-yl-ethylcarbamoyl]-2-(4-ethoxy-phenyl)-ethyl]-amide;

N—[(R)-1-[(S)-1-(4-Aminomethyl-benzylcarbamoyl)-2-thiazol-4-yl-ethylcarbamoyl]-2-(4-ethoxy-phenyl)-ethyl]-4-methyl-benzamide;

3-Methyl-1H-pyrrole-2-carboxylic acid [(R)-1-[(S)-1-(4-aminomethyl-benzylcarbamoyl)-2-benzo[b]thiophen-3-yl-ethylcarbamoyl]-2-(4-ethoxy-phenyl)-ethyl]-amide;

3-Amino-thiophene-2-carboxylic acid [(R)-1-[(S)-1-(4-aminomethyl-benzylcarbamoyl)-2-thiazol-4-yl-ethylcarbamoyl]-2-(4-ethoxy-phenyl)-ethyl]-amide;

3-Acetylamino-thiophene-2-carboxylic acid [(R)-1-[(S)-1-(4-aminomethyl-benzylcarbamoyl)-2-benzo[b]thiophen-3-yl-ethylcarbamoyl]-2-(4-ethoxy-phenyl)-ethyl]-amide;

N—[(R)-1-[(S)-1-(4-Aminomethyl-benzylcarbamoyl)-2-pyridin-3-yl-ethylcarbamoyl]-2-(4-ethoxy-phenyl)-ethyl]-3-methyl-benzamide;

N—[(R)-1-[(S)-1-(4-Aminomethyl-benzylcarbamoyl)-2-pyridin-3-yl-ethylcarbamoyl]-2-(4-ethoxy-phenyl)-ethyl]-2-methyl-benzamide;

3,5-Dimethyl-1H-pyrrole-2-carboxylic acid [(R)-1-[(S)-1-(4-aminomethyl-benzylcarbamoyl)-2-phenyl-ethylcarbamoyl]-2-(4-ethoxy-phenyl)-ethyl]-amide;

N—[(R)-1-[(S)-1-(4-Aminomethyl-3-methyl-benzylcarbamoyl)-2-pyridin-3-yl-ethylcarbamoyl]-2-(4-ethoxy-phenyl)-ethyl]-benzamide;

3-Acetylamino-thiophene-2-carboxylic acid [(R)-1-[(S)-1-(4-aminomethyl-benzylcarbamoyl)-2-thiophen-3-yl-ethylcarbamoyl]-2-(4-ethoxy-phenyl)-ethyl]-amide;

3-Amino-thiophene-2-carboxylic acid [(R)-1-[(S)-1-(4-aminomethyl-benzylcarbamoyl)-2-benzo[b]thiophen-3-yl-ethylcarbamoyl]-2-(4-ethoxy-phenyl)-ethyl]-amide;

3-Acetylamino-thiophene-2-carboxylic acid [(R)-1-[(S)-1-(4-aminomethyl-benzylcarbamoyl)-2-benzo[b]thiophen-3-yl-ethylcarbamoyl]-2-(4-ethoxy-phenyl)-ethyl]-amide;

3-Chloro-thiophene-2-carboxylic acid [(R)-1-{[(S)-1-(4-aminomethyl-benzylcarbamoyl)-2-phenyl-ethyl]-methyl-carbamoyl}-2-(4-ethoxy-phenyl)-ethyl]-amide;

N—[(R)-1-[(1S,2R)-1-(4-Aminomethyl-benzylcarbamoyl)-2-hydroxy-2-phenyl-ethylcarbamoyl]-2-(4-ethoxy-phenyl)-ethyl]-benzamide;

3-Chloro-thiophene-2-carboxylic acid [(R)-1-[(1S,2R)-1-(4-aminomethyl-benzylcarbamoyl)-2-hydroxy-2-phenyl-ethylcarbamoyl]-2-(4-ethoxy-phenyl)-ethyl]-amide;

N-{(R,S)-1-[(S)-1-(4-Aminomethyl-benzylcarbamoyl)-2-phenyl-ethylcarbamoyl]-2-[4-(2,2,2-trifluoro-ethoxy)-phenyl]-ethyl}-benzamide;

or a pharmaceutically acceptable salt or solvate thereof.

12. A compound as claimed in claim 1, the compound being:

N—[(R)-1-[(S)-1-(4-Aminomethyl-benzylcarbamoyl)-2-phenyl-ethylcarbamoyl]-2-(4-ethoxy-phenyl)-ethyl]-benzamide;

Naphthalene-1-carboxylic acid [(R)-1-[(S)-1-(4-aminomethyl-benzylcarbamoyl)-2-phenyl-ethylcarbamoyl]-2-(4-ethoxy-phenyl)-ethyl]-amide;

N—[(R)-1-[(S)-1-(4-Aminomethyl-benzylcarbamoyl)-2-phenyl-ethylcarbamoyl]-2-(4-ethoxy-phenyl)-ethyl]-4-chloro-benzamide;

N—[(R)-1-[(S)-1-(4-Aminomethyl-benzylcarbamoyl)-2-phenyl-ethylcarbamoyl]-2-(4-ethoxy-phenyl)-ethyl]-2,4-dichloro-benzamide;

N—[(R)-1-[(S)-1-(4-Aminomethyl-benzylcarbamoyl)-2-phenyl-ethylcarbamoyl]-2-(4-ethoxy-phenyl)-ethyl]-nicotinamide;

N—[(R)-1-[(S)-1-(4-Aminomethyl-benzylcarbamoyl)-2-phenyl-ethylcarbamoyl]-2-(4-ethoxy-phenyl)-ethyl]-3,4-difluoro-benzamide;

N—[(R)-1-[(S)-1-(4-Aminomethyl-benzylcarbamoyl)-2-phenyl-ethylcarbamoyl]-2-(4-ethoxy-phenyl)-ethyl]-isonicotinamide;

Thiophene-3-carboxylic acid-[(R)-1-[(S)-1-(4-aminomethyl-benzylcarbamoyl)-2-phenyl-ethylcarbamoyl]-2-(4-ethoxy-phenyl)-ethyl]-amide;

Thiophene-2-carboxylic acid [(R)-1-[(S)-1-(4-aminomethyl-benzylcarbamoyl)-2-phenyl-ethylcarbamoyl]-2-(4-ethoxy-phenyl)-ethyl]-amide;

Cyclohexanecarboxylic acid [(R)-1-[(S)-1-(4-aminomethyl-benzylcarbamoyl)-2-phenyl-ethylcarbamoyl]-2-(4-ethoxy-phenyl)-ethyl]-amide;

Isoxazole-5-carboxylic acid [(R)-1-[(S)-1-(4-aminomethyl-benzylcarbamoyl)-2-phenyl-ethylcarbamoyl]-2-(4-ethoxy-phenyl)-ethyl]-amide;

Pyridine-2-carboxylic acid [(R)-1-[(S)-1-(4-aminomethyl-benzylcarbamoyl)-2-phenyl-ethylcarbamoyl]-2-(4-ethoxy-phenyl)-ethyl]-amide;

(R)—N—[(S)-1-(4-Aminomethyl-benzylcarbamoyl)-2-phenyl-ethyl]-2-(4-chloro-benzenesulfonylamino)-3-(4-ethoxy-phenyl)-propionamide;

N—[(R)-1-[(S)-1-(4-Aminomethyl-benzylcarbamoyl)-2-phenyl-ethylcarbamoyl]-2-(4-ethoxy-phenyl)-ethyl]-4-methyl-benzamide;

N—[(R)-1-[(S)-1-(4-Aminomethyl-benzylcarbamoyl)-2-phenyl-ethylcarbamoyl]-2-(4-ethoxy-phenyl)-ethyl]-3,4-dichloro-benzamide;

N—[(R)-1-[(S)-1-(4-Aminomethyl-benzylcarbamoyl)-2-phenyl-ethylcarbamoyl]-2-(4-ethoxy-phenyl)-ethyl]-3-chloro-benzamide;

N—[(R)-1-[(S)-1-(4-Aminomethyl-benzylcarbamoyl)-2-phenyl-ethylcarbamoyl]-2-(4-ethoxy-phenyl)-ethyl]-4-methoxy-benzamide;

N—[(R)-1-[(S)-1-(4-Aminomethyl-benzylcarbamoyl)-2-phenyl-ethylcarbamoyl]-2-(4-ethoxy-phenyl)-ethyl]-4-fluoro-benzamide;

3-Methyl-thiophene-2-carboxylic acid [(R)-1-[(S)-1-(4-aminomethyl-benzylcarbamoyl)-2-phenyl-ethylcarbamoyl]-2-(4-ethoxy-phenyl)-ethyl]-amide;

3-Methyl-1H-pyrrole-2-carboxylic acid [(R)-1-[(S)-1-(4-aminomethyl-benzylcarbamoyl)-2-phenyl-ethylcarbamoyl]-2-(4-ethoxy-phenyl)-ethyl]-amide;

3-Amino-thiophene-2-carboxylic acid [(R)-1-[(S)-1-(4-aminomethyl-benzylcarbamoyl)-2-phenyl-ethylcarbamoyl]-2-(4-ethoxy-phenyl)-ethyl]-amide;

N—[(R)-1-[(S)-1-(4-Aminomethyl-benzylcarbamoyl)-2-phenyl-ethylcarbamoyl]-2-(4-propoxy-phenyl)-ethyl]-benzamide;

N—[(R)-1-[(S)-1-(4-Aminomethyl-benzylcarbamoyl)-2-pyridin-2-yl-ethylcarbamoyl]-2-(4-ethoxy-phenyl)-ethyl]-benzamide;

N—[(R)-1-[(S)-1-(4-Aminomethyl-benzylcarbamoyl)-2-(3,4-dichloro-phenyl)-ethylcarbamoyl]-2-(4-ethoxy-phenyl)-ethyl]-benzamide;
N—[(R)-1-[(S)-1-(4-Aminomethyl-benzylcarbamoyl)-2-(4-fluoro-phenyl)-ethylcarbamoyl]-2-(4-ethoxy-phenyl)-ethyl]-benzamide;
N—[(R)-1-[(S)-1-(4-Aminomethyl-benzylcarbamoyl)-2-pyridin-3-yl-ethylcarbamoyl]-2-(4-ethoxy-phenyl)-ethyl]-benzamide;
N—[(R)-1-[(S)-1-(4-Aminomethyl-benzylcarbamoyl)-2-thiophen-2-yl-ethylcarbamoyl]-2-(4-ethoxy-phenyl)-ethyl]-benzamide;
N—[(R)-1-[(S)-1-(4-Aminomethyl-benzylcarbamoyl)-2-thiophen-3-yl-ethylcarbamoyl-2-(4-ethoxy-phenyl)-ethyl]-benzamide;
N—[(R)-1-[(S)-1-(4-Aminomethyl-benzylcarbamoyl)-2-benzo[b]thiophen-3-yl-ethylcarbamoyl]-2-(4-ethoxy-phenyl)-ethyl]-benzamide;
N—[(R)-1-[(S)-1-(4-Aminomethyl-3-fluoro-benzylcarbamoyl)-2-phenyl-ethylcarbamoyl]-2-(4-ethoxy-phenyl)-ethyl]-benzamide;
N—[(R)-1-[(S)-1-(4-Aminomethyl-3-chloro-benzylcarbamoyl)-2-phenyl-ethylcarbamoyl]-2-(4-ethoxy-phenyl)-ethyl]-benzamide;
Pyridine-2-carboxylic acid [(R)-1-[(S)-1-(4-aminomethyl-benzylcarbamoyl)-2-thiophen-2-yl-ethylcarbamoyl]-2-(4-ethoxy-phenyl)-ethyl]-amide;
N—[(R)-1-[(S)-1-(4-Aminomethyl-benzylcarbamoyl)-2-pyridin-2-yl-ethylcarbamoyl]-2-(4-ethoxy-phenyl)-ethyl]-4-methoxy-benzamide;
Pyridine-2-carboxylic acid [(R)-1-[(S)-1-(4-aminomethyl-3-chloro-benzylcarbamoyl)-2-phenyl-ethylcarbamoyl]-2-(4-ethoxy-phenyl)-ethyl]-amide;
N—[(R)-1-[(S)-1-(4-Aminomethyl-benzylcarbamoyl)-2-pyridin-3-yl-ethylcarbamoyl]-2-(4-ethoxy-phenyl)-ethyl]-4-methoxy-benzamide;
Thiophene-2-carboxylic acid [(R)-1-[(S)-1-(4-aminomethyl-benzylcarbamoyl)-2-pyridin-3-yl-ethylcarbamoyl]-2-(4-ethoxy-phenyl)-ethyl]-amide;
N—[(R)-1-[(S)-1-(4-Aminomethyl-benzylcarbamoyl)-2-pyridin-3-yl-ethylcarbamoyl]-2-(4-ethoxy-phenyl)-ethyl]-4-methyl-benzamide;
N—[(R)-1-[(S)-1-(4-Aminomethyl-benzylcarbamoyl)-2-(3,4-difluoro-phenyl)-ethylcarbamoyl]-2-(4-ethoxy-phenyl)-ethyl]-benzamide;
3-Chloro-thiophene-2-carboxylic acid [(R)-1-[(S)-1-(4-aminomethyl-benzylcarbamoyl)-2-phenyl-ethylcarbamoyl]-2-(4-ethoxy-phenyl)-ethyl]-amide;
3-Chloro-thiophene-2-carboxylic acid [(R)-1-[(S)-1-(4-aminomethyl-benzylcarbamoyl)-2-pyridin-3-yl-ethylcarbamoyl]-2-(4-ethoxy-phenyl)-ethyl]-amide;
N—[(R)-1-[(S)-1-(4-Aminomethyl-benzylcarbamoyl)-2-(1H-indol-3-yl)-ethylcarbamoyl]-2-(4-ethoxy-phenyl)-ethyl]-benzamide;
N—[(R)-1-[(S)-1-(4-Aminomethyl-benzylcarbamoyl)-2-benzo[b]thiophen-3-yl-ethylcarbamoyl]-2-(4-ethoxy-phenyl)-ethyl]-isonicotinamide;
3-Acetylamino-thiophene-2-carboxylic acid-[(R)-1-[(S)-1-(4-aminomethyl-benzylcarbamoyl)-2-phenyl-ethylcarbamoyl]-2-(4-ethoxy-phenyl)-ethyl]-amide;
3-Methyl-thiophene-2-carboxylic acid [(R)-1-[(S)-1-(4-aminomethyl-benzylcarbamoyl)-2-pyridin-3-yl-ethylcarbamoyl]-2-(4-ethoxy-phenyl)-ethyl]-amide;
or a pharmaceutically acceptable salt or solvate thereof.

13. A pharmaceutical composition comprising a compound of claim 1 and a pharmaceutically acceptable carrier, diluent or excipient.

14. A compound as claimed in claim 1, the compound being N—[(R)-1-[(S)-1-(4-Aminomethyl-benzylcarbamoyl)-2-phenyl-ethylcarbamoyl]-2-(4-ethoxy-phenyl)-ethyl]-benzamide or a pharmaceutically acceptable salt or solvate thereof.

15. A compound as claimed in claim 1, the compound being 3-Chloro-thiophene-2-carboxylic acid [(R)-1-[(S)-1-(4-Aminomethyl-benzylcarbamoyl)-2-pyridin-3-yl-ethylcarbamoyl]-2-(4-ethoxy-phenyl)-ethyl]-amide or a pharmaceutically acceptable salt or solvate thereof.

16. A compound as claimed in claim 1, the compound being N—[(R)-1-[(S)-1-(4-Aminomethyl-3-methyl-benzylcarbamoyl)-2-phenyl-ethylcarbamoyl]-2-(4-ethoxy-phenyl)-ethyl]-benzamide or a pharmaceutically acceptable salt or solvate thereof.

17. A compound as claimed in claim 1, the compound being N—[(R)-1-[(S)-1-(4-Aminomethyl-benzylcarbamoyl)-2-pyridin-3-yl-ethylcarbamoyl]-2-(4-ethoxy-phenyl)-ethyl]-4-methyl-benzamide or a pharmaceutically acceptable salt or solvate thereof.

\* \* \* \* \*